United States Patent
Rufo et al.

(10) Patent No.: US 11,581,099 B1
(45) Date of Patent: Feb. 14, 2023

(54) AUTOMATED HOME SYSTEM FOR SENIOR CARE

(71) Applicant: HAPPIE HOME, INC., Henderson, NV (US)

(72) Inventors: Anthony P. Rufo, Las Vegas, NV (US); Phyllis K. Rufo, Las Vegas, NV (US); William J. McMaster, San Jose, CA (US); James P. Kosta, Reno, NV (US); Dylan S. Petty, Reno, NV (US)

(73) Assignee: HAPPIE HOME, INC., Henderson, NV (US)

( * ) Notice: Subject to any disclaimer, the term of this patent is extended or adjusted under 35 U.S.C. 154(b) by 728 days.

(21) Appl. No.: 16/717,943

(22) Filed: Dec. 17, 2019

Related U.S. Application Data

(63) Continuation-in-part of application No. 15/971,011, filed on May 4, 2018, now abandoned.
(Continued)

(51) Int. Cl.
*G16H 80/00* (2018.01)
*H04L 12/28* (2006.01)
(Continued)

(52) U.S. Cl.
CPC ............ *G16H 80/00* (2018.01); *G05B 15/02* (2013.01); *G06N 20/00* (2019.01); *G16H 10/60* (2018.01);
(Continued)

(58) Field of Classification Search
None
See application file for complete search history.

(56) References Cited

U.S. PATENT DOCUMENTS

| | | | |
|---|---|---|---|
| 9,934,366 B1 * | 4/2018 | Zanuzoski | G16H 20/13 |
| 10,751,259 B1 * | 8/2020 | Dutta | A61J 7/0472 |
| 2002/0153411 A1 * | 10/2002 | Wan | G16H 20/10 |
| | | | 235/375 |
| 2011/0187549 A1 | 8/2011 | Balasingam | |

(Continued)

OTHER PUBLICATIONS

Tsai et al, Smart Medication Dispenser: Design, Architecture, and Implementation, 2005, IEEE Systems Journal, vol. 5, No. 1, pp. 99-110 (Year: 2005).*

(Continued)

*Primary Examiner* — Gregory Lultschik
(74) *Attorney, Agent, or Firm* — Snell & Wilmer L.L.P.

(57) ABSTRACT

An improved home automation system is provided to facilitate senior care, as well as to facilitate care for individuals suffering from Alzheimer's disease or other dementias. A home control unit is provided that is connected to, and interfaces with, a combination of health equipment, smart home appliances, a smart medicine cabinet, a smart pantry, wearable sensors, motion detectors, video cameras, microphones, video monitors, speakers, smart thermostat, lighting, floor sensors, bed sensors, smoke detectors, glass breakage detectors, door sensors, and other perimeter sensors. A distributed computational architecture is provided having a CPU associated with each video camera and an associated proximate microphone and speaker, wherein speech detection and processing, and video processing, is performed by each such CPU in conjunction with its associated video camera, microphone, and speaker. Remote backup for such distributed speech processing is selectively provided by a remote server based upon confidence scopes generated by each such CPU. The distributed computational architecture is also utilized for video processing to facilitate peer-to-peer video conferencing communication using industry standard (Continued)

formats and to reduce latency and response times that would otherwise be encountered using remote servers.

9 Claims, 83 Drawing Sheets

Related U.S. Application Data

(60) Provisional application No. 62/510,474, filed on May 24, 2017.

(51) Int. Cl.
| | | |
|---|---|---|
| *G16H 40/67* | (2018.01) | |
| *H04N 7/14* | (2006.01) | |
| *H04N 7/18* | (2006.01) | |
| *G16H 10/60* | (2018.01) | |
| *G05B 15/02* | (2006.01) | |
| *G06N 20/00* | (2019.01) | |

(52) U.S. Cl.
CPC ......... *G16H 40/67* (2018.01); *H04L 12/2825* (2013.01); *H04N 7/141* (2013.01); *H04N 7/181* (2013.01); *H04L 2012/2849* (2013.01)

(56) References Cited

U.S. PATENT DOCUMENTS

2018/0342329 A1* 11/2018 Rufo ................ G08B 25/10
2020/0410433 A1* 12/2020 Rahilly ............. G06Q 50/08

OTHER PUBLICATIONS

Becker et al, SmartDrawer: RFID-Based Smart Medicine Drawer for Assistive Environments, 2009,PETRA'09: Proceedings of the 2nd International Conference on PErvasive Technologies Related to Assistive Environments, Article: 49, pp. 1-8 (Year: 2009).*

Pang et al, Intelligent Packaging and Intelligent Medicine Box for Medication Management towards the Internet-of-Things, 2013, ICACT Transactions on Advanced Communications Technology(TACT) vol. 2, Issue 6, pp. 352-360 (Year: 2013).*

Wan, Magic Medicine Cabinet: A Situated Portal for Consumer Healthcare, 1999, Gellersen, HW. (eds) Handheld and Ubiquitous Computing. HUC 1999. Lecture Notes in Computer Science, vol. 1707, pp. 352-355 (Year: 1999).*

* cited by examiner

AUTOMATED HOME SYSTEM FOR SENIOR CARE

CROSS-REFERENCE TO RELATED APPLICATIONS

This application is a continuation-in-part of, and claims priority to and the benefit of, application Ser. No. 15/971,011, filed May 4, 2018 and entitled "HAPPIE HOME SYSTEM," which claims priority to and the benefit of provisional patent application No. 62/510,474, filed May 24, 2017 and entitled "HAPPIE HOME SYSTEM," both of which are hereby incorporated by reference.

FIELD

The present invention relates to home automation systems to facilitate senior care, and in particular, care for individuals suffering from Alzheimer's disease or other dementias.

BACKGROUND

There is a need for improved home automation systems to facilitate senior care, as well as to facilitate care for individuals suffering from Alzheimer's disease or other dementias. There is a need for automated systems that focus on caregivers as an integral part of a patient's post release care, patient satisfaction & wellness. In addition, there is a need for home automation systems that utilize machine learning and artificial intelligence in connection with remote caregiver access to facilitate senior care. Advanced home automation systems designed to facilitate senior care may also have advantageous applications in other circumstances as well.

Alzheimer's disease is a degenerative brain disease and the most common cause of dementia. Dementia is characterized by a decline in memory, language, problem-solving, and other cognitive skills that affects a person's ability to perform everyday activities.

According to the Alzheimer's Association, the number of Americans suffering from Alzheimer's disease is significant and growing. The 2016 Alzheimer's Disease Facts and Figures, published by the Alzheimer's Association, states that an estimated 5.4 million Americans were living with Alzheimer's disease in 2016. This includes an estimated 5.2 million people age 65 or older, and approximately 200,000 individuals under age 65 who have younger-onset Alzheimer's. According to the Alzheimer's Association, one in nine people age 65 or older have Alzheimer's disease, and about one-third of people over age 85 have Alzheimer's disease. The Alzheimer's Association's estimates of the number of individuals age 65 and older with Alzheimer's disease comes from a study using the latest data from the 2010 U.S. Census and the Chicago Health and Aging Project. As the elderly population is expected to increase, the number of Americans living with Alzheimer's disease is expected to increase. In fact, the Alzheimer's Association expected the number of people affected by the disease to escalate rapidly as the baby boom generation ages, and that the number of people age 65 and older with Alzheimer's disease may nearly triple by 2050, barring the development of medical breakthroughs to prevent or cure the disease.

The number of people with symptoms of dementia include more individuals than just those suffering from Alzheimer's disease. For example, vascular dementia, previously known as multi-infarct or post-stroke dementia, accounts for about 10 percent of dementia cases. Another example is dementia with Lewy bodies ("DLB"), in which Lewy bodies are abnormal aggregations of protein alpha-synuclein in neurons, and when Lewy bodies develop in the brain cortex, dementia can result. Yet another example is Parkinson's disease dementia ("PD"), where alpha-synuclein aggregates appear in an area deep in the brain called the substantia nigra, and are thought to cause degeneration of the nerve cells that produce dopamine. Other examples of dementia include frontotemporal lobar degeneration ("FTLD"), in which nerve cells in the frontal lobe and temporal lobes of the brain may become markedly atrophied, upper layers of the cortex typically become soft and spongy, and have protein inclusions (usually tau protein or the transactive response DNA-binding protein). Two more less common types of dementia are Creutzfeldt-Jakob disease, and normal pressure hydrocephalus.

Other common causes of dementia-like symptoms are depression, delirium, side effects from medications, thyroid problems, certain vitamin deficiencies, and excessive use of alcohol. Different causes of dementia are associated with distinct symptom patterns and brain abnormalities. Some people with dementia, especially those in the older age groups, have brain abnormalities associated with more than one cause of dementia, and such a condition is referred to as mixed dementia.

Alzheimer's and other dementias can take a devastating toll on caregivers. In 2015, the Alzheimer's Association estimated that 15.9 million family and friends provided 18.1 billion hours of unpaid care to those with Alzheimer's and other dementias. Forty-one percent of caregivers have a household income of $50,000 or less. On average, care contributors lose over $15,000 in annual income as a result of reducing or quitting work to meet the demands of caregiving, according to the Alzheimer's Association. Nearly sixty percent of Alzheimer's and dementia caregivers rate the emotional stress of caregiving as high or very high; about forty percent suffer from depression. One in five caregivers cut back on their own doctor visits because of their care responsibilities. And among caregivers, seventy-four percent report they are "somewhat" to "very" concerned about maintaining their own health since becoming a caregiver. The Alzheimer's Association estimated that Alzheimer's and other dementias would cost the United States approximately $236 billion in 2016.

Alzheimer's disease is the 6th leading cause of death in the United States. It kills more people than breast cancer and prostate cancer combined.

In addition to people who may be suffering from Alzheimer's and other dementias, many otherwise-healthy senior citizens can benefit from improved home automation systems to facilitate their living and provide convenient services for them.

According to the website at aPlaceforMom.com, each year in the United States more than 125,000 people die from a failure to properly take their medications, adding approximately $100 billion in preventable additional hospitalization, emergency room, and repeat physician visit costs to the health care system. According to the same source, at least 10% of all hospital admissions are a result of this problem. That website states: (1) up to twenty-three percent of nursing home admissions may be due to an elderly person's inability to self-manage his or her prescription medications at home; (2) over twenty-one percent of all drug-related health complications are caused by patients failing to adhere to their medication regimens, whether by accident, negligence, or intent; (3) up to fifty-eight percent of all seniors make some kind of error when taking their medications, with twenty-six percent making mistakes with potentially serious consequences; and (4) in studies of elderly patients on long-term cholesterol-lowering statin therapy, researchers found that fifty-seven percent had stopped taking them after six months, and seventy-four percent had stopped by the end of five years.

There may be different reasons why people fail to take their medication properly; most commonly, they simply forget to do so. In some instances, people may think that they feel better and discontinue the medication prematurely. Or in some instances, people may stop because they experience bothersome side effects, or because they decide that they do not actually need the medication. In other instances, people may believe the drug treatment does not seem to have an immediate effect, so they decide the medicine is not working and stop. Or in other instances, people may believe that the medicine seems to work very well, so they decide to take more of it per dose, or they decide to take the prescribed dose more often. Or they may find the cost of the drugs to be too burdensome, and decide to take the medication less often in order to conserve money. In general, people usually do not fully understand how a drug is supposed to work, and do not fully understand the health consequences that occur when they do not follow the drug regimen correctly or discontinue it altogether.

The importance of taking medications properly cannot be overemphasized. The consequences of not following a prescribed medication regimen can be especially serious for seniors. The consequences may include loss of life as a result of drug complications or mistakes. The risk of being prematurely forced into a nursing home increases with each emergency room visit or hospitalization. Therefore, it is desirable to avoid emergency room visits and hospitalization that result from the failure to take medications properly.

The U.S. Centers for Disease Control and Prevention defines aging in place as the ability to live in one's own home and community safely, independently, and comfortably, regardless of age, income, or ability level. Generally, every senior citizen would like to keep his or her independence for as many years as possible. Most adults would prefer to age in place—that is, remain in their home of choice as long as possible.

The average senior takes about seven different medications (both prescribed and over-the-counter) every day, so it may not be surprising that many senior citizens find it difficult to remember and keep track of the medicines they are supposed to be taking. It is helpful to have a caregiver present who can ensure that someone is taking his prescriptions on time and on dose. However, that is not always possible.

The costs and burdens associated with caregiving are much broader than the above discussion concerning caregiving associated with persons suffering from Alzheimer's and other dementias. According to the Family Caregiver Alliance, National Center on Caregiving, approximately 43.5 million caregivers have provided unpaid care to an adult or child in the last twelve months, and approximately 39.8 million caregivers provide care to adults with a disability or illness. Unpaid individuals (for example, a spouse, partner, family member, friend, or neighbor) who are involved in assisting others with activities of daily living and/or medical tasks provided an estimated economic value of $470 billion for caregiving in 2013, up from $450 billion in 2009, and $375 billion in 2007. The economic impact of caregiving has been steadily growing, and that growth is expected to continue in the future.

According to the Family Caregiver Alliance, National Center on Caregiving, regardless of employment status, unpaid caregivers report that positive activities in their respective daily lives are reduced by 27.2% as a result of their caregiving responsibilities. This effect is three times greater in their personal lives than in their professional lives.

In view of the growing economic and societal impact of these conditions upon the country, and the growing number of affected individuals, there is a need for innovative solutions to facilitate caregiving for persons suffering from dementia and Alzheimer's disease, to facilitate caregiving for seniors and other adults, to address other problems associated with senior citizen living, and to improve the quality and safety of home living in general.

OBJECTS AND FEATURES OF THE INVENTION

It is an object of the present invention to provide an automated system to facilitate caregiving associated with elderly persons, or senior citizens.

It is also an object of the present invention to provide an automated system to facilitate caregiving for persons suffering from dementia or Alzheimer's disease.

It is another object of the present invention to provide embodiments that take advantage of machine learning and artificial intelligence in an automated system to provide caregiving for senior citizens and for persons suffering from dementia or Alzheimer's disease.

The present invention includes an embodiment providing a system for aged or senior care. An alternative embodiment provides a system for injured or ill persons or those receiving outpatient care or physical or mental therapy. An alternative embodiment provides a system for persons having memory or cognitive challenges due to mental impairment, TBI, dementia, or other conditions.

An alternative embodiment provides a system for athletes and physically active adults, as well as those who focus on staying in top physical and mental condition for a healthy active lifestyle.

An alternative embodiment provides a system for young people or those requiring occasional assistance or oversight. Yet another alternative embodiment provides a system for infants and small children under the care of a nanny or baby sitter.

Additional embodiments of the present invention may be employed to improve the quality and safety of home living in general.

SUMMARY OF THE INVENTION

A preferred embodiment of the present invention provides an improved home automation system to facilitate senior care, as well as to facilitate care for individuals suffering from Alzheimer's disease or other dementias.

In accordance with the present invention, technology is provided as an enabler for allowing adults to age in place. Broadly speaking, technology is provided in the categories of communication, health and wellness, learning, and security. Caregiving technology may be employed to help those who care for older adults provide that care in the most effective way, and to alleviate some of the burdens associated with caregiving.

Remote access is provided for a caregiver to check on the status of a senior citizen, and to communicate with the senior citizen, who is the resident at the home that is utilizing an automation system to facilitate senior care according to the present invention. Machine learning, and artificial intelligence, is advantageously used to either alert a caregiver to circumstances that require attention, or in the absence of caregiver involvement, to automatically take predetermined actions in response to a set of inputs or circumstances.

BRIEF DESCRIPTION OF THE DRAWINGS

FIG. 88 is a rear view of the remote smart medicine cabinet shelf holder shown in FIG. 87, with a shelf in place in the holder.

DETAILED DESCRIPTION OF ONE OR MORE PREFERRED EMBODIMENTS

In accordance with a first embodiment of the present invention, a home automation system is provided comprising a home unit 103, for communication, safety and companionship. A home automation system in accordance with the present invention is sometimes referred to as the HAPPIE system. HAPPIE is an acronym which stands for "Helping All People Promote Independence Everyday." The HAPPIE system functions as a monitoring and management portal in a home or facility where a person may be in need of part time or on demand assistance, yet still has the ability and desire to remain primarily independent.

Figure 1:
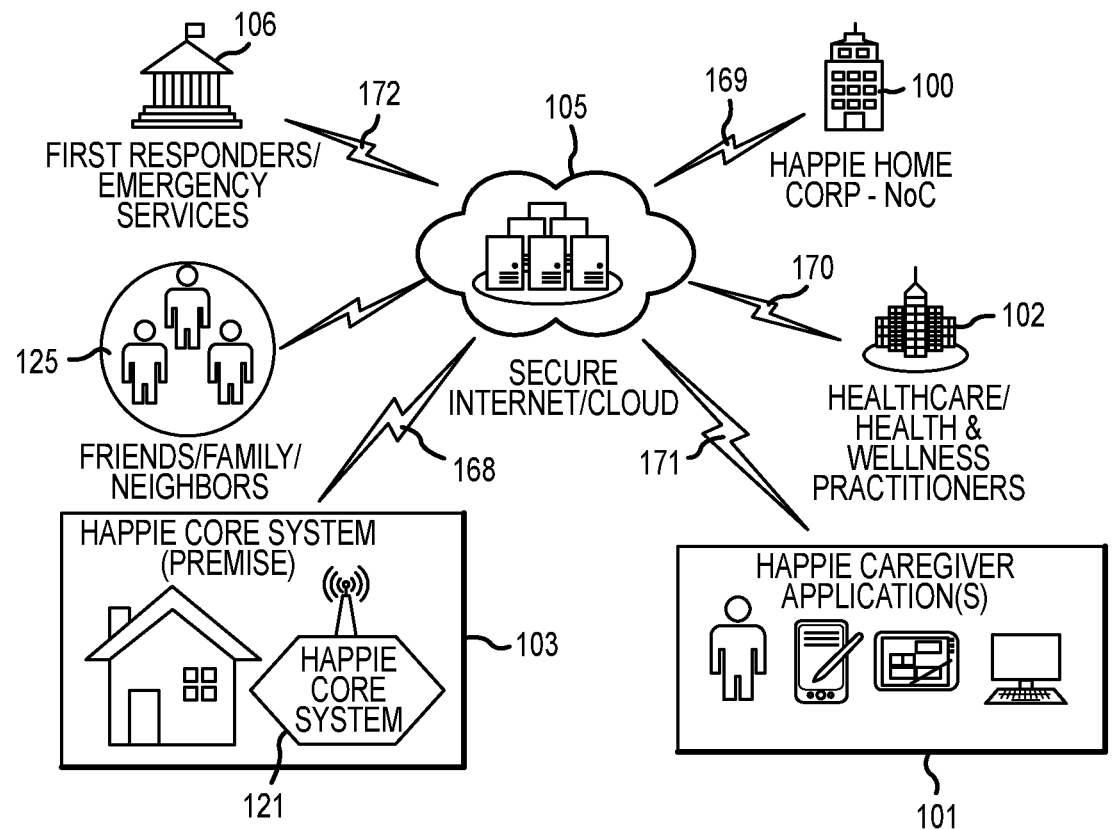
FIG. 1 is a schematic diagram of various components of a first embodiment of a system in accordance with the present invention.

The main components of a first embodiment of the HAPPIE system are shown in FIG. 1. The HAPPIE home unit 103 is in communication with the Internet or cloud 105. The cloud 105 is a wide-area network, providing high speed communication with other equipment connected to the cloud 105. The cloud or Internet 105 provides a communication network through which others may communicate with or access the HAPPIE home unit 103. The communication link 168 provided between the HAPPIE home unit 103 and the Internet 105 is preferably a high speed two-way communication link.

A caregiver portal 101 is provided in communication with the cloud 105 over a high speed two-way communication link 171. One or more persons, who serve a caregiver role for the person who is the resident at the HAPPIE home unit 103, may communicate with and monitor the resident using the caregiver portal 101. A central server 100 may be provided, which includes a central data store 175 and other administrative capabilities. The central server 100 is in communication with the cloud 105 using a two-way high speed communication link 169.

Referring to FIG. 1, a doctor portal 102 or communication interface for healthcare providers 102 is provided in communication with the cloud 105 over a high speed two-way communication link 170. A physician or nurse, for example, may communicate with the resident of the HAPPIE home unit 103 via the cloud 105 using the doctor portal 102. This feature of the system facilitates medical care for the resident of the HAPPIE home unit 103 without requiring the resident to travel to a clinic or doctor's office.

As shown in FIG. 1, one of more emergency responder portals 106 are also provided, which are in communication with the HAPPIE home unit 103 via the cloud or network 105. A high speed two-way communication link 172 is preferably provided in order to permit emergency responders to not only have voice communication with the HAPPIE home unit 103, but also receive streaming video and receive data from sensors 130. Emergency responder portals 106 may include high speed two-way communications links with police, fire, ambulance, and other emergency services.

In addition, one or more family communications portals 125 may be provided to facilitate communications with friends and family, as illustrated in FIG. 1. In addition to providing a communications link with the resident of the HAPPIE home unit 103, the family portal 125 allows a friend or family member to monitor or check on the status of the resident.

Figure 2:
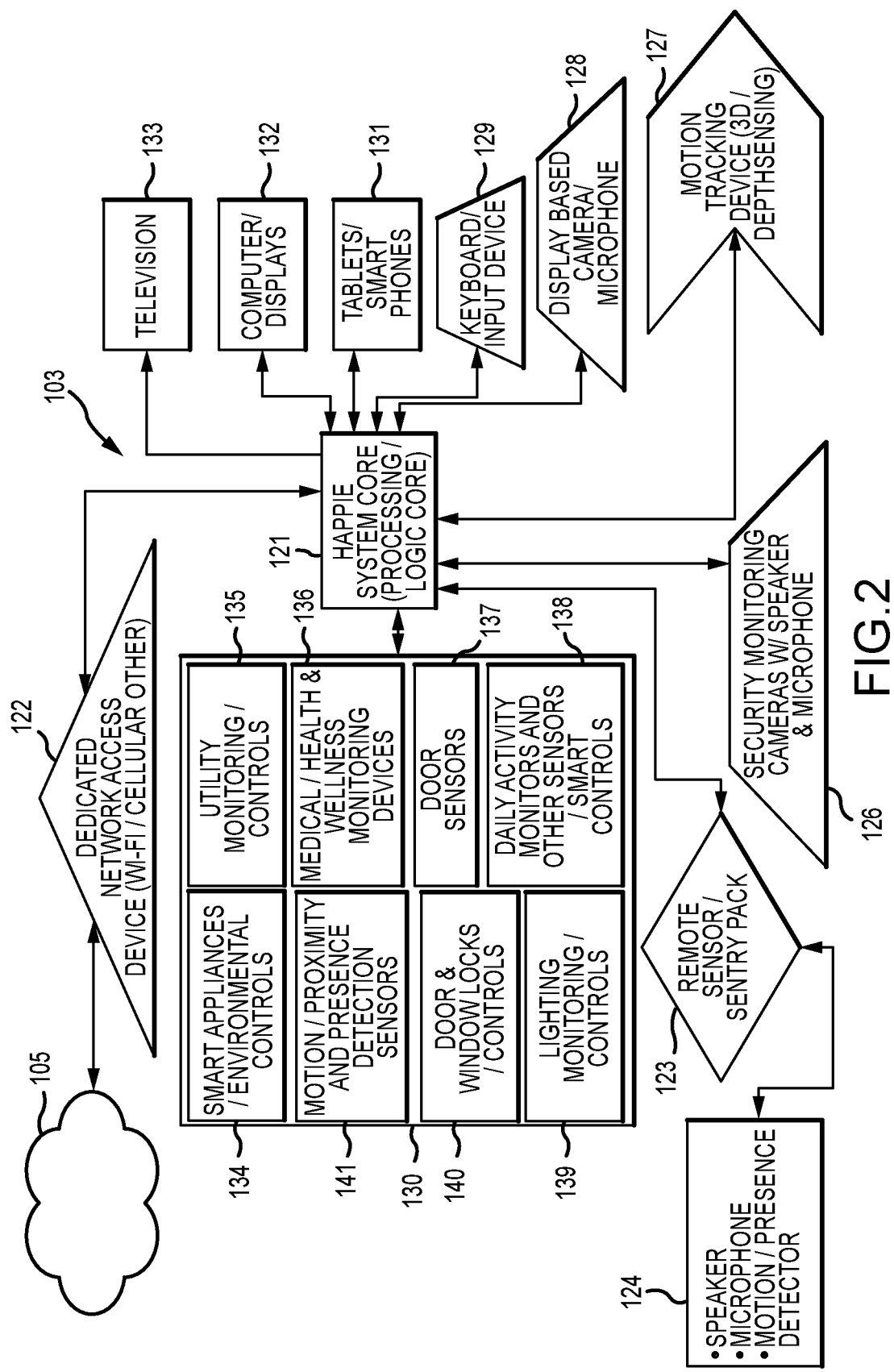
FIG. 2 is a block diagram of components of the home unit located at the home premises.

FIG. 2 is a schematic block diagram of the HAPPIE home unit 103 that is located at the home premises. The HAPPIE home unit 103 includes a HAPPIE system core 121, or computational and logic unit 121, that provides processing and logic functionality, and preferably includes artificial intelligence capability. Alternatively, the HAPPIE system core 121 may be a CPU 121. The HAPPIE system core 121 is connected to, or in communication with, an array of sensors and controllers 130 for monitoring conditions at the home premises, and for controlling appliances and equipment at the home premises.

The array of sensors and controllers 130 may include smart appliances and environmental controls 134, for example, a smart refrigerator, a smart washer, a smart air conditioning system, or a smart heater. The array of sensors and controllers 130 may include utility monitoring and controls 135, such as a water monitor, a natural gas monitor and controller, electricity monitor and controls, and similar devices. The array of sensors and controllers 130 may include medical and health and wellness monitoring devices 136, for example, wearable exercise monitors, wearable heart monitors, blood pressure monitors, pulse monitors, temperature readers, Fitbit™ devices 164, weight scales, and similar devices.

The array of sensors and controllers 130 shown in FIG. 2 may include door sensors 137, as well as lighting monitoring and control 139. The array of sensors and controllers 130 may include daily activity monitors and related sensors and smart controls 138. In addition, window and door locks and controls 140 are provided. The array of sensors and controllers 130 may include motion, proximity and presence detection sensors 141.

The array of sensors and controllers 130 send data to the HAPPIE system core 121 for processing, and for storage. The HAPPIE system core 121 also sends commands and signals to the array of sensors and controllers 130 to activate certain functions or actions.

The HAPPIE system core 121 is connected to security monitoring cameras 126 with associated speakers and microphones. The HAPPIE system core 121 is also connected to remote sensor & sentry pack 123. The remote sensor & sentry pack 123 controls speaker, microphone, and motion-presence detector unit 124.

As illustrated in FIG. 2, the HAPPIE system core 121 may be provided with peripherals for input and output, such as television 133, computer display 132, and keyboard or input device 129. A display based camera and microphone 128 are connected to the HAPPIE system core 121.

Wireless handheld computing devices may also provide input to, and receive output from, the HAPPIE system core 121, such as the tablet or smart phone 131 shown in FIG. 2. A motion tracking device 127, including 3D and depth sensing, is connected to the HAPPIE system core 121.

The HAPPIE system core 121 has a communication link with a network access device 122, such as an Ethernet interface, WiFi radio or interface, Bluetooth, cellular transceiver, or other similar device. The network access device 122 provides communication with the cloud or Internet 105. In addition, local wireless network communication is provided within the home using a WiFi hotspot 109 connected to the HAPPIE system core 121.

The HAPPIE home unit 103 is made up of the HAPPIE system core 121, a WiFi hot spot 109, a battery back-up 110, cameras 112, speakers 157, microphones 113, intelligent heat detectors 194, motion detectors 152, and smoke detectors 150 that can be strategically deployed inside the residence and around the property. A resident interacts with the HAPPIE home unit 103 with voice commands or a natural voice interface. The HAPPIE home unit 103 communicates with the resident by displaying text messages, text alerts, text reminders, video messages, and live streaming video displayed by the HAPPIE home unit 103 on a television or on video monitors 156. Audio messages, audio alerts and audio reminders are broadcast by the HAPPIE home unit 103 through speakers 157 and can be heard throughout the home.

Figure 3:
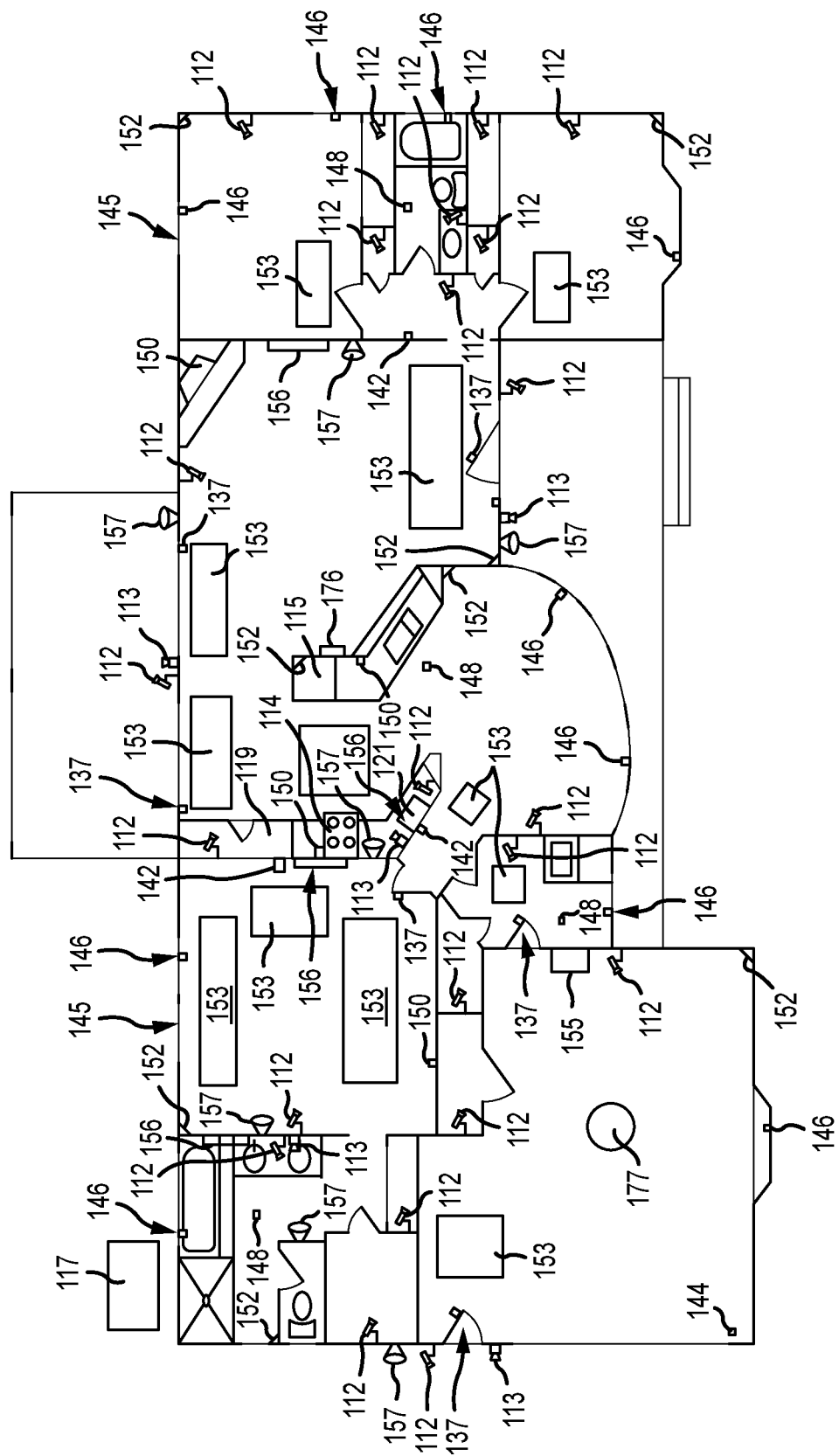
FIG. 3 shows a floor plan and illustrates an example of the location of sensors and other components at the home premises.

FIG. 3 shows an example of a floor plan, and provides a schematic diagram of a suitable home installation of sensors 130 and other components at the home controlled by the HAPPIE home unit 103. A plurality of video cameras 112 are provided, which are all connected to the HAPPIE system core 121 of the HAPPIE home unit 103. The video cameras 112 are capable of recording video, which may be stored in the local database 108. Video data from the video cameras 112 may be streamed over the Internet 105 to, for example, the doctor portal 102, the caregiver portal 101, or to the HAPPIE server 100 for storage in a central database 175. The video cameras 112 facilitate two-way video communication with the resident of the home controlled by the HAPPIE home unit 103. In the event of a security breach, video data from the video cameras 112 may also be automatically provided by the HAPPIE home unit 103 to a law enforcement portal 106, or in the event of a fire, video data may be automatically provided by the HAPPIE home unit 103 to other first responders 106, such as the fire department.

Figure 6:
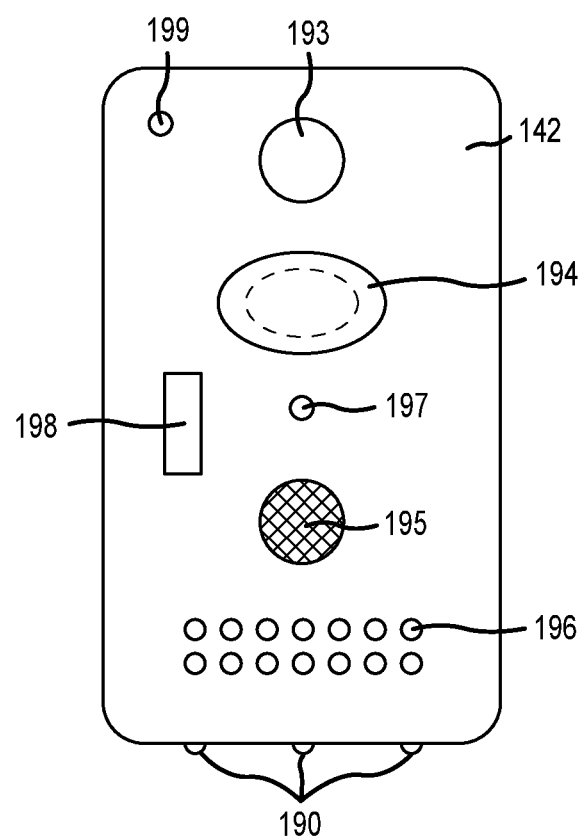
FIG. 6 shows a front view of a mic pack device.

In addition to, or as an alternative to, the video cameras 112, a plurality of mic packs 142 may be included at the premises. Each mic pack 142 also has a video camera 193, as shown in FIG. 6. Each mic pack 142 is connected to the HAPPIE system core 121.

Each mic pack device 142 shown in FIG. 3 includes a microphone 195. In addition, additional microphones 113 may be located at the home controlled the HAPPIE home unit 103. Alternatively, every camera 112 may have a microphone associated with it. The microphones 113 and 195 are used to receive voice commands, for speech recognition, and to facilitate two-way voice communication with the resident of the home. The microphones 113 and 195 are also used to receive audio which is used, in accordance with a speech recognition sub-module running on the HAPPIE system core 121 of the HAPPIE home unit 103, to identify persons present at the home premises, and to distinguish between the resident, and other persons who may be visiting the home. In addition, it can be used to identify unauthorized persons, and in appropriate circumstances, as data upon which the HAPPIE home unit 103 may make a determination to automatically generate an emergency call to a law enforcement portal 106. It should be understood that all two-way voice communication with the resident of the home preferably is hands free on the part of the resident, and sufficient microphones 113 are provided to enable the resident to speak in a normal voice anywhere in the home and effectively communicate via the HAPPIE home unit 103.

A plurality of speakers 157 are provided at various locations in the home. In addition, or as an alternative to speakers 157, each mic pack 142 includes a speaker 196. The speakers 157 and 196 may be used to play audio files from the HAPPIE home unit 103, and to facilitate voice communication with the resident of the home. The speakers 157 are preferably connected to a home entertainment system 120 through the HAPPIE system core 121 of the HAPPIE home unit 103, and may be used to play music for the resident, or to play audio from a television program or movie.

A plurality of video displays or televisions 156 are provided in the home. The video displays are connected to the HAPPIE system core 121. The video displays 156 are used to display information generated by the HAPPIE home unit 103, as described more fully in connection with FIG. 8 through FIG. 21, and FIG. 23 through FIG. 39. The video displays 156 are used to facilitate video conferencing with the resident of the home. The video displays 156 may be used to surf the Internet 105 using a conventional web browser running on the HAPPIE home unit 103. In addition, the video displays and televisions 156 are preferably connected to the home entertainment system 120 through the HAPPIE system core 121 of the HAPPIE home unit 103, and may be used to show a television program or movie, or otherwise used for entertainment purposes.

Referring to FIG. 3, motion sensors 152 are located in the home, and connected to the HAPPIE system core 121. In addition, each mic pack 142 preferably includes one or more motion sensors 192. Motion sensors 152 and 192 are used to detect the presence of the resident, and to determine the whereabouts of the resident in the event that the HAPPIE home unit 103 receives an inquiry from the caregiver portal 101 or from a family member 125. Motion sensors 152 and 192 are also used by the security system module running on the HAPPIE system core 121 in the HAPPIE home unit 103 to protect against intruders or unauthorized entry. As explained more fully herein, data from the motion sensors is stored in a local database 108 and used to determine patterns of movement by the resident. When the resident deviates significantly from his or her established patterns of movement, the HAPPIE home unit 103 makes an intelligent determination of whether a response may be warranted. For example, in the case of significant inactivity, the HAPPIE home unit 103 may trigger an alert to the caregiver portal 101 requesting investigation into whether there may be a slip or a fall situation.

As shown in FIG. 3, floor sensors 153 are provided to detect any person who walks across the floor sensors 153. The floor sensors 153 are connected to the HAPPIE system core 121.

A magnetic sensor or detector 177, connected to the HAPPIE system core 121, is provided in the garage to detect the presence of an automobile or other vehicle. The garage door has a garage door sensor and controller 144 for detecting when the garage door is opened, and for controlling the opening and closing of the garage door. The HAPPIE home unit 103 may use data from the vehicle sensor 177 to determine whether the resident's car is parked in the garage. Video data from a camera 112 located in the garage may also be used for that purpose, either in addition to the automobile sensor 177, or as an alternative to it. Sound picked up by a microphone 113 located in or near the entrance to the garage is used by the HAPPIE home unit 103 to verify whether an automobile has entered into the garage, or has departed from the garage, in combination with data from an appropriate video camera 112 located in the garage, data from the garage door sensor 144, and data from the vehicle sensor 177. An automobile interface 155, connected to the HAPPIE system core 121, is preferably provided in the garage for data communication with, and to obtain diagnostic and service information from, the resident's automobile or other vehicle.

Bed sensors 151 may be provided connected to the HAPPIE system core 121, and operable to detect when the resident is lying on his bed. This may be useful to family members or caregivers who use the HAPPIE home unit 103 to check on the status and well-being of the resident. In addition to detecting the presence of the resident in bed, the bed sensors 151 measure the weight of the resident, and that data is stored in the local database 108. The HAPPIE home unit 103 automatically generates an alert to the caregiver portal 101 or the doctor portal 102 in the event that the resident's weight deviates beyond an upper limit and a lower limit set in configuration parameters within the HAPPIE home unit 103. A sudden increase in weight may indicate excessive fluid retention, which may be strenuous on the heart. A rapid weight loss can sometimes be a warning sign for cancer or other disorders.

Toilet seat sensors 151 may be provided on the toilet seat, which are connected to the HAPPIE system core 121, and operable to detect when the resident is sitting on the toilet. If the toilet seat sensors 151 do not detect any activity involving the resident sitting on the associated toilet seat, it may indicate a health condition that could require further attention from the caregiver or medical personnel. The HAPPIE home unit 103 automatically generates an alert to the caregiver portal 101 or the doctor portal 102 in the event that the resident's lack of activity (indicated by an absence of any sensor activity detected concerning the toilet seat sensors 151), extends beyond a predetermined period of time, which may be set in configuration parameters within the HAPPIE home unit 103.

Glass breakage detectors 146 are connected to the HAPPIE system core 121, and provide data to the HAPPIE home unit 103 indicative of a glass breakage event. This data may be used by the HAPPIE home unit 103 to determine that a security breach has occurred, and to set off appropriate alarms using the speakers 157, and to summon help via an emergency services portal 106. In addition, window sensors 145 are provided on any window that can be opened, in order to determine when the associated window is in a closed or open state. The window sensors 145 are connected to the HAPPIE system core 121. Other perimeter sensors 143 connected to the HAPPIE system core 121 may also be provided for detecting intruders.

Water and flood sensors 148 capable of detecting water leakage or flooding may be provided at appropriate locations, as shown in FIG. 3, connected to the HAPPIE system core 121. Data received from the water sensors 148 may be used by the HAPPIE home unit 103 to determine whether the home is flooding, and to automatically generate appropriate warnings to the resident and/or summon help.

Fire and smoke sensors 150 are provided at appropriate locations in the home to detect fire or smoke conditions. The fire and smoke sensors 150 are connected to the HAPPIE system core 121 of the HAPPIE home unit 103. Upon detection of dangerous fire or smoke conditions, the HAPPIE home unit 103 will automatically generate an emergency message to the fire department 106, and will broadcast an alarm and warning over the speakers 157, and display an alert on the video monitors and televisions 156. Automatic emergency messages will also be generated to the caregiver portal 101 and to family and friends 125. Data received from the temperature sensor on the smart thermostat 176, and data received from intelligent heat sensors 194 on mic packs 142, may also be used by the HAPPIE home unit 103 in its determination and identification of a dangerous fire or smoke condition. If suitable coverage of intelligent heat sensors 194 is provided throughout the home, the HAPPIE home unit 103 will use data from such intelligent heat sensors 194, and available data concerning the present location of the resident, to automatically determine the best escape route for the resident, and will broadcast escape instructions over the speakers 157, as well as display a map on the video monitors and televisions 156 showing the optimum escape route. The escape information is also displayed on any connected smart phone 111. Emergency responders 106 also receive the same information, so that they know the escape route that the resident is expected to have taken if he or she followed the instructions provided by the HAPPIE home unit 103.

Using artificial intelligence, the HAPPIE home unit 103 uses data from the motion detectors 152 and 192, data from the video cameras 112 and 193, data from the floor sensors 153, data from the microphones 113 and 195, and data from the intelligent heat sensors 194 on the mic packs 142, to identify and determine the location of the resident, as well as to detect and identify any other persons who may be present at the home. In addition, the resident may wear a HAPPIE bracelet 158 which can be detected by the HAPPIE home unit 103 to determine the location of the resident.

A plurality of door sensors or control units 137 are provided, as shown in FIG. 3. The door sensors 137 are connected to the HAPPIE system core 121 of the HAPPIE home unit 103. The door sensors 137 detect when a door is opened, and transmit appropriate data to the HAPPIE system core 121 when a detection is made. In addition, the door sensors 137 control door locks. The door sensors are responsive to data or commands received from the HAPPIE system core 121 to cause the associated door to lock or to unlock, depending upon the command received by the door sensor 137. When the resident arrives home, the resident may, from outside the residence, speak a command to the HAPPIE home unit 103 that is picked up by a microphone 113 near the door, and using speech recognition, verbally provide a security code to unlock the door 137. Alternatively, or in addition thereto, the HAPPIE home unit 103 may use 3D facial recognition upon data from a video camera 112 near the door, and/or voice pattern recognition from a microphone 113 near the door, in order to identify the resident and make a determination to unlock the door unit 137. Facial recognition software modules such as Real Python or OpenFace may be used for facial recognition functions.

The HAPPIE system core 121 of the HAPPIE home unit 103 is connected to controllers for lights 159 in the home. The HAPPIE home unit can turn lights 159 on or off, or dim them. The HAPPIE home unit 103 includes sensors for sensing the level of lighting in a room, and is operative to adjust the lights 159 based upon data associated with lighting levels, and also control motorized window shades or coverings to selectively increase or decrease the amount of outside light entering a room based upon the time of day, the day of the week, the resident's schedule, and other configuration data.

Referring to FIG. 3, the HAPPIE home unit 103 controls air conditioning unit 117. A smart thermostat 176 is provided, connected to the air conditioning unit 117, and also connected to the HAPPIE home unit 103. Smart thermostat 176 is capable of sensing temperature and humidity and other environmental conditions. Other temperature and humidity sensors 149, connected to the HAPPIE system core 121, may be provided in the home, if desired. The HAPPIE home unit 103 controls and adjusts the operation of the air conditioning unit 117 based upon configuration parameters that allow for operational characteristics determined by the time of day, the day of the week, temperature and humidity data from sensors 149, whether the resident is home (which the HAPPIE home unit 103 may automatically sense), and schedule information stored in the local database 108 (which permits the HAPPIE home unit 103 to, for example, adjust the air conditioning unit 117 to cool the home before the resident is scheduled to return home so that the home will already be at a comfortable temperature when the resident arrives). The HAPPIE home unit 103 controls and adjusts the operation of lights based upon configuration parameters that allow for operational characteristics determined by the time of day, the day of the week, whether the resident is home (which the HAPPIE home unit 103 may automatically sense), and schedule information stored in the local database 108 (which permits the HAPPIE home unit 103 to, for example, turn on the lights just before the resident is scheduled to arrive at home, or to turn off the lights when the resident leaves the home, or to turn lights on or off in any given room based upon the movement of the resident from one room to the next).

Figure 4:
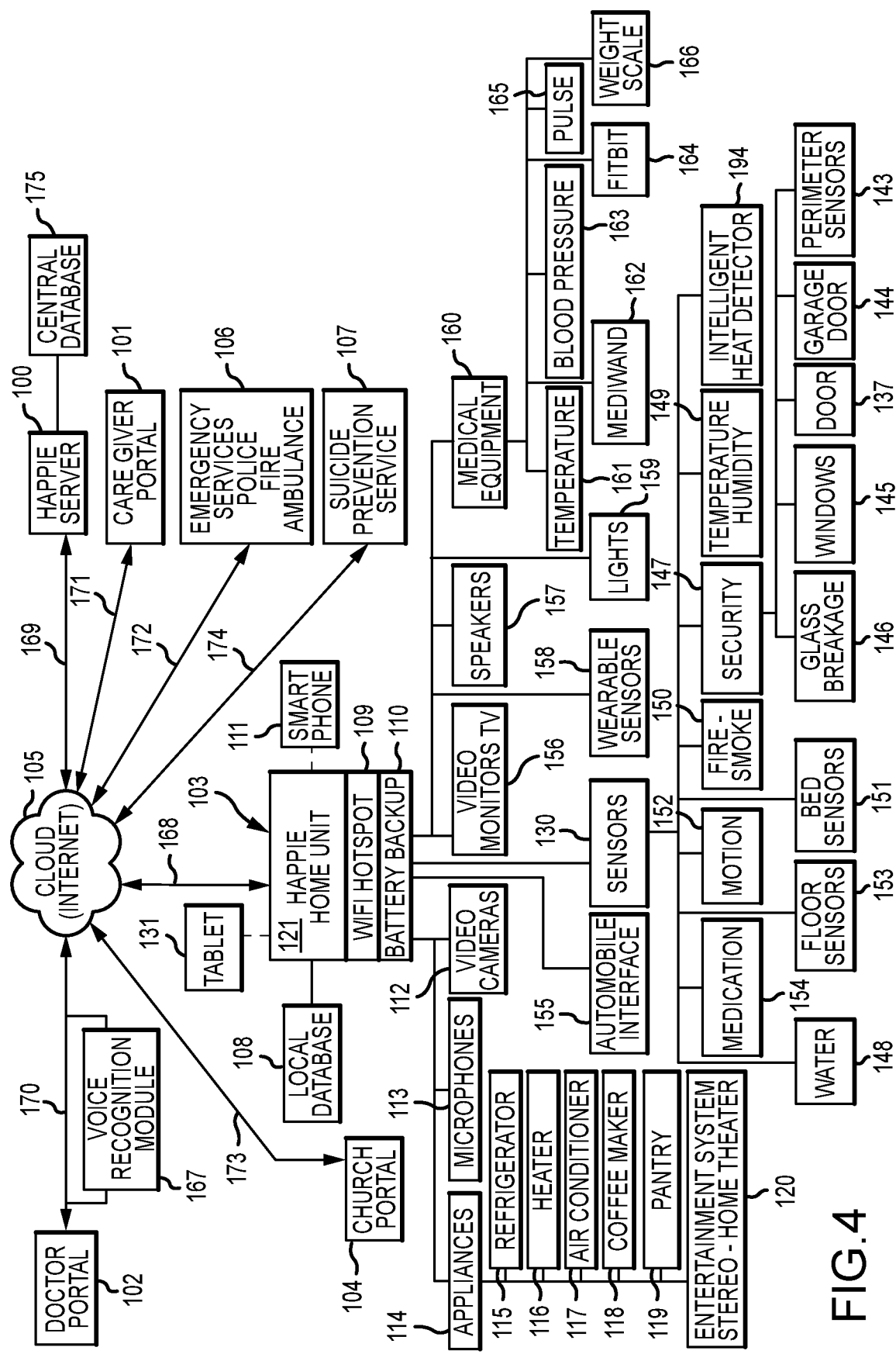
FIG. 4 is a block diagram of various components of an embodiment of a system in accordance with the present invention.

As illustrated schematically in FIG. 4, the automated system of this invention includes a HAPPIE server 100 that is connected to the Internet or cloud 105. The HAPPIE server includes a central database 175. Alternatively, data storage may be provided in the cloud 105. Although the Internet 105 is a preferred networking configuration, other wide area network configurations could be employed, or the Internet 105 may take the form of the cloud 105, or local area networks substituted for the Internet 105. The communication link 169 connecting the HAPPIE central server 100 to the Internet 105 is a high speed two-way communication link.

A caregiver portal 101 is also connected to the Internet 105 over a two-way high speed communication link 171. In addition, a doctor portal 102 is preferably provided connected to the Internet 105 via a two-way high speed communication link 170. In an especially preferred embodiment, a church portal 104 is also included, and the communication link with the church portal 104 is a high speed two-way communication link 173. In a preferred embodiment, all communications links used in this invention are secure links having data encryption.

A preferred embodiment of a HAPPIE home unit 103 according to the present invention is shown connected to the Internet 105 in FIG. 4 over a two-way high speed communication link 168. The HAPPIE home unit 103 includes a HAPPIE system core 121. The HAPPIE home unit 103 comprises a local database 108 connected to, or in communication with, the HAPPIE system core 121. A WiFi hotspot 109 is preferably included in the home unit 103, but can alternatively be provided as a separate wireless communication connection unit 109. In the illustrated embodiment, the home unit 103 and WiFi hotspot 109 have battery backup 110 to provide power to the HAPPIE home unit 103, including the HAPPIE system core 121, and WiFi hotspot 109 in the event of a main power failure. Those skilled in the art will appreciate that a plurality of WiFi hotspots 109 may be provided, if needed, for good wireless coverage throughout the property, both inside and out, depending upon the size of the home.

A smart phone 111 may be connected to the home unit 103, and used to configure, or control the home unit 103, or used to display data received from the home unit 103, or used to input data into the home unit 103. Connection between smart phone 111 and home unit 103 is preferably via WiFi hotspot 109, but connection may alternatively be established via a cable, such as a cable with one end plugged into a USB port on the HAPPIE home unit 103 and the other end plugged into the smart phone 111. Alternatively, other wireless computing devices may be substituted for smartphone 111, such as a tablet device 131, like an Apple iPad® tablet device, or an Apple iPod Touch® device, or any similar wireless handheld computing device 131.

Emergency services 106 may be connected in various ways to the system, including connection directly or indirectly with the HAPPIE server 100. Emergency services 106 preferably include ambulance, fire, and police (or other law enforcement agencies). In the illustrated embodiment shown in FIG. 4, connection is provided via the Internet or cloud 105. However, emergency services 106 may alternatively be connected by telephone, (for example, via the public switched telephone network, or PSTN), by radio link, by a cellular link, by satellite, or by dedicated communication lines.

In some instances, a communication link with a suicide prevention service 107 may desired, and can be optionally provided, as appropriate.

In a preferred embodiment, the HAPPIE home unit 103 is connected to various sensors and input devices to provide data and analog information that may be processed by the HAPPIE system core 121 in the HAPPIE home unit 103, or may be transmitted to the HAPPIE server 100, or may be stored in the local database 108, or may alternatively be communicated to the caregiver portal 101, the doctor portal 102, and under some circumstances, to emergency services 106. For example, video cameras 112 are provided for selectively transmitting video via the HAPPIE home unit 103 to the caregiver portal 101, the doctor portal 102, the church portal 104, the HAPPIE server 100, and if needed, to emergency services 106. Microphones 113 are connected to the HAPPIE home unit 103 for providing two-way audio and voice communication to the caregiver portal 101, the doctor portal 102, the church portal 104, the HAPPIE server 100, and if needed, to emergency services 106. The combination of a microphone 113 and video camera 112 permits two-way video conferences between the resident living at the HAPPIE home unit 103, and the caregiver portal 101, the doctor portal 102, the church portal 104, the HAPPIE server 100, and if needed, to emergency services 106. The functions performed by the video cameras 112 and the microphones 113 will be further described below in connection with various modules included in software executed by the HAPPIE system core 121 in a preferred HAPPIE home unit 103.

Smart appliances 114 with sensors and detectors are provided connected through the HAPPIE home unit 103. For example, in the illustrated system shown in FIG. 4, a smart refrigerator 115 is provided. The smart refrigerator 115 has a sensor on the door that detects when the door is opened, and transmits associated data to the HAPPIE home unit 103 indicating such detection when it occurs. The refrigerator 115 preferably has sensors inside that can detect when food is removed or placed inside the refrigerator 115, and one or more internal cameras that allow a visual inspection of the contents of the refrigerator 115 without opening the door of the appliance 115. A visual recognition module may be provided on the HAPPIE home unit 103 to analyze the images of the interior of the refrigerator 115 to determine what food is contained in the refrigerator 115, and to automatically calculate nutritional statistics, such as calorie intake, vitamin requirements met, carbohydrate and protein consumption, and other nutritional statistics. In addition, the images of the interior of the refrigerator 115 may be analyzed to automatically determine what groceries are needed from the market, and to automatically generate a shopping list or automatically place an order to an online grocery store ordering system. The HAPPIE home unit 103 can automatically determine when routine maintenance for appliances is needed, and automatically generate a message to the HAPPIE server 100 or to the caregiver portal 101 indicating that maintenance service is due. The automatic generation of routine maintenance messages is triggered by date or on a periodic basis. For example, the calendar module may include reminders spaced every six months that it is time for routine six month replacement of air conditioning filters. Alternatively, maintenance messages may be triggered on an as needed basis, such as the replacement of a water filer for the smart refrigerator 115.

In the illustrated system shown in FIG. 4, a smart heater 116 is provided, which may be remotely controlled by the HAPPIE home unit 103, and which provides data to the HAPPIE home unit 103 concerning the operation and settings of the heater 116, such as temperature and operational characteristics. Similarly, an air conditioner 117 is provided, which may be remotely controlled by the HAPPIE home unit 103, and which provides data to the HAPPIE home unit 103 concerning the operation and settings of the air conditioner 117, such as temperature and operational characteristics. Both the heater 116 and the air conditioner 117 preferably provide alternative manual controls that may be manually controlled or set from the local premises. The HAPPIE home unit 103 maintains records concerning use of the heater 116 and the air conditioner 117 and automatically determines when routine maintenance is needed, and generates a message to the HAPPIE server 100 to order maintenance service. Alternatively, the HAPPIE home unit 103 may order service directly for the heater 116 and the air conditioner 117, as well as other appliances such as the refrigerator 115.

In the illustrated system shown in FIG. 4, a smart coffee maker 118 is provided which communicates data concerning its operation and settings to the HAPPIE home unit 103, and which may be remotely controlled by the HAPPIE home unit 103. The data from the smart coffee maker 118 may include data concerning coffee consumption. This data may be communicated to the HAPPIE home unit 103, and recorded in the local database 108. The data concerning coffee consumption may be used, with other data concerning calorie intake, vitamin requirements met, and carbohydrate and protein consumption, to calculate and analyze nutritional statistics. The HAPPIE home unit may provide such information stored on local database 108, if desired, to medical personnel via the doctor portal 102.

In the illustrated system shown in FIG. 4, a smart pantry 119 is provided with sensors to detect when the pantry is opened or otherwise accessed, and sensors to detect when food supplies are removed or restocked in the pantry 119. One or more internal cameras may be provided in the pantry 119 to allow a visual inspection of the contents of the pantry 119. A visual recognition module may be provided on the HAPPIE home unit 103 to analyze the images of the interior of the pantry 119 to determine what food supplies are contained in the pantry 119, to automatically calculate nutritional statistics, and to automatically determine when additional food supplies need to be obtained. This data may be communicated to the HAPPIE home unit 103, and recorded in the local database 108. The data may be communicated to the HAPPIE central server 100 and recorded on the central database 175 as well. The HAPPIE home unit may provide such information stored on local database 108, if desired, to medical personnel via the doctor portal 102. The information stored on the local database 108 may be used by the HAPPIE home unit 103 to automatically generate appropriate messages or orders for groceries and supplies, which may be ordered directly from a grocery store or other retail outlet via the Internet 105.

Using information from the smart pantry 119, the smart refrigerator 115, coffee maker 118, and other related appliances 114, the HAPPIE home unit 103 may include a nutritional analysis module that calculates estimated nutritional information for a local user. The HAPPIE home unit 103 can generate recommendations for changes in the local user's diet, if desired, in order to achieve nutritional goals, or weight control, or fitness objectives. At any given time, the local user can obtain from the HAPPIE home unit 103 a current calculation of nutritional information for the day, for the current week, or for any other period. A module provided by the HAPPIE home unit 103 can, if requested, analyze the current inventory in the refrigerator 115 and the pantry 119 to generate recipes using currently available food supplies or which may assist in meeting certain predetermined nutritional goals or calorie intake.

The HAPPIE home unit 103 includes an array of sensors and controllers 130. As shown in FIG. 4, medication sensors 154 are included. Medication sensors 154 may include secure medication dispensers, unsecure medication dispensers, medication services such as PillPack™, and smart medication dispensers. Secure medication dispensers are used for controlling potentially addictive opioid class medications. Smart pill dispensers 154 monitor medication dispensed through the use of built-in weight-based dosage calculators comparing pre-and-post dispenser weight to ensure accurate dosing. Similarly, data concerning vitamins and other dietary supplements may be automatically recorded by the HAPPIE home unit 103 using medication sensors 154. Data concerning medication (and dietary supplements) taken by the resident is automatically generated by the medication sensors 154 and is stored on the local database 108. Data concerning medication (and dietary supplements) taken by the resident may also be selectively transmitted to a doctor or nurse via the doctor portal 102, to a caregiver via the caregiver portal 101, or to a family member via the family portal 125. Reminders are provided to the resident when medication is due to be taken. The HAPPIE home unit 103 insures that the correct medications are taken by the resident at the correct time, and in the correct dosage. Tight integration between the calendar module, the wellness module, and the medication monitoring module enables the intelligence built into the HAPPIE home unit 103 to confirm that the resident is complying with medication guidelines. For example, in the case of certain medications that need to be taken with a meal, the HAPPIE home unit 103 can ascertain whether the medication is taken when the resident is having a meal, and the calendar module and medication module can be configured to generate a reminder for the medication when the resident is having a meal, or can remind the resident it is time for a meal when the dose of medication is due. Similarly, in the case of certain medications that need to be taken on an empty stomach, the HAPPIE home unit 103 can ascertain whether the medication is being taken on an empty stomach based upon the data stored in the local database 108 concerning when the resident last had a meal or a snack.

Medical equipment 160 may be connected to the HAPPIE system core 121 in the HAPPIE home unit 103. Such medical equipment 160 may include a smart thermometer 161 for taking the resident's temperature, and communicating data indicative of the temperature measurement to the HAPPIE system core 121 for storage on the local database 108, and/or for transmission to the doctor portal 102, to the caregiver portal 101, or to a family member 125. Blood pressure equipment 163 may also be connected to the HAPPIE system core 121 in the HAPPIE home unit 103, for generating data indicative of the resident's measured blood pressure. A pulse monitor 165 may be provided connected to the HAPPIE system core 121. A weight scale 166 connected to the HAPPIE system core provides data indicative of the measured weight of the resident, which is stored on the local database 108, and if desired, selectively transmitted to the doctor portal 102, the caregiver portal 101, or to the HAPPIE server 100 for storage on a central database 175. A Medwand™ device 162 may also be provided connected to the HAPPIE system core 121. Other health or medical devices may be connected as well, such as a Fitbit™ device 164.

Referring to FIG. 4, an automobile interface 155 is provided to receive data from an automobile or other vehicle at the residence where the HAPPIE home unit 103 is located. The connection is preferably facilitated by a wireless device plugged into the car's diagnostic port, which has been standard on automobiles since 1996. The HAPPIE home unit 103 is able to maintain the automobile's trip log, parked location, and records concerning engine diagnostics using the automobile interface 155. The HAPPIE home unit 103 uses data received from the automobile interface 155 in order to automatically schedule automobile service and maintenance, determine whether the resident is at home, track trips, and generate records for tax returns or accounting purposes. In addition, the wireless device plugged into the automobile's diagnostic port may connect to a smart phone, including the driver's smart phone, and using the cellular telephone network and/or Internet 105, may communicate the automobile's location and/or when the automobile is parked to the HAPPIE home unit 103. The HAPPIE home unit 103 can disable the vehicle under circumstances where the resident has restricted driving privileges. For example, if the resident is restricted from driving after dark, the HAPPIE home unit 103 may calculate the time of sunset and sunrise, based upon the GPS location of the home, and calculate the end and beginning of twilight, and then use that data to disable the vehicle during hours of darkness (between the end of evening twilight and the beginning of morning twilight). If the automobile is not home, the HAPPIE home unit 103 may use communication link 168 to obtain information concerning the automobile's location. This information may be made available to a caregiver via the caregiver portal 101, or to family members via a family member portal 125.

Figure 7:
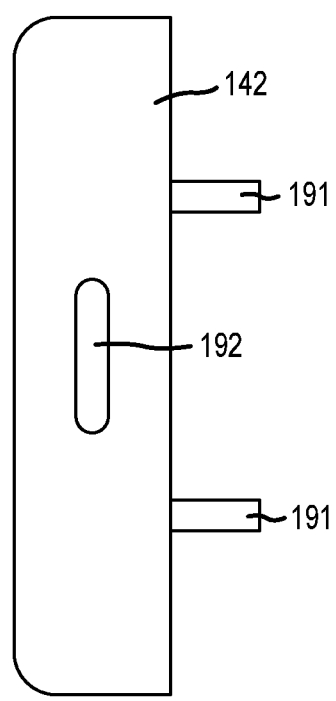
FIG. 7 shows a side view of a mic pack device.

FIG. 6 shows a front view of a mic pack device 142. FIG. 7 shows a side view of the mic pack device 142 illustrated in FIG. 6. A mic pack device 142 contains sensors, and communication functionality, and may be conveniently deployed at various advantageous locations on the home premises by plugging in prongs 191 into a conventional electrical outlet or standard wall socket. Preferably, a mounting screw 197 may be used to attach the mic pack 142 to the electrical outlet to safeguard against accidental unplugging of the device 142 from the power source. In FIG. 6, the mounting screw 197 is shown on the front of the mic pack device 142. An indicator light 199 is provided that lights up to indicate that the mic pack 142 is connected to electrical power. The mic pack device 142 includes a motion sensor or motion detector 192 on each side, as shown in FIG. 7.

Referring to FIG. 6, the mic pack device 142 includes a camera 193. The camera 193 may have a wide view. In a preferred embodiment, the camera 193 has a view of view that is 120 degrees or greater. The camera 193 preferably works well in daylight, lamp light, and low light conditions, and has thermal imaging and infrared night vision capability. The camera 193 can capture still images and live video. An intelligent heat detector or sensor 194 is provided on the front of the mic pack device 142. A microphone 195 and speaker 196 are included for audio communication with the resident at the HAPPIE home unit 103, or for communication with other persons at the home premises. A smart USB port 198 may be provided for charging mobile devices such as a smartphone 111. A night light 190 is preferably included.

The mic pack also includes wireless or WiFi connectivity for connection to the HAPPIE home unit 103 via wireless connection or WiFi hotspot 109. The mic pack 142 can send still image or stream live video over the wireless connection to the HAPPIE home unit via the WiFi hotspot 109, which can be stored on the database 108. Still images and video recorded on the database 108 can be played back by the HAPPIE home unit 103 and displayed on video monitors 156, as well as displayed on the remote caregiver portal 101, or on the caregiver's smartphone 178, or on the resident's smartphone 111, or to a remote viewer over the cloud 105. Similarly, live video can be streamed from the camera 193 and displayed on the video monitors 156, on the remote caregiver portal 101, on the caregiver's smartphone 178, on the resident's smartphone 111, or on a display device of a remote viewer connected over the cloud 105. The mic pack 142 communicates with the HAPPIE system core 121, and can send audio signals from the microphone 195 to the HAPPIE system core 121, and can produce audio sounds with the speaker 196 from signals received from the HAPPIE system core 121.

The mic pack 142 is provided with a CPU logic core, built into the housing of the mic pack 142. Each CPU in a mic pack 142 controls the camera 193 in that mic pack 142. Significant video processing for the camera 193 is performed by the CPU on the mic pack 142, with periodic updates concerning the processed video being sent to the HAPPIE home unit 103 via WiFi connection 109. In addition, audio transcoding and speech recognition for audio received by the microphone 195 is performed by the CPU on the mic pack 142. The transcoding process for a video and audio stream is very CPU intensive. In accordance with the present invention, a design approach is utilize in which video and audio processing is distributed among CPUs associated with each camera 193 and microphone 195 in order to off-load those intensive computational tasks from the HAPPIE home unit 103.

The CPU on the mic pack 142 converts the format of the video from the camera 193. For example, the CPU on the mic pack 142 converts the format of the video from ONVIF frames generated by the camera 193 to H264 video. The CPU on the mic pack 142 takes each video frame, analyzes it, and encodes it into an H264 stream. In the H264 stream, each video frame is a delta on the last frame. The motion of each "block" on the screen is analyzed (pan, zoom, rotate, etc.), the chroma (color) is analyzed and optimized to reduce the number of colors when possible, and the luma (luminescence or black and white) is analyzed and compressed. Then the frame is compared to the previous frame and any redundant data is removed. The resulting H264 stream is very optimized. This reduces the amount of network traffic for video data.

The CPU on the mic pack 142 also processes still frame images taken with the associated camera 193. A still frame image is compressed in color space (reduce colors) and separated into chroma and luma channels. The chroma is then reduced in scale, since color data is not as important as outlines and shading offered by the luma channel. These two images are compressed as JPEGs and sent to the HAPPIE home unit 103 for analysis.

The CPU on the mic pack 142 organizes video from camera 193 into a WebRTC stream or other standard video streaming format. WebRTC is an industry standard for video conferencing. In the present example, WebRTC is advantageous because it is commonly used by Skype™, Facebook™, Google Chrome™ and others for video conferencing. A doctor or hospital may already be using a WebRTC client, such as Skype™, which would allow them to easily add a resident using a HAPPIE home unit 103 to their Skype™ user list. The WebRTC standard allows for peer-to-peer video connections that do not need to run through a remote server. The use of peer-to-peer video conferencing connections provides significant advantages in response times, network traffic, and latency. For a HAPPIE home unit 103, in many cases it is expected that a caregiver, medical professional, and family member who video-conferences with the resident will be located in a nearby neighborhood, in the same metropolitan area, or in relatively close proximity to the resident. The video and audio stream employed in a peer-to-peer video conferencing connection does not have to travel to a remote server and then back again to the other party connected to the conference. The transmission delay is greatly reduced by eliminating the remote server from the connection. The HAPPIE home unit 103 is typically located behind a secure firewall, which typically prevents a third party from creating a connection to the HAPPIE home unit 103. In order to circumvent this problem, the HAPPIE home unit 103 creates an outgoing connection from each peer, and then gets these connections to join together, in a manner known to those skilled in the art as a standard WebRTC peer-to-peer discovery and firewall traversal, in order to achieve peer-to-peer connections behind a firewall.

In addition, the WebRTC system provided by the HAPPIE home unit 103 will continue to analyze the quality of service of the connection during peer-to-peer video conferencing, and the latency, and may suggest new routes for the video conference. The peers involved in the peer-to-peer connection can then seamlessly switch to the new route. This is advantageous if the remote peer, who is involved in the peer-to-peer connection with the resident using the HAPPIE home unit 103, is using a mobile cell phone and is driving or moving between cell towers. This is advantageous because it can be used to circumvent problems caused by network equipment failures or sudden network congestion.

In a preferred embodiment, all video cameras 112 have an associated CPU for video processing, and to improve speech recognition performance, each camera 112 is provided with an associated microphone 113 whose audio is also processed by the associated CPU. The associated CPU performs its own voice recognition and sends the results and confidence scores to the HAPPIE home unit 103. The HAPPIE home unit 103 will receive speech-to-text results from every remote associated CPU processing unit that hears an individual speak on its associated microphone 113. The accompanying confidence data associated with each word and branch of the spoken phrase allows the HAPPIE home unit 103 to decide which microphone 113 heard the individual best and which words (derived from varying speech recognition results received from each device) were most likely spoken. The results of the final processing of the speech by the HAPPIE home unit 103 can then be played back over the speaker 195 associated with that camera 193 and mic pack 142, and if desired, over speakers 157 as well. The identification of the microphone that achieved the best speech recognition results may also be used in an algorithm to determine the approximate location of the individual who is speaking, and to assist in pointing the cameras 112.

Although all voice processing is preferably handled locally by the CPU associated with each microphone 195 and 113, the HAPPIE home unit 103 allows remote fallback audio processing. This has the advantage of doing first pass voice recognition processing on the local system provided by the CPU on each mic pack 142, or with the HAPPIE home unit 103 itself, and the voice recording does not need to be sent to a remote server 100 and then wait for the response from the remote server 100. Sending voice to a remote server 100 has two major downsides when it comes to voice recognition. First, the spoken phrase needs to be complete in order to send it to the remote server 100, whereas in local processing, the phrase can be interpreted in real-time as the audio is being spoken. Waiting for the spoken phrase to be completed before the audio can be sent to a remote server 100 for processing can introduce a significant delay. Second, the voice recording needs to be sent to the remote server 100, processed, and then the result is sent back. This round-trip can typically take two to three seconds. The voice recognition processing cannot begin at the remote server 100 until the audio is received, and because the audio is not sent until the completion of the spoken phrase, and no matter how fast the remote server 100 is of processing the audio, the remote server 100 is unable to respond any quicker that the latency associated with the transmission to and from the remote server, which is usually noticeable under the best of circumstances. Conventional commercial systems like iOS and Android occupy this inherent delay with sound effects and spinning graphics on the screen of the phone, which appear to cover up the delay and distract the user during the delay.

The HAPPIE home unit 103 transcribes the spoken phrase locally, and in the event of a poor confidence score, the HAPPIE home unit 103 will send it up to the remote server 100. In that event, the HAPPIE home unit 103 may play an audible prompt to the resident, for example, "Just a moment." When the remote server 100 interprets the audio phrase, and sends back the results to the HAPPIE home unit 103 via the Internet 106, this data is used to train the local voice model employed by the HAPPIE home unit 103 for voice recognition of the resident's voice (or the voices of others frequently present at the residence). During initial operation, some residents using a HAPPIE home unit 103, who may have an unusual accent or speech pattern, may hear the delay prompt more often. But the local voice model employed by the HAPPIE home unit 103 will adapt to them over time. The remote server 100 will record these instances in a central database 175, and the central HAPPIE server 100 can look for phrases that are commonly misinterpreted and introduce an updated voice model to be distributed to local HAPPIE home units 103.

The HAPPIE home unit 103 may use audio processing to play audio through the built-in speaker 195 on the mic pack 142. As audio comes in from a remote video conference peer, the audio typically needs to be converted from one of the formats allowed by WebRTC to the type of audio necessary for the speaker 195. In some instances, this means cutting the incoming audio into chunks that can be played easily. When this is required, the audio files may not play back-to-back seamlessly. Instead, the HAPPIE home unit 103 breaks audio on pauses, looking for the end of a sentence, and then breaks that audio into discrete files. This process works better with equipment that was designed for file-based playback instead of stream-based playback, and provides better seamless playback of audio during a WebRTC video conferencing session.

This distributed approach to video processing and audio processing provides significant advantages. The computational time available to the processor in the HAPPIE home unit 103 is free from the demands of CPU intensive video processing performed by each mic pack 142. Otherwise, the number of cameras 112 that could be handled by a single HAPPIE home unit 103 would be limited to the computational and processing power of the HAPPIE home unit 103. Instead, this distributed processing results in an unlimited number of cameras 193 that may be associated with a single HAPPIE home unit 103 and which may be incorporated into the residence. This scalability allows a HAPPIE home unit 103 to monitor any home, regardless of its size or number of floors. Using this approach to scalability with distributed processing of video and audio, a single HAPPIE home unit 103 could control all cameras installed in patient or resident's rooms in an assisted living facility, memory care facility, hospice care facility, medical clinic or hospital. In practice, a Raspberry Pi 3 computer has provided satisfactory results for the CPU used in the mic pack 142, and for a CPU associated with each video camera 112 and corresponding microphone 113.

The CPU in the mic pack 142, and the CPU associated with each video camera 112, includes artificial intelligence with machine vision to detect common events and activities. These may include, but are not limited to, a slip, trip, fall, someone on the ground. In addition, the CPU in the mic pack 142 may access data stored in the database 108 of common objects like people, pets, phones, lighting and doors, for purposes of detecting such objects. The HAPPIE home unit 103 will send still images from the cameras 193 and 112 to the remote server 100 at predetermined intervals of time. These images will be scanned by a machine learning algorithm on the remote server 100. The remote HAPPIE server 100 will look for things like a door that is left open, or a prone body on the floor. If nothing is detecting, the still images will be saved for a few days in case it is necessary to access them because of the occurrence of an event at the residence. Otherwise, the images may be routinely destroyed to conserve storage in the central database 175. The CPU associated with each camera 193 and 112 will be responsible for uploading images to the server 100. Machine learning algorithms are used in the remote server 100 to look for things like multiple people in the house, objects being moved, gait analysis, movement and routine patterns, confused behavior (wandering room to room), lack of movement and exercise, etc. As part of the still image upload to the remote server 100, combined motion events on the cameras 193 and 112 and usage on the HAPPIE home unit 103, as well as possible sound received by microphones 113 within the home, the HAPPIE server 100 will assemble a "pattern" for the resident. This should include the resident's normal waking hours, the resident's activities like watching TV, how often the resident eats, normal times for opening the doors, etc. The pattern can be tracked over time, and appropriate alerts generated to a caregiver and family members via the caregiver portal 101 if the resident's pattern changes significantly. Data associated with any relevant patterns uncovered by the machine learning algorithms will be transmitted to the HAPPIE home unit 103, and in appropriate circumstances, to the caregiver via the caregiver portal 101.

The indicator light 199 on the mic pack 142 includes different colors to signify different conditions. For example, the indicator light 199 may light up yellow to indicate that power is being supplied, but the mic pack 142 is not connected to the HAPPIE home unit 103. The indicator light 199 may light up green to indicate that power is being supplied, and the mic pack 142 is connected to the HAPPIE home unit 103 via WiFi hot spot 109. The indicator light 199 may light up red to indicate that a fault condition has occurred.

In a preferred embodiment, the mic pack 142 has blue tooth connectivity. The mic pack device 142 preferably has near field communication functionality that allows the mic pack 142 to sync, wirelessly and without contact, with wearable fitness and health sensors 158, wellness trackers such as a smart watch or Fitbit™ device 164, and other health monitoring equipment and devices 160, such as a heart rate monitor 165. Monitored functions include heart rate, heart rate variability, respiration rate, blood pressure, body temperature, oxygen saturation, glucose levels, steps walked, and sleep quality.

Blue tooth connectivity enables the mic pack 142 to act as a near field communication device for contactless synchronization with wearable fitness tracker 164, wearable health sensor 158, other wellness trackers and health monitoring equipment 160, as well as remote health monitoring devices like heart rate 165, blood pressure 163, and glucose meters. The mic pack 142 features an open API standard for synch functionality to enable third-party applications to communicate with the HAPPIE home unit 103. Using a wireless connection with the HAPPIE home unit 103 via WiFi hotspot 109, the mic pack device 142 is provided with time sync capability with the HAPPIE home unit 103 clock, remote clocks, and Internet based clocks, to accurately time stamp each download or data acquired from wearable fitness tracker 164, wearable health sensor 158, other wellness trackers and health monitoring equipment 160. The mic pack device 142 preferably is provided with an open standard interface to permit connectivity and operation with other systems in addition to the HAPPIE home unit 103.

The HAPPIE home unit 103 has the ability to monitor the power levels on battery powered devices, and to notify the resident when a battery needs replacement or recharging. In addition, the HAPPIE home unit 103 has the ability to send a message to the caregiver portal 101 or the family portal 125 concerning battery status, and to recommend a recharge or a replacement of a battery.

The operation of the HAPPIE system may be described in connection with FIG. 8, which shows a screen shot of a first home screen 200. The first home screen 200 includes a weather/time/date display area 201. This area 201 preferably displays the current time at the home premises. The current weather conditions are also displayed, along with the date and day of the week in the weather/time/date display area 201.

The first home screen 200 includes a calendar button or icon 202 to activate a calendar software module. A medication button or icon 203 is provided to activate a medication software module, as shown in FIG. 8. A wellness button or icon 204 is provided to facilitate activation of a wellness software module. Similarly, a smart home button or icon 205 is provided to initiate or activate a smart home software module. A memory strength button or icon 206 is preferably included to activate a memory strength software module.

In all cases where an icon or button is described in connection with a screen shot, it will be understood by those skilled in the art that, in a touch screen implementation, the button or icon may be activated by pressing that area of the touch screen display. In addition, for example in a PC implementation, the button or icon may be alternatively activated by clicking with a mouse, or by using keyboard shortcuts. In a preferred embodiment, voice recognition is also used by the HAPPIE system, and each software module can be activated using speech. Thus, the resident who lives at the HAPPIE home unit 103 may control, activate, and interface with the HAPPIE system, and the software modules described herein, using natural speech that is detected by microphones 113 located at appropriate locations on the premises, and the natural speech is analyzed and recognized using a voice recognition software module.

Figure 8:
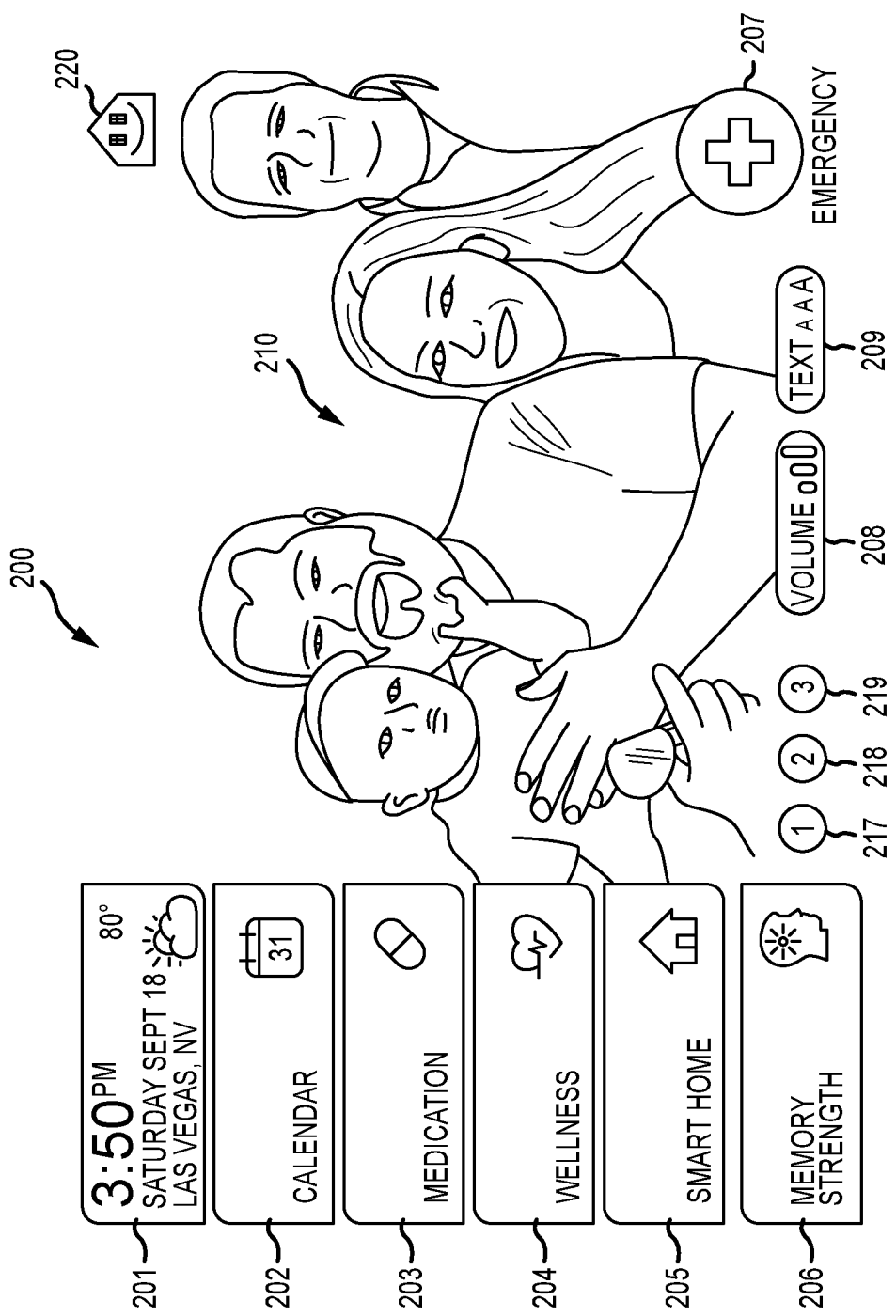
FIG. 8 is a screen shot showing a first home screen.

As shown in FIG. 8, the first home screen 200 has an emergency button or icon for automatically dialing 9-1-1 when it is pressed or activated. The first home screen 200 preferably includes a volume control or icon 208 for adjusting audio volume, and a text size adjustment button or icon 209 for adjusting the size of text displayed.

Each screen includes a home screen icon 220 that may be activated to return the user to the first home screen 200. Repeated activation of the home screen icon 220 causes the HAPPIE home unit 103 to display the second home screen 211, and successive home screens.

In the example illustrated in FIG. 8, the first home screen may include wall paper of a desktop display of a family photo. In the case of a resident who may suffer from dementia, displaying an image of family members may assist the resident in remembering who they are, and aid in recognition.

Figure 9:
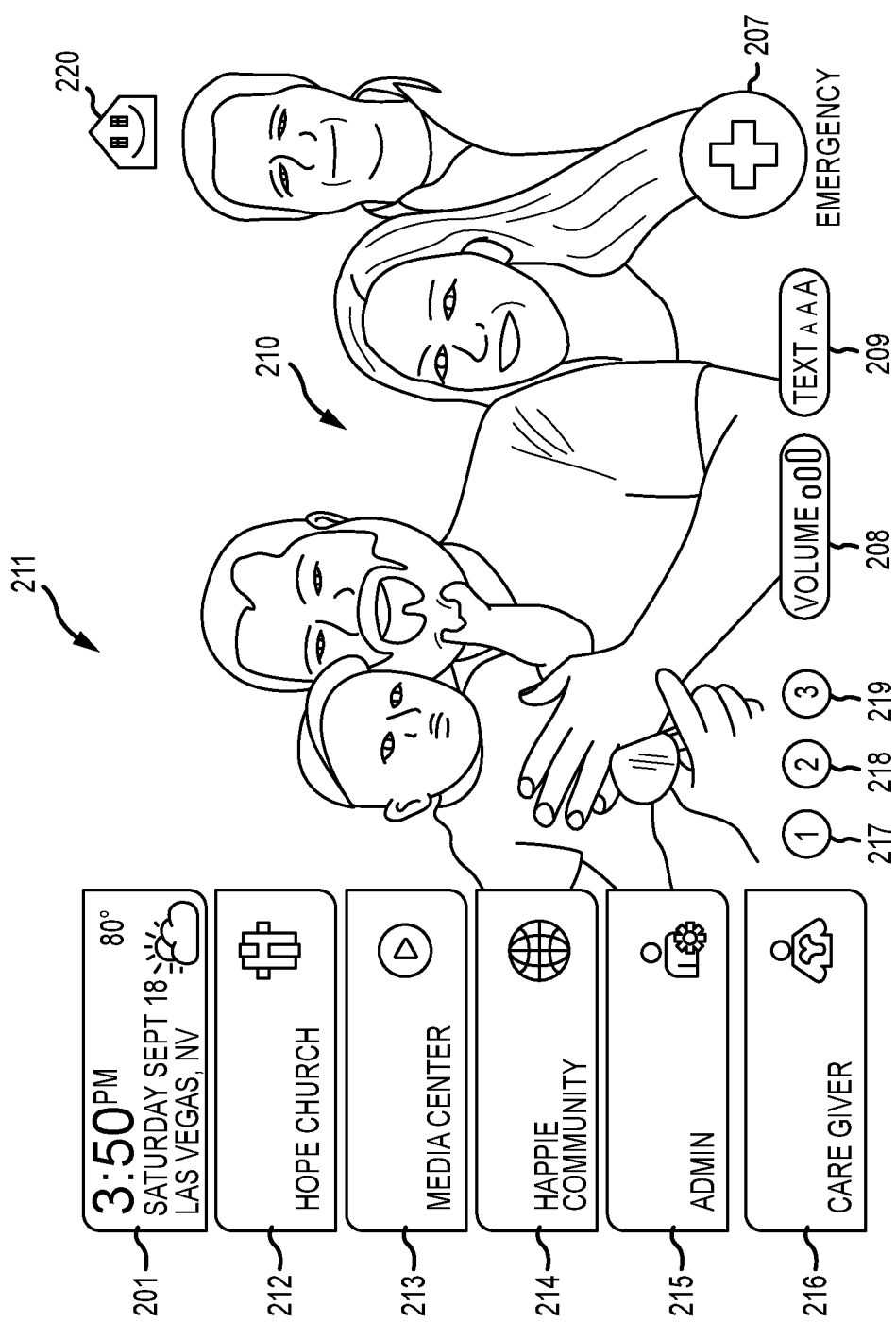
FIG. 9 is a screen shot showing a second home screen.

The first home screen 200 includes a plurality of screen selection buttons 217, 218 and 219. A second screen selection button 218 selects a second home screen 211. FIG. 9 shows a screen shot of the second home screen 211.

Referring to FIG. 9, the second home screen 211 may include the weather/time/date display area 201. The second home screen 211 has a church button 212 for activating a church software module. The second home screen 211 includes a media center button 213 for activating a media center software module. The second home screen 211 includes an admin button 215 for activating an administrative software module. The second home screen 211 also has a HAPPIE community button 214 for activation of a HAPPIE community software module.

The second home screen 211 includes a plurality of screen selection buttons 217, 218 and 219. A first screen selection button 217 selects the first home screen 200 shown in FIG. 8. Pressing or clicking a third screen selection button 219 activates a third home screen, to allow for a plurality of menus presenting a plurality of options and functionality, which can be displayed on a series of home screens to provide convenient and easily operated buttons and icons using the limited display area of a handheld computing device, such as a tablet 131 (e.g., an iPad® tablet), or a smart phone device 111 (e.g., an iPhone® smart phone).

Figure 10:
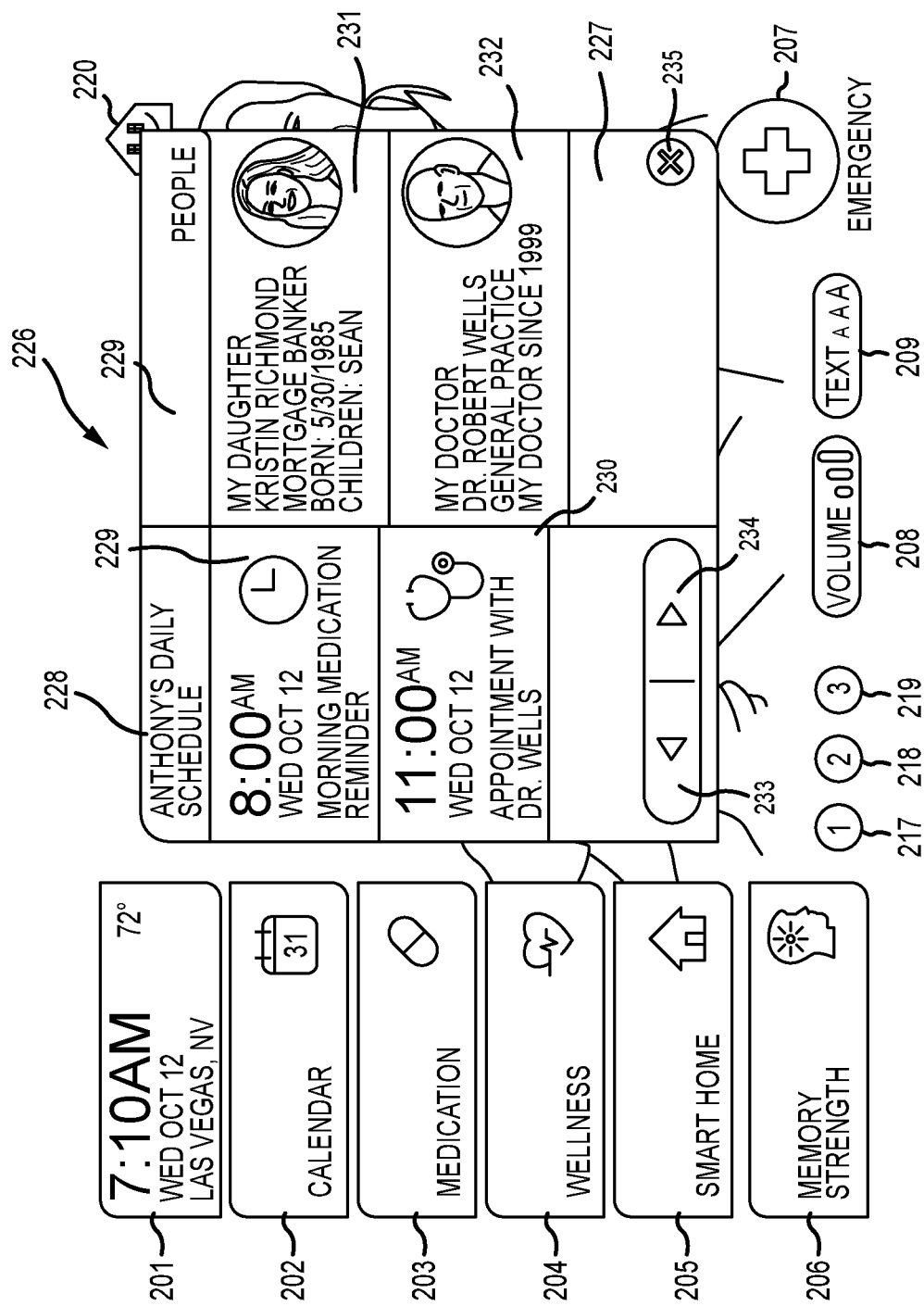
FIG. 10 is a screen shot showing a first screen for a calendar module.

Referring to FIG. 8, when the calendar button 202 is activated, by touching the screen 200, or by mouse clicking the button 202, or by an associated voice command, the calendar software module is activated. A first calendar module screen shot 226 is shown in FIG. 10. In the first calendar screen shot 226, a daily schedule window 227 is selectively displayed to show the schedule for any date. The default display 227 is for the current date. The left column 228 displays appointments 230 and reminders 229 and other data relating to the day's schedule. The right column 229 may be used to display information concerning associated people, for example, to display information for a first person 231 associated with a reminder 229, and to display information for a second person 232 associated with an appointment 230.

The calendar module contains a contact information for the people 231 and 232 in the resident's or user's life. Family, friends, neighbors, authorized caregivers, aides, in-home help, medical professionals, maids, service personnel, resident managers, and more. Contact profiles are personalized to include name, address, phone number, email, photo, date-of-birth, relationship, employment, and duration of time known to the user, as shown in the example illustrated in FIG. 10. These association definitions are designed to be of value to users with Alzheimer's, dementia, cognitive impairment, and head trauma injuries. In addition, contact profiles preferably include each person's 3D facial image and voice pattern recognition. The 3D facial image and voice pattern recognition information allow the HAPPIE home unit 103 to automatically identify any known person who enters the residence at the HAPPIE home unit 103, based upon a pattern recognition of the person's voice sensed by microphones 113 at the residence, and based upon analysis of 3D facial image data compared with the image of the person recorded by video cameras 112 at the residence. The calendar module includes functionality for importing contact information from any smart phone or handheld computing device using any conventional format. The HAPPIE home unit 103 includes configuration controls by which the resident or user, or someone configuring the system on behalf of such resident or user, can determine how much of this information to display on their video monitor or television 156 when the HAPPIE home unit 103 books an appointment associated with that person, or when an outbound call or text message is generated to that person, or an inbound call, text message, or video message is received from that person.

Referring to FIG. 10, a forward button 234 is provided for advancing the display of the daily schedule 227. A back button 233 is provided for navigating to previous daily schedule information 227. Activating a close button 235 closes the daily schedule display 227.

Figure 11:
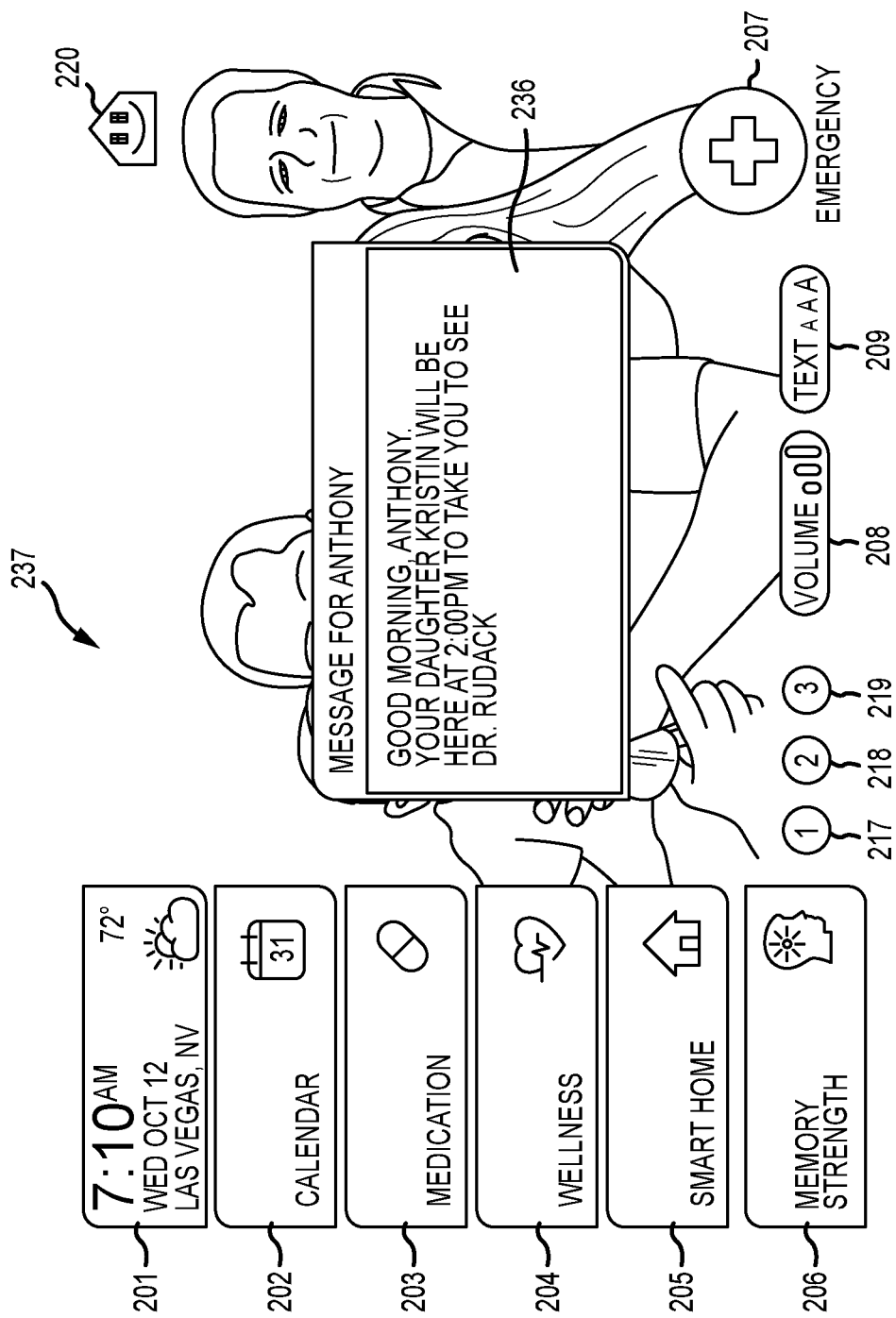
FIG. 11 is a screen shot showing a second screen for the calendar module.

In addition to providing information concerning reminders 229 in the daily schedule 227 shown in FIG. 10, when the time associated with a reminder arrives, a reminder window 236 is displayed, as shown in a second calendar screen shot 237 illustrated in FIG. 11. Moreover, a voice message (or other audio alert) associated with the reminder 236 may be played over speakers 157 at the premises controlled by the HAPPIE home unit 103.

Figure 12:
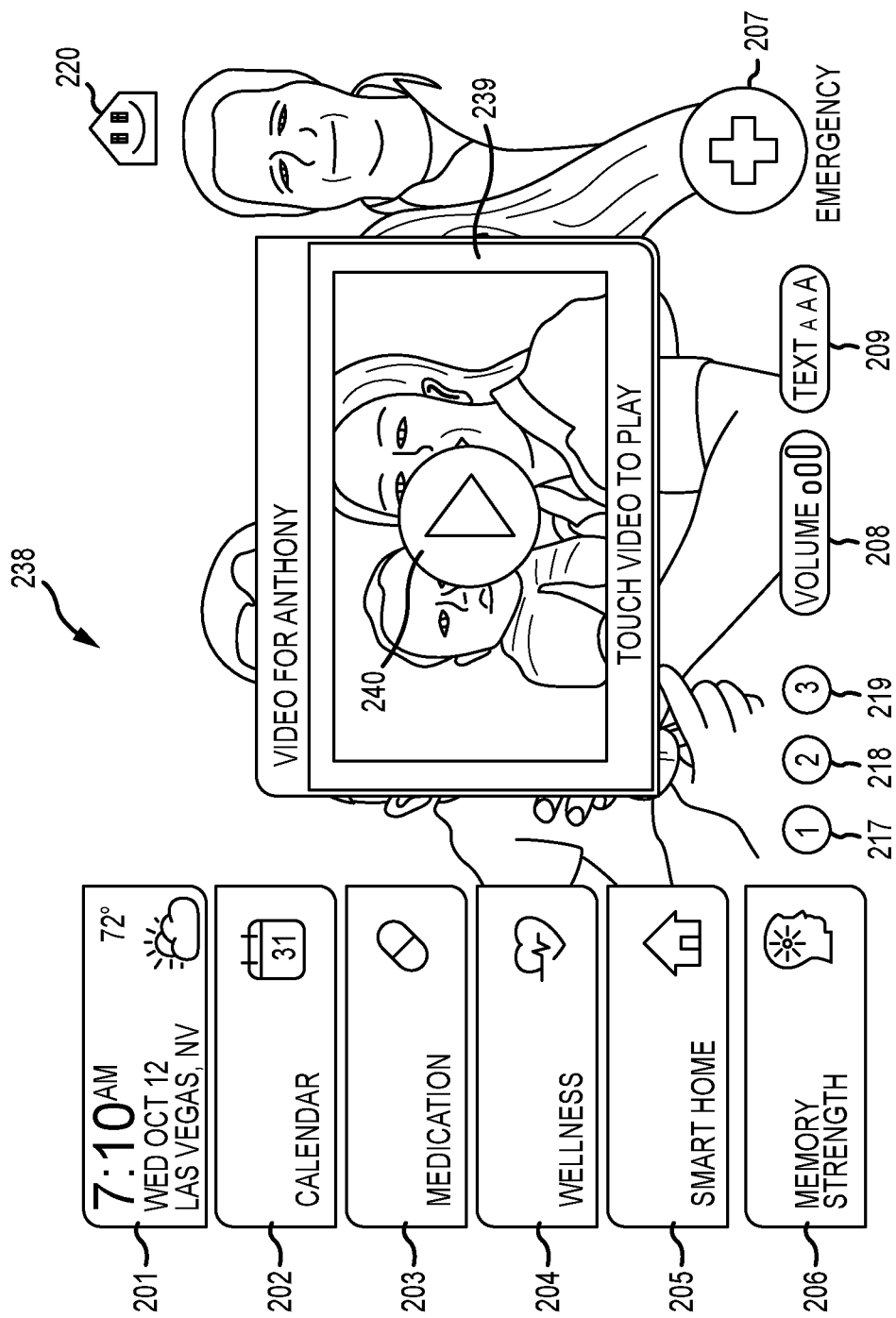
FIG. 12 is a screen shot showing a third screen for the calendar module.

FIG. 12 shows a third calendar screen shot 238. A video message may be stored in the local database 108, and at a scheduled time, the calendar module may automatically open a video window 239 to show the video. A play button 240 may be provided for the resident or user to activate in order to play the video 239. Alternatively, the calendar module may be configured to play the video 239 automatically. For example, a video message 239 to remind the resident of an important event may be automatically played, or a video message 239 such as a happy birthday message or a happy father's day message, may be automatically played at a predetermined time configured in the calendar module.

The HAPPIE home unit 103 may receive data from the Internet 105 concerning appointments and reminders for storage in the local database 108 and for incorporation into data associated with the calendar module. The calendar module includes an importation sub-module that can load contact details from a smart phone or mobile device. The calendar module includes functionality for importation of appointment data and meeting requests from Microsoft, Google, Yahoo, Apple, iPhone, Android, and others calendar applications. The calendar module includes similar appointment setting capabilities and functions of popular digital planners.

Figure 13:
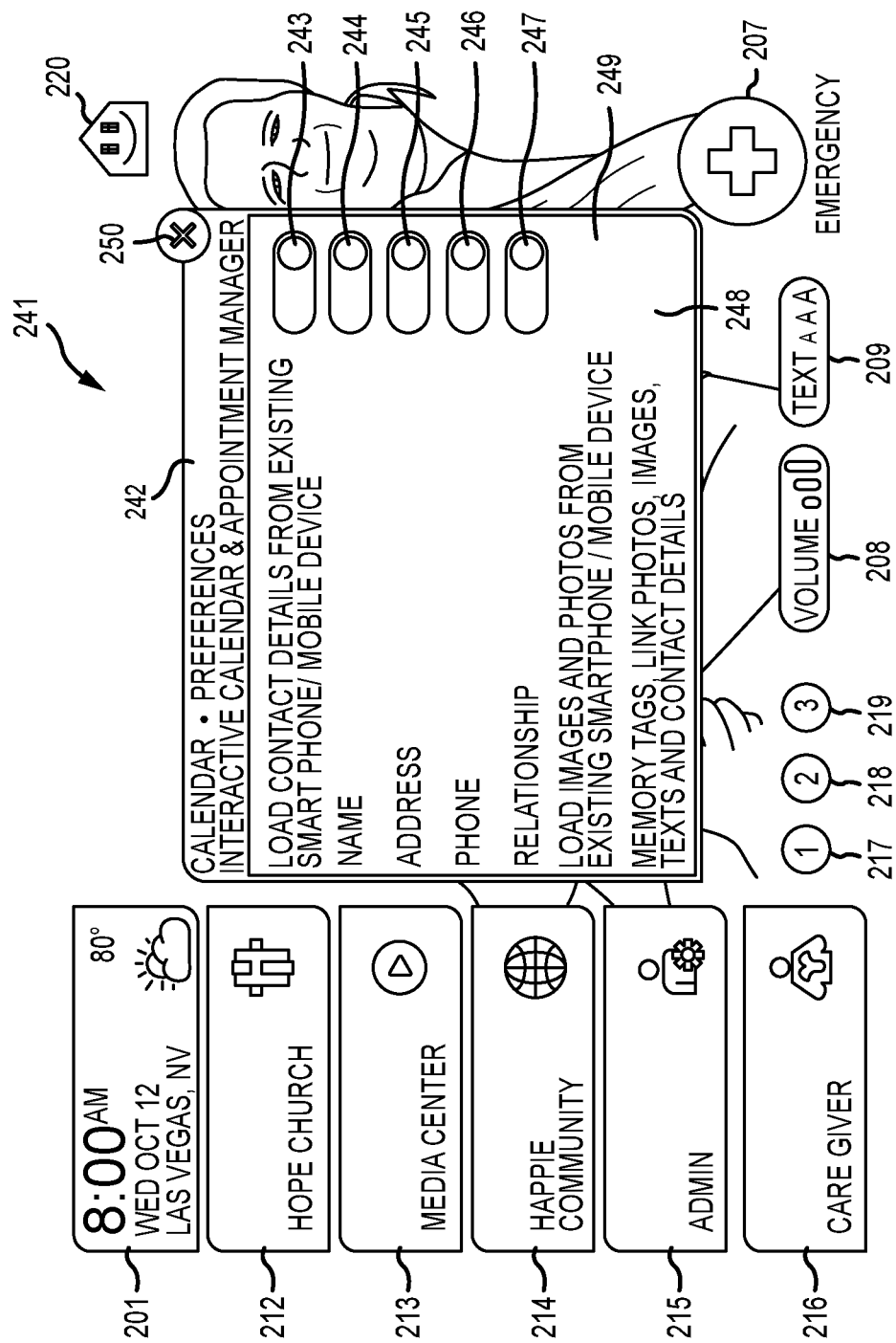
FIG. 13 is a screen shot showing a fourth screen for the calendar module.

FIG. 13 shows a fourth calendar screen shot 241, illustrating a calendar preferences and configuration window 242. The calendar preferences window 242 has a first toggle 243 for loading contact details from an existing contacts app on a smart phone 111, tablet computer 131, or other mobile device, or a laptop. The calendar preferences window 242 has a second toggle 244 that may be used to selectively display the name associated with a person in the contact information stored on the local database 108. The calendar preferences window 242 has a third toggle 245 that may be used to selectively display the address associated with a person in the contact information stored on the local database 108. The calendar preferences window 242 has a fourth toggle 246 that may be used to selectively display the phone number associated with a person in the contact information stored on the local database 108. The calendar preferences window 242 has a fifth toggle 247 that may be used to selectively display relationship identifying information associated with a person in the contact information stored on the local database 108.

The calendar preferences window 242 has a sixth toggle 248 that may be used to load images and photos from an existing smart phone or mobile device. The calendar preferences window 242 has a seventh toggle 249 that may be used to selectively use memory tags, link photos, images, texts, and contact details. A close button 250 is provided in FIG. 13 to close the calendar preferences window 242.

Figure 14:
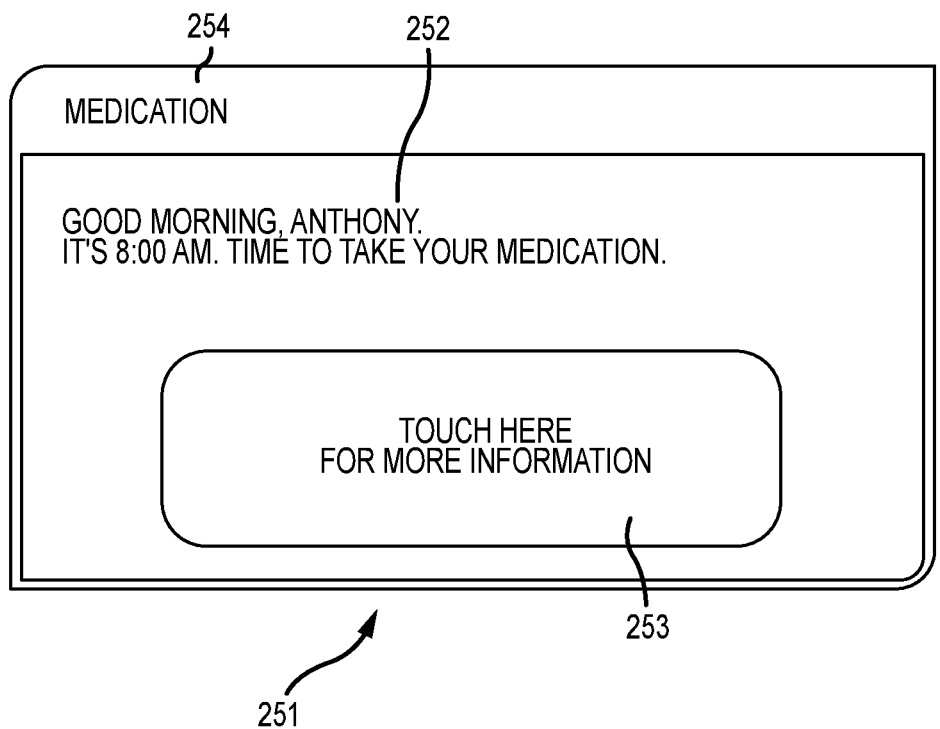
FIG. 14 is a screen shot showing a first screen for a medication module.

FIG. 14 is a screen shot 251 showing a medication reminder window 254 for a software medication module running on the HAPPIE home unit 103. Unlimited medication calendar events can be delivered in any combination of text alerts 252, audio file alerts, and video file alerts 254. The HAPPIE home unit 103 automatically generates the medication reminder window 254, to be displayed on video monitors and televisions 156, when medicine is scheduled to be taken by the resident. The medication monitoring module activated by medication button 203 is designed to eliminate the common errors, omission and challenges a patient or resident may have in being sure he or she takes the exact correct medication by day, time of day, and dosage to greatly minimize the effects of under or over medicating one's self.

The medication module 203 is integrated with the calendar module 202. Medication times and dosages can be conveniently entered into the resident's calendar, and stored in the local database 108, on a day, week, month, and year at a time basis. Unlimited calendar alerts for medication are available over adjustable time intervals leading up to the calendar event, and may be delivered by text, audio file, or video file.

A caregiver can use the caregiver portal 101 to remotely enter medication reminders, notifications, and alert settings into the local database 108 to be stored as a calendar event for the calendar module. Calendar events can be added, modified or deleted by remotely accessing the caregiver portal 101. Alternatively, calendar events can be added, modified or deleted by direct access to the HAPPIE home unit 103 locally at the home.

Figure 15:
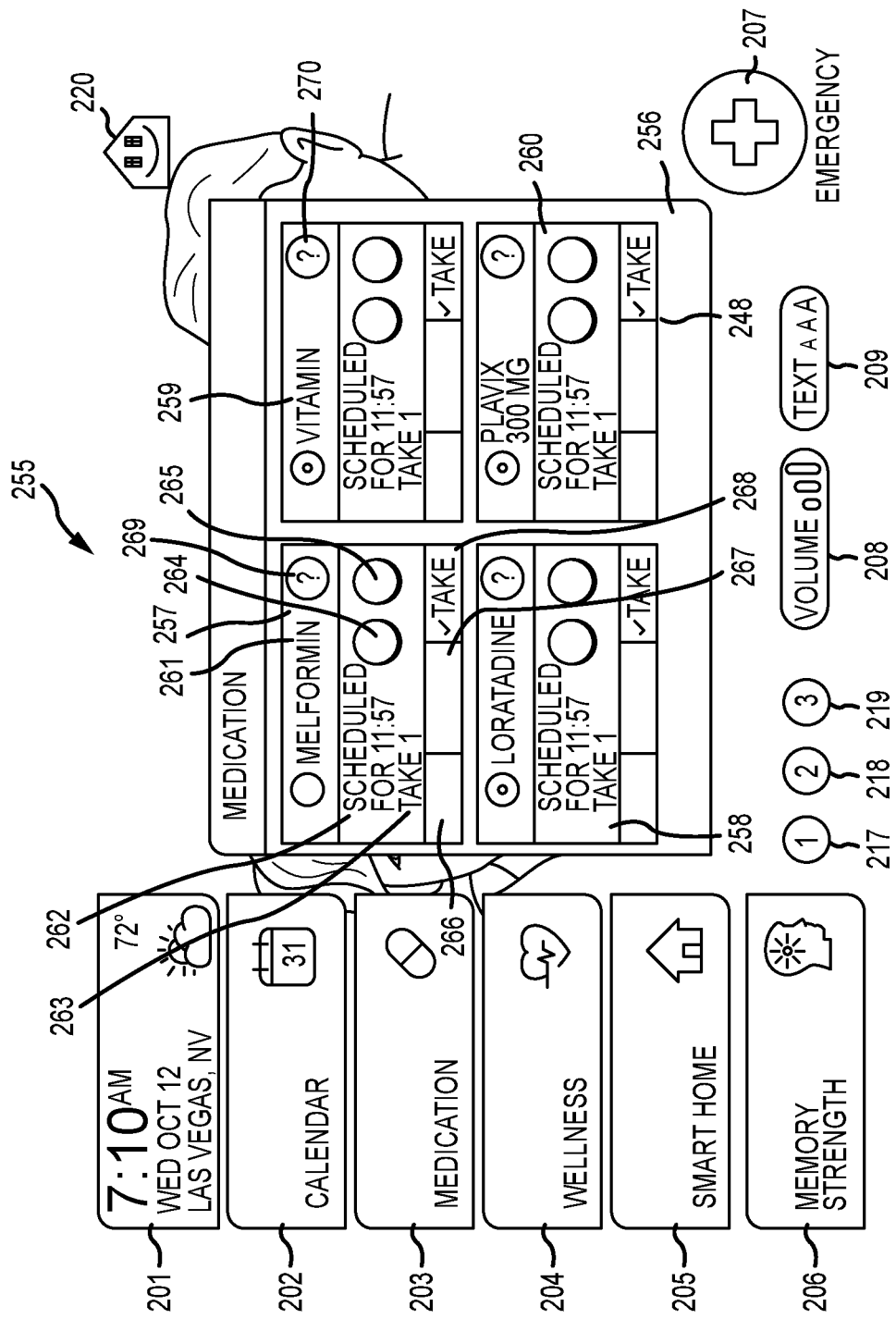
FIG. 15 is a screen shot showing a second screen for the medication module.

When the medication button 203 is activated, a medication screen 255 shown in FIG. 15 displays the next series of medicines scheduled to be taken by the resident. The medication screen 255 includes a medication information window 256 that, in the example shown in FIG. 15, displays a first medicine dose window 257 for metformin, a second medicine dose window 258 for loratadine, a third medicine dose window 259 for a vitamin, and a fourth medicine dose window 260 for plavix.

Referring to FIG. 15, a medicine dose window 257 shows the scheduled time 262 to take the dose, and information 263 concerning how many pills to take. Images of the front and back of each pill based medication, vitamin, and supplement are stored in the local database 108 of the HAPPIE home unit 103. As shown in FIG. 15, a front image 264 of the pill is displayed in the medicine dose window 257, and a back image 265 of the pill is displayed. Images of the pill are also displayed on any connected smart phone 111, during an alert, or selectively displayed on smart phone 111 at any time upon request. The same information may be displayed on video monitors and televisions 156 at the home.

Each medicine dose window 257 has a skip button 266, associated with a "skip" function, a snooze button 267, associated with a "snooze" function, and a take button 268, associated with a "take" function, respectively. The skip button 266, the snooze button 267, and the take button 268 can be activated by pressing the respective button on a touch screen, or by clicking a mouse, or by voice command. Alternatively, the resident can verbally comment to the HAPPIE home unit 103 that he or she has taken the scheduled medication, or that he or she wants to snooze the taking of the medication for a specific period (e.g., snooze for 15 minutes), or that he or she wants to snooze the taking of the medication until a specific time (e.g., remind me at 3 o'clock PM). Another option is for the patient to verbally command the HAPPIE home unit 103 to skip the current medication time and dosage all together.

Figure 22:
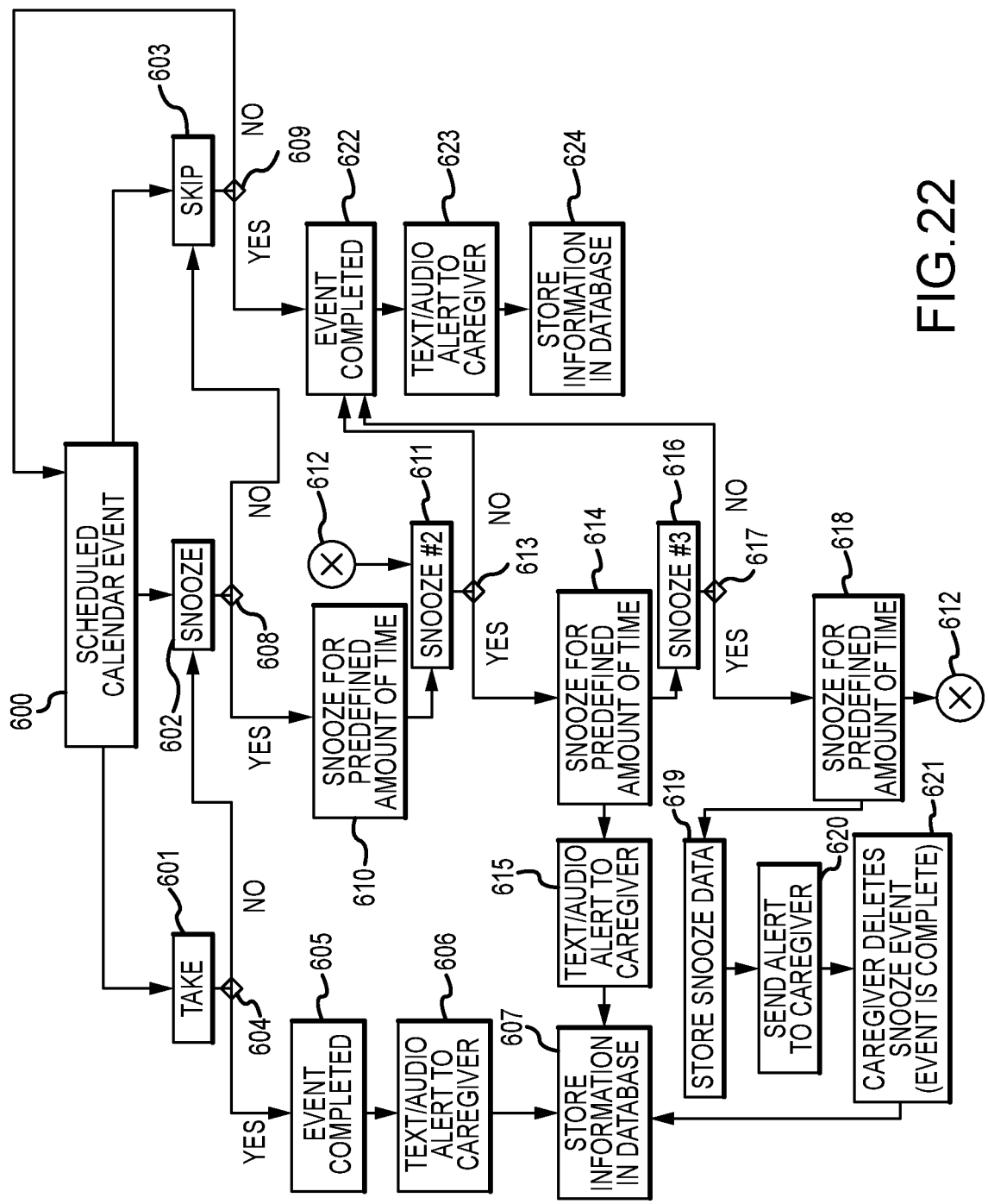
FIG. 22 is a flow chart showing the operation of the "take," "snooze," and "skip" functions in the medication module.

FIG. 22 is a flow chart showing the operation of the "take" 601, "snooze" 602, and "skip" 603 functions in the medication module. The taking of medication may be accomplished using a scheduled calendar event 600. When a calendar event 600 involving taking medication comes due at the corresponding time of day and on the specified date, the resident has an option to take the medicine, to snooze the medication reminder, or to skip taking this dose of the medication.

Referring to FIG. 22, the program flow branches to 601, and a determination 604 is made concerning whether the resident takes the medication. If the determination 604 is "yes," then the flow branches to execute appropriate event complete routines 605. The software checks medication sensors 154 to make sure the pill was removed from the associated medication dispenser. Alternatively, the software may analyze video of the resident to ascertain whether the medication was actually taken by the resident.

The HAPPIE home unit 103 integrates with secure and unsecure medication dispensers 154 (e.g. pill boxes), medication services (e.g. PillPack™), and smart medication dispensers. Smart pill dispensers 154 monitor medication dispensed through the use of built-in weight-based dosage calculators comparing pre-and-post dispenser weight to ensure accurate dosing. The verbal commands of the resident, and information generated by medication sensors 154, are recorded in the local database 108 and used to positively track and verify the resident's compliance with scheduled medication.

In the event of a discrepancy in the information received from the medication sensors 154 or the analysis of video, and the resident's indication that the medication was taken, in step 607 shown in FIG. 22, data concerning the discrepancy will be stored in the local database 108, and if appropriate depending upon configuration settings, in step 606 a text alert or audio alert may be sent to the caregiver via the caregiver portal 101. In addition, in the case of a resident suffering from dementia or conditions that warrant additional confirmation, a video camera 112 will record a video record of the resident taking the medication, which video data may also be stored in the local database 108 in step 607. Under normal circumstances, when the medication is taken, in step 606 a text alert or audio alert may be sent to the caregiver portal 101, which can be optionally relayed to the caregiver's smart phone 178.

Referring to FIG. 22, if the medication is not taken in step 604, then the flow branches to the snooze step 602. A determination is made in step 608 whether the reminder to take the medication should be snoozed or not. If a determination is made in step 608 not to snooze the reminder, then the flow branches to the skip step 603 to determine in step 609 whether the dose of medication in question will be skipped. If a determination is made in step 608 to snooze the medication reminder, the flow branches to step 610, and the resident or the caregiver can specify on the fly how long to snooze the reminder, or whether to snooze the reminder until a specified time. Alternatively, the medication module may be configured with a default predetermined time for a snooze event in case no length of time is specified.

After the specified predetermined period of snooze time configured in step 610, flow branches to step 611 where a reminder or alert to provided to the resident concerning the associated dose of medication. In step 613, a determination is made whether to snooze the medication alert again. If the medication reminder is again snoozed, flow branches to step 614 where the medication alert is snoozed for a predetermined length of time. An alert is also preferably generated in step 615, and a text message or audio message is sent, in step 615, to the caregiver via the caregiver portal 101, in order to notify the caregiver that the medication reminder was snoozed multiple times, and in step 607 the data is stored in the local database 108. In addition, from step 614 shown in FIG. 22, the flow branches to step 616 where, after a predetermined amount of time has elapsed, a medication reminder is generated to the resident. A determination is made in step 617 whether to snooze the medication reminder again. If it is snoozed, flow branches to step 618 where the alert is snoozed for a predetermined length of time. If the flow reaches step 618, then in step 619, data concerning the number of times that the medication reminder has been snoozed is stored in the local database 108. In step 620, a text message or audio message is sent to the caregiver via the caregiver portal 101 to alert the caregiver concerning the number of times that the medication reminder has been snoozed. After a predetermined number of snooze events, in step 621, the caregiver has the discretion to delete the event, making the determination that the dose of medication in question will not be taken and the HAPPIE home unit 103 stops reminding the resident concerning the scheduled dose of medication. Assuming the event is not deleted by the caregiver in step 621, after the predetermined time has elapsed in step 618, the flow loops back to step 611 as indicated by reference numeral 612.

In the skip step 603 shown in FIG. 22, a determination is made in step 609 whether the resident decides to skip the dose of medication. If the determination in step 609 is "yes," then the flow proceeds to step 622 where event completion tasks are performed. In the event that a dose of medication is skipped, in step 623 a text message or audio message is sent to the caregiver via the caregiver portal 101 to alert the caregiver that the dose of medication was skipped. This may prompt the caregiver to communicate with the resident to determine why the medication was skipped, whether it was causing significant side effects, or whether there was some other reason for skipping the scheduled dose. Flow proceeds to step 624, and data is stored in the local database concerning the skipped dose of medication.

In step 609, if a determination is made not to skip the dose of medication associated with a medication reminder, flow loops back to step 600. Referring to FIG. 22, in step 613, if a determination is made not to snooze the reminder, the flow proceeds to step 622, as described above. Similarly, if in step 617 a determination is made not to snooze the reminder, the flow proceeds to step 622.

The status of medication taken, based upon the verbal commands of the resident, or the responses to the "take," "snooze," and "skip" steps described above, may also be stored in the central database 175. That data is accessible from the caregiver portal 101, or from the doctor portal 102. Trend analysis performed by the HAPPIE home unit 103 can be used to trigger multiple preset and customizable reminders, notifications, and alerts to advise the caregiver or the doctor of the exact status of adherence by the resident to physician directives regarding medication.

The HAPPIE home unit 103 can be remotely configured, using the caregiver portal 101, to use the video cameras 112 to record a video of the resident taking the medication, and either store the video data in the local database 108, transmit the video data to the caregiver portal 101, or store the video data in the central database 175 for later retrieval by the caregiver portal 101 or the doctor portal 102.

All skip, snooze, and medication taken status information is provided to the caregiver portal 101. A caregiver software module running on the caregiver portal 101 uses data associated with the resident's skip, snooze, and medication taken status information to interact with alert functions in the caregiver portal 101. Prescription refill notifications can be programed into the calendar module and stored on the local database 108, and linked to a caregiver alert feature provided by the caregiver software module at the caregiver portal 101. The calendar module may be personalized remotely via the caregiver portal 101, or directly on the HAPPIE home unit 103, in order to meet the needs of the caregiver and the resident.

Figure 16:
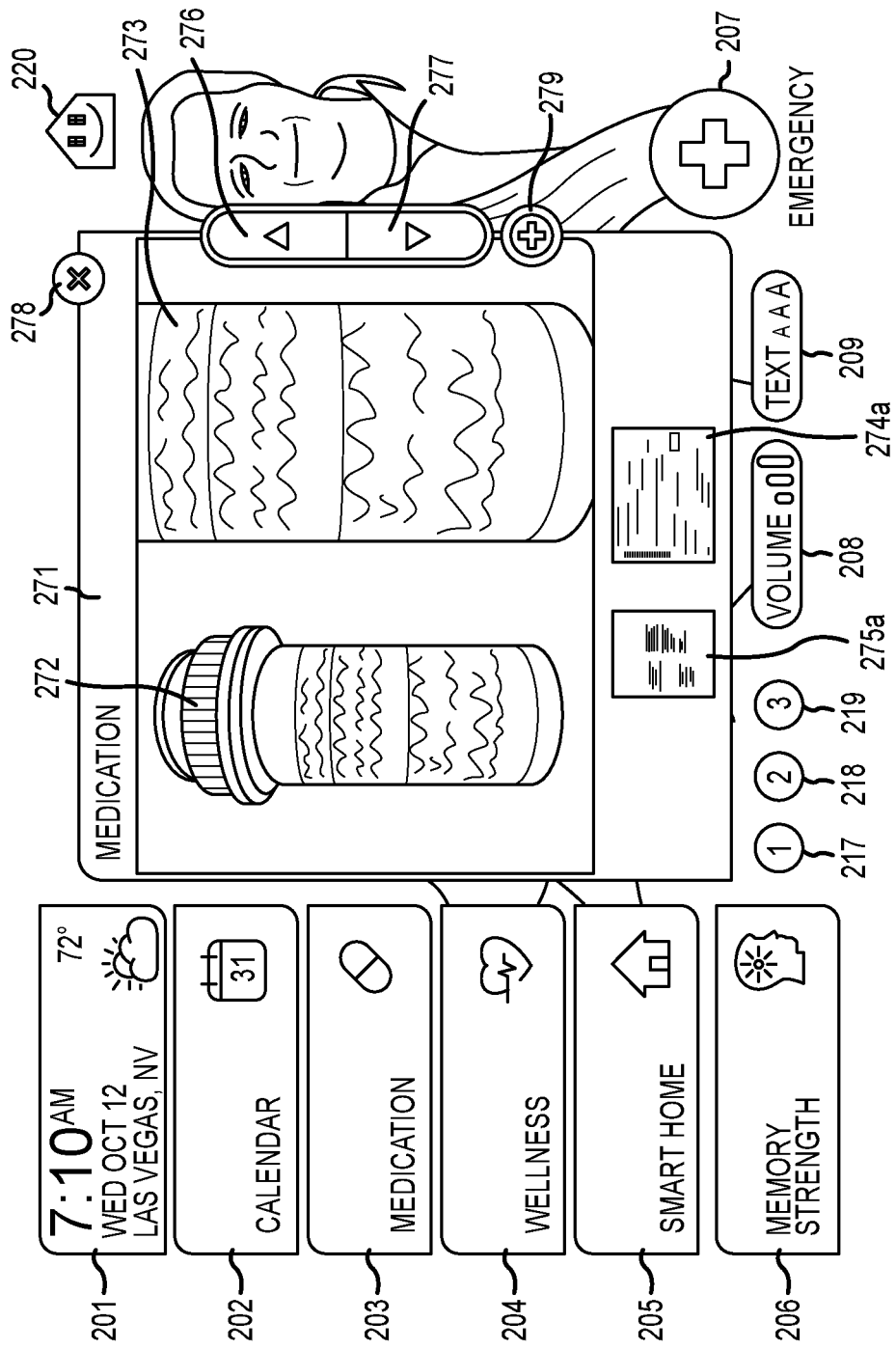
FIG. 16 is a screen shot showing a third screen for the medication module.
Figure 17:
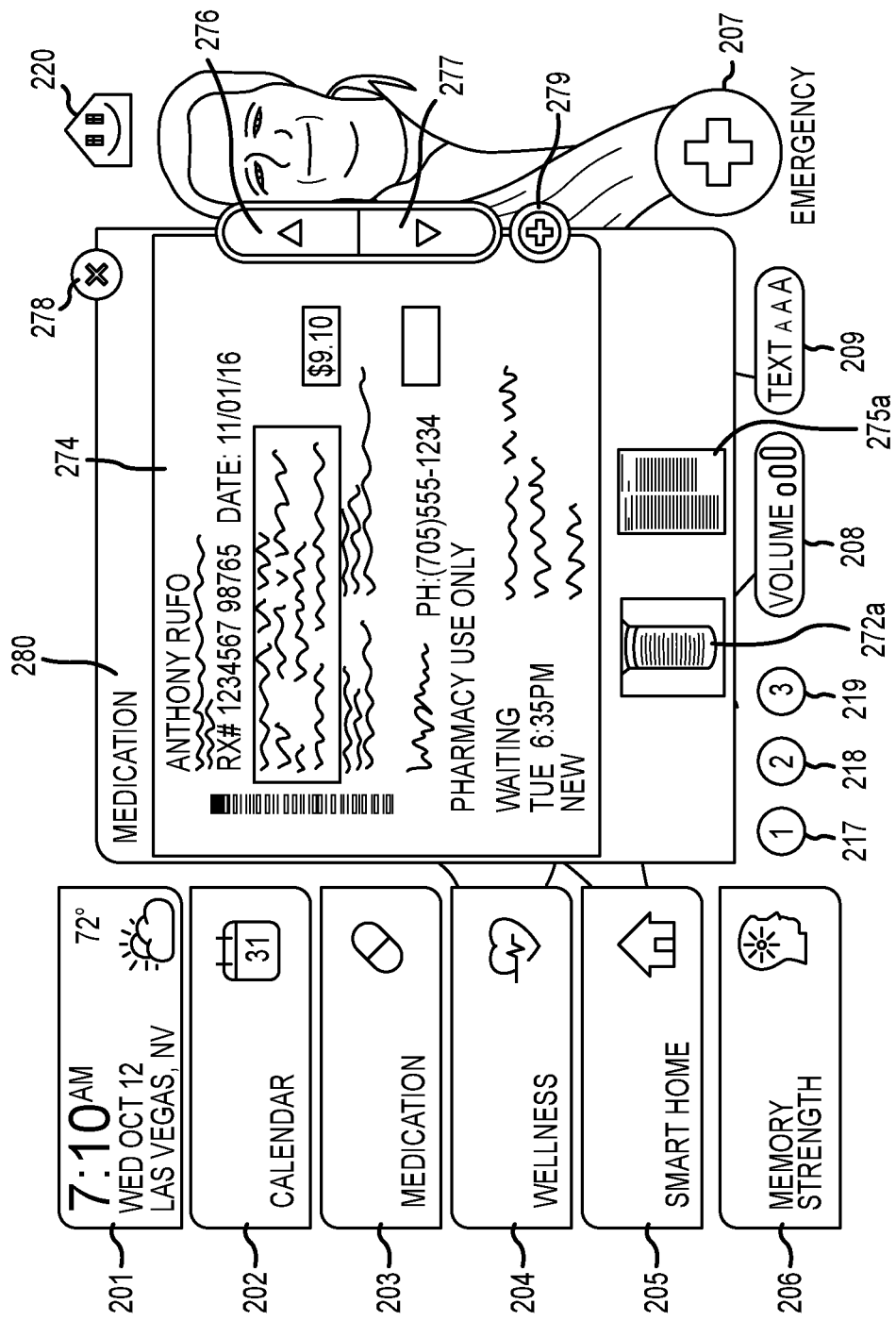
FIG. 17 is a screen shot showing a fourth screen for the medication module.
Figure 18:
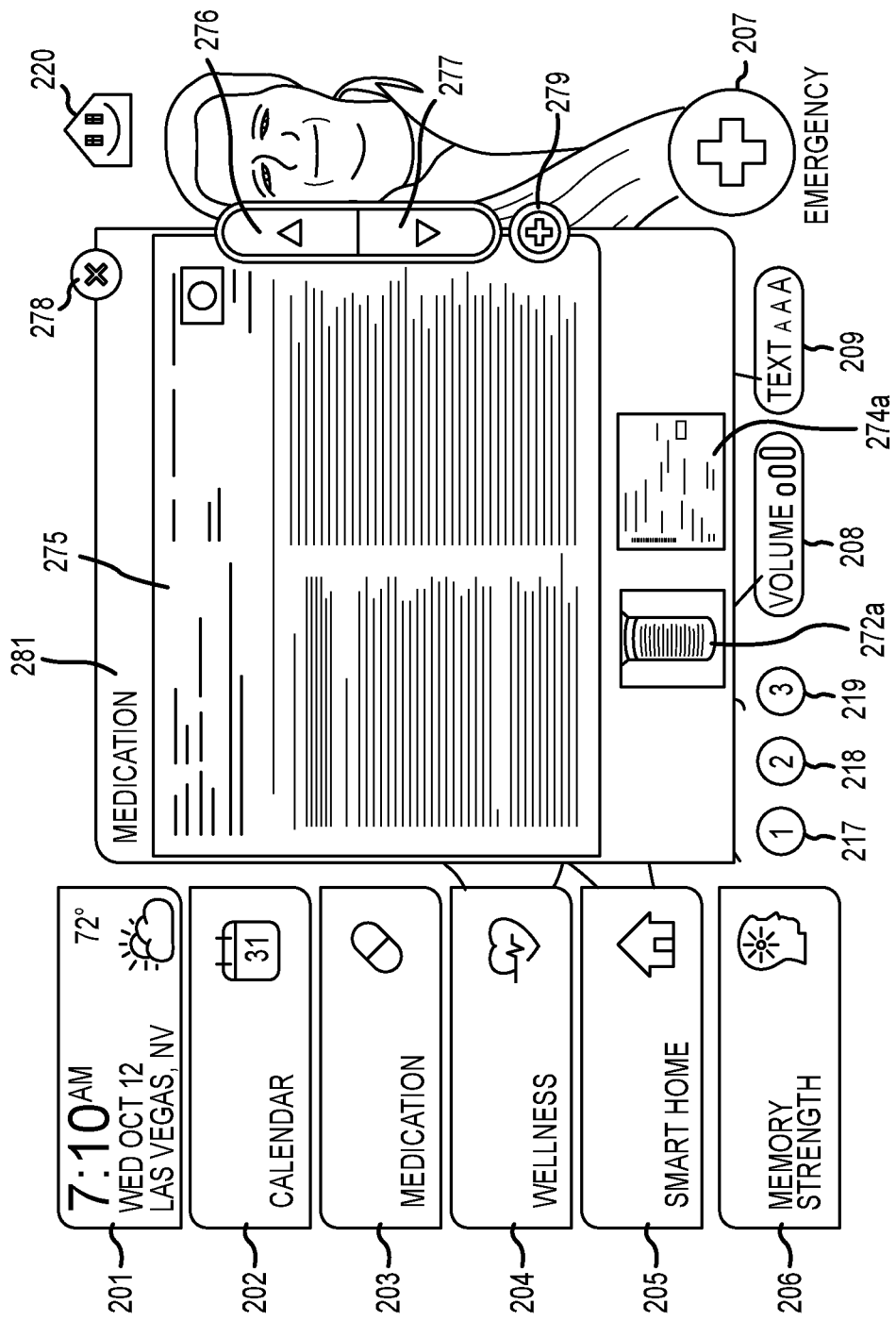
FIG. 18 is a screen shot showing a fifth screen for the medication module.

Referring to FIG. 14, a first medication information button 253 is provided with medication alerts, and when pressed or otherwise activated, the HAPPIE system core 121 will selectively display a cascading series of additional screens, such as the screens shown in FIG. 16, FIG. 17, and FIG. 18, which provide more information concerning the medication that is scheduled to be taken. Referring to FIG. 15, a second medication information button 269 is provided to invoke the same functionality, and to provide additional information concerning the medicine, vitamin or supplement associated with first medicine dose window 257. A medication information button is associated with each medicine dose window. For example, FIG. 15 illustrates a third medication information button 270 associated with third medicine dose window 259. In addition to activating a medication information button 253, 269 or 270 with a touch on a touch screen, or a mouse click, or keyboard shortcut, the resident can request more information concerning a particular medicine, vitamin, or supplement with a voice command or using speech recognition.

The HAPPIE home unit 103 stores additional data for each medicine, vitamin, or supplement, on the local database 108. Medications with bar coded packaging can be scanned with a bar code reader or smart phone 111 and tracked into the local database 108 of the HAPPIE home unit 103. A scan function may be activated for the HAPPIE home unit 103 to scan a barcode on a medication package for entry into the local database 108, or to take an image of a medicine bottle, pharmacy label, or written medication description, to manually add such information to the local database 108. If needed, a complete database of information for every available medicine, vitamin, and supplement, is stored and available on the central database 175, and complete verified information provided by the pharmacy or the manufacturer can be retrieved from the central database 175 over the Internet 105 when a barcode is scanned by the resident's smart phone 111. The central database 175 includes images of pills, and in other instances, images of tubes of cream, liquid, syrup, vial, dropper, syringe, and inhalers. The resident can request the HAPPIE home unit 103 to selectively display the medication bottle 272, the push-through blister pack, the pharmacy label 274, and a written medication description 275, to further help avoid an error in medication. Medications in non-pill form are displayed by dosage and dispenser.

If the resident requests more information concerning a particular medicine, the HAPPIE home unit 103 will selectively display a series of screens shown in FIG. 16, FIG. 17, and FIG. 18, providing additional information for the associated medicine, vitamin, or supplement. Referring to FIG. 16, a first medication info window 271 is displayed that shows an image of the medication bottle 272. A close-up image of the medication bottle 273 is also provided in the example illustrated in FIG. 16. Referring to FIG. 17, a second medication info window 280 is displayed that shows an image of the pharmacy label 274. Referring to FIG. 18, a third medication info window 281 is displayed that shows the written medication description 275 for the associated medicine.

The resident can easily navigate between the first, second, and third medication info windows 271, 280 and 281 using a scroll up button 276 and a scroll down button 277. For example, when the first medicine info window 271 is displayed, as shown in FIG. 16, the resident can scroll to the second medicine info window 280 shown in FIG. 17 by activating the scroll down button 277. The resident can selectively scroll between the first, second, and third medication info windows 271, 280 and 281 in either order by selectively activating either the scroll up button 276 or the scroll down button 277.

In addition, the first medicine info window 271 shown in FIG. 16 includes a second thumbnail image 274a of the pharmacy label 274 shown in the second medicine info window 280, and pressing or clicking on that second thumbnail image 274a causes the HAPPIE home unit 103 to display the second medicine info window 280 showing the pharmacy label 274, as illustrated in FIG. 17. Similarly, the first medicine info window 271 shown in FIG. 16 includes a third thumbnail image 275a of the written description 275 shown in the third medicine info window 281, and pressing or clicking on that third thumbnail image 275a causes the HAPPIE home unit 103 to display the third medicine info window 281 showing the written medication description 275 shown in FIG. 18. The second medicine info window 280 shown in FIG. 17 similarly includes a first thumbnail image 272a of the medication bottle image 272, and a third thumbnail image 275a of the written medication description 275, which provide similar navigation to the first medicine info window 271 and the third medicine info window 281, respectively. Similarly, the third medicine info window 281 shown in FIG. 18 similarly includes a first thumbnail image 272a of the medication bottle image 272, and a second thumbnail image 274a of the pharmacy label 274, which provide similar navigation to the first medicine info window 271 and the second medicine info window 280, respectively.

A plus button 279 is provided for increasing the size of the image of the written description 275, or the image of the pharmacy label 274, or the image of the medication bottle image 272, respectively, in order to make it easier to read. A close button 278 is provided to close the first, second, and third medication info window 271, 280 and 281, respectively, as the case may be.

A resident or caregiver may access all medication information associated with a resident from the resident's smart phone 111 or from the caregiver's smart phone 178, respectively, during a doctor visit to accurately communicate medication type, dosage, prescribing doctor, duration of time the resident has been on the medication, as well as refills remaining. Details of vitamins and supplements taken by the resident may be stored on the central database 175 and accessed by the caregiver using the caregiver portal 101, or may be stored on storage associated directly with, or connected directly to, the caregiver portal 101. Now, a complete understanding of vitamins, supplements and medicine taken, regardless of doctor or self-medication can be shared with medical professionals.

The HAPPIE home unit 103 manages the medication refill cycle by communicating a prescription refill need between the prescribing doctor, pharmacy and health insurance carrier to calculate the out-of-pocket payment due and required of the resident. Examples of other medical supplies tracked by the HAPPIE home unit 103 include bed pads, adult diapers, braces, personal care, wound care, specialty garments, oxygen, walkers, crutches, wheel chair rentals, and hospital bed rentals can be managed directly within the HAPPIE home unit 103 or using the caregiver portal 101.

Figure 19:
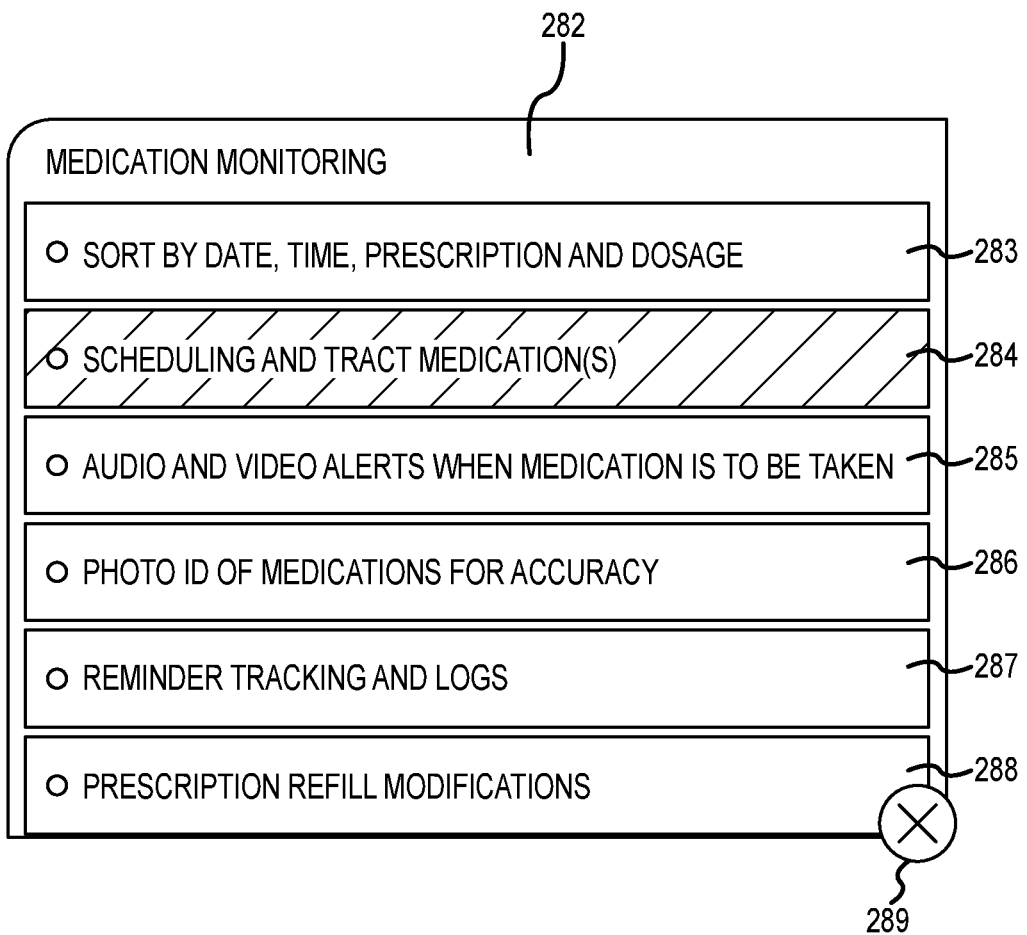
FIG. 19 is a screen shot showing a sixth screen for the medication module.

FIG. 19 shows a medication information configuration window generated by the medication module associated with the medication button 203. The HAPPIE home unit 103 allows the resident or a caregiver to configure medication monitoring and reporting parameters. An example of a medication monitoring configuration window 282 is shown in FIG. 19. In the illustrated example, the medication monitoring configuration window 282 includes a first menu item for sorting by data, time, prescription, and dosage 283. The medication monitoring configuration window 282 includes a second menu item for scheduling and tracking medications 284. The medication monitoring configuration window 282 includes a third menu item for audio and video alerts to be displayed when medication is to be taken 285. The medication monitoring configuration window 282 includes a fourth menu item for configuring a photo ID of medications used for accuracy 286. The medication monitoring configuration window 282 includes a fifth menu item for reminder tracking and logs of medication taken, when it was taken, how much, etc. 287. The medication monitoring configuration window 282 includes a sixth menu item for configuring prescription refill modifications 288. A close button 289 is also provided.

A mobile phone application operative to run on a smart phone 111 is provided for interoperability and connection with the HAPPIE home unit 103. The mobile phone application can also be run on the caregiver's smart phone 178.

Figure 20:
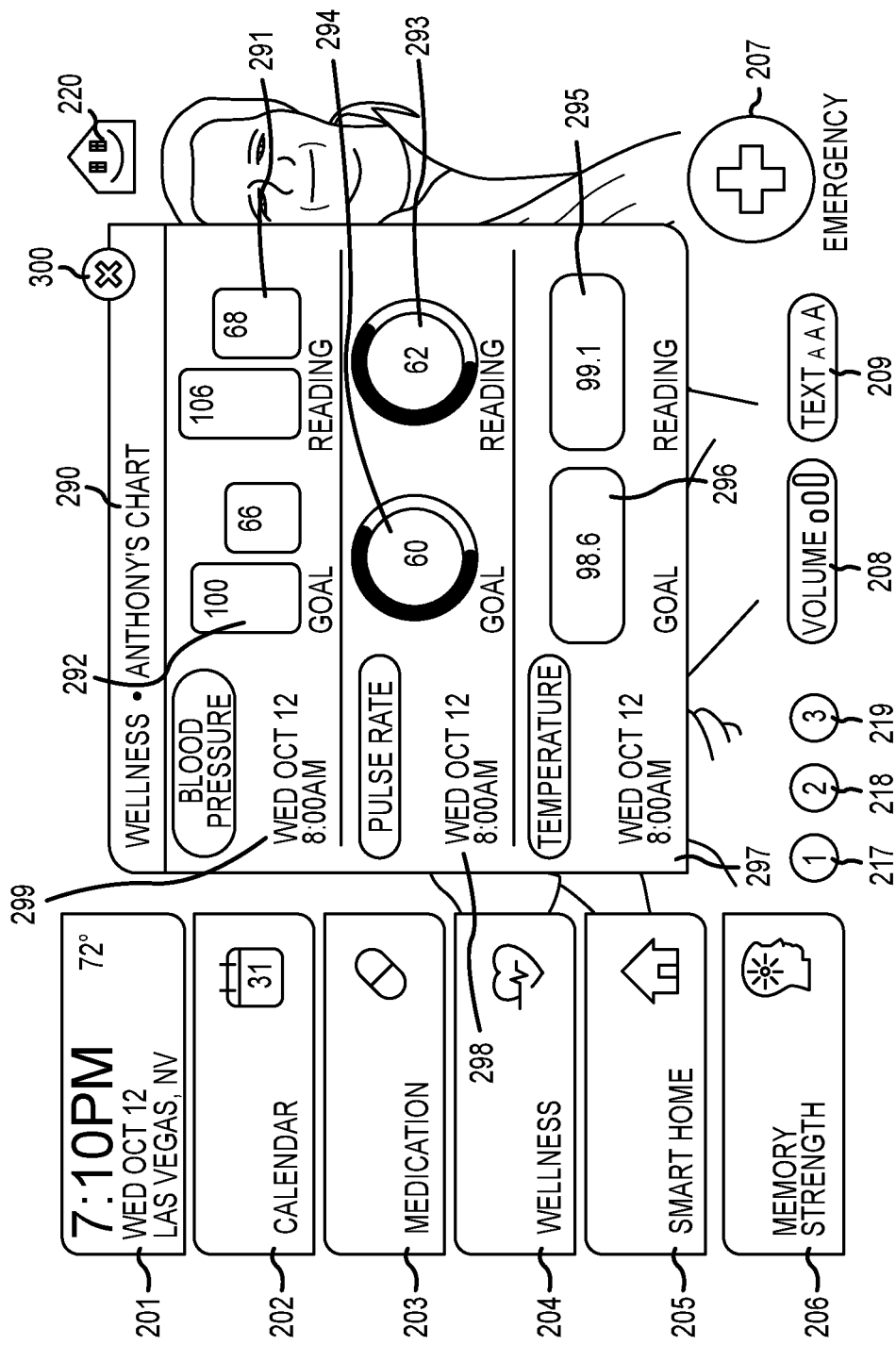
FIG. 20 is a screen shot showing a first screen for a wellness module.

FIG. 20 shows a first wellness screen 290, which may be displayed when the wellness button 204 is used to active the wellness software module, or the wellness module is activated by voice command or speech recognition. The wellness module integrates with wearable medical devices 158 and 164, medical equipment sensors 161, 163 and 165, and other devices, including medical implants, to collect data concerning the resident. The wellness module may be used to track health data for the resident, regardless of the condition of his or her health. The ability of the HAPPIE home unit 103 to track wellness data is only limited by the number of devices the resident wishes to wear, or the number of medical devices that the resident has implanted. Wearable devices 158 can be used to track nearly everything from body posture to physical activity, pain management, fall monitoring, sunlight exposure, and length and quality of sleep. Wearable devices 158 can be used to track heart rate, rhythm, blood oxygen level, respiratory rate, glucose monitoring, skin temperature, and more. The versatility and portability of wearable devices appeals to residents who wish to improve their overall health through the collection of actionable data trends. In addition, the HAPPIE home unit 103 also allows a resident with health issues or who is under the care of a doctor to cut down on in-person medical office visits by allowing the resident's doctor to securely and remotely connect with the HAPPIE home unit 103 using the doctor portal 102 to examine the resident in the resident's home.

Referring to FIG. 20, a blood pressure reading 291 is shown displayed on the wellness screen 290. The blood pressure reading 291 is taken using a wearable device or using some other blood pressure sensor 163 that is connected to the HAPPIE home unit 103. A corresponding blood pressure goal 292 may be displayed for comparison, and the time 299 of the blood pressure reading is recorded. A pulse rate reading 293 (taken by a connected pulse rate sensor 165) is shown, with a corresponding pulse rate goal 294 and the time 298 that the pulse rate was measured. A temperature reading 295 (taken with a connected temperature sensor 161) is shown, and a corresponding temperature goal 296 may also be displayed. The time 297 that the temperature was measured is also recorded. All of this data is preferably stored in the local database 108. A close button 300 is provided to close the wellness window 290.

The wellness module allows a resident or user to implement training regimes for races, events, and competitions, to set and track goals, to track workout intensity, to receive reminders, to set their activities to specific music tracks (using the entertainment system 120), and to review consolidated graphic reporting and trend analysis using the data stored in the local database 108. The HAPPIE home unit 103 provides integration with an intelligent pantry 119 and smart refrigerator 115 to simplify the tracking of food consumed and to automatically calculate the calorie consumption and nutritional value of food consumed against goals and objectives. Consolidated consumption reporting is available to the resident, but may also optionally be made available to a caregiver through the caregiver portal 101.

Although the wellness module works well with wearable devices 158, the HAPPIE home unit 103 may also connect with medical devices that are implanted in the resident. For example, a resident with type 1 diabetes may wear or have implanted a glucose monitoring system. Conventional glucose monitoring systems set off an alarm when the resident's glucose goes below or above a set limit. If the resident is asleep when this happens, the resident may typically wake up shaking and sweating, and have to drink some glucose, or calculate a dose of insulin and administer the correct amount of insulin with an insulin pump or by an injection. Although the resident may then be able to go back to sleep, the resident will often wake up the next morning feeling terrible. There is also the danger that the resident will not wake up when a glucose monitor alarm goes off, which could have serious consequences.

In contrast, in this example of a resident with type 1 diabetes, the HAPPIE home unit 103 may receive real-time readings from a glucose monitor 158, and calculate or project glucose levels for the next few hours. When the HAPPIE home unit 103 determines that insulin needs to be administered in order to maintain glucose levels within an optimum range, the HAPPIE home unit 103 may automatically command an insulin pump implanted in the resident or otherwise connected to the resident to administer the correct dose of insulin, even while the resident is still sleeping. With the HAPPIE home unit 103 performing this function, the resident can sleep through the night and never needs to wake up to administer insulin or to drink sugar. In effect, the HAPPIE home unit 103 may function, in these circumstances, as an automatic pancreas.

Figure 21:
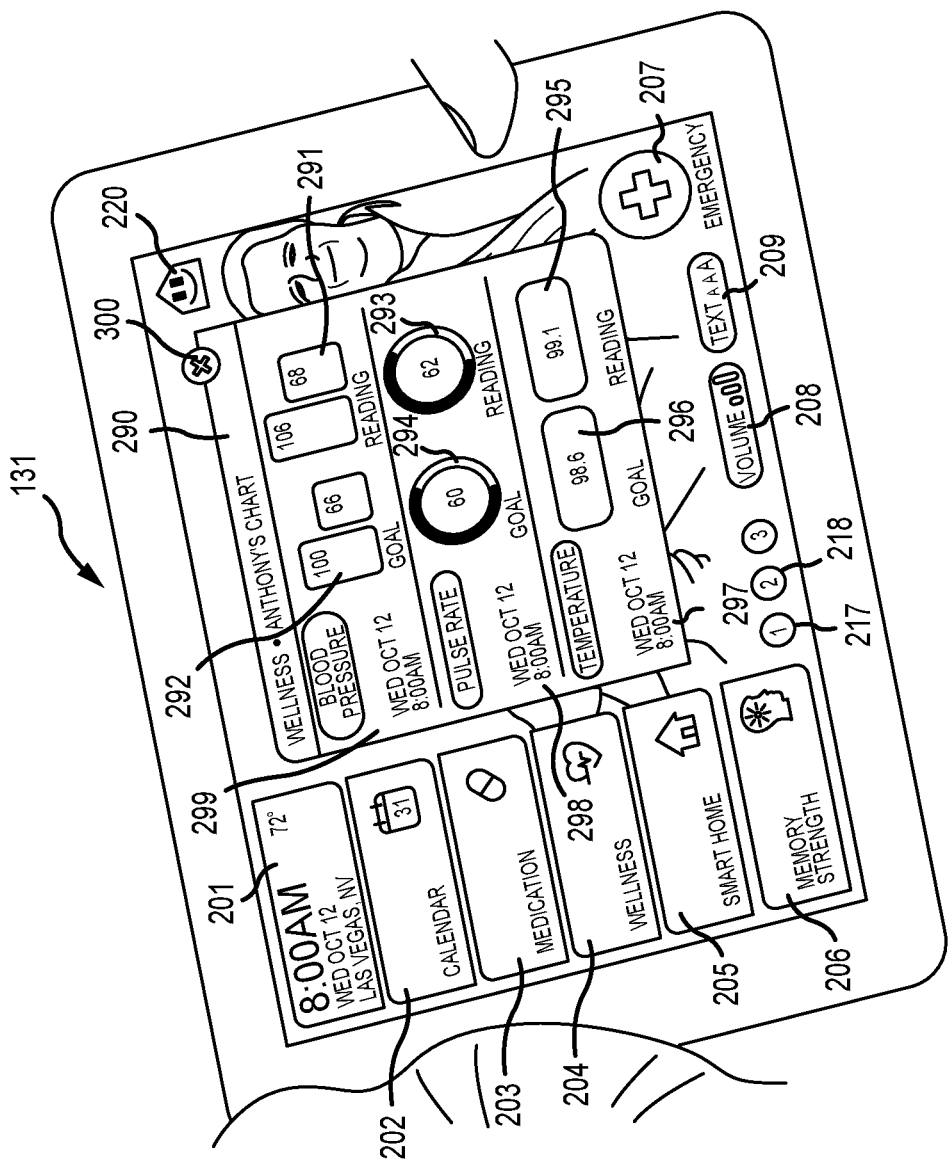
FIG. 21 is a perspective view of a screen shot for the wellness module displayed on a handheld wireless computing device, such as a tablet computer.

FIG. 21 shows a perspective view of a first wellness screenshot displayed on a wireless handheld computing device, such as a tablet computer 131.

Figure 23:
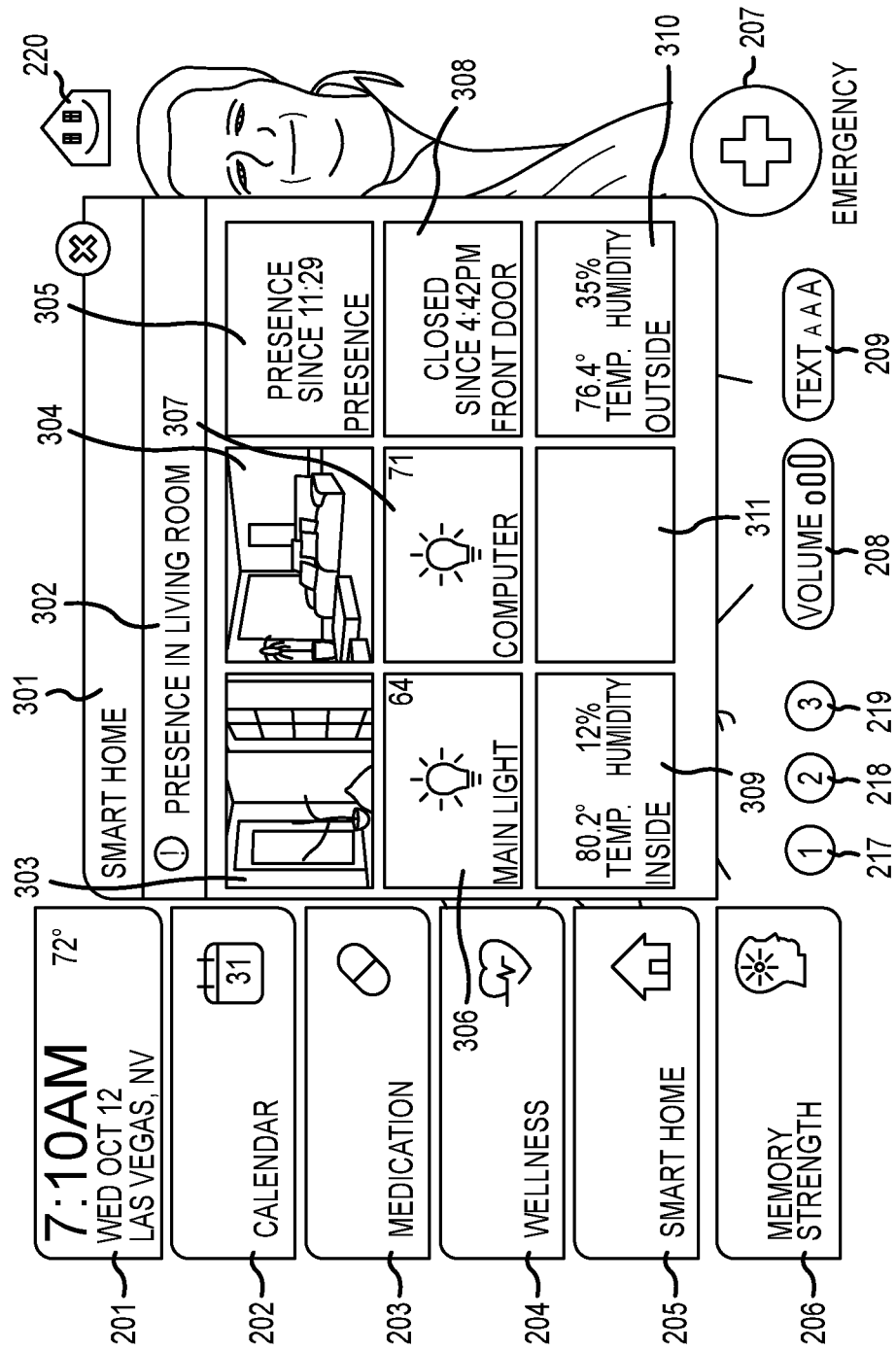
FIG. 23 is a screen shot showing a first screen for a smart home module.

FIG. 23 shows a first smart home screen 301, which may be displayed when the smart home button 205 is used to active the smart home software module, or the smart home module is activated by voice command or speech recognition. The smart home module controls a plurality of cameras 112, microphones 113, speakers 157, motion detectors 152, intelligent heat detectors 194, and glass breakage detectors 146, which are placed throughout the residence, for example, as shown in FIG. 3. Weather resident and waterproof outdoor cameras 112, drones, satellite imagery, and outside motion detectors 141, 152 may be used to cover the front yard, backyard, and perimeter of the property, as well as access to the residence using door sensors 137 and garage door sensor 144. Sensors control window coverings 140 to adjust the amount of sun light entering the home to keep the home cooler in the summer and warmer in the winter. Sensors 134 are provided to monitor HVAC 117, lighting 139, gas 135, water 135, thermostat 149, video doorbell 126, pool alarm to prevent accidental drowning, freeze alarm, and water leak detection 148. Bed sensors 151, floor sensors 153, and chair sensors measure presence and weight. Sensors 134, 114, 115 and 118 to monitor appliance access and performance can schedule maintenance, prevent downtime, and reduce ownership costs.

Referring to FIG. 23, the first smart home screen 301 displays a status bar which may be used to display the detected presence of the resident, and which room is currently occupied by the resident. A status window 305 also displays the current status of the resident, and how long the resident has been present in the home as well and the length of time in each room. In the example illustrated in FIG. 23, the door status window 308 indicates that the resident has been present since 11:29 AM. This information is stored in the local database 108. This information can be configured so that the current location of the resident is available externally to a caregiver via the caregiver portal 101 to allow the caregiver to check on the status and location of the resident at any time. This information may also be provided, in an emergency, to an emergency services portal 106, so that the police or firemen will have information concerning the location of the resident in the home during an emergency.

A first camera image window 303 is shown in FIG. 23, which is provided to display image information from an associated video camera 112 directed at the rear door. A second camera image window 304 is provided to display image information from an associated video camera 112 directed at the living room. The status of light sensors 139 is displayed in first light status window 306. The status of lighting controls 159 in individual rooms is displayed in second light status window 307. A door status window 308 is provided to display the current status of the front door, for example, whether the door is open, closed, locked, or unlocked. The door status window 308 also shows how long the door has maintained that status. In the example illustrated in FIG. 23, the door status window 308 indicates that the door has been closed since 4:42 PM.

As shown in FIG. 23, the first smart home screen 301 also includes an inside environmental conditions window 309. In the illustrated example, the inside environmental conditions window 309 displays the inside temperature and humidity. An outside environmental conditions window 310 is provided, which displays the outside temperature and humidity. The first smart home screen 301 has a third camera image window 311, which in the example shown in FIG. 23, displays image information from an associated video camera 112 directed at the backyard. A close button 312 is provided to facilitate closing the first smart home screen 301.

The smart home software module provides integration with local law enforcement, amber alerts, home security, alarm companies, and home warranty companies. For example, in the event that an emergency call to 9-1-1 is dialed, the HAPPIE home unit 103 automatically connects police and fire departments via an emergency services portal 106 to enable them to access video cameras 112, microphones 113, and speakers 157. Authorities are also automatically provided with access to floor plans, together with information from the local database 108 sufficient to identify residents of the home premises, versus an unauthorized intruder.

The smart home software module provides intruder detection. The HAPPIE home unit 103 can perform voice recognition based upon audio received from microphones 113. The HAPPIE home unit 103 can perform 3D facial recognition based upon video received from video cameras 112. The local database stores information sufficient to identify the resident, and other authorized persons such as family members, caregivers, friends, cleaning personnel, servicemen, etc. Intruder detection automatically activates cameras 112, microphones 113, and speakers 157. The HAPPIE home unit 103 calls out the intruder's estimated height, weight and apparel while taking 3D images of the intruder's face, which are stored in local database 108, and transmitted to central database 175. The smart home software module, during an intruder alert, will automatically send image data and audio data concerning the intruder directly to the police via an emergency service portal 106. The HAPPIE home unit 103 may also audibly describe the intruder's appearance out loud over the speakers 157, and uses the speakers 157 and video monitors 156 to advise the intruder that his or her image has been transmitted to the police.

In the event of local weather or security alerts, the HAPPIE home unit 103 broadcasts warnings that the home of a patient or subscriber may be in the path of a tornado, hurricane, wildfire, flood, mud slide, etc.

Figure 24:
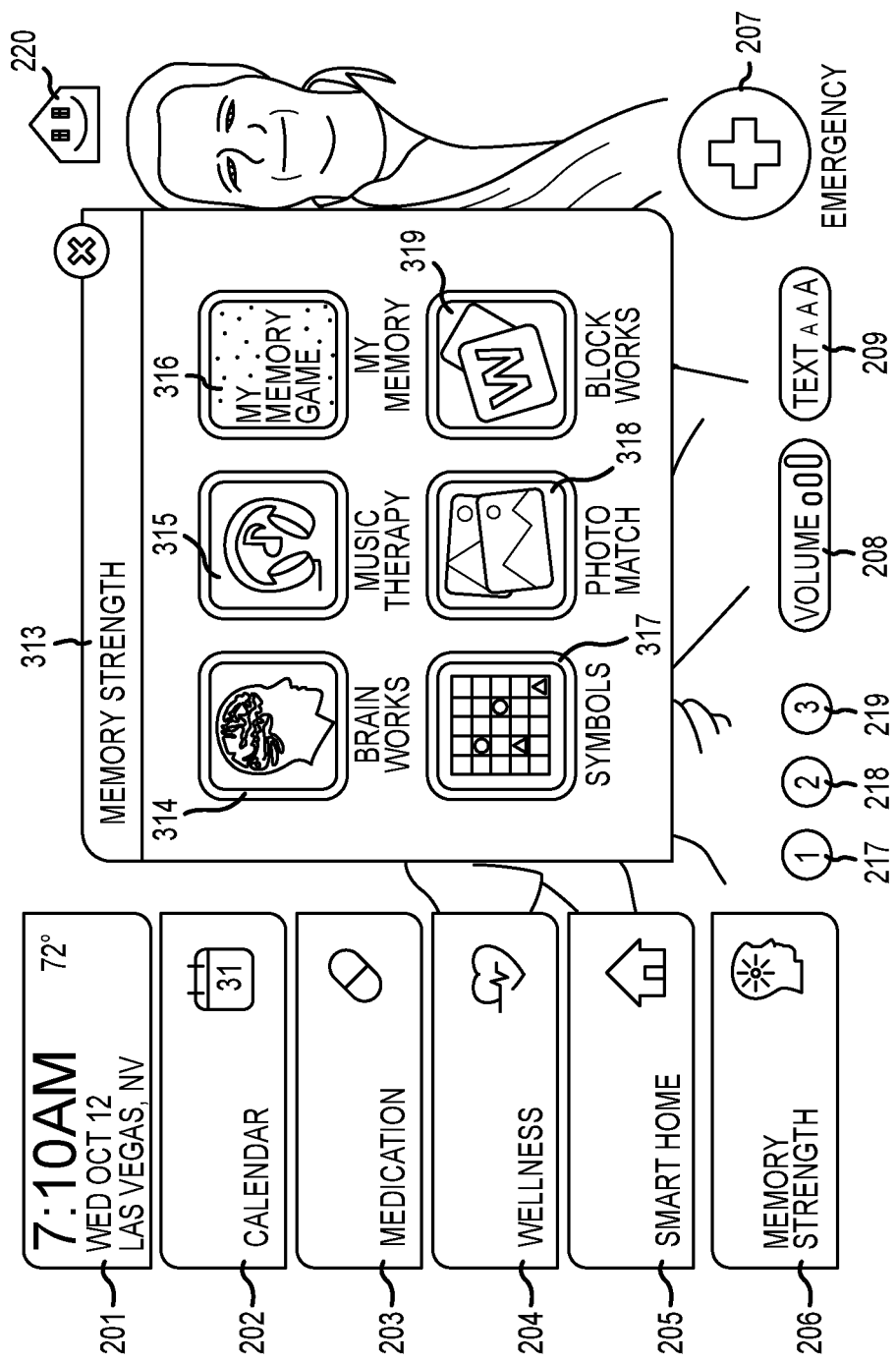
FIG. 24 is a screen shot showing a first screen for a memory strength module.

FIG. 24 shows a first memory strength screen 313, which may be displayed when the memory strength button 206 is used to active the memory strength software module, or the memory strength module is activated by voice command or speech recognition. The memory strength module helps users take advantage of proven scientific games, monitoring and testing to help them to slow the effects of aging on memory and improve memory function. The ability for one to remain mentally sharp is enhanced with proper nourishment, sleep, exercise, stress relief, relaxation and staying connected socially.

A resident can experiment with applications from partners, leaders in industry, and academia to personalize a plan that yields the best results for the resident. For example, game and testing content contributors may include, but not limited to, UNLV, Cleveland Clinic, Healthy Brains.org, and Luminocity.com. In the example shown in FIG. 24, a brain works icon 314, a music therapy icon 315, and a my memory game icon 316 are provided on the first memory strength screen 313 for activating associated memory strength or brain workout modules included in the memory strength software module. In addition, a symbols icon 317, a photo match icon 318, and a block works icon 319 are also provided for activating associated memory strength or brain workout modules included in the memory strength software module.

Brain health assessment testing provided by the memory strength module may be used to set a base line for the resident, which is stored in the local database 108, and the baseline data can be compared to all future testing. Data associated with the resident's performance of memory strength and brain workout modules can be cataloged on the local database 108, and retrieved by a doctor using the doctor portal 102, for diagnosis and treatment. Brain health scores stored on the local database 108, and detailed personalized reporting provided by the HAPPIE home unit 103, is available to the resident locally, to a caregiver via the caregiver portal 101, and to medical professionals via the doctor portal 102. Intelligence built into the HAPPIE home unit 103 can be used to assess the health of the resident's brain on a routine basis and to provide personalized recommendations about how to enhance the resident's brain health.

Music therapy, memory games, and other approved content like foreign language tutorials, on-line education, a testing center for personal and professional certifications, DMV services, home schooling curriculum, and more can also be stored in the entertainment system 120 and accessed through the memory strength module or through a media center module activated by the media center button 213 shown in FIG. 13.

Referring to FIG. 9, when the church button 212 is activated, by touching the screen 200, or by mouse clicking the button 202, or by an associated voice command, a church or faith-based module is activated in the HAPPIE home unit 103. The church (faith-based) module is designed to be the home-bound ministry and hospice care for the 21st century. It provides a resident with streamed video-casts of worship services as well as events like live or recorded concerts, baptisms, weddings and funerals performed at the resident's church.

Importantly, the HAPPIE home unit 103 provides a high speed two-way communication link 173 with the church portal 104. Not only does the resident have the ability to receive video and audio information from the church portal 104, but the resident can also communicate with the church portal 104, including sending prayer requests, confessions, feedback, and other communications to the church portal 104. The resident can actively participate in a bible study session, and use the two-way communications link with the church portal 104 to ask questions, or to provide a testimonial, or otherwise participate.

Figure 25:
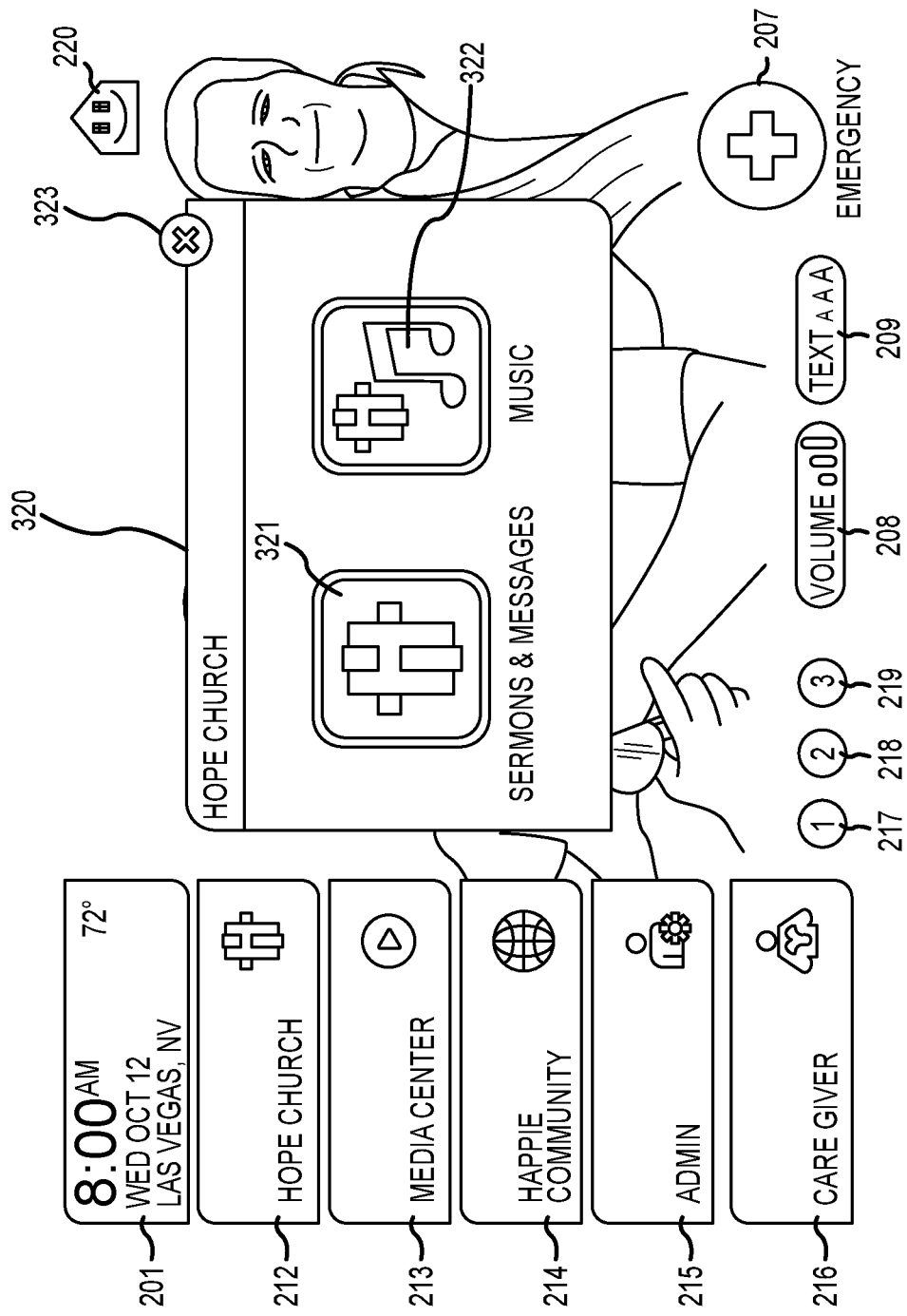
FIG. 25 is a screen shot showing a first screen for a church module.

A first church module screen shot is shown in FIG. 25, having a first church window 320. A sermons icon 321 is provided for accessing sermons and spiritual messages. A music icon 322 is provided for accessing music, including music stored locally on the local database 108, music stored on the home entertainment system 120, and music streamed from the Internet 105. A close button 323 is also provided.

Figure 26:
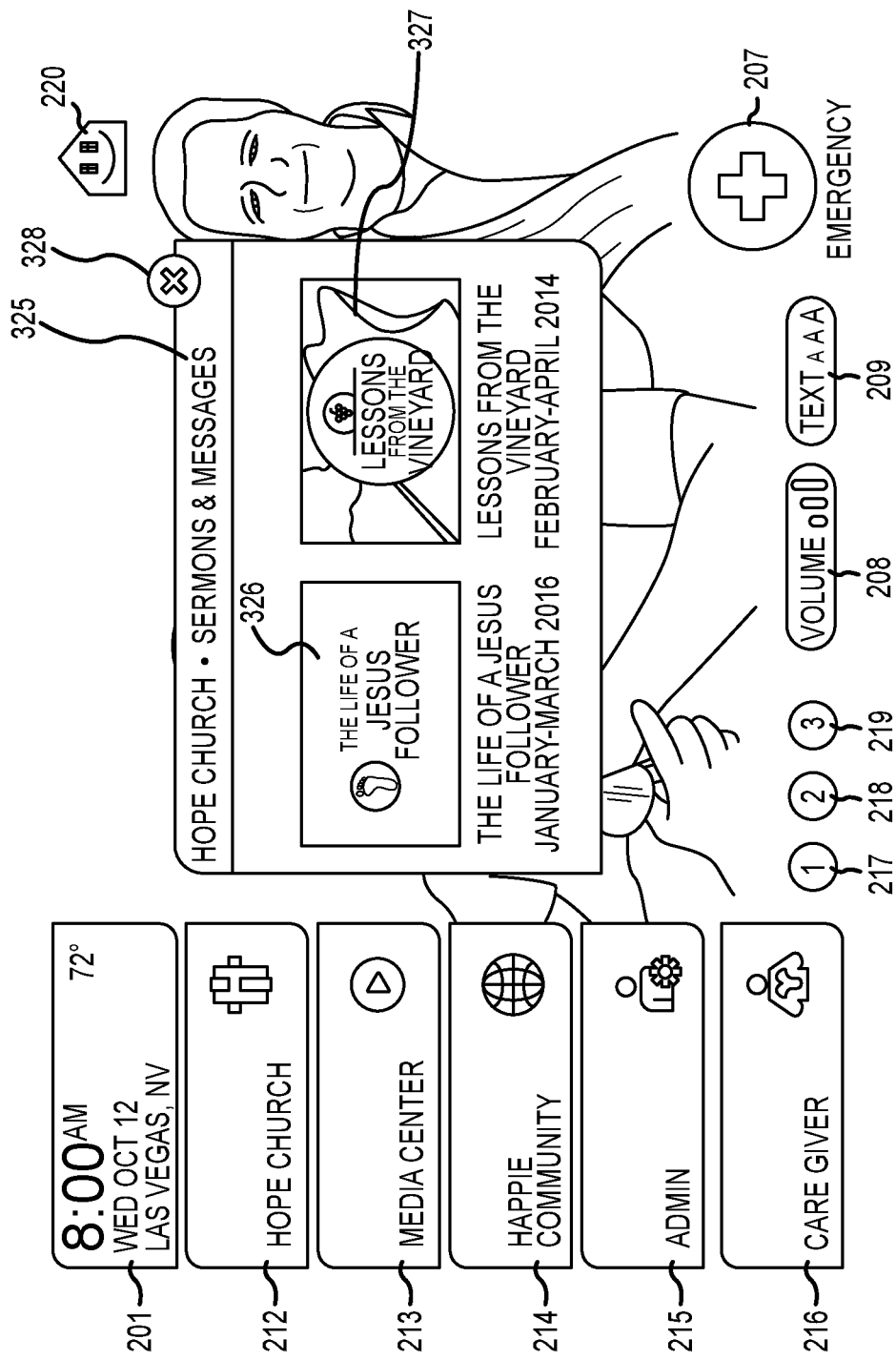
FIG. 26 is a screen shot showing a second screen for the church module.

FIG. 26 shows a second church module screen shot having a second church window 325, which is opened when the sermons icon 321 is activated. A first sermon series icon 326 is provided to access a first list of a series of sermons or spiritual messages have a common theme or connection. A second sermon series icon 327 is provided to access a second list of a series of sermons or spiritual messages have a common theme or connection. A close button 328 is also provided.

Figure 27:
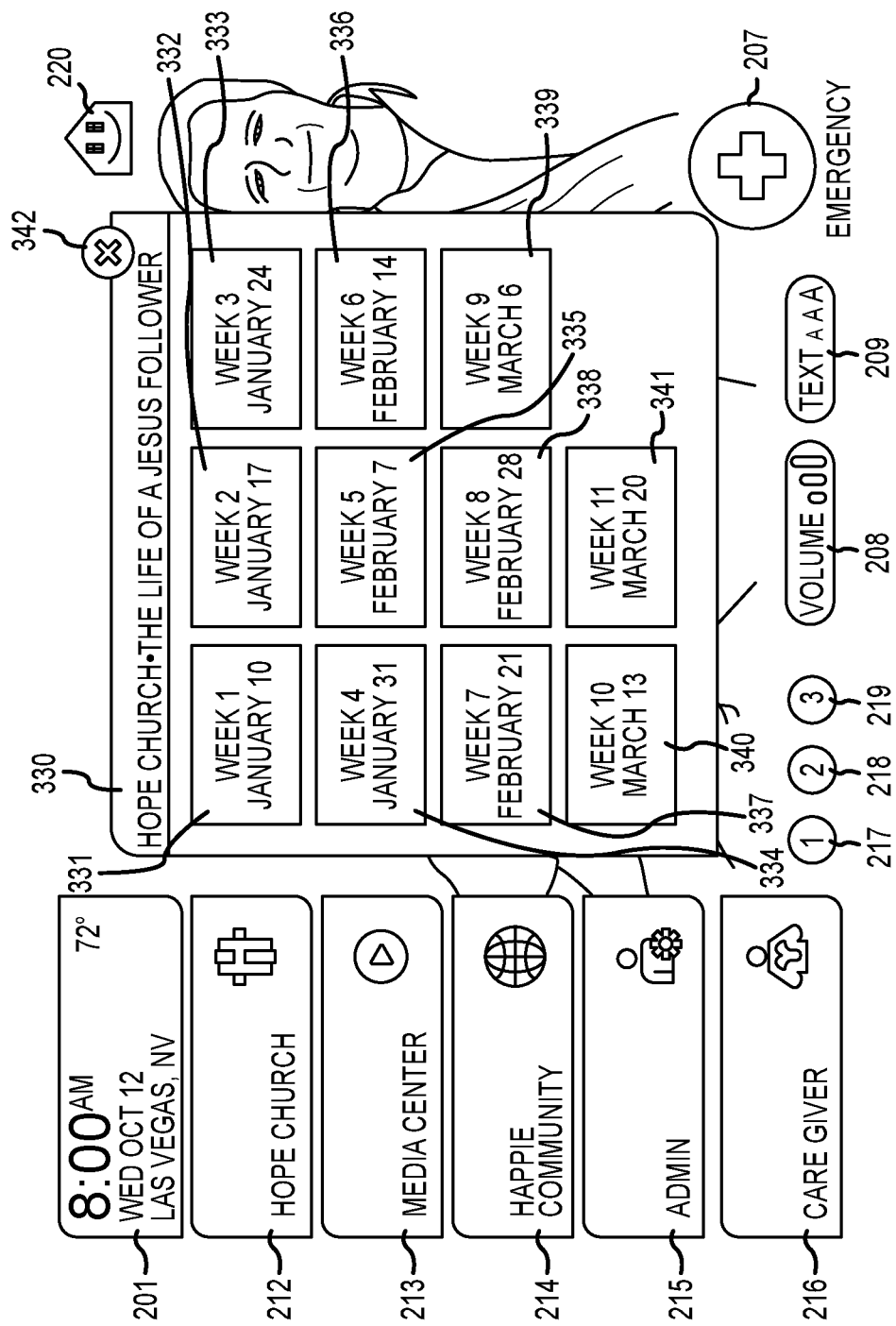
FIG. 27 is a screen shot showing a third screen for the church module.

If the first sermon series icon 326 is activated, a third church module screen shot having a third church window 330, which opened, as shown in FIG. 27. In the third church window 330, icons are provided which are linked to individual recorded sermons or messages for each sermon in the first series. A first sermon icon 331 is provided, which is linked to and associated with a recorded sermon that is the first sermon in the first series. The associated data for the recorded sermon may be stored in a database associated with the church portal 104, or may be recorded on the local database 108, or may be recorded on another database such as central database 175. Similarly, a second sermon icon 332 is provided linked to recorded data for a second sermon in the first series. A third sermon icon 333 is provided linked to recorded data for a third sermon in the first series. Similarly, a fourth sermon icon 334, a fifth sermon icon 335, a sixth sermon icon 336, a seventh sermon icon 337, an eight sermon icon 338, a ninth sermon icon 339, a tenth sermon icon 340, and an eleventh sermon icon 341 are provided, with each being similarly linked to respective sermons or spiritual messages in the first series. Finally, a close button 342 is provided.

Figure 28:
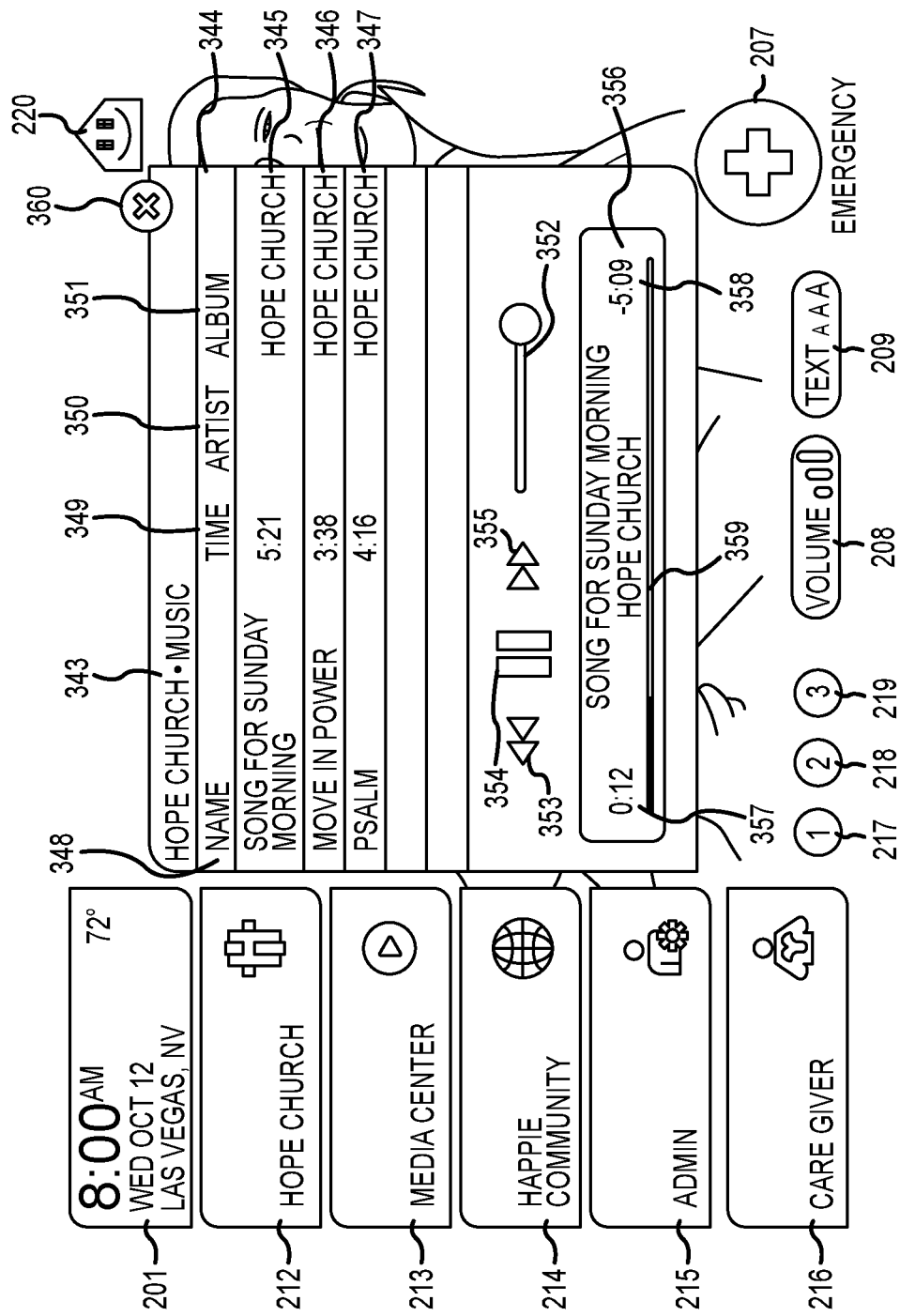
FIG. 28 is a screen shot showing a fourth screen for the church module.

Referring to FIG. 25, if the music icon 322 is activated, a fourth church window 343 is opened, as shown in the fourth church module screen shot shown in FIG. 28. The fourth church window 343 shown in FIG. 28 displays a title bar 344 showing the name and other information for each song provided on the list displayed in the fourth church window 343. The title bar 344 provides a heading for the song name 348, the time 349 that the song plays, the artist 350, and the name of the album 351. In the illustrated example, the list includes a first song information bar 345, a second song information bar 346, and a third song information bar 347. In the event that more songs are included in the list, additional song information bars will be provided for each additional song, and a scroll bar may appear if the number of songs is too many to be displayed in a single screen.

The fourth church window 343 shown in FIG. 28 also has a music volume control 352. A first control icon 353 is provided to skip back to a previous song, a second control icon 354 is provided to pause the music, and a third control icon 355 is provided to skip to the next song. A status bar 356 is provided to show the status of the playback of the current song. The status bar 356 displays the time 357 that the song has been playing, and the time 358 remaining for the current song. a progress bar 359 is provided to visually show how much of the song has played. The status bar 352 also displays the name of the current song, and the album, as shown in FIG. 28. A close button 360 is shown.

Music requests may be linked to the church music library or a personal play list stored on the local database 108 of the HAPPIE home unit 103. Access to pre-recorded material, music, messages and sermons, which may alternatively be stored on the home entertainment system 120, are also made available.

Remote 2-way interaction with the church for the submission of prayer requests, feedback and donations. Alerts for services and events. Links to Calendar allow for the recording of services, alerts, and special events. Automate television on/off settings and set to record services and web casts up to 12 months in advance. Users have the option to connect directly with a Christian Counselor directly through the HAPPIE church module. Two-way hands-free communication is facilitated through the microphones 113, the speakers 157, and a video interface comprising video cameras 112 and video monitors 156. The contact details of a Christian counselor may be stored in the local database 108 of the HAPPIE home unit 103. The resident may use a specific command such as "HAPPIE, connect me to my Christian counselor" or "HAPPIE call Billy O'Donnell" to have the HAPPIE home unit 103 automatically establish communication with the specified person. Residents have the ability to store video recordings in the local database 108 with access controlled by voice recognition, 3D facial recognition, or both.

Figure 29:
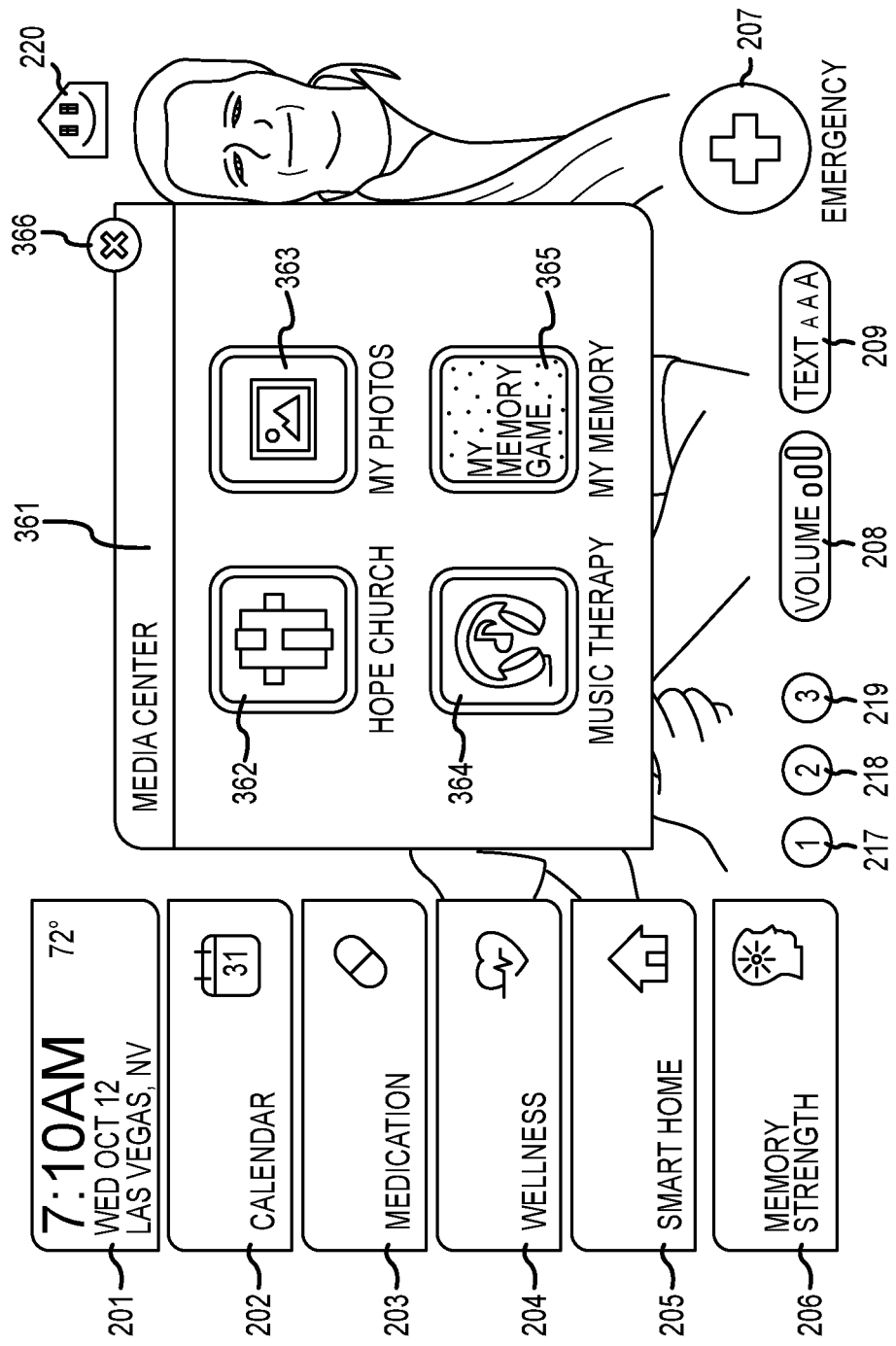
FIG. 29 is a screen shot showing a first screen for a media center module.

FIG. 29 is a screen shot showing a first screen for the media center module, showing a first media center window 361. In the illustrated example, a church icon 362 is shown that is linked to spiritual music that is recorded on the entertainment system 120, recorded on the local database 108, recorded on the central database 175, or available from the church portal 104. A photo icon 363 is provide that is linked to personal photos, images, and videos recorded on the local database 108. A music therapy icon 364 is provided for access to music therapy recordings. A memory icon 365 is provided for activating memory games and brain exercises. A close button 366 is also shown to close the first media center window 361.

The media center is designed to enable the user to easily access stored video messages, greetings and well wishes from family and friends. Users enjoy life moments by viewing personal photos, family photos, video and home movie and to access security camera recordings. Users will access their personal movie and music playlists for enjoyment when linked to in-home entertainment components. The media center provides access to the Memory Strength and Church Module (recorded events).

Figure 30:
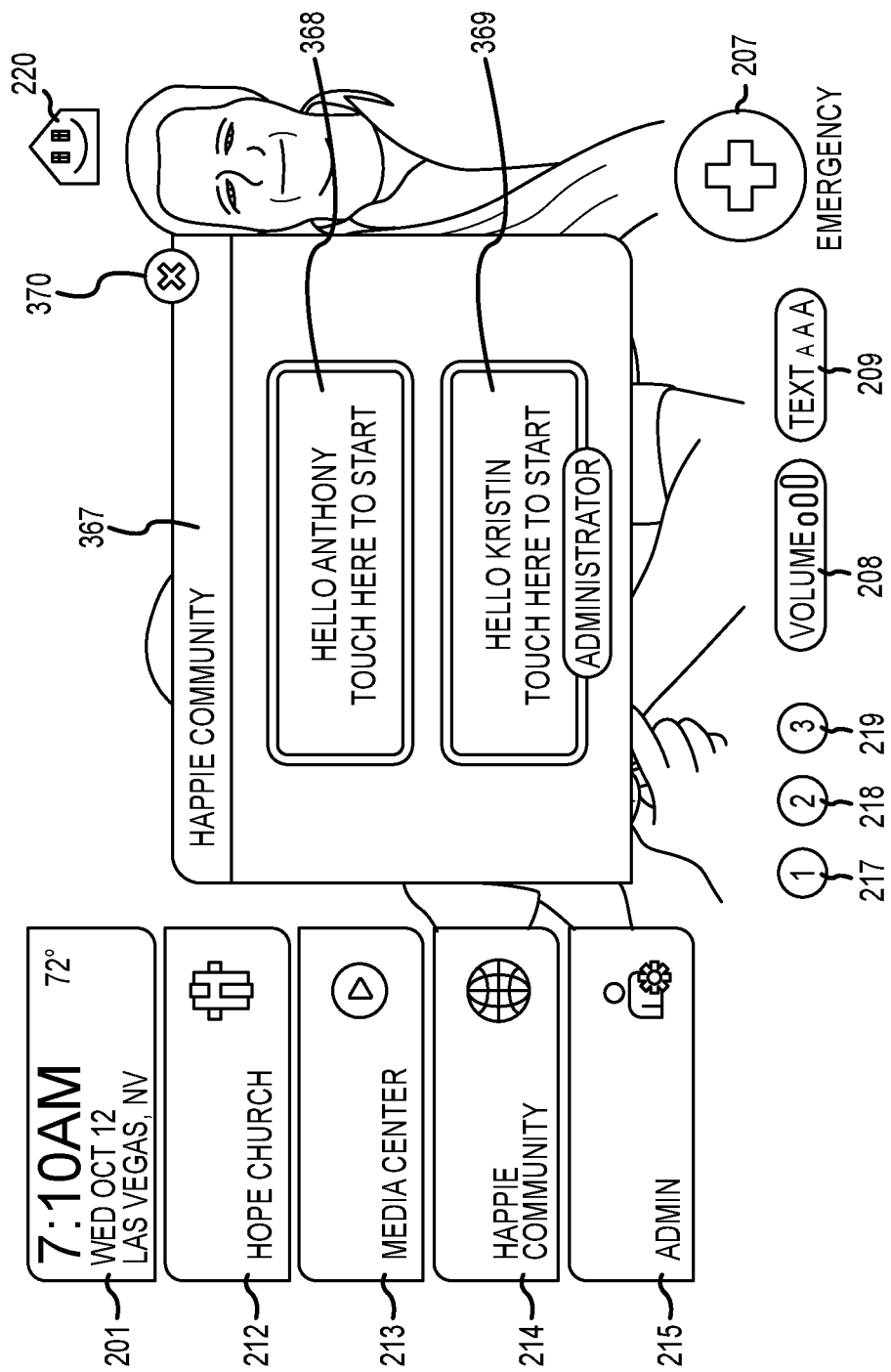
FIG. 30 is a screen shot showing a first screen for a community module.

FIG. 30 shows a screen shot of a first community window 367 for the community module. Access to the community module features dual authentication of an eight plus character password plus voice or facial recognition verification. FIG. 30 illustrates a log-in window 367, showing a log-in button 368 for the resident, and a log-in button 369 for the caregiver or administrator. The community module is designed to provide a resident with access to virtual patient and caregiver support groups. The resident has the option to engage in the community under his or her name, or to do so anonymously. The log-in window 367 may be closed using the close button 370 shown in FIG. 30.

The community module provides general access to the Internet 105 for the resident, with search engine and browser functionality. The community module provides the resident with subject matter alerts from published web articles and news stories that may be of interest to the resident. The HAPPIE home unit 103 includes an artificial intelligence component to track the resident's Internet searches, and other communications, and to provide analysis of the resident's subject matter interest for the purpose of identifying appropriate subject matter alerts for the resident. Optional integration with social media sites is available if desired by the resident.

Figure 31:
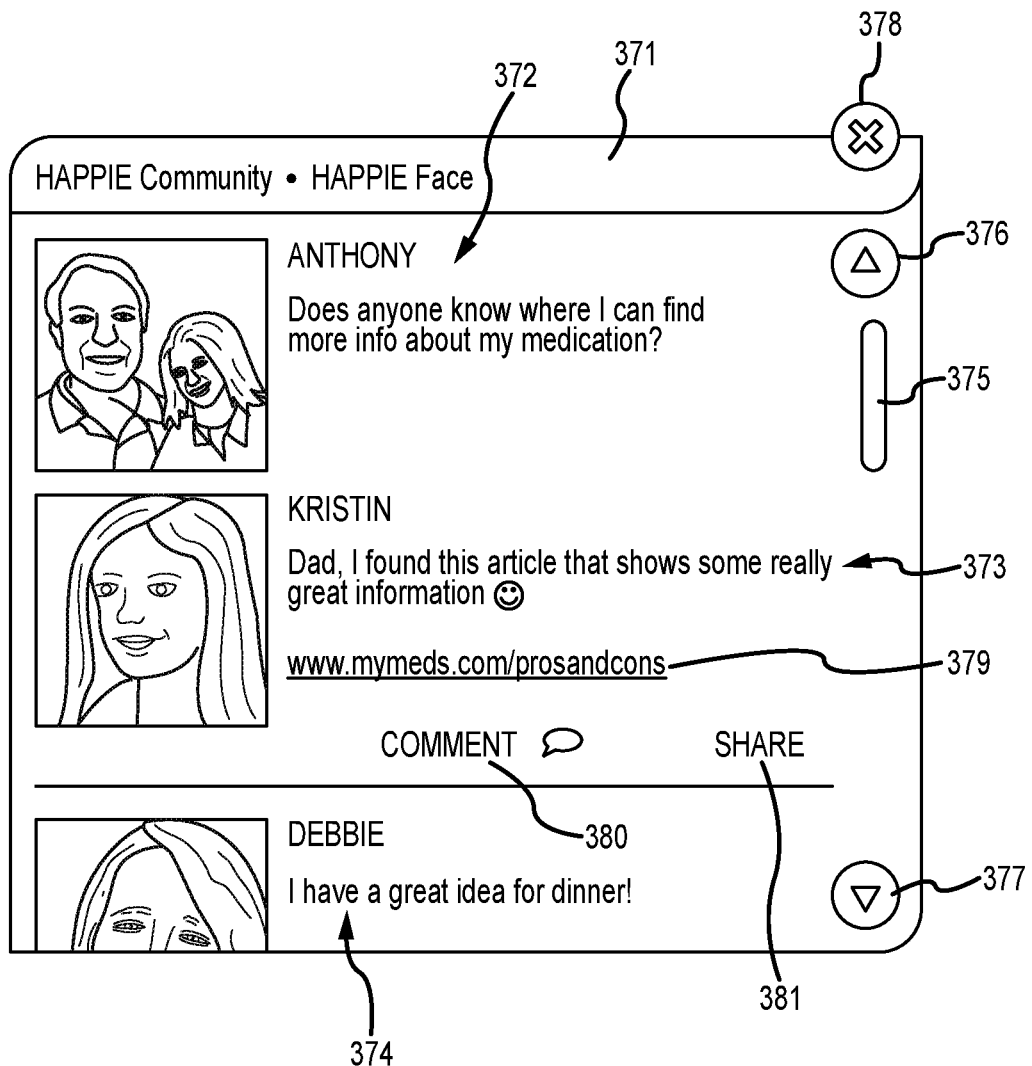
FIG. 31 shows a message board window for the community module.

FIG. 31 shows a second community window 371 provided by the community module, which is a message board for the resident. In the illustrated example, the message board includes a first message 372 sent by the resident to the community, a second message 373 sent to the resident by a family member, and a third message 384 sent to the resident from his spouse. As shown in the second message 373, a message may include an embedded link 379 to a web page. A comment icon 380 may be provided to facilitate generating a comment linked to the article referenced in the second message 373, and a share icon 381 for sharing the article with others. A scroll bar 375 is provided for scrolling through the resident's messages, with a scroll button 376 and a scroll down button 377. The second community window 371 may be closed using the close button 378.

Figure 32:
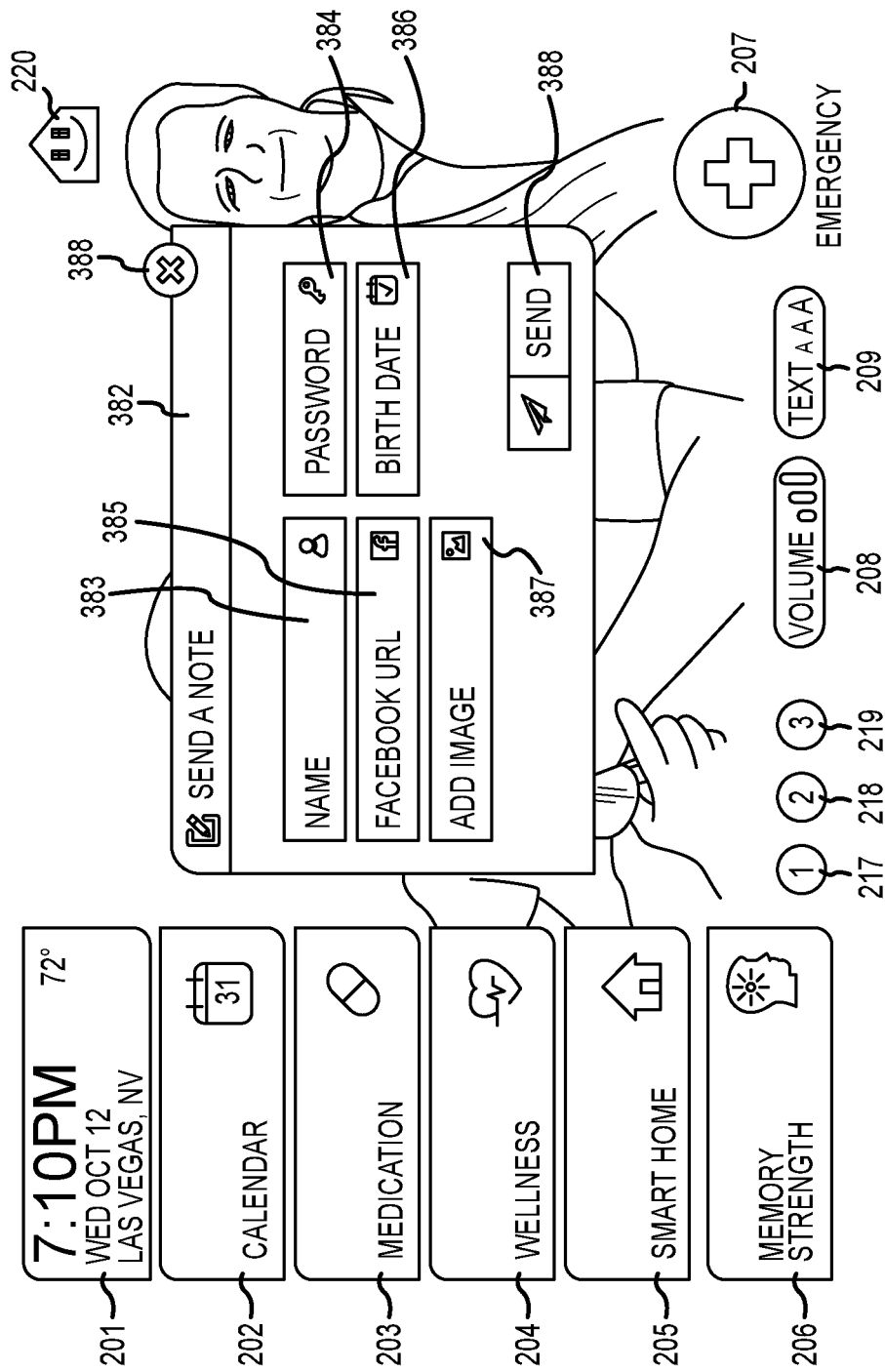
FIG. 32 is a screen shot showing a third screen for the community module.

FIG. 32 is a screen shot of a third community window 382 provided by the community module. This is an example of a user interface for sending a note or message. The third community window 382 includes fields for name 383, password 384, Facebook URL 385, birth date 386, and to add an image 387. A send button 388 causes the message to be sent. A close button 389 is provided.

The community module provides a search engine for restaurants and public venues, with customer and community reviews, and further provides data concerning restaurants and public venues with special accommodations based upon being friendly to those with a specified medical condition or disability. The community module provides review ratings, menus, on-line orders and ticket purchases for restaurants and public venues.

The community module provides the resident with access to a community that may act as an extension of the telemedicine services provided by doctors, hospitals and those in the HAPPIE users medical community. A subscription based system may be used to provide the resident with access to medical diagnosis and condition web sites that have been vetted for quality and accuracy of the content. DNA testing and results associated with the resident may be integrated into a patient profile for the resident in order to facilitate medical diagnosis and potential areas of interest or topics of concern.

A resident can use the community module to reconcile his or her medical bills, insurance payments and health savings account (HAS) account to know true out-of-pocket costs for medical care. The community module provides secure access to bank accounts and other financial accounts. The community module also provides secure bill paying, expense and payment tracking, an HAS interface, and Medicare tracking.

The community module also provides caregiver support groups, including live chat and video conferencing for caregivers. The community module provides limited access chat groups, text messaging, and video conferencing for multiple caregivers associated with a patient or subscriber that they have in common, where access to the group is limited to authorized caregivers. The community module provides caregivers with subject matter alerts from published web articles and news stories. Consolidation of all medical records are made available for secure sharing amongst doctors and medical professionals via the doctor portal 102, and for caregivers via the caregiver portal 101.

Figure 33:
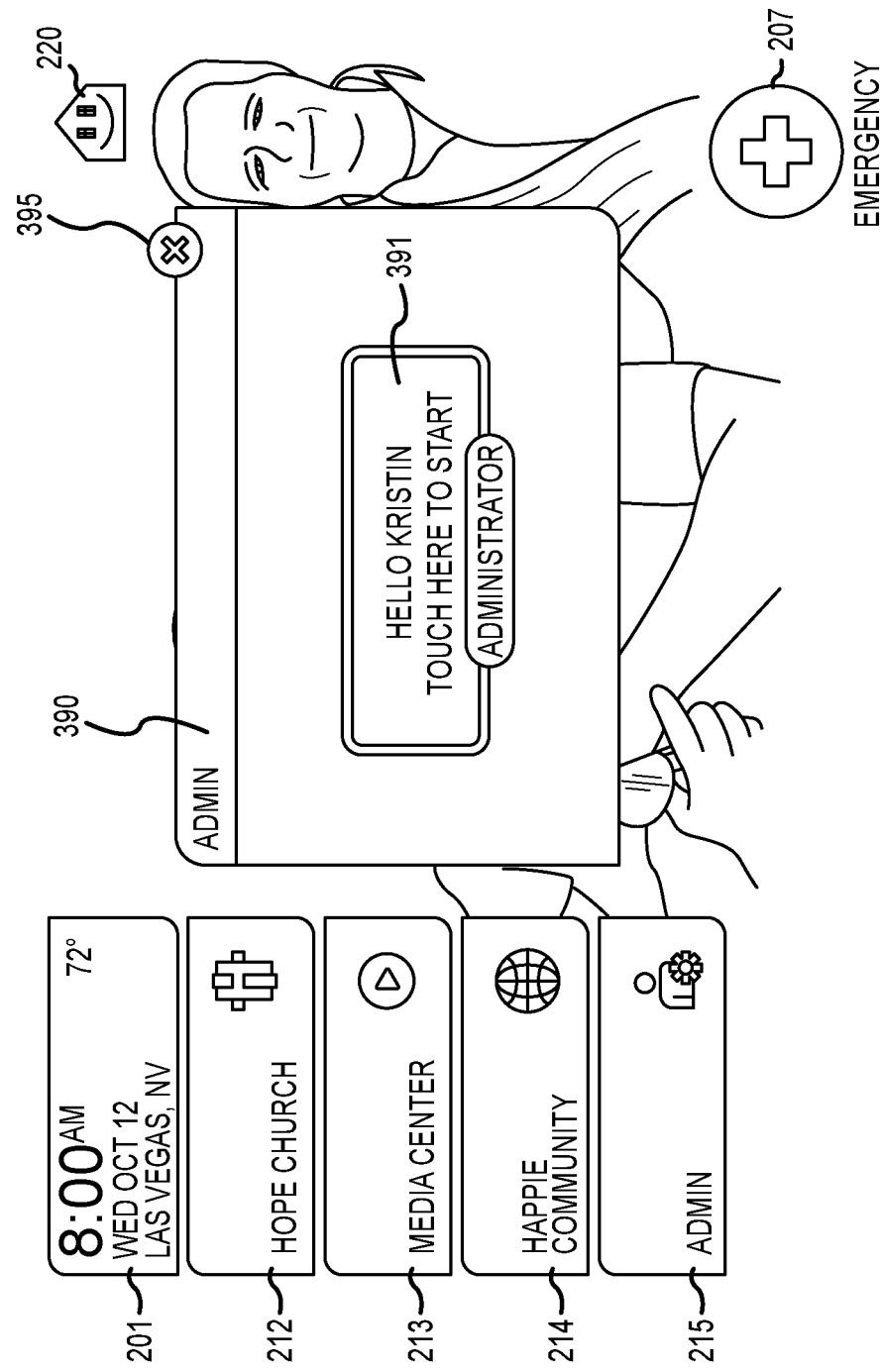
FIG. 33 is a screen shot showing a first screen for an admin module.

FIG. 33 shows a first admin window 390 that may be displayed for a software admin module running on the HAPPIE home unit 103, and which is activated by the admin button 215. The first admin window 390 provides a log-in button 391 for the administrator to indicate whether he or she wishes to log-in to the admin module as an administrator. A close button 395 is provided in the event the administrator decides to abort the log-in process.

Figure 34:
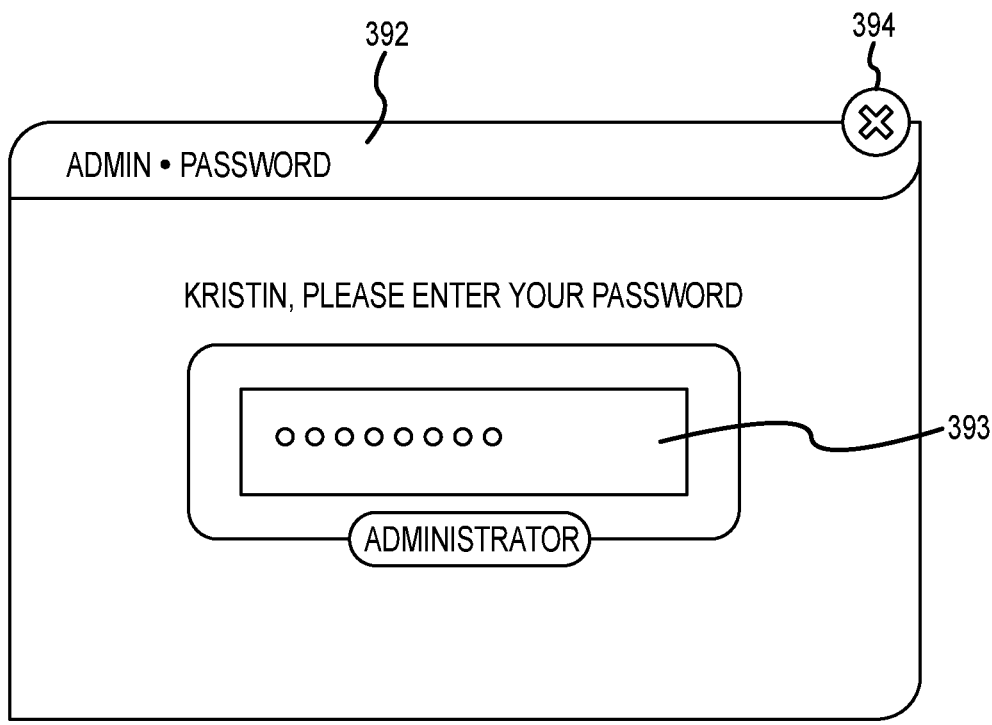
FIG. 34 shows a log-in window for the admin module.

FIG. 34 shows a second admin window 392 for the administrator to enter his or her password in a password entry box 393, in the event that the administrator activates the log-in button 391 shown in FIG. 33. A close window 394 is provided.

Figure 35:
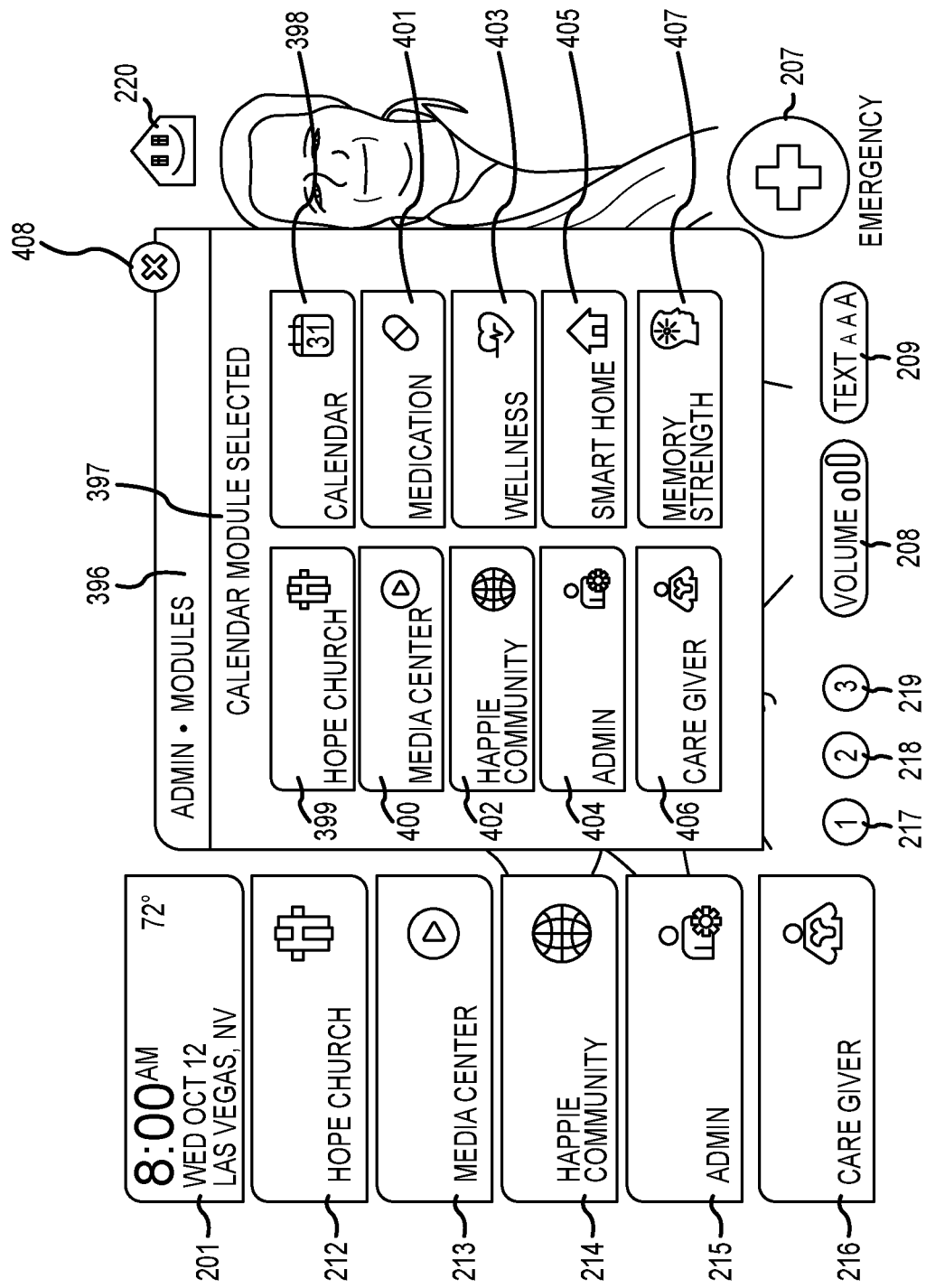
FIG. 35 is a screen shot showing a third screen for the admin module.

If the administrator successfully enters a valid password, a third admin window 396 is displayed, as shown in FIG. 35. Using the third admin window 396, the administrator may select an administration module associated with each module of the HAPPIE home unit 103. In the illustrated example, the calendar selection button 398 has been activated, and an information bar 397 displays a text confirmation concerning which administration module has been selected. The third admin window 396 includes a church selection button 399, a media center selection button 400, a medication selection button 401, a community selection button 402, a wellness selection button 403, an admin selection button 404, a smart home selection button 405, a caregiver selection button 406, and a memory strength selection button 407, each of which activates an associated corresponding administrative module. A close button 408 is provided for closing the third admin window 396.

Figure 36:
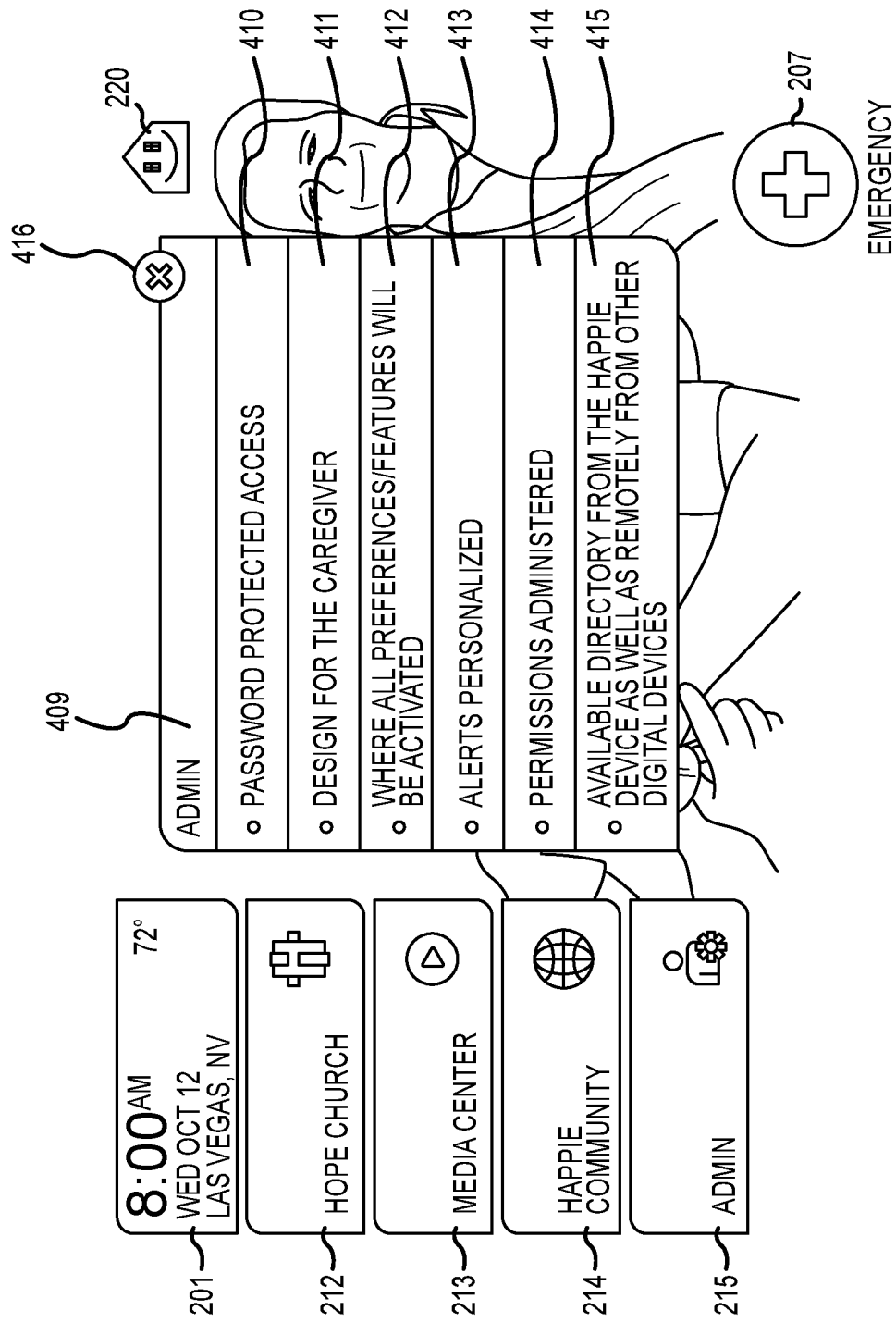
FIG. 36 is a screen shot showing a fourth screen for the admin module.

FIG. 36 is a fourth admin window 409, and shows an example of a typical window opened when the administrator selects one of the module buttons shown in FIG. 35. The fourth admin window 409 provides a first administrative data entry box 410 for entering configuration settings for an associated module in the HAPPIE home unit 103. In the illustrated example, a second administrative data entry box 411, a third administrative data entry box 412, a fourth administrative data entry box 413, and fifth administrative data entry box 414, and a sixth administrative data entry box 415 are shown. A close button 416 is provided to close the fourth admin window 409 and save the configuration data entered in the respective administrative data entry boxes 410, 411, 412, 413, 414, and 415.

Figure 5:
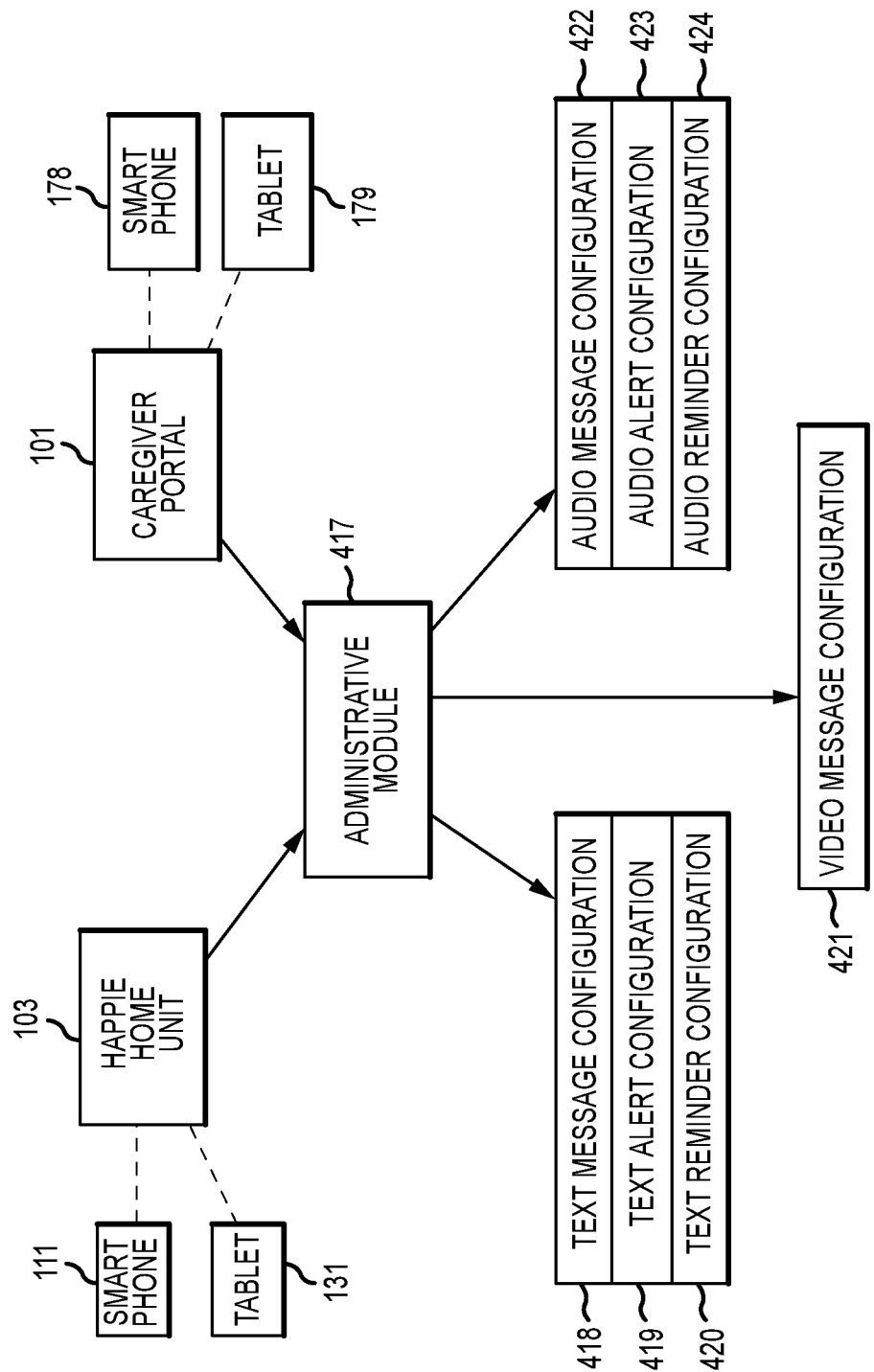
FIG. 5 is a block diagram illustrating software architecture concerning an administrative module.

The administration module 417 can be operatively accessed from the HAPPIE home unit 103 as shown in FIG. 5. Alternatively, the administration module 417 can be operatively accessed from the caregiver portal 101. The administrative module 417 provides the caregiver with direct access to customization and personalization features for all modules within the HAPPIE home unit 103. Access to the administration module 417 features dual authentication of an eight-plus character password, plus voice or facial recognition verification. The HAPPIE home unit 103 is unable to accept any changes to current settings from anyone unable to provide adequate authentication. In a preferred embodiment, adequate authentication consists of two of these three authentication methods, either an eight-plus character password plus voice recognition, or an eight-plus character password plus facial recognition. The administrative module can be used to set configuration data and preferences for text messages 418, configuration data and preferences for text alerts 419, and configuration data and preferences for text reminders 420. Configuration data and preferences for video messages 421 can be set by the administrative module 417. The administrative module can be used to set configuration data and preferences for audio messages 422, configuration data and preferences for audio alerts 423, and configuration data and preferences for audio reminders 424. Each module in the HAPPIE home unit 103 features its own set of pre-programed alerts and notifications. Access to the administration module shown in FIG. 5 features dual authentication of an eight-plus character password plus voice or 3D facial recognition verification.

The HAPPIE home unit 103 includes a caregiver module that may be operated locally by activating the caregiver button 216, or which may be operated remotely from the caregiver portal 101. In accordance with the present invention, the caregiver portal 101 is a "window" into the home of the resident for whom the caregiver provides care and attention. Using the caregiver portal 101, a caregiver can view the data, audio and video collected by the in-home sensors 130 to determine the status of the home and the resident.

Figure 37:
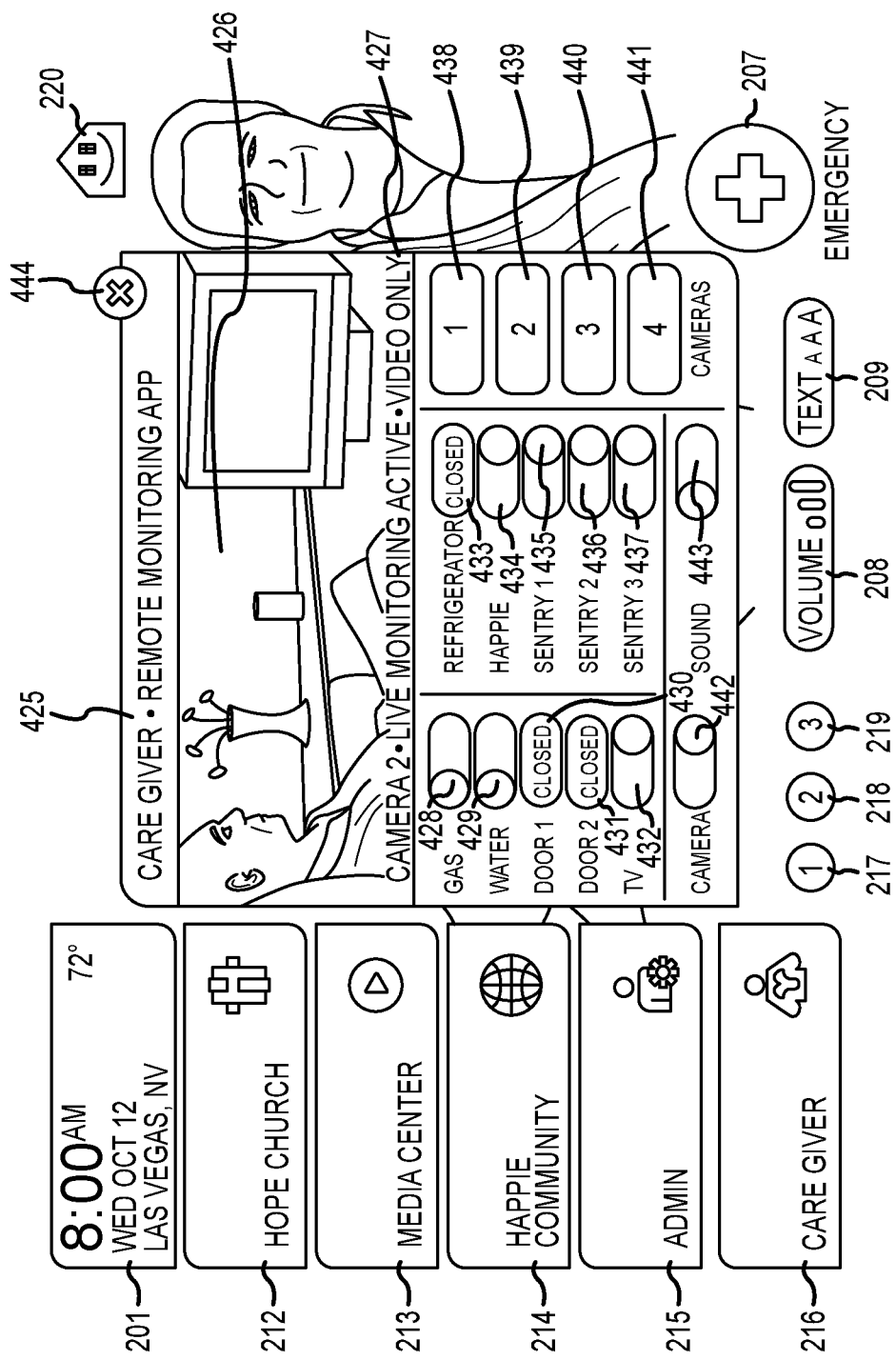
FIG. 37 is a screen shot showing a first screen for a caregiver module.

For example, a first caregiver window 425 is shown in FIG. 37. Using the caregiver module via the caregiver portal 101, a caregiver can control home heating 116 and home air conditioning 117, lighting 159, power window coverings 140, natural gas 135, and water consumption 148, the status of doors 137 and windows 145. Referring to FIG. 37, the first caregiver window 425 selectively displays a live video window 426 from one of the video cameras 112 in the home. The caregiver can select which camera 112 to display in the live video window 426. A first camera selection button 438 is provided for selecting live video from a camera 112 associated with the first camera selection button 438. A second camera selection button 439 is provided for selecting live video from a camera 112 associated with the second camera selection button 439. In the example shown in FIG. 37, the live video from camera two has been selected, and that second camera selection button 439 is highlighted in the first caregiver window 425. A sound control 443 is provided, and in the illustrated example, the sound is turned off, so that audio picked up by microphones 113 is not currently being transmitted to the caregiver. Text shown in a video information display bar 427 identifies which video camera 112 is currently being displayed, and in the illustrated example, states that the module is in the "video only" mode, because the sound control 443 is turned off. A third camera selection button 440 is provided for selecting live video from a camera 112 associated with the third camera selection button 440. A fourth camera selection button 441 is provided for selecting live video from a camera 112 associated with the fourth camera selection button 441. A camera control 442 permits the caregiver to turn the video feed from video cameras 112 "off" or "on."

The first caregiver window 425 shown in FIG. 37 has a gas control 428 and a water control 429 that both display the current status of gas and water, respectively, and further allow the caregiver to control both by turning them "off" or "on." A first door control 430 displays the status of a door in the home, and the caregiver can remotely lock or unlock the door associated with the first door control 430. A second door control 431 is provided, which indicates the status of a second door in the home associated with the second door control 431. The caregiver can similarly remotely lock or unlock the door associated with the second door control 431.

The first caregiver window 425 shown in FIG. 37 includes a television control 432, which indicates that the television 156 is "on," and the television control 432 allows the caregiver to remotely turn the television 156 "off," or back "on." A refrigerator status 433 shows the current status of the door of the smart refrigerator 115 in the home. The security system can be remotely controlled by the caregiver. A first sentry area control 435 may be used to selectively turn "off" or turn "on" a first portion of the security alarm system for the resident's home. A second sentry area control 436 may be used to selectively turn "off" or turn "on" a second portion of the security alarm system for the resident's home. And a third sentry area control 437 may be used to similarly selectively turn "off" or turn "on" a third portion of the security alarm system for the resident's home. The first caregiver window 425 may be closed using close button 444.

Figure 38:
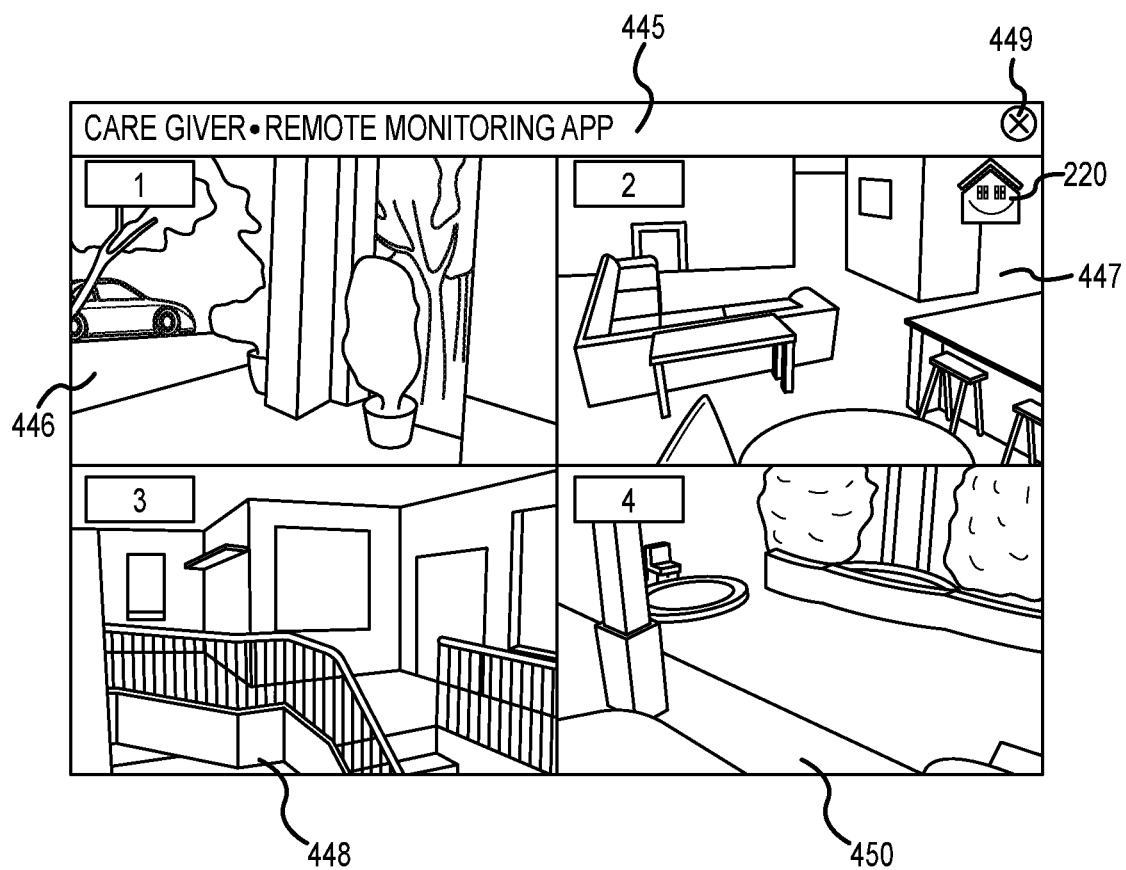
FIG. 38 shows video windows for the caregiver module.

FIG. 38 illustrates a second caregiver window 445. The second caregiver window 445 allows the caregiver to simultaneously remotely view live video feed from a plurality of video cameras 112. In the illustrated example, a first video window 446 shows the live video from a video camera 112 associated with the first video window 446. A second video window 447 shows the live video from a video camera 112 associated with the second video window 447. A third video window 448 shows the live video from a video camera 112 associated with the third video window 448. And a fourth video window 450 shows the live video from a video camera 112 associated with the fourth video window 450. A close button 449 is provided to close the third video window 448.

Using the caregiver portal 101 in connection with the HAPPIE home unit 103, a caregiver can discretely look in on the resident by activating the cameras 112 placed throughout the home. A caregiver can use the caregiver portal 101 to call the resident and speak to him or her directly through accessing speakers 157 and microphones 113 in the home. The resident may speak from anywhere in the home, hands free, and in his or her natural voice.

Notifications, reminders and alerts are configured and formatted by the caregiver, using the caregiver portal 101, based upon actions, activities, and statuses the caregiver wishes to monitor within the residence and on the property grounds. These alerts provide actionable information that tell the caregiver of something requiring attention or action, versus the caregiver having to query multiple solutions and services to compile the findings needed to understand the status or condition of the resident they care for as well as the home he or she resides in. Sensors in the pantry 119, kitchen 115, and medical equipment 160 connect with the HAPPIE home unit 103, and software modules are provided to "push" actionable alerts out to the caregiver's smart phone 178, tablet 179, or computer 180, via the caregiver portal 101.

All data sent between the HAPPIE home unit 103 and the caregiver portal 101 is preferably encrypted. In addition, all data at rest is also encrypted, including all data stored on the local database 108, all data pertaining to the resident that is stored on the central database 175, and all data stored at the caregiver portal 101.

Although the various modules of the HAPPIE home unit 103 have been separately described, full integration is provided among the modules, including the calendar module, the wellness module, the church module, the media center module, and the community module.

Intelligent software components within the HAPPIE home unit 103 include 3D facial recognition, voice pattern recognition and intelligent movement pattern and routine mapping fed by sensors and motion detectors throughout the home. At the caregiver's discretion, 3D facial images and voice map recordings are stored on the local database 108 in the personal profiles of the resident, caregivers, family members, visiting help, aides, nurses, doctors, and other persons known to the resident. The HAPPIE home unit 103 can identify, greet, track, and record all persons, by name, who enter or exit the resident's home, regardless of whether the resident is present. The HAPPIE home unit 103 recognizes the resident and caregivers using 3D facial recognition, voice recognition, data from a HAPPIE bracelet 158 worn by the resident, etc., and greets them by name. Greeting settings within the HAPPIE home unit 103 can be set to activate a verbal greeting the first time a person is seen in a twenty-four hour period, or multiple times within a twenty-four hour period. Greeting settings dictate how often the resident is addressed by name. The goal is for the HAPPIE home unit 103 to become familiar to the resident where he or she looks upon the HAPPIE home unit 103 as a digital companion, and not simply a computer, hardware or new technology.

The HAPPIE home unit 103 can be integrated with robots and other motorized hardware to control the robots and other devices, thereby performing the role of their "brain" to control the robots' function. Sensors 130, motion detectors 152 and 195, cameras 112, satellite or drone imagery, all continually feed resident activities into the local database 108 for analysis and pattern definition by the HAPPIE home unit 103. This allows the caregiver to drill down a view of the perimeter of the residence, into the residence, and within a room at the residence. The longer the HAPPIE home unit 103 is in use in a home, the more accurately the HAPPIE home unit 103 is able to understand and predict the resident's typical daily routine. Wake times, meal times, exercise, movement throughout the home, exiting the home, time away, return times, and sleep times, all contribute to the user profile for the resident, which is stored in the local database 108 within the HAPPIE home unit 103, and optionally stored in a central database 175 at the central server 100. Caregivers can rely on this data to set notifications, reminders and alerts linked to behavior that needs to be taken, e.g., medication times as well as out-of-pattern or omission of activity, e.g., if the resident is not seen by the video cameras 112 within a historic wake time period, and which can be monitored via the caregiver portal 101 using the caregiver's smart phone 178, the caregiver's tablet 179, or the caregiver's computer 180.

Notifications, reminders and alerts may be defined and customized by the caregiver. Caregivers establish the alert trigger point (time, day, event, inactivity), frequency and recipients of the alert event. The same alert can be sent to multiple recipients simultaneously. A default set of pre-set alerts are preferably configured on a module-by-module basis and installed on the HAPPIE home unit 103 prior to installation in the home. An unlimited number of custom alerts can be defined and deployed by the caregiver. Administration of the alert function can be managed through the caregiver portal 101 or directly on the HAPPIE home unit 103. All administrative functions within the HAPPIE home unit 103, including alerts in use, are backed up to the central database 175 via the cloud 105 on a predetermined routine basis, such as by using a batch processing configuration.

The HAPPIE home unit 103 manages both non-emergency and emergency medical assistance (e.g. health and wellbeing) requests by the resident and caregiver. Residents may verbally activate a non-emergency alert by simply speaking aloud within the home. Pre-defined voice commands may be configured in the HAPPIE home unit 103 by the caregiver, and stored in the local database 108. It can be a simple as a "HAPPIE, get help" command to cause the HAPPIE home unit 103 to make a phone call, send a text or simultaneously send both voice and text messages to one or more caregivers at one or more caregiver portals 101. In addition, the caregiver can access the HAPPIE home unit 103, installed in a residence, using the caregiver's smart phone 178, the caregiver's wireless handheld computing device or tablet 179, or the caregiver's computer 180 at the caregiver portal 101. The caregiver can activate the television, cameras, microphones, speakers, and mic packs 142 throughout the home. The caregiver's voice will be heard throughout the resident's home when the caregiver calls out. An example of which could be "mom, are you OK". The resident can verbally respond, hands free, from anywhere inside the home, because the microphones 113 will pick up the resident's voice so that the resident can be heard by the caregiver at the caregiver portal 101. In addition, the caregiver can turn on a television 156 and override the current programming to activate a video-audio conference, or "facetime" communication, with the resident over the television 156 using an associated speaker 157, an associated microphone 113, and an associated video camera 112.

Figure 39:
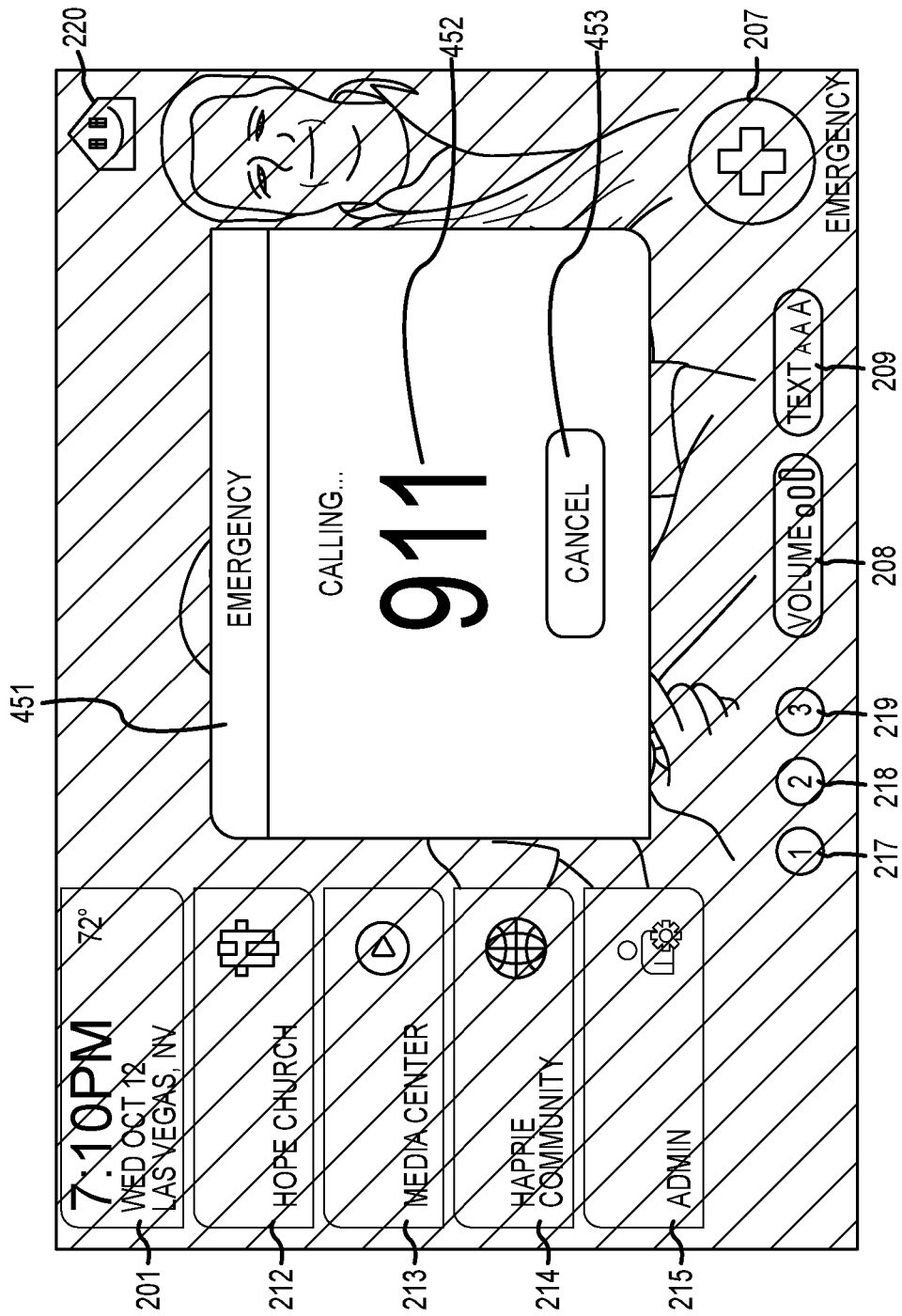
FIG. 39 is a screen shot showing a screen display during an emergency call.

Emergency assistance requests contain enhanced functionality. The HAPPIE home unit's 103 natural voice interface 180 can determine the difference between an emergency and non-emergency request for help, based upon the stress level and tonal inflection detected in the resident's voice at the time of the request. In addition, the HAPPIE home unit 103 "listens" for slurred speech or incoherent sentence structure that may indicate the resident is experiencing a medical emergency and will automatically make the emergency assistance request to emergency services 106 on behalf of the resident. The motion detectors 152, intelligent heat detectors 194 and mic packs 142 connected to the HAPPIE system core 121 can determine the difference between user inactivity and a fall which may render the resident injured and unconscious. The HAPPIE home unit 103 will automatically make an emergency assistance request to emergency responders 106 on behalf of the resident should he or she fall and be unable to request help himself or herself. FIG. 39 shows an example of an emergency call window 451 that may be displayed when the HAPPIE home unit 103 makes an emergency call. A text alert 452 displays a warning that the HAPPIE home unit 103 is calling 9-1-1. A cancel button 453 is provided to cancel the call. During an emergency call, other areas of the screen are greyed out and deactivated, as shown in FIG. 39.

Should the resident elect to use a voice command, a more specific request may be used in order to request emergency services 106 to be dispatched to the residence. For example, a "HAPPIE, get help now!" or similar pre-programed command may be used. In all emergency request scenarios, a text notification will be sent to the caregiver via the caregiver portal 101, to family members via the family portal 125, to the primary care physician via the doctor portal 102, and to specialist or other medical personnel. An emergency message sent to the caregiver portal 101 will also be displayed on the caregiver's smart phone 178 and the caregiver's tablet device 179. Points of integration include, but are not limited to, medical and ambulatory services portal 106, suicide prevention hotline portal 107, fire and police departments portal 106, as well as the caregiver portal 101.

The HAPPIE home unit 103 automates non-medical emergency assistance requests on behalf of the resident and caregiver. The HAPPIE home unit 103 monitors the security of the residence regardless of whether anyone is home. Motion detection sensors 152, heat detection sensors 194, fire and smoke detection sensors 150, water sensors 148, window sensors 145, door sensors 137, and mic packs 142, all feed data to the HAPPIE home unit 103 that is stored in the local database 108; and the data is also fed via the cloud 105 to a central data store 175 maintained by the central server 100. Intelligent software continually monitors the data to compare the values to representative data corresponding to a fully secure residence. If the data comparison deviates beyond limits set by configuration parameters, an alert is automatically generated to the caregiver portal 101, the family members portal 125, and under certain circumstances, (for example, if smoke or a fire is detected), automatically to the emergency services portal 106.

The HAPPIE home unit 103 activates all cameras 112, microphones 113, and speakers 157 in the event of the receipt of data indicative of a breach of a door sensor 137, a breach of a window sensor 145, or the detection of glass breakage by a glass breakage sensor 146.

The video cameras 112 may include thermal imaging capability. In addition, mic packs 142 include motion sensors 192, video cameras 193, and intelligent thermal sensors 194. The HAPPIE home unit 103 may use thermal imaging data to determine how many intruders have entered the home and their location within the home. As a deterrent to intruders, the HAPPIE home unit 103 may be configured to automatically display, during an intruder alert, the image of an intruder on all televisions and video monitors 156 inside the home. The HAPPIE home unit 103 broadcasts the description of the intruders verbally, out loud, through all speakers 157 describing each intruder's approximate height, weight, clothing, and other identifying characteristics, and announces that the authorities have been notified, in order to scare the intruder into leaving the home.

3D facial image and recording of the intruder's voice are logged into the local database 108 for retrieval and identification purposes, and may be transmitted in real-time to an emergency services portal 106 for use by the authorities. The HAPPIE home unit 103 alerts the police via the emergency services portal 106 of the detection of a break-in and transmits the intruder's image and other identifying information to the police. Caregiver(s) are notified of the break in via the caregiver portal 101, and may be directed to stay away from the home until the caregiver receives the "all clear" from the police. If the resident is not home during the intruder alert, the resident will be similarly warned. Police dispatch operators will automatically have access to the HAPPIE home unit 103, its cameras 112, microphones 113, and motion detectors 152, in the event of an emergency that is phoned in by the resident or the caregiver from inside the residence. A floor plan of the home is automatically transmitted to the emergency services portal 106 by the HAPPIE home unit 103 via the cloud 105, in order to allow police to understand the layout of the home and the location of the resident and location of the intruders prior to their arrival on the scene.

The HAPPIE home unit 103 automates non-medical emergency assistance requests (e.g. fire in the home) on behalf of the resident and caregiver. Intelligent heat detectors 194, fire and smoke detectors 150, and video cameras 112 work in concert to pinpoint any fire's point-of-origin sooner than a conventional smoke detector alone could do. The HAPPIE home unit 103 announces the fire threat over the speakers 157 to all who may be present within the residence and the need to evacuate the home, while simultaneously contacting the caregiver via the caregiver portal 101, and automatically contacting appropriate emergency responders, such as a fire department, via the emergency services portal 106.

Although the HAPPIE home unit 103 has been described as having a number of modules, additional modules may be provided in the HAPPIE home unit 103 in accordance with the invention. Additional modules may include a physical therapy module, an occupational therapy module, a speech-language pathology or therapy module, a job skills assessment and development module, a job finding module, and a dating or match-making module.

A physical therapy module in accordance with the present invention is designed to enable a patient to achieve greater results than current methods. The HAPPIE home unit 103 displays the actual live or video recorded therapy routine prescribed to the patient on a split television screen or video monitor 156. The resident who participates in the physical therapy mimics the routine as he or she performs the exercise in real-time. The resident's performance is displayed on the split screen television 156, and recorded by video cameras 112 connected to the HAPPIE home unit 103 for storage in the local database 108. The resident mimics the therapist's routine displayed on the video monitors 156 for improved accuracy of movement. The time, duration, intensity and accuracy of the resident patient's routine are all measured and logged by the HAPPIE home unit 103 in the local database 108 for review by the patient, caregiver or authorized medical professional. For example, a doctor or physical therapist can use the doctor portal 102 to access the recorded video data stored on the local database 108. The HAPPIE home unit 103 uses artificial intelligence to graph past performance, effectiveness of the most current session, graph the effectiveness of the current session, and project future performance and time to recovery.

This physical therapy module provided by the HAPPIE home unit 103 allows a resident to effectively continue physical therapy, if needed, even after an insurance company caps the number of sessions that the insurance is willing to pay for. Therapy routines may be categorized and sorted by injury type, live or recorded routines, surgery type, body part, and treatment.

An occupational therapy module may be provided in accordance with the present invention to aid health care professionals in the assessment of a resident with physical, mental, or cognitive disorders, and to facilitate the delivery of treatment to the resident to help in his or her development, recovery, or maintenance of daily living and work skills. Routines, exercises and therapies prescribed by a therapist can be implemented in the HAPPIE home unit 103 for easy access by the resident. The HAPPIE home unit 103 will contain the therapy schedule, which may be implemented in the calendar module. Audio and video alerts, messages, and reminders can be established by the caregiver to assist the resident to stay on track with his or her therapy. Artificial intelligence built into the HAPPIE home unit 103 will evaluate the performance of all exercises, routines and therapies, and provide meaningful feedback and scores to the resident, the caregiver, and the therapist.

Occupational therapists also focus much of their work on identifying and eliminating environmental barriers to independence and participation in daily activities. Occupational therapists work with clients of all ages, ranging from infants to the elderly, with a focus on adapting the environment, modifying the task, teaching the skill, and educating the client/family to increase participation in and performance of daily activities, particularly those that are meaningful to the client. The combination of the HAPPIE home unit 103 and use of cameras 112, microphones 113, and sensors 130, can provide improved tracking, reporting and feedback regarding the resident's environment and ability to adapt to modified tasks. Occupational therapists often work closely with professionals in physical therapy, speech therapy, nursing, social work and the community. Many of which, upon the caregiver's approval and authorization, will have the unique ability to collaborate and synchronize the delivery of care they have collectively designed prescribed for a resident.

A speech-language pathology or therapy module may be provided in the HAPPIE home unit 103. Speech-language pathology or therapy is a field of expertise practiced by a clinician or therapist who specializes in the evaluation and treatment of communication, cognition, voice and swallowing disorders. Therapists will use a doctor portal 102 to connect to the HAPPIE home unit 103 for communication with the resident, and to facilitate remote therapy sessions over the Internet 105. The HAPPIE home unit 103 controls a split screen television display on a television 156 that may be advantageously used in physical therapy sessions by a speech therapists. The therapist and resident can perform treatments, routines and exercises in real time. Video cameras 112, speakers 157, and microphones 113 work in concert with the voice recognition feature within the HAPPIE home unit 103 to track and monitor a resident's progress when practicing at home and off-line, and the sessions may be recorded and stored on the local database 108.

Speech-language therapy provided by the present system may include word-finding issues, either as a result of a specific language problem such as a language delay, or a more general issue such as dementia. Speech-language therapy provided by the present system may include therapy for structural language impairments, including difficulties creating sentences that are grammatical (syntax) and meaningful (semantics). Speech-language therapy provided by the present system may include therapy for literacy impairments (reading and writing) related to the letter-to-sound relationship (phonics), the word-to-meaning relationship (semantics), and understanding the ideas presented in a text (reading comprehension). Speech-language therapy provided by the present system may include therapy for voice difficulties, such as a raspy voice, a voice that is too soft, or other voice difficulties that negatively impact a person's social or professional performance. Artificial intelligence built into the HAPPIE home unit 103 will evaluate the performance of all exercises, routines and therapies, and provide meaningful feedback and scores to the user, the caregiver, and therapist, while maintaining a record of each exercise, routine and therapy on the local database 108.

The HAPPIE home unit 103 may include an aptitude assessment module that allows the resident to take interest tests to determine what sort of jobs the resident may be interested in, or to take tests to determine what type of jobs may be of interest to the resident, or for which the resident may have an aptitude.

The HAPPIE home unit 103 may include a job skills assessment and development module that assists the resident in assessing the resident's job skills and qualifications. The job skills assessment and development module may link to data in the central database 175 concerning available jobs, and the required qualifications, skills, and experience. The HAPPIE home unit is operative to match the resident with available jobs, and to assist in automatically generating and submitting an application, as well as scheduling an appointment for an interview. If needed, the HAPPIE home unit 103 may provide the resident with training programs and job skills development. The HAPPIE home unit 103 may also administer skills testing to demonstrate that the resident qualifies for a particular job.

The HAPPIE home unit 103 may include a dating or match-making module. Many match-making websites and services rely upon a user's self-identification and self-assessment to try to match people. Unfortunately, people's self-assessment and description of themselves for such purposes is not always reliable, and the image that people sometimes try to project is not always who they really are. The HAPPIE home unit 103 has extensive data concerning the resident's activities, interests, energy level, DNA profile, medical condition, education level, and preferences. For example, if the resident is a night owl, the resident may not be well matched with an early morning person, and the HAPPIE home unit 103 has a record of the daily waking hours of the resident in order to determine such personal characteristics. The dating or match-making module provided by the HAPPIE home unit 103 can more effectively discretely match a resident with another compatible person who also lives in a home having a HAPPIE home unit, and can more effectively identify compatible people based upon comprehensive factual information about each person that is not colored by the tendency of many people to try to project an image of themselves under such circumstances that may not be completely reliable or accurate.

The HAPPIE home unit 103 tracks web searches by computer, sites accessed, and downloads received. The HAPPIE home unit 103 also tracks smart phone and WiFi usage. Automobile GPS integration is provided by the HAPPIE home unit 103 to schedule maintenance and repairs. The HAPPIE home unit 103 may be used to analyze words used in text messages, tweets, and emails sent by the resident. Research has shown that a person's risk of diabetes may be predicted based upon the words used such communications. In addition, the HAPPIE home unit 103 may include in the analysis data from the resident's consumption of food, data from the smart refrigerator 115, data from the smart pantry 119, and other relevant health data, including DNA test data recorded in the resident's profile and stored in the local database 108. If the HAPPIE home unit 103 determines that the data analysis indicates a risk of diabetes, or any other relevant condition, the HAPPIE home unit 103 may generate a message to the resident with a recommendation for appropriate testing. In addition, the HAPPIE home unit 103 may be configured to automatically generate an alert to be sent to the caregiver portal 101 or the doctor portal 102.

The HAPPIE home unit 103 includes data reporting, data analytics, and data trend analysis. Artificial intelligence built into the HAPPIE home unit 103 preferably performs a continual analysis on the data collected and stored in the local database 108. Data collection includes data received from, but not limited to, the sensors 130, microphones 113, cameras 112, and mic packs 142 located throughout the home. Reporting formats include numeric and graphic representations, and can be viewed as a past-to-the-present format, a specific point-in-time format, as well as current-to-future projections.

For example, sensors 130 that feed into the physical health side of the wellness module may include medical equipment 160, wearable sensors 158, a Medwand™ 162, temperature sensors 161, blood pressure sensors 163, a Fitbit™ device 164, pulse sensors 165, and weight scales 166. Sensors that feed the nutritional side of the wellness module may include appliances 114, a smart refrigerator 115, a smart coffee maker 118, and smart pantry sensors 119. Data from the medication module will include data concerning time, dosage and frequency of vitamins, supplements and medications taken. The resident can speak to the HAPPIE home unit 103 about how he or she is feeling at any given moment, and the resident's comments will be recorded and added to the local database 108. All of this data may be included and displayed in the reporting and trend analysis.

For example, the resident may state that he or she is dizzy at 2:14 pm on Tuesday the 21st of March, energetic at 10:14 am on Wednesday the 22nd of March, and has a headache or severe joint pain at 12:14 pm on Thursday the 23rd. The trend analysis performed by the HAPPIE home unit 103 may be able to pinpoint the cause as a missed medication, the wrong dosage, a missed meal, consuming something off of the resident's nutritional plan, over exertion while exercising, or even the onset of a cold or the flu. The HAPPIE home unit 103 is able to provide analytics that would be otherwise unavailable to the caregiver or medical professional without the comprehensive data collection performed as a routine by the HAPPIE home unit 103. Based upon the data analysis, the HAPPIE home unit 103 may, if appropriate, generate text, video, or audio alerts and messages to be received by the caregiver on the caregiver's smart phone 178, or which can be accessed by the caregiver from the caregiver portal 101 or by medical professionals from the doctor portal 102.

The HAPPIE home unit 103 is able to intelligently detect the location of the resident in the premises, based upon voice recognition and/or 3D facial recognition sub-modules provided in the HAPPIE home unit 103. In some embodiments, a resident may value privacy, and is that type of an application, the video cameras in every corner of the house may be considered too invasive. In such instances, the HAPPIE home unit 103 includes configuration settings for operation of the video cameras based upon the location of the resident. Based upon the configuration settings, the HAPPIE home unit 103 may be configured to turn off video cameras in rooms where the resident is located for privacy. Or the HAPPIE home unit 103 configuration settings may be set to turn off all internal video cameras while the resident is at home.

Alternatively, in instances where privacy is a concern, a HAPPIE bracelet 158 may be provided for the resident to wear. The HAPPIE home unit 103 includes configuration settings for operation of the video cameras 112 based upon location detection of the bracelet 158. The HAPPIE home unit 103 detects the location of the bracelet 158 in the residence, and automatically secures or turns off the cameras 112 in the room where the resident is detected (as the resident moves around the premises). Video data from the cameras 112 is stored on the local database 108 using encryption. Video data from the cameras 112 is transmitted over the Internet 105 encrypted. When video data from the cameras 112 is stored on a central database 175, the data is encrypted.

The bracelet 158 preferably includes a panic button. In an emergency, the resident can press the panic button, to invoke a panic override mode, and the HAPPIE home system 103 will override the configuration setting, and record video in every room, including where the resident is located. The system also automatically calls for emergency help when the panic button on the bracelet 158 is activated. Alternatively, the panic override mode may be activated by voice commands or speech recognition.

In a preferred embodiment, the software running on the HAPPIE home unit 103 is configured with a architecture providing separate stand-alone modules with defined API interfaces. Each module is capable of running alone, and data passed to the module and returned from the module, is configured in a API interface having defined data structures and formats. This provides a significant advantage, because other third-party software modules may be substituted for any of the modules provided in accordance with a preferred embodiment of the invention. For example, if a third-party wishes to use its own voice-recognition software module, instead of the HAPPIE home unit's voice recognition module, the third-party voice recognition module can be readily interfaced with the defined API interface for the voice recognition functionality.

The HAPPIE Home unit 103 features an open API standard to allow products and services of third-party hardware and software technology companies, service providers, and an ever-growing community of freelancing developers, to be interfaced with the HAPPIE home unit 103. This facilitates the creation of innovative third-party applications that add functionality and additional value to the HAPPIE home unit 103. Open APIs are favored, because they simultaneously increase the production of new ideas by third-parties without requiring direct investment in development efforts. The HAPPIE home unit 103 may also incorporate tailored APIs to target specific developer audiences that are deemed to be most effective in creating valuable new applications.

The API interface architecture also provides the ability to turn individual modules used in the HAPPIE home unit 103 on and off, which results in flexibility to personalize the experience for each resident. For example, a 35-year old resident may wish to begin with the smart home module 663 while enjoying the flexibility to add the wellness module 662 at a later date. As circumstances change, a resident may turn on, or add, additional modules to the operation of the resident's particular HAPPIE home unit 103. For example, an unexpected automobile accident may result in the resident suffering a broken leg. During the recuperation and healing period, the resident may wish to turn on, and add, the calendar module 650, the medication module 660, and the physical therapy module 665. Once healed, the resident may, at his or her option, shut off the additional modules, if desired.

The doctor portal 102 is preferably provided with a voice recognition module 167 that monitors communications over the communications link 170 with the doctor portal 102. The voice recognition module 167 translates speech into text, and records the communications with the doctor to be stored in the local database 108. Then if a question ever arises concerning a doctors diagnosis or instructions, the data recorded on the local database 108 may be consulted. Artificial intelligence in the HAPPIE home unit 103 analyzes the speech recognition, and if a medication is prescribed by the doctor, the HAPPIE home unit 103 may automatically communication with a pharmacy concerning the medication, and the calendar module will automatically insert into the resident's calendar an alert for picking up the medication at the pharmacy, medication reminders for each dose, and as well as an alert for ordering a refill of the medication when needed.

Figure 40:
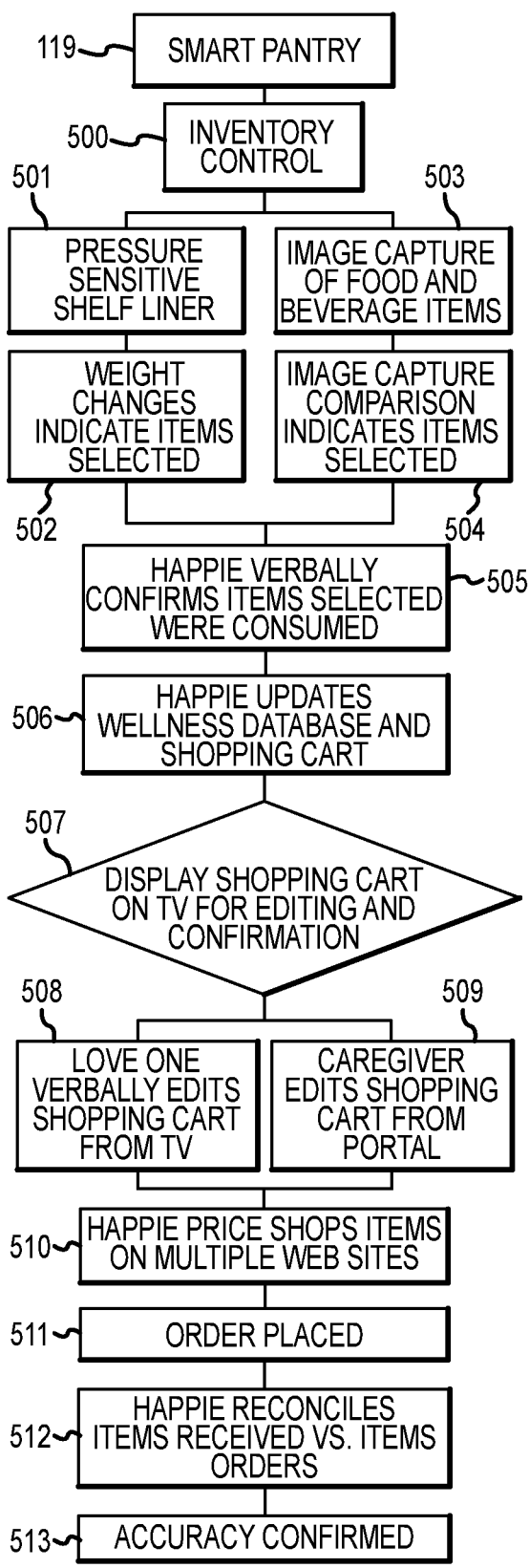
FIG. 40 is a flowchart illustrating a method associated with a smart pantry.

Referring to FIG. 40, in one advantageous embodiment, the HAPPIE home unit 103 includes a smart pantry 119 coupled to sensors 130 and a smart pantry module 500 in communication with a remote accessible caregiver interface 101. It may also optionally communicate with an app running on the resident's smart phone 111 or a caregiver's smartphone 178.

Figure 41:
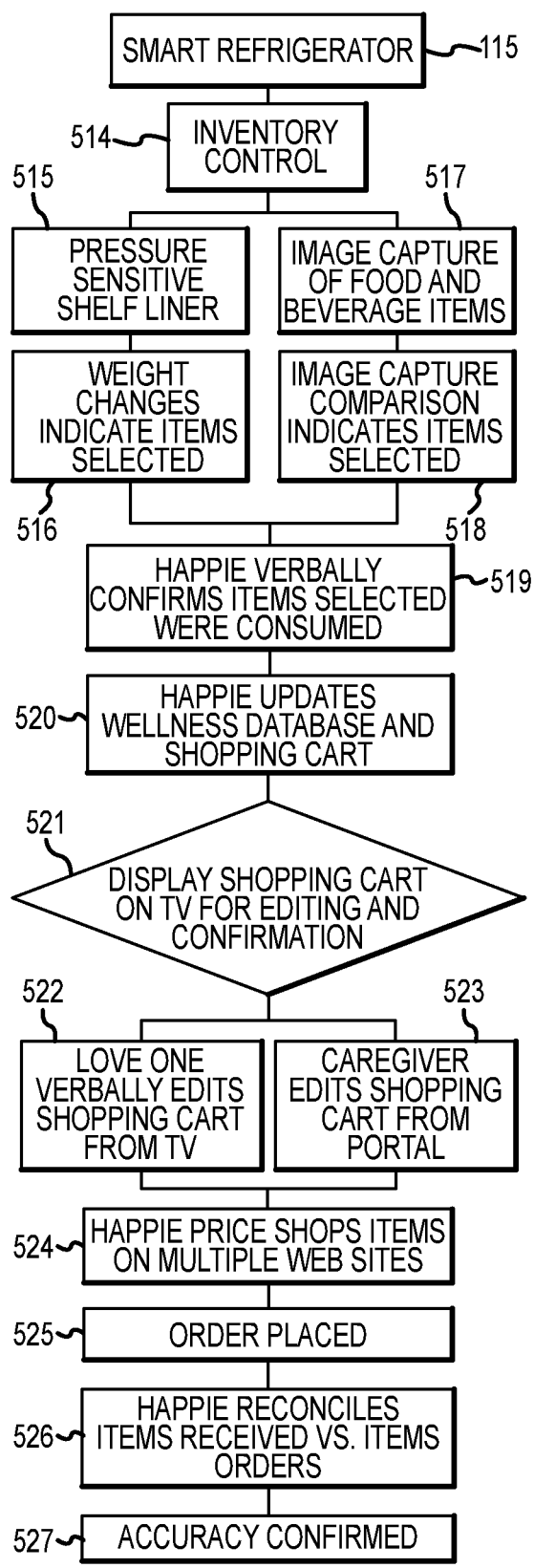
FIG. 41 is a flowchart illustrating a method associated with a smart refrigerator.

The smart pantry module 500 tracks food and beverage consumption, and preferably has access to inventory data stored on the database 108 from the smart refrigerator module 514 (shown in FIG. 41). Three inventory control methods for the smart pantry 119 are available in the smart pantry module 500, which are not mutually exclusive. Video cameras 112 may be provided inside the smart pantry 119, and a comparison of images of the items in inventory may be made between images taken prior to consumption of food and images taken after consumption of food. The smart pantry module 500 may analyze the image of each food or beverage item to determine the identity of the item, or alternatively, stickers containing readable codes uniquely identifying each food or beverage item may be affixed to each inventory item. A second alternative is a sensor based system using sensors 130, where the foods and beverages are stored on pressure and weight sensitive pads and shelf liners provided in the smart pantry 119. In a third alternative, a caregiver or the resident can manually scan items in inventory with a bar code scanner. Combinations of these three alternatives may also be employed. Food and beverage reorder thresholds may be established in an alert system in the HAPPIE home unit 103 and stored in the database 108. Once minimum values are met, the HAPPIE home unit 103 will reach out to preferred on-line or brick and mortar retailers, stores and web sites, and place orders for delivery to the residence.

Preferably, food and beverage storage maps are provided specifying and describing the placement of food and beverage items on the shelves for the smart pantry 119 and the smart refrigerator 115. In a sensor based system, the HAPPIE home unit 103 then assumes that a sensor detecting the weight of an item at a specified location designated in the food and beverage storage maps for a particular food or beverage item as an indication of the presence in inventory of the corresponding item.

Video images of food and beverage inventories taken by the cameras 112 in the smart pantry 119 are stored within the database 108 provided for the HAPPIE home unit 103. In addition, metadata is stored associated with each video image, including the time that the image was taken, and location information associating the field of view in the video image with one or more corresponding food and beverage storage maps.

The smart pantry module 500 may be activated by a door sensor and/or motion detectors which provide a signal to the HAPPIE home unit 103 indicating that the smart pantry 119 has been accessed, and that a food or beverage item from the inventory may be selected for consumption. The HAPPIE home unit 103 may verify that images of inventory items in the smart pantry 119 are stored in the database 108 for the last time that the smart pantry 119 was accessed. Referring to FIG. 40, in step 503, new images taken of the inventory items in the smart pantry 119 afterwards. In step 504, data derived from that image capture may be compared with the data derived from previous images stored in the database 108 to make a determination of which inventory items were removed or consumed, and the inventory stored in the database 108 may be updated accordingly. In one embodiment, a new video image is taken by video cameras 112 within the pantry 119 after a predetermined delay in time. In practice, a specified delay of 15 minutes may provide good results. The two images are compared in step 504, and the comparison identifies what items, if any, were accessed for consumption.

Alternatively, when the smart pantry module 500 is activated by a door sensor and/or motion detectors providing a signal to the HAPPIE home unit 103 indicating that the smart pantry 119 has been accessed, in step 501 shown in FIG. 40, weight sensitive pads and shelf liners may provide a signal to the smart pantry module 500 to indicate that an item has been selected from the pantry 119. In step 502, the weight changes are compared to data stored in the database 108 associated with one or more corresponding food and beverage storage maps to make a determination concerning which inventory items were removed from the pantry 119. As noted above, the use of video images and sensors is not mutually exclusive, and both may be used in an especially preferred embodiment.

Optionally, the HAPPIE home unit 103 may be configured to verbally verify the food consumed, as shown in step 505 in FIG. 40. For example, the HAPPIE home unit 103 may use a speech synthesizer, or may retrieve a voice recording from the database 108, and play the audio over speakers 157. The HAPPIE home unit 103 may ask, for example, "Did you drink the full 12 oz. of water you selected?" Or, for example, the HAPPIE home unit 103 may ask, "Did you finish the 12 oz. of soup you selected?" The resident, or alternatively a caregiver, may respond in a normal speaking voice, which is picked up by microphones 113. The HAPPIE home unit 103 may record the response in the database 108, and preferably, a speech recognition module is used to analyze the response.

Optionally, the HAPPIE home unit 103 may be configured to verbally ask if the resident wishes to add this item to the current shopping list, as shown in step 506 in FIG. 40. The HAPPIE home unit 103 may use a speech synthesizer, or may retrieve a voice recording from the database 108, and play the audio over speakers 157. The resident, or alternatively a caregiver, may respond in a normal speaking voice, which is picked up by microphones 113. The HAPPIE home unit 103 may record the response in the database 108, and preferably, a speech recognition module is used to analyze the response.

Referring to FIG. 40, in step 506, the HAPPIE home unit 103 updates the shopping list. This may be done automatically, or in accordance with the response received from the resident or caregiver.

Under circumstances where a caregiver is not present at the residence, the caregiver can optionally receive alerts at the caregiver portal 101 each time a food item or beverage is consumed. In addition, the caregiver can optionally receive alerts at the caregiver portal 101 when meals are missed or skipped, or when a predetermined number of hours have lapsed without the resident accessing the smart pantry 119 or the smart refrigerator 115.

Referring to FIG. 40, in step 507, at any time the resident or a caregiver can ask the HAPPIE home unit 103 to display the current shopping list on the resident's TV or video monitor 156, or on the caregiver's portal 101, respectively. As shown in step 508 of FIG. 40, the resident may verbally ask the HAPPIE home unit 103 to change quantities of the items on the shopping list, or to delete or add items as desired. Similarly, in step 509, the caregiver may change quantities of the items on the shopping list, or to delete or add items as desired, remotely using the caregiver portal 101.

Some food and beverage items may be assigned expiration dates. If the item in inventory is not consumed before the expiration date, the HAPPIE home unit 103 will notify the resident and/or a caregiver that the inventory item has expired and must be discarded, and the HAPPIE home unit 103 updates the shopping list accordingly.

In step 510, the HAPPIE home unit 103 price shops food and beverage items on multiple websites or by remotely accessing databases associated with food and beverage suppliers or sellers. The HAPPIE home unit 103 can be configured to shop for items based upon price and brand, and to factor in alternative shipping methods, and fees, and take into consideration any differences in sales tax or other expenses, in order to identify the best overall value when determining where to purchase each item.

At predetermined intervals, or when inventory items drop below a predetermined minimum level, in step 511, the HAPPIE home unit 103 places orders for food and beverage items using the shopping list stored in the database 108, or based upon inventory levels of each food or beverage item as compared with inventory maintenance quotas. Optionally, the HAPPIE home unit 103 may be configured to require caregiver approval before an order is placed, and at the time that authorization is requested from the caregiver, allow the caregiver to edit the shopping list via the caregiver portal 101. The caregiver may also be provided with the capability to override any choice concerning the purchase of food and beverage items, including where the items are purchased, brand substitutions, and any other characteristic of the purchase.

In step 512, when ordered items are received, the HAPPIE home unit 103 reconciles the items that were received with the items as ordered, and notes any missing or incorrect items. If the comparison does not reveal any errors, the accuracy of the fulfillment of the order is confirmed in step 513.

Referring to FIG. 41, in one advantageous embodiment, the HAPPIE home unit 103 includes a smart refrigerator 115 coupled to sensors 130 and a smart refrigerator module 514 in communication with a remote accessible caregiver interface 101. It may also optionally communicate with an app running on the resident's smart phone 111 or a caregiver's smartphone 178.

The smart refrigerator module 514 tracks food and beverage consumption, and preferably has access to inventory data stored on the database 108 from the smart pantry module 500 (shown in FIG. 40). Three inventory control methods for the smart refrigerator 115 are available in the smart refrigerator module 514. Video cameras 112 may be provided inside the smart refrigerator 115, and a comparison of images of the items in inventory may be made between images taken prior to consumption of food and images taken after consumption of food. The smart refrigerator module 514 may analyze the image of each food or beverage item to determine the identity of the item, or alternatively, stickers containing readable codes uniquely identifying each food or beverage item may be affixed to each inventory item. A second alternative is a sensor based system using sensors 130, where the foods and beverages are stored on pressure and weight sensitive pads and shelves provided in the smart refrigerator 115. In a third alternative, a caregiver or the resident can manually scan items in inventory with a bar code scanner. Combinations of these three alternatives may also be employed. Food and beverage reorder thresholds may be established in an alert system in the HAPPIE home unit 103 and stored in the database 108. Once minimum values are met, the HAPPIE home unit 103 will reach out to preferred on-line or brick and mortar retailers, stores and web sites, and place orders for delivery to the residence.

Video images of food and beverage inventories taken by the cameras 112 in the smart refrigerator 115 are stored within the database 108 provided for the HAPPIE home unit 103. In addition, metadata is stored associated with each video image, including the time that the image was taken, and location information associating the field of view in the video image with one or more corresponding food and beverage storage maps.

The smart refrigerator module 514 may be activated by a door sensor and/or motion detectors which provide a signal to the HAPPIE home unit 103 indicating that the smart refrigerator 115 has been accessed, and that a food or beverage item from the inventory may be selected for consumption. The HAPPIE home unit 103 may verify that images of inventory items in the smart refrigerator 115 are stored in the database 108 for the last time that the smart refrigerator 115 was accessed. Referring to FIG. 41, in step 517, new images are taken of the inventory items in the smart refrigerator 115 after the smart refrigerator 115 is accessed. In step 518, data derived from that image capture may be compared with the data derived from previous images stored in the database 108 to make a determination of which inventory items were removed or consumed, and the inventory stored in the database 108 may be updated accordingly. In one embodiment, a new video image is taken by video cameras 112 within the smart refrigerator 115 after a predetermined delay in time. In practice, a specified delay of 15 minutes may provide good results. The two images are compared in step 518, and the comparison identifies what items, if any, were accessed for consumption.

Alternatively, when the smart refrigerator module 514 is activated by a door sensor and/or motion detectors providing a signal to the HAPPIE home unit 103 indicating that the smart refrigerator 115 has been accessed, in step 515 shown in FIG. 41, weight sensitive shelves or shelf liners may provide a signal to the smart refrigerator module 514 to indicate that an item has been selected from the refrigerator 115. In step 516, the weight changes are compared to data stored in the database 108 associated with one or more corresponding food and beverage storage maps to make a determination concerning which inventory items were removed from the smart refrigerator 115. As noted above, the use of video images and sensors is not mutually exclusive, and both may be used in an especially preferred embodiment.

Optionally, the HAPPIE home unit 103 may be configured to verbally verify the food consumed from the smart refrigerator 115, as shown in step 519 in FIG. 41. For example, the HAPPIE home unit 103 may use a speech synthesizer, or may retrieve a voice recording from the database 108, and play the audio over speakers 157. The HAPPIE home unit 103 may ask, for example, "Did you drink the full 12 oz. of water you selected?" Or, for example, the HAPPIE home unit 103 may ask, "Did you finish the 12 oz. of soup you selected?" The resident, or alternatively a caregiver, may respond in a normal speaking voice, which is picked up by microphones 113. The HAPPIE home unit 103 may record the response in the database 108, and preferably, a speech recognition module is used to analyze the response.

Optionally, the HAPPIE home unit 103 may be configured to verbally ask if the resident wishes to add this item to the current shopping list, as shown in step 522 in FIG. 41. The HAPPIE home unit 103 may use a speech synthesizer, or may retrieve a voice recording from the database 108, and play the audio over speakers 157. The resident, or alternatively a caregiver, may respond in a normal speaking voice, which is picked up by microphones 113. The HAPPIE home unit 103 may record the response in the database 108, and preferably, a speech recognition module is used to analyze the response.

Referring to FIG. 41, in step 520, the HAPPIE home unit 103 updates the shopping list. This may be done automatically, or in accordance with the response received from the resident or caregiver.

Under circumstances where a caregiver is not present at the residence, the caregiver can optionally receive alerts at the caregiver portal 101 each time a food item or beverage is consumed. In addition, the caregiver can optionally receive alerts at the caregiver portal 101 when meals are missed or skipped, or when a predetermined number of hours have lapsed without the resident accessing the smart refrigerator 115.

Referring to FIG. 41, in step 521, at any time a caregiver or the resident can request the HAPPIE home unit 103 to display the current shopping list on the caregiver's portal 101, or on the resident's TV or video monitor 156, respectively. As shown in step 523 of FIG. 41, the caregiver may remotely change quantities of the items on the shopping list, or to delete or add items as desired, using the caregiver portal 101. Similarly, in step 522, the resident may verbally ask the HAPPIE home unit 103 to change quantities of the items on the shopping list, or to delete or add items as desired.

Some food and beverage items may be assigned expiration dates. If the item in inventory is not consumed before the expiration date, the HAPPIE home unit 103 will notify the resident and/or a caregiver that the inventory item has expired and must be discarded from the smart refrigerator 115, and the HAPPIE home unit 103 updates the shopping list accordingly.

The remaining steps 524, 525, 526, and 527, shown in FIG. 41, are the same as those described in connection with similar steps in FIG. 40. In step 524, the HAPPIE home unit 103 price shops food and beverage items on multiple websites or by remotely accessing databases associated with food and beverage suppliers or sellers.

At predetermined intervals, or when inventory items drop below a predetermined minimum level, the HAPPIE home unit 103 places orders for food and beverage items, as shown in step 525, using the shopping list stored in the database 108, or based upon inventory levels of each food or beverage item as compared with inventory maintenance quotas.

In step 526, when ordered items are received, the HAPPIE home unit 103 reconciles the items that were received with the items as ordered, and notes any missing or incorrect items. In step 527, if the comparison does not reveal any errors, the accuracy of the fulfillment of the order is confirmed.

In the case of food and beverages generally, the HAPPIE home unit 103 may be configured to initiate restocking orders to replenish items in the smart pantry 119 and in the smart refrigerator 115 on a predetermined day of the week, on a predetermined date, and at a set time, or after a predetermined number of days have passed, or when a sale is detected. In addition, the HAPPIE home unit 103 may be configured to time purchased on certain days that discounts are given, for example, such as senior day at participating supermarkets that offer discounts to seniors on certain days.

In an advantageous embodiment, the HAPPIE home unit 103 includes a smart medicine cabinet coupled to sensors for medicine 154 that function similarly to the smart pantry 119 and smart pantry module 500, and the smart refrigerator 115 and smart refrigerator module 514, in communication with the caregiver portal 101. An example of a smart medicine cabinet is disclosed in US patent application publication No. US 2011/0187549 A1, to Balasingam, entitled SMART MEDICINE CABINET, which is incorporated herein by reference.

The smart medicine cabinet tracks medicine to make sure that the resident is taking medicine as prescribed, and the information concerning the resident's medication is stored on the database 108. In a preferred embodiment, multiple redundant inventory control methods for the smart medicine cabinet are used. Video cameras 112 may be provided inside the smart medicine cabinet, and a comparison of images of the medicine in inventory may be made between images taken prior to the resident taking his or her daily medication, and images taken after the medicine is taken. The smart medicine cabinet may analyze the image of each medicine to determine the identity of the item, or alternatively, stickers containing readable codes uniquely identifying each medicine may be affixed to each bottle or container of medicine. In addition, a sensor-based system using sensors 154 is provided, where the medicine is stored in dosage containers or in medicine bottle placed on pressure and weight sensitive pads 154 provided in the smart medicine cabinet. Medication storage maps may be utilized to designate specific locations for specific corresponding medications, in order to assist in the identification of the corresponding medication with the corresponding or associated sensors 154. A caregiver or the resident can also manually scan items in inventory with a bar code scanner. Information for refilling prescriptions may be stored in the database 108 for use to generate alerts concerning prescription refills in the HAPPIE home unit 103. Once minimum values are met, the HAPPIE home unit 103 will reach out to the caregiver via the caregiver portal 101, or directly to the appropriate doctor via the doctor portal 102, with notices concerning needed prescription refills.

Video images of medication inventories taken by the cameras 112 in the smart medicine cabinet are stored within the database 108 provided for the HAPPIE home unit 103. In addition, metadata is stored associated with each video image, including the time that the image was taken, and location information associating the field of view in the video image with one or more corresponding medication storage maps.

The smart medicine cabinet may be activated by a door sensor and/or motion detectors which provide a signal to the HAPPIE home unit 103 indicating that the smart medicine cabinet has been accessed. The HAPPIE home unit 103 may verify a schedule for medication stored in the database 108 to determine whether scheduled medication is due, or whether the smart medicine cabinet is being accessed for unscheduled medication. The HAPPIE home unit 103 will play an audio prompt for the resident when the smart medicine cabinet is accessed. If the smart medicine cabinet is accessed at a time when scheduled medication is due to be taken, the HAPPIE home unit 103 will play an audio prompt over speakers 157 listing the medicine that is due to be taken as a reminder to the resident. If the smart medicine cabinet is accessed at a time when scheduled medication is due to be taken, the HAPPIE home unit 103 will play an audio prompt over speakers 157 inquiring about the resident's health and the reason for accessing the smart medicine cabinet. The response from the resident is received via speakers 157 and analyzed and stored in the database 108. For example, if the resident is accessing the smart medicine cabinet for aspirin for a headache, the HAPPIE home unit 103 will store such information concerning the resident's medical history, and if relevant, will make such information stored on the database 108 available to a caregiver or doctor.

New images are taken of the inventory items in the smart medicine cabinet after the smart medicine cabinet is accessed. Data derived from that image capture may be compared with the data derived from previous images stored in the database 108 to make a determination of what medicine was taken, and when, and the inventory concerning medicine that is stored in the database 108 is updated accordingly. In one embodiment, a new video image is taken by video cameras 112 within the smart medicine cabinet after a predetermined delay in time, for example, after 15 minutes. The before and after images are compared, and the comparison identifies what medicine was accessed and taken by the resident.

In addition, weight sensitive pads 154 associated with each medicine or with each set dosage container provide a signal to the smart medicine cabinet to indicate that a particular medicine has been removed from the smart medicine cabinet. The weight changes are compared to data stored in the database 108 associated with one or more corresponding medicine storage maps to make a determination concerning which medicine was removed from the smart medicine cabinet. Both video images and sensors 154 are used in a preferred embodiment.

The HAPPIE home unit 103 is preferably configured to verbally verify the medicine taken from the smart medicine cabinet. For example, the HAPPIE home unit 103 may use a speech synthesizer, or may retrieve a voice recording from the database 108, and play the audio over speakers 157. The HAPPIE home unit 103 may ask, for example, "Did you take your prescribed dose of aspirin?" The resident, or alternatively a caregiver, may respond in a normal speaking voice, which is picked up by microphones 113. The HAPPIE home unit 103 may record the response in the database 108, and preferably, a speech recognition module is used to analyze the response.

The HAPPIE home unit 103 stores in the database 108 the amount of each medication on hand, and the prescribed times and dosage for each medicine. The HAPPIE home unit 103 automatically updates the information stored in the database 108 as each dose is taken by the resident.

Under circumstances where a caregiver is not present at the residence, the caregiver can optionally receive alerts at the caregiver portal 101 each time the resident takes any medication, or accesses the smart medicine cabinet. In addition, the caregiver receive alerts at the caregiver portal 101 when any prescribed medication is not taken when due, or if any medicine is taken incorrectly, either at the wrong time or in the wrong amount.

At any time a caregiver or the resident can request the HAPPIE home unit 103 to display the current amount of each medicine in the smart medicine cabinet and the schedule for taking medication. In the case of the caregiver, this may be displayed on the caregiver's portal 101. In the case of the resident, this may be displayed on the resident's TV or video monitor 156.

Some medications may be assigned expiration dates. If a medicine in inventory is not taken before the expiration date, the HAPPIE home unit 103 will notify the resident and/or a caregiver that the medication has expired and must be discarded from the smart medicine cabinet.

Two different embodiments of a front door for a smart medicine cabinet are described below in connection with FIG. 58 and FIG. 59. Either embodiment may be used in accordance with the present invention. The two described embodiments feature different information display capabilities, but are otherwise operationally the same.

Figure 58:
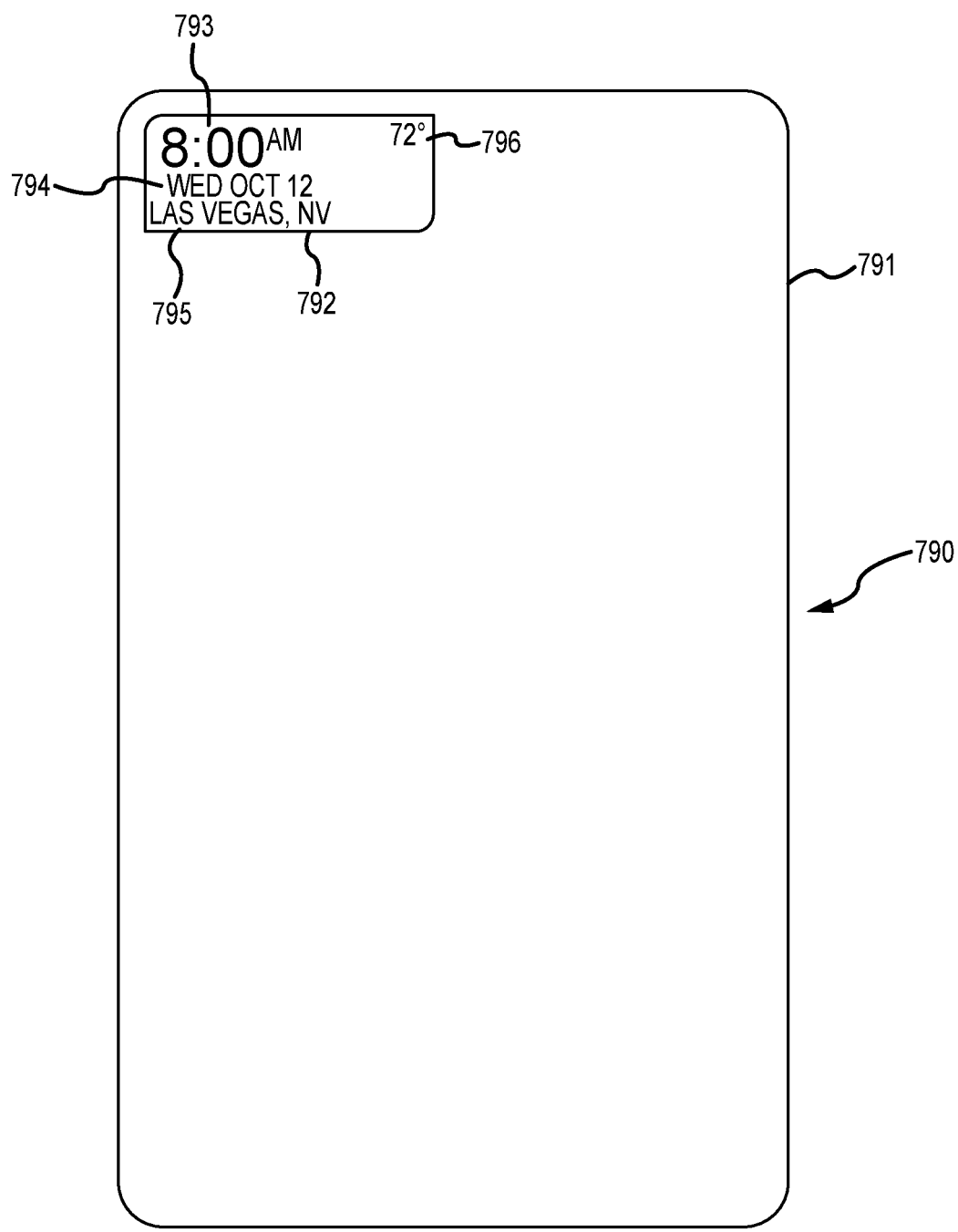
FIG. 58 is a front view illustrating one embodiment of a door for a smart medicine cabinet.

FIG. 58 illustrates a first embodiment of a door 791 for a smart medicine cabinet 790. In the example illustrated in FIG. 58, the exterior surface of the door 791 of the smart medicine cabinet 790 is reflective like a standard mirror when the door 791 is closed. The smart medicine cabinet 790 is connected to the HAPPIE home unit 103. The door 791 may include a display area 792 displaying the local time 793, the date 794, and the location 795. The display area 792 can also include a display of the temperature 796.

Figure 59:
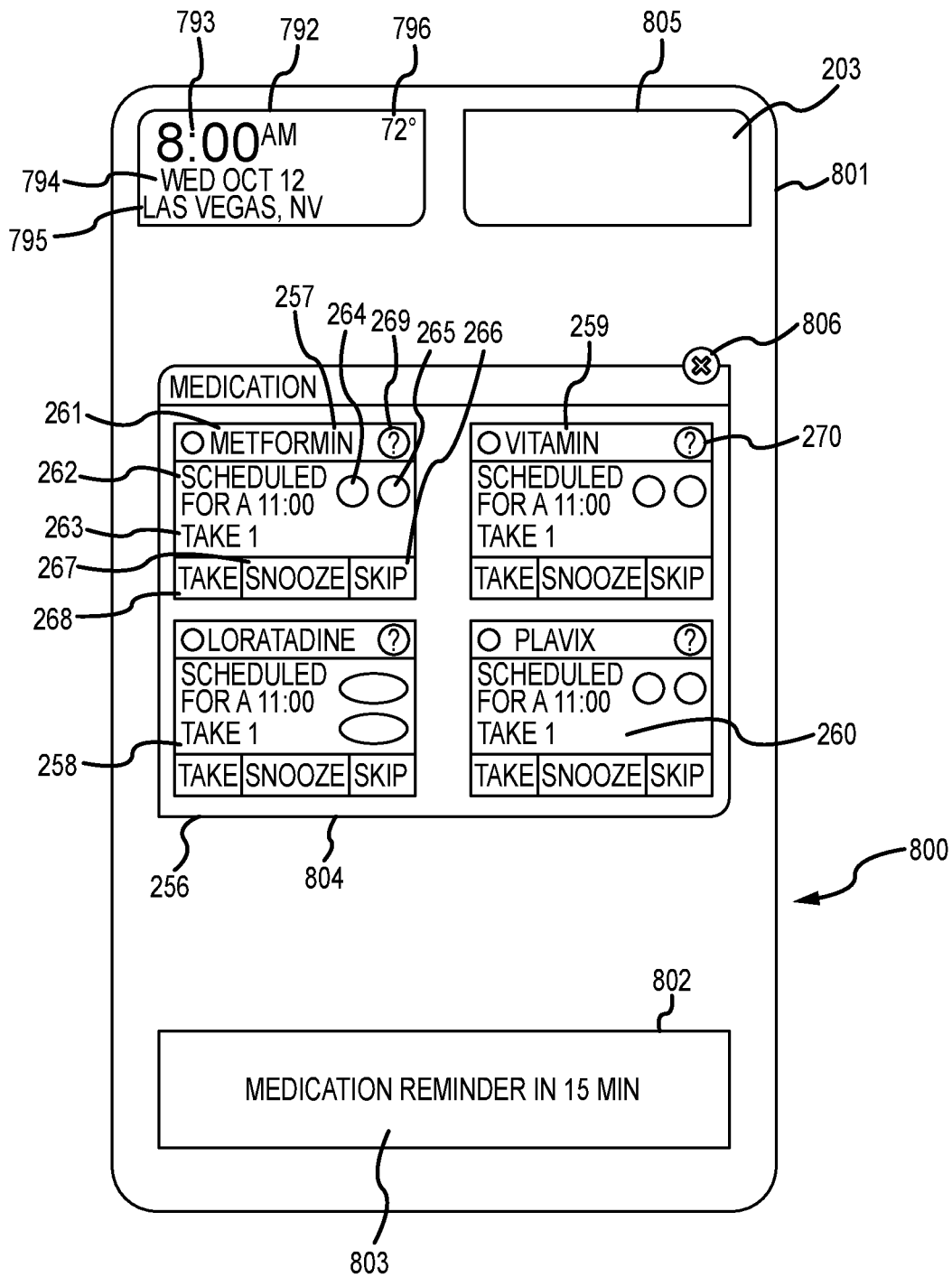
FIG. 59 is a front view illustrating a second embodiment of a door for a smart medicine cabinet.

FIG. 59 illustrates a second embodiment of a door 801 for a smart medicine cabinet 800. The operation of the display area 792 is the same as described in connection with the first example illustrated in FIG. 58. However, the door 801 shown in FIG. 59 also includes a message display area 802 in which text messages 803 may be displayed by the HAPPIE home unit 103 concerning scheduled medication. In the illustrated example shown in FIG. 59, in the message display area 802 the HAPPIE home unit 103 is displaying a scrolling message 803 as follows: "Medication reminder in 15 min". Alternatively, the message display area 802 on the door 801 of the smart medicine cabinet 800 may display the message shown in FIG. 14, which would be simultaneously displayed on the TV or video monitors 156 for the HAPPIE home unit 103 in this example.

The door 801 of a smart medicine cabinet 800 shown in FIG. 59 has a second display area 805 that may be used to display the active medication module 203 shown in FIG. 8. The door 801 also includes a third display area 804 that duplicates the same image displayed on the TV or video monitors 156 for the HAPPIE home unit 103. In the example shown in FIG. 59, in which the medication module 203 is active, the third display area 804 displays similar information to that shown in FIG. 15 that is simultaneously displayed on the TV or video monitors 156 for the HAPPIE home unit 103, although certain information may be rearranged in the third display area 804 as shown in the illustrated example. The third display area 804 is operative to display any of the information that is displayed on the TV or video monitors 156 for the HAPPIE home unit 103, for example, such as the displays illustrated in FIG. 16, FIG. 17, and FIG. 18. For example, images of the correct medicine container 272 corresponding to the medication that is scheduled to be taken will appear in the third display area 804, similar to the example shown FIG. 16. The door 801 of the smart medicine cabinet 800 is preferably a touch screen, and can communicate data to the HAPPIE home unit 103 in response to the resident touching predetermined areas of the display area 804, for example, in response to the resident touching the skip button 266, the snooze button 267, or the take button 268, respectively.

In addition, the second display area 805 may also be used to display the calendar module 202, the smart home module 205, the wellness module 204, or any of the other modules available to the HAPPIE home unit 103, and the third display area 804 will similarly display the corresponding information associated with the respective active module similar to what would be concurrently displayed on the video monitors or TV 156. In an embodiment employing a touch screen for the door 801, the resident may touch the second display area 805 to alternatively scroll through successive modules 202, 203, 204, 205 to selectively display on the door 801 information associated with the respective modules 202, 203, 204, 205, or any other module available on the HAPPIE home unit 103.

Thus, in both embodiments illustrated in FIG. 58 and FIG. 59, the door 801 and 791 of the smart medicine cabinet 800 doubles as a display and monitor 156 visually displaying information communicated from the HAPPIE home unit 103 and the resident. The message area 802 shown in FIG. 59 may be used to display any appropriate message, alert, calendar reminder, incoming email, or other information from the HAPPIE home unit 103. All messaging from the HAPPIE home unit 103 that may be displayed on the video monitors or TV 156 can be replicated and displayed on the door 801 of the smart medicine cabinet 800.

When it is time for the resident to take scheduled medication, the HAPPIE home unit 103 sends a message to the smart medicine cabinet 790. At this point, the interior of the smart medicine cabinet 790 is illuminated, and the door 791 appears transparent, revealing illuminated medication containers inside the smart medicine cabinet 790. In a preferred embodiment, the door 791 becomes transparent when it is time to take a scheduled medication. The illuminated medication containers inside the smart medicine cabinet 790 can be seen through the door 791 without opening the door 791.

An optional remote locking mechanism may be provided for the door 801 or the door 791. The operation of the remote locking mechanism is the same for both the door 801 and the door 791, and for convenience, will only be henceforth described with respect to door 801, it being understood that the description is equally applicable to door 791. The remote locking mechanism may be selectively activated by the HAPPIE home unit 103 to lock or unlock the door 801 of the smart medicine cabinet 800. The HAPPIE home unit 103 may be configured to unlock the door 801 of the smart medicine cabinet 800 only at specific time intervals that coincide with a predetermined medication schedule established by the caregiver or a medical professional. The caregiver may establish the predetermined medication schedule remotely, and transmit the predetermined medication schedule to the HAPPIE home unit 103 via the caregiver portal 101. The caregiver may selectively activate the door 801 remotely via the caregiver portal 101. Similarly, a medical professional may establish the predetermined medication schedule remotely, and transmit the predetermined medication schedule to the HAPPIE home unit 103 via the doctor portal 102. The HAPPIE home unit 103 may be configured to permit the medical professional to selectively activate the door 801 of the smart medicine cabinet 800 remotely via the doctor portal 102. The provision of a remotely controllable locking mechanism on the door 801 of the smart medicine cabinet 800 may be used to reduce unauthorized access to controlled substances and opioids which may be stored in the smart medicine cabinet 800.

Wide-angel video cameras 112 are mounted in the smart medicine cabinet. The video cameras 112 offer a security feature, because the video cameras 112 record a 3D image of the person accessing the medications in the smart medicine cabinet 800. Facial recognition technology built into HAPPIE Home unit 103 will verify that the resident, who was prescribed the medications, is the person who is actually taking the medication. Access by an unauthorized person will result in the logic and computing unit 121 capturing a 3D map of that person's facial features and storing the captured data for that 3D map in the database 108 for identification at a later time.

An optional locking mechanism built into the smart medicine cabinet door, and hinges may be pre-programed to unlock the smart medicine cabinet 800 at specific time intervals that coincide with the medication monitoring schedule established by the caregiver or medical professional. This feature helps reduce unauthorized access to controlled substances and opioids.

A power supply 1300 is mounted to the rear, exterior of the smart medicine cabinet 800. It powers the front door monitor display, pressure sensitive pads, lights, optional locking mechanism and communication protocols. The smart medicine cabinet 800 establishes two-way communication with the HAPPIE Hone unit 103 via WiFi, Bluetooth or a hard line (CAT-5) connection.

Figure 60:
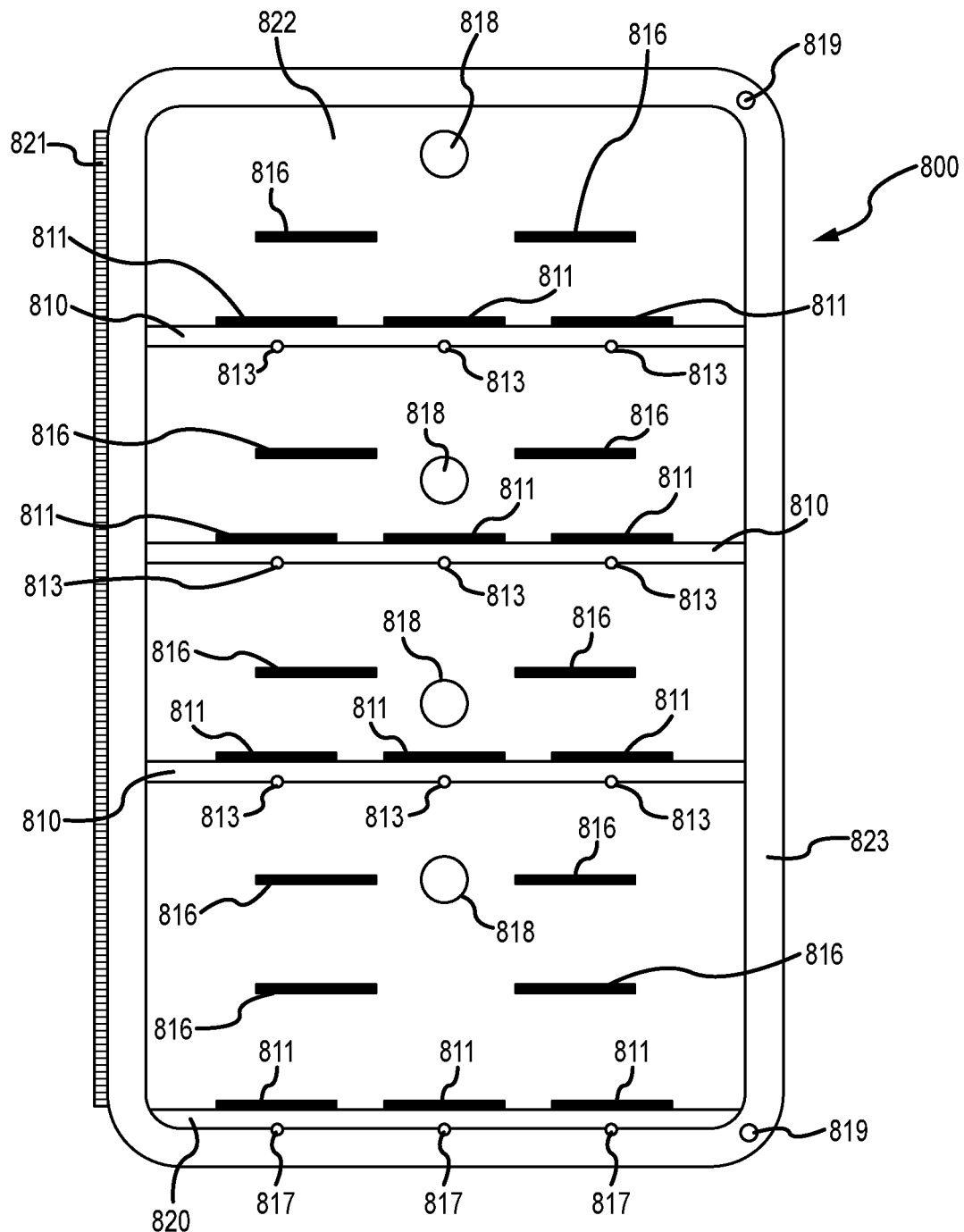
FIG. 60 is a front view of the interior of the smart medicine cabinet according to FIG. 59 with the door open.

FIG. 60 is a front view of the interior of the smart medicine cabinet 800.

Figure 61:
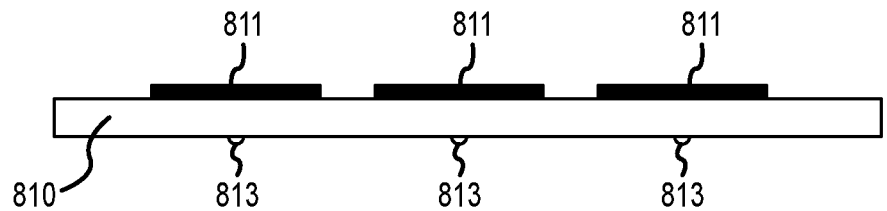
FIG. 61 is a front view of a shelf of the smart medicine cabinet according to FIG. 60.

FIG. 61 is a front view of a shelf 810 in the smart medicine cabinet 800. The shelf 810 has a plurality of pressure sensitive pads 811 adapted to receive containers of medicine. The pressure sensitive pads 811 may also include weight sensors 158 capable of precisely weighing a dose of medication. Referring to the top view of the shelf 810 shown in FIG. 62, a light ring 812 is provided around each pressure sensitive pad 811. When the resident is scheduled to take a particular medication, the light ring 812 corresponding to the correct medicine selectively illuminates under the corresponding medicine container, and around the pressure sensitive pad 811 corresponding to the correct medicine container, that is to be taken at the predetermined scheduled time. The pressure sensitive pad 811 is sensitive enough to detect the difference in the weight of the corresponding medicine container before the resident takes a predetermined dose of medicine, and the weight of the corresponding medicine container after the resident takes a predetermined dose of medicine.

Figure 64:
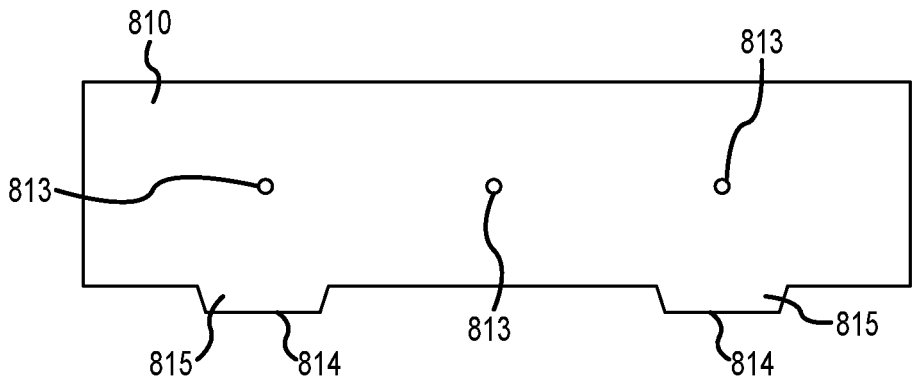
FIG. 64 is a bottom view of the shelf of the smart medicine cabinet shown in FIG. 61.

Referring to the bottom view of the shelf 810 shown in FIG. 64, a plurality of small lights 813 are mounted to the underside of the shelf 810. The small lights 813 may also be used to illuminate the interior of the smart medicine cabinet 800, and may be used to identify medications in non-standard containers, such as ointments, salves, drops, syrups, syringes, or inhalers. One of the small lights 813 may be selectively activated by the computational and logic unit 121 of the HAPPIE home system 103 to selectively illuminate the medicine container, on a second shelf immediately below the first shelf 810 containing the small light 813, which container corresponds to the correct medicine container that contains a dose of medicine that is to be taken by the resident at a predetermined scheduled time.

Figure 62:
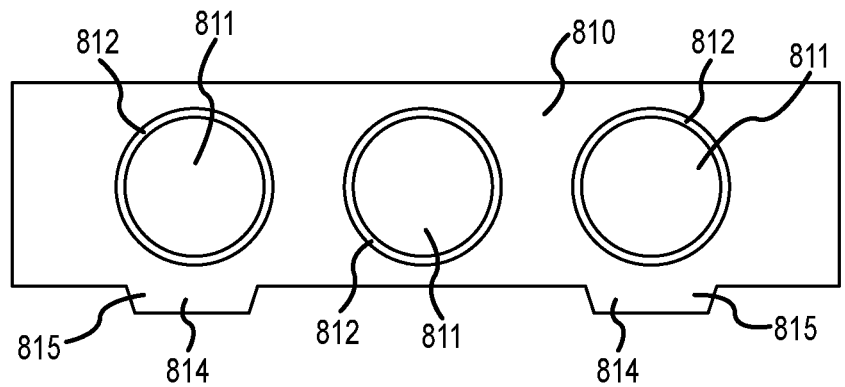
FIG. 62 is a top view of the shelf of the smart medicine cabinet shown in FIG. 61.

Referring to the top view of the shelf 810 shown in FIG. 62, each shelf 810 has one or more tabs 815 that extend to the interior rear wall of the smart medicine cabinet 800. Referring to the rear view of the shelf 810 shown in FIG. 63, at least one tab 815 on a shelf 810 is provided with a power & communication port 814. The power & communication port 814 provides a power port for electrical power to be provided to the pressure sensitive pads 811, the light rings 812, and the small lights 813. The power & communication port 814 also provides a communication port for data from the pressure sensitive pads 811 to be transmitted to the HAPPIE home unit 103, either by a hardwired network cable such as a CAT5 cable, or by a wireless connection such as a WiFi connection to the WiFi hotspot 109, or via a Bluetooth connection, or any other suitable connection capable of conveying information from the pressure sensitive pads 811 to the HAPPIE home unit 103. The power & communication port 814 may take the form of a USB port.

Referring to FIG. 60, each shelf 810 is preferably adjustable, and may be positioned in any one of a plurality of predetermined shelf positions. Each predetermined shelf position has one or more power & communication ports 816 corresponding to power & communication ports 814 on the associated shelf 810. A power & communication port 816 connects to and supplies electrical power to a corresponding power & communication port 814 on the shelf 810. The power & communication port 816 also supplies data communication through the corresponding power & communication port 814 on the shelf 810.

In the illustrated example, a bottom shelf 820 is provided. The bottom shelf 820 need not be adjustable. In the case of the bottom shelf 820, bottom lights 817 are provided on the front edge of the bottom shelf 820. The pressure sensitive pads 811 and corresponding light rings 812 provided on the bottom shelf 812 are the same as the pressure sensitive pads 811 and corresponding light rings 812 provided on shelf 810. A hardwired power connection may be provided for the bottom lights 817, the pressure sensitive pads 811, and the corresponding light rings 812 on the bottom shelf 820. A hard-wired communication circuit may be provided on the bottom shelf 820 with the pressure sensitive pads 811, since the bottom shelf 820 does not need to be adjustable.

A plurality of wide-angle video cameras 818 are mounted in the back panel 822 of the smart medicine cabinet 800. The wide-angle video cameras 818 may be used to image the contents of the smart medicine cabinet 800, and the images used by the HAPPIE home unit 103 to identify the medicines that are in inventory in the smart medicine cabinet 800. The wide-angle video cameras 818 also offer a security feature as well. The wide-angle video cameras 818 may be used to take an image of the person accessing the medications. Facial recognition technology provided in HAPPIE home unit 103 can be employed to verify that the resident, who was prescribed the medications, is the person actually taking the medication. Access by an unauthorized person will result in the HAPPIE home unit 103 capturing a map of that person's facial features and storing the map in the database 108 for identification at a later time.

Referring to FIG. 60, contacts 819 are provided in the sidewalls 823 of the smart medicine cabinet 800 to sense when the door 801 is opened. Data from the contacts 819 may be communicated to the HAPPIE home unit 103. A hinge 821 is provided for mounting the door 801.

During operation, medication containers are illuminated by small lights 813, bottom lights 817, and light rings 812. The wide-angle video cameras 818 record all activity inside the smart medicine cabinet 800, and the video data from those wide-angle video cameras 818 is stored in the database 108. The pressure sensitive pads 811 operate to weigh and record the difference in the weight of a medicine container before and after medicine has been taken, and the associated data is recorded in the database 108.

Figure 65:
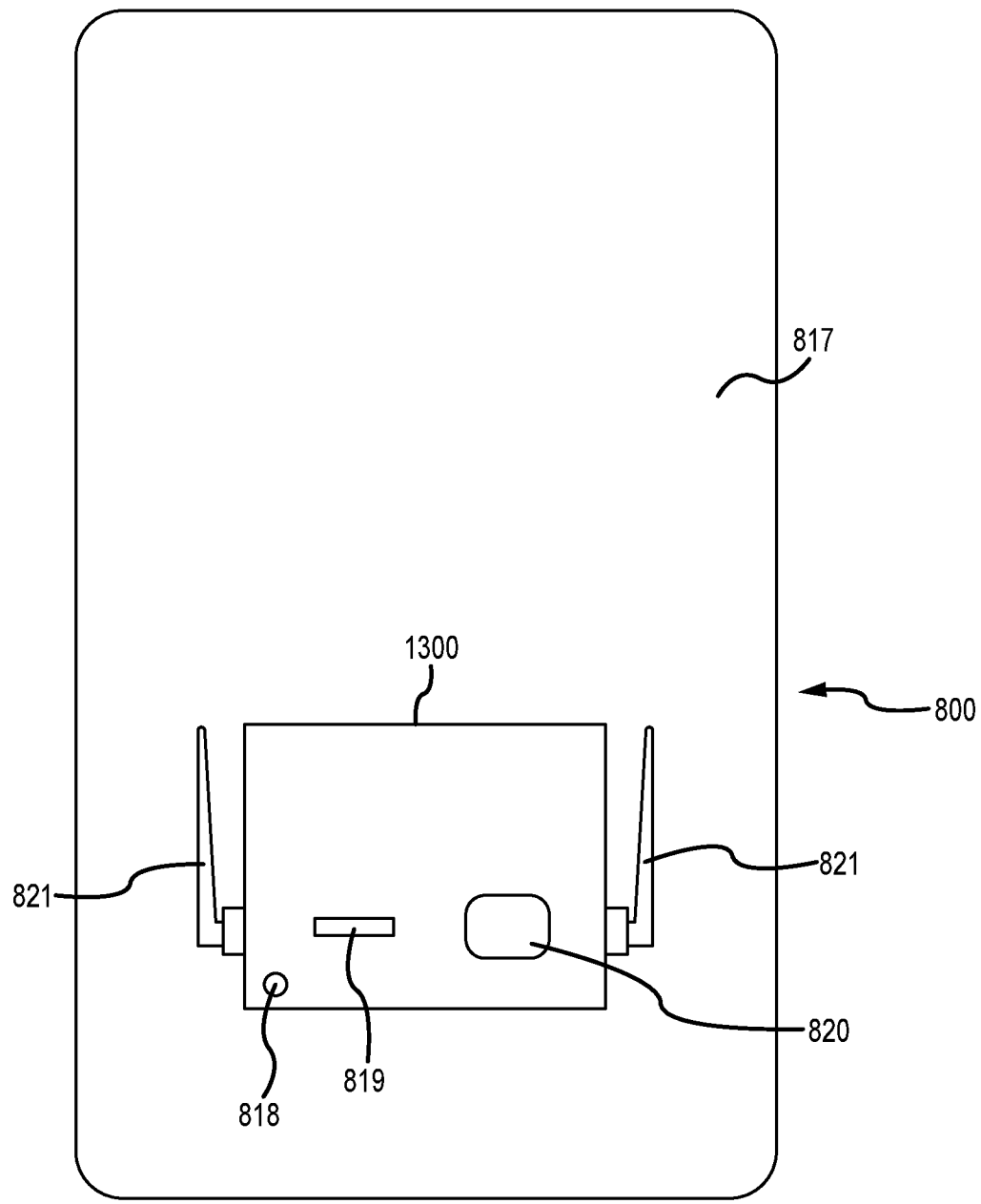
FIG. 65 is a rear view of the smart medicine cabinet shown in FIG. 60.

FIG. 65 shows a rear view of the smart medicine cabinet 800. A power supply 1300 is mounted to the rear exterior wall 817 of the smart medicine cabinet 800. The power supply 816 preferably includes a power connection 818 to conventional household AC power. The power supply 816 provides electrical power to the front door 801 to power the display 792, 802, 804, and 805 provided on the door 801. The power supply 816 provides electrical power to the pressure sensitive pads 811, light rings 811, small lights 813, power & communication ports 814, and in the event the door 801 is provided with a locking mechanism, to that locking mechanism.

Referring to FIG. 65, a USB port 819 may be provided for communication between the HAPPIE home unit 103 and the smart medicine cabinet 800. A network connection 820, such as a CAT5 port, may also be provided for communication between the HAPPIE home unit 103 and the smart medicine cabinet 800. Alternatively, the smart medicine cabinet 800 may have antennas 821 for wireless communication, such as WiFi communication, to the HAPPIE home unit 103 via WiFi hotspot 109 or any alternative wireless connection. The smart medicine cabinet 800 may establish two-way communicate with the HAPPIE home unit 103 via WiFi using antennas 821, or via a hard line (CAT-5) connection plugged into port 820, or via Bluetooth.

As discussed above, the medication accessing experience is the same between the first embodiment of the door 791 and the second embodiment of the door 801.

In an alternative embodiment, intelligence is built into the smart medicine cabinet 800 to allow micro-scale measurements and adjustments for medication dosage. In this alternative embodiment, the HAPPIE Home computational and logic unit 121 is connected to temperature and humidity sensors 149, and also may be connected to atmospheric pressure sensors to provide data that may be used in connection with weight and dosage measurements by weight sensors 154 associated with the smart medicine cabinet 800 that are used to measure each dose of medication before it is taken by the resident, or to measure the remaining number of pills, capsules, or medication remaining in the smart medicine cabinet 800 for each respective medication. With data from temperature, humidity, and atmospheric pressure sensors, the HAPPIE Home computational and logic unit 121 may perform calculations to adjust measurements of medication doses for variations in temperature, humidity, and atmospheric pressure, in order to automatically compensate for these factors. In addition, the HAPPIE Home computational and logic unit 121 is also connected to a GPS unit, or Global Positioning System receiver, that provides positional data such as latitude, longitude, and altitude for the resident's location, or such data may be input into the database 108 during an initial configuration of the system, since is it unlikely to change unless the resident moves to a new home. The HAPPIE Home computational and logic unit 121 may also perform calculations to adjust measurements of medication doses for any impact that latitude, longitude, and altitude may have upon dosage measurements. For example, differences in altitude may impact precise weight measurements, and if a medication dose is prescribed by weight, adjustments may be made based upon the altitude of the resident's home, if necessary. One additional advantage of having a GPS unit connected to the system is that it may also provide accurate time calibration for the system clock.

Figure 57:
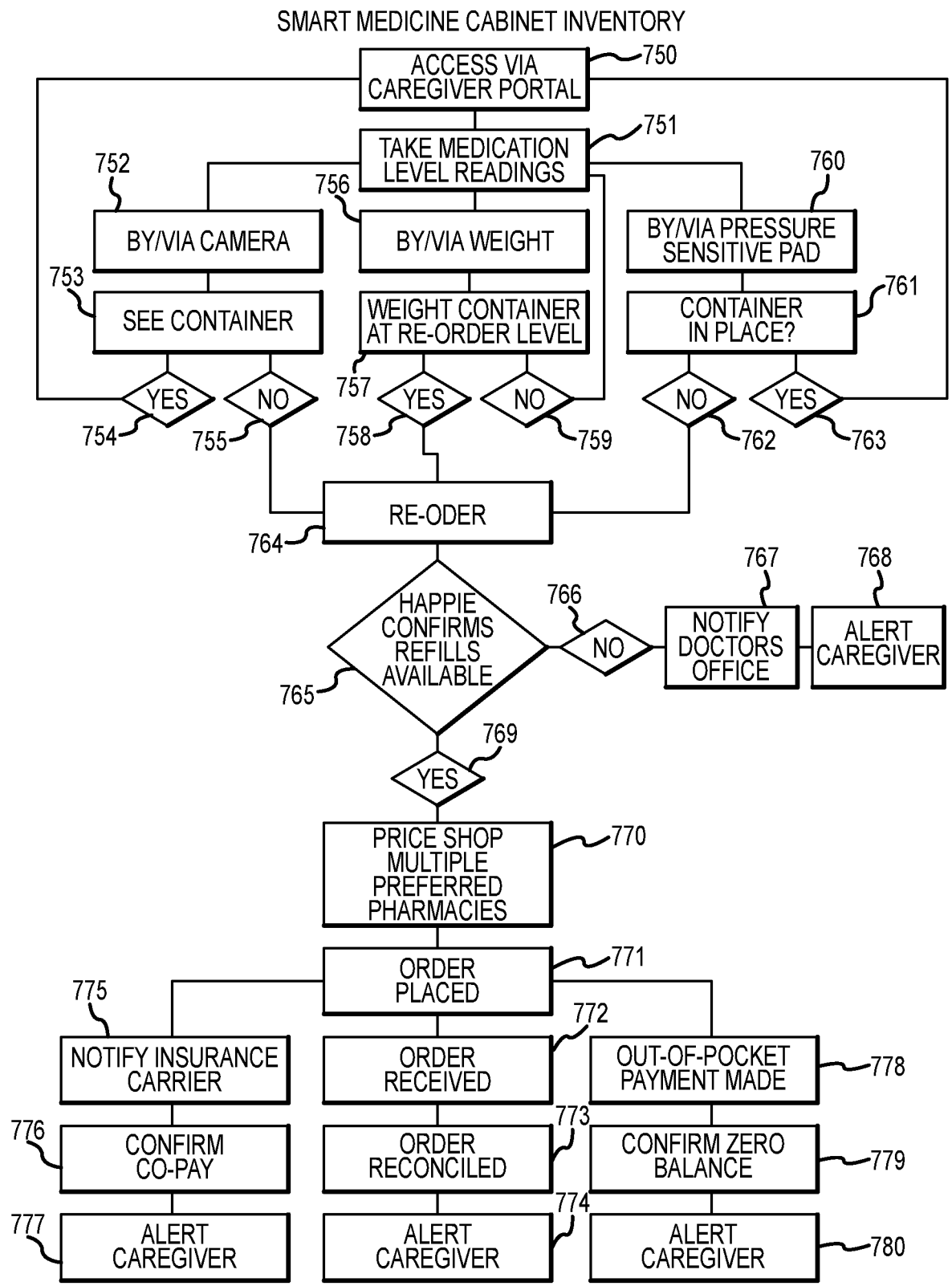
FIG. 57 is a flowchart illustrating the operation of a smart medicine cabinet for inventory.

FIG. 57 is a flowchart illustrating the operation of a smart medicine cabinet in accordance with one embodiment of the invention. In step 750, the smart medicine cabinet 800 can be accessed from the caregiver portal 101, for example, in order to take inventory concerning the contents of the smart medicine cabinet 800. In step 751, medication level readings may be requested, using cameras 818 provided in the smart medicine cabinet 800, using the pressure sensitive pads 811 in the smart medicine cabinet 800, and using other sensors 130 in the smart medicine cabinet 800, such as weight sensors 154. In step 752, one or more video cameras 818 in the smart medicine cabinet 800 may be used to image the medicine present in inventory, and to identify each medicine based upon images of the medicine in step 753. For each medicine, if the medicine is visible and can be identified as being in inventory in step 754, the method may loop back to step 750. If the required medicine is not located in step 755, the HAPPIE home unit 103 may re-order a refill in step 764.

In the case of some types of medicine, it may be desirable to inventory the medicine using weight sensitive sensors 154, as indicated in step 765 in FIG. 57. In step 757, a determination is made whether the medicine is at a weight sensed by the sensor 154 that is indicative of a re-order level. If the weight indicates in step 758 that the medicine needs to be re-ordered, then the HAPPIE home unit 103 may re-order a refill in step 764. If the weight sensed by sensor 154 indicates that the medicine container is sufficiently full and is not at the re-order level, as indicated in step 759, the method loops back to step 751, as shown in FIG. 57.

Referring to FIG. 57, in the case of some types of medicine, it may be desirable to inventory the medicine in the smart medicine cabinet 800 using an associated pressure sensitive pad 811, as indicated in step 760. In step 761, a determination is made concerning whether the pressure sensitive pad 811 indicates that the medicine container is in place. If the container is detected by the pressure sensitive pad 811, as indicated in step 763, the method loops back to step 750. If the container is not detected by the pressure sensitive pad 811, as indicated in step 762, the method proceeds to step 764, and the HAPPIE home unit 103 may re-order a refill.

When a refill for a medicine is ordered in step 764 shown in FIG. 57, the HAPPIE home unit 103 then determines in step 765 whether a refill is available. If a refill is not available, the HAPPIE home unit 103 notifies the doctor's office in step 767, and in step 768, alerts the caregiver via the caregiver portal 101. If a refill in available, as indicated in step 769, the HAPPIE home unit 103 proceeds to step 770 to find the best available price for the needed medicine.

Referring to FIG. 57, in step 771, an order is placed for the medicine. When the order is received in step 772, the order is automatically reconciled in step 773 by the HAPPIE home unit 103, and in step 774 the caregiver is alerted via the caregiver portal 101. When the order for medicine is placed in step 771, the HAPPIE home unit 103 also transmits a notification to the relevant insurance carrier in step 775. The HAPPIE home unit 103 verifies the co-pay terms and conditions in step 776, and in step 777 alerts the caregiver via the caregiver portal 101. When the order for medicine is placed in step 771, the HAPPIE home unit 103 may also make any payment required in step 778. In the event that funds are not available in step 778 to make a required payment, the HAPPIE home unit 103 confirms the absence of funds in step 779, and in step 780, alerts the caregiver via the caregiver portal 101.

Figure 66:
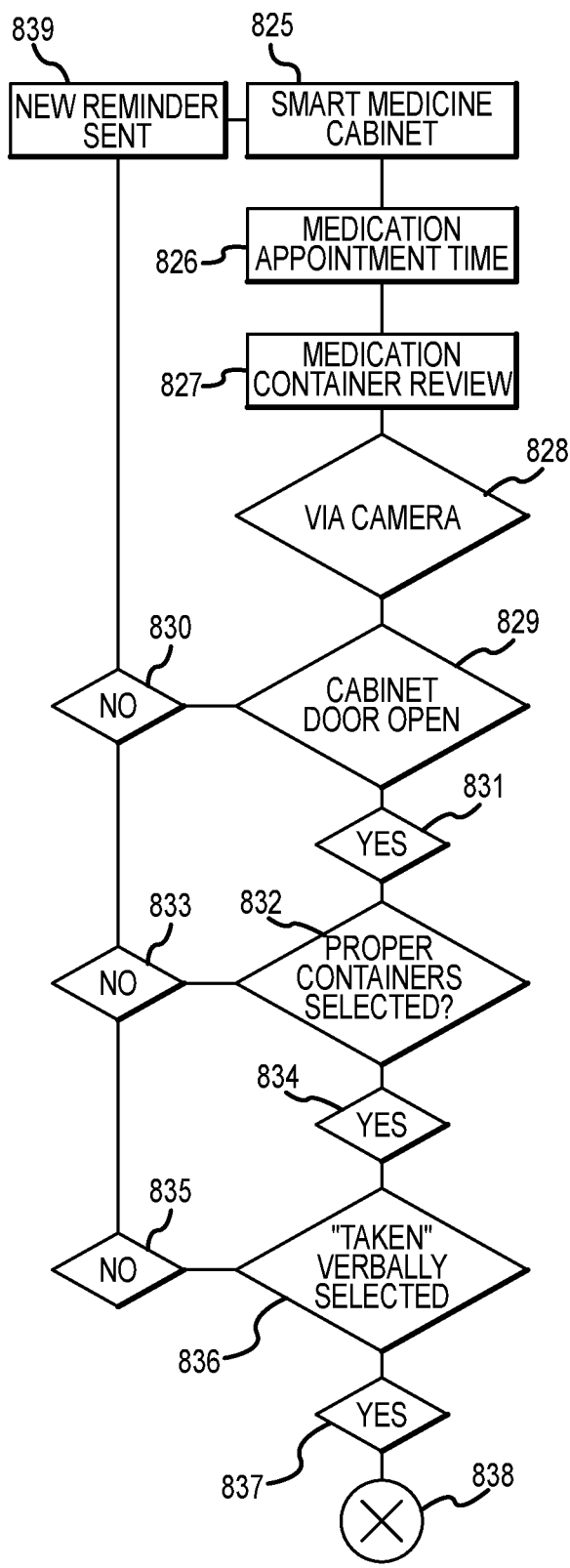
FIG. 66 is a flowchart illustrating the operation of a smart medicine cabinet for scheduled medication.

FIG. 66 is a flowchart illustrating a method of operation of a smart medicine cabinet 800 for scheduled medication. The illustrated method starts in step 825 by the HAPPIE home unit 103 establishing a connection with the smart medicine cabinet 800. In step 826, the HAPPIE home unit 103 determines that the time has arrived for scheduled medication to be taken by the resident. In step 827, the HAPPIE home unit 103 accesses information stored in the database 108 concerning the scheduled medication. In step 828, the HAPPIE home unit 103 uses video cameras 818 to image the contents of the smart medicine cabinet 800, and specifically to selectively image the medicine container that contains the scheduled dose of medicine to be taken by the resident.

In step 819, a determination is made whether the door 801 of the smart medicine cabinet 800 has been opened by the resident. Contacts 819 may be used by the HAPPIE home unit 103 to sense whether the door 801 has been opened. If after a predetermined delay or wait time the door 801 has not been opened, as indicated in step 830, the method loops back to step 839, and the HAPPIE home unit 103 sends a new reminder to the resident concerning the scheduled dose of medicine.

If a determination is made in step 829 that the door 801 of the smart medicine cabinet 800 has been opened, as indicated in step 831, the method proceeds to step 832 to determine whether the proper medicine container has been selected by the resident. The smart medicine cabinet 800 preferably spotlights the correct medicine container by selectively illuminating the corresponding small light 813, ring light 812, or bottom light 817 for the correct medicine container. If the resident does not select the proper medicine container, as indicated in step 833, the method may loop back to step 839 for the HAPPIE home unit 103 to remind the resident to take the predetermined dose of scheduled medicine. Alternatively, and in addition to the method described in connection with FIG. 66, the HAPPIE home unit 103 may play a prompt over speakers 157 to alert the resident that he or she has not selected the correct medicine container. The HAPPIE home unit 103 may also signal the resident, for example, by flashing the small light 813, ring light 812, or bottom light 817 for the correct medicine container. If the resident does select the proper medicine container, as indicated in step 834, the method proceeds to step 836 to request a confirmation from the resident that the scheduled dose of medicine has been taken.

If verbal confirmation is received from the resident that the scheduled dose of medicine has been taken, as indicated in step 837, the method proceeds to step 838 and ends. In the illustrated example, if verbal confirmation is not received from the resident that the scheduled dose of medicine has been taken, as indicated in step 835, the method loops back to step 839. Alternatively, if verbal confirmation is not received from the resident that the scheduled dose of medicine has been taken, the HAPPIE home unit 103 may analyze video data from the video cameras 818 to determine whether the scheduled dose of medicine was taken.

Figure 67:
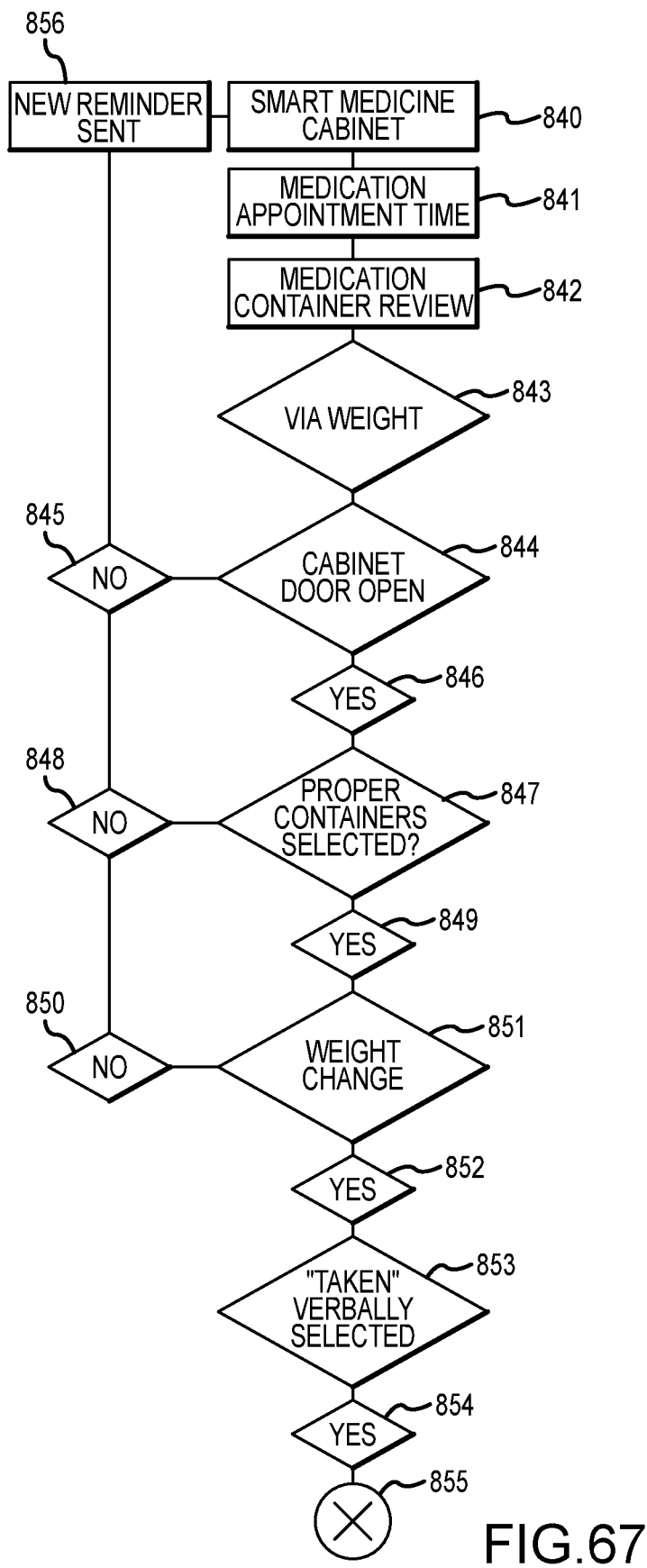
FIG. 67 is a flowchart illustrating the operation of a smart medicine cabinet for scheduled medication.

FIG. 67 is a flowchart illustrating a method of operation of the smart medicine cabinet 800 for scheduled medication. The illustrated method starts in step 840 by the HAPPIE home unit 103 establishing a connection with the smart medicine cabinet 800. In step 841, the HAPPIE home unit 103 determines that the time has arrived for scheduled medication to be taken by the resident. In step 842, the HAPPIE home unit 103 accesses information stored in the database 108 concerning the scheduled medication. In step 843, the HAPPIE home unit 103 uses weight sensors 130 to weigh the medicine containers in the smart medicine cabinet 800, and specifically to selectively weigh the medicine container that contains the scheduled dose of medicine to be taken by the resident.

In step 844, a determination is made whether the door 801 of the smart medicine cabinet 800 has been opened by the resident. Contacts 819 may be used by the HAPPIE home unit 103 to sense whether the door 801 has been opened. If after a predetermined delay or wait time the door 801 has not been opened, as indicated in step 845, the method loops back to step 856, and the HAPPIE home unit 103 sends a new reminder to the resident concerning the scheduled dose of medicine.

If a determination is made in step 844 that the door 801 of the smart medicine cabinet 800 has been opened, as indicated in step 846, the method proceeds to step 847 to determine whether the proper medicine container has been selected by the resident. The smart medicine cabinet 800 preferably spotlights the correct medicine container by selectively illuminating the corresponding small light 813, ring light 812, or bottom light 817 for the correct medicine container. If the resident does not select the proper medicine container, as indicated in step 848, the method may loop back to step 856 for the HAPPIE home unit 103 to remind the resident to take the predetermined dose of scheduled medicine. Alternatively, and in addition to the method described in connection with FIG. 67, the HAPPIE home unit 103 may play a prompt over speakers 157 to alert the resident that he or she has not selected the correct medicine container. The HAPPIE home unit 103 may also signal the resident, for example, by flashing the small light 813, ring light 812, or bottom light 817 for the correct medicine container.

If the resident does select the proper medicine container, as indicated in step 849, the method proceeds to step 851 for the HAPPIE home unit 103 to compare the weight of the medicine container, as sensed by sensors 130, before the medicine container was selected by the resident, and after it was replaced by the resident, to determine whether there is a difference in weight that corresponds to the resident having removed the correct dose from the container. If there is no difference in weight, as indicated in step 850, the method loops back to step 856, and the HAPPIE home unit 103 sends a new reminder to the resident concerning the scheduled dose of medicine. If the correct difference in weight is detected, as indicated in step 852, the method proceeds to step 853 for a verbal confirmation from the resident that the scheduled dose of medicine was taken.

If verbal confirmation is received from the resident that the scheduled dose of medicine has been taken, as indicated in step 854, the method proceeds to step 855 and ends. Alternatively, if verbal confirmation is not received from the resident that the scheduled dose of medicine has been taken, the HAPPIE home unit 103 may send a message concerning the event to a caregiver via the caregiver portal 101.

Figure 68:
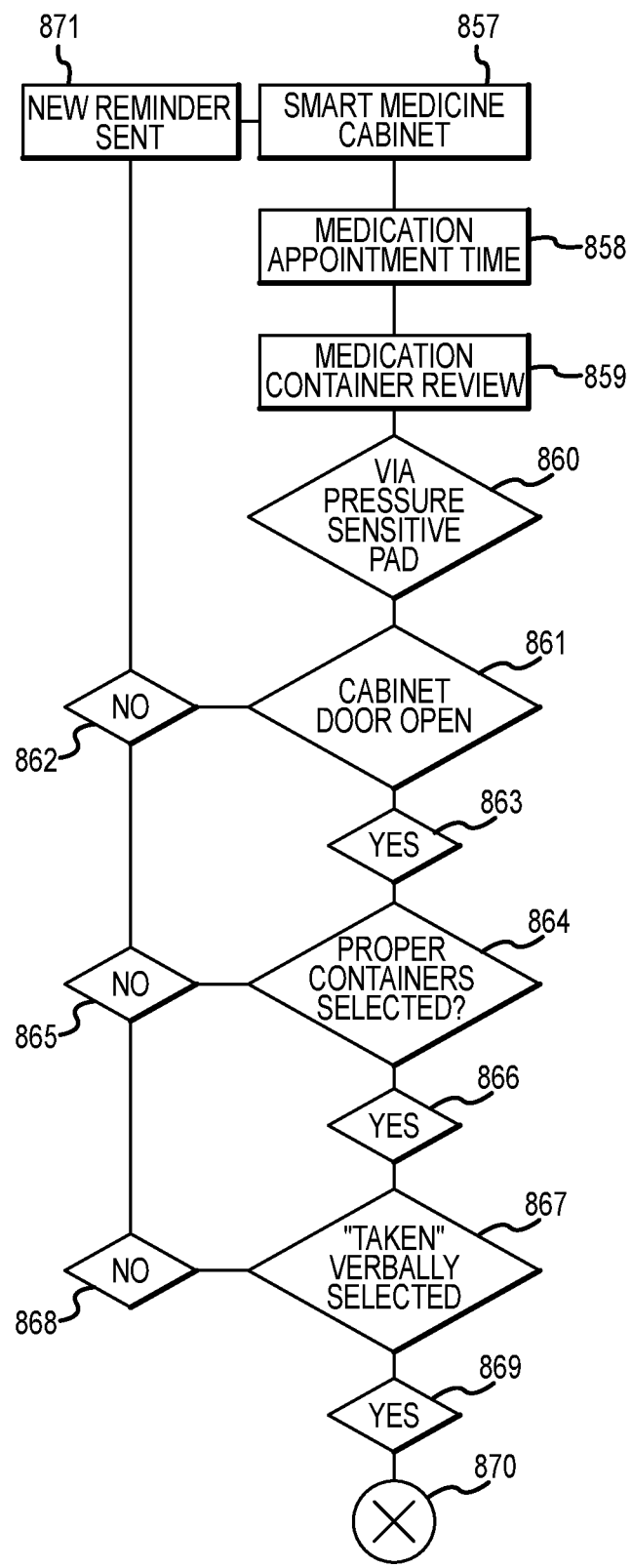
FIG. 68 is a flowchart illustrating the operation of a smart medicine cabinet for scheduled medication.

FIG. 68 is a flowchart illustrating a method of operation of the smart medicine cabinet 800 for scheduled medication. The illustrated method starts in step 857 when the HAPPIE home unit 103 establishes a connection with the smart medicine cabinet 800. In step 858, the HAPPIE home unit 103 determines that the time has arrived for scheduled medication to be taken by the resident. In step 859, the HAPPIE home unit 103 accesses information stored in the database 108 concerning the scheduled medication. In step 860, the HAPPIE home unit 103 uses the pressure sensitive pads 811 in the smart medicine cabinet 800 to selectively detect the medicine container that contains the scheduled dose of medicine to be taken by the resident.

In step 861, a determination is made whether the door 801 of the smart medicine cabinet 800 has been opened by the resident. As discussed above, contacts 819 may be used by the HAPPIE home unit 103 to sense whether the door 801 has been opened. If after a predetermined delay or wait time the door 801 has not been opened, as indicated in step 862, the method loops back to step 871, and the HAPPIE home unit 103 sends a new reminder to the resident concerning the scheduled dose of medicine.

If a determination is made in step 861 that the door 801 of the smart medicine cabinet 800 has been opened, as indicated in step 863, the method proceeds to step 864 to determine whether the proper medicine container has been selected by the resident. The smart medicine cabinet 800 preferably spotlights the correct medicine container by selectively illuminating the corresponding small light 813, ring light 812, or bottom light 817 for the correct medicine container. If the resident does not select the proper medicine container, as indicated in step 865, the method may loop back to step 871 for the HAPPIE home unit 103 to remind the resident to take the predetermined dose of scheduled medicine. Alternatively, and in addition to the method described in connection with FIG. 68, the HAPPIE home unit 103 may play a prompt over speakers 157 to alert the resident that he or she has not selected the correct medicine container. The HAPPIE home unit 103 may also signal the resident, for example, by flashing the small light 813, ring light 812, or bottom light 817 for the correct medicine container. If the resident does select the proper medicine container, as indicated in step 866, the method proceeds to step 867 to request a confirmation from the resident that the scheduled dose of medicine has been taken.

If verbal confirmation is received from the resident that the scheduled dose of medicine has been taken, as indicated in step 869, the method proceeds to step 870 and ends. In the illustrated example, if verbal confirmation is not received from the resident that the scheduled dose of medicine has been taken, as indicated in step 868, the method loops back to step 871. Alternatively, if verbal confirmation is not received from the resident that the scheduled dose of medicine has been taken, the HAPPIE home unit 103 may compare the weight of the medicine container, as sensed by pressure sensitive pads 811, before the medicine container was selected by the resident, and after it was replaced by the resident, to determine whether there is a difference in weight that corresponds to the resident having removed the correct dose from the container.

The methods described in connection with FIG. 66, FIG. 67, and FIG. 68, may be combined, and the HAPPIE home unit 103 may simultaneously use data from video cameras 818, from pressure sensitive pads 811, and from other sensors 130, to process a resident's access to the smart medicine cabinet 800 for scheduled medication, and to verify and confirm that the correct dose of the scheduled medication has been taken by the resident.

Figure 69:
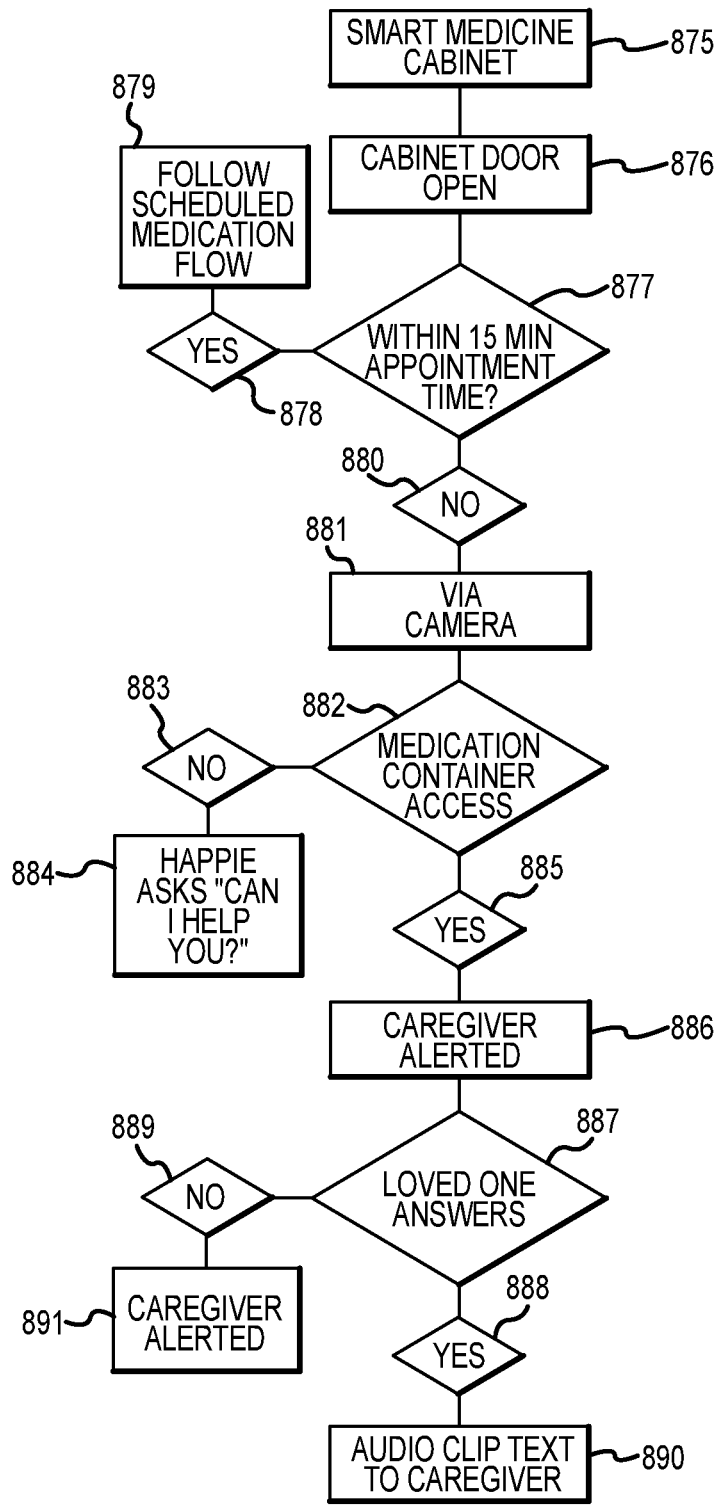
FIG. 69 is a flowchart illustrating the operation of a smart medicine cabinet for unscheduled medication.

FIG. 69 is a flowchart illustrating a method of operation of the smart medicine cabinet 800 for unscheduled medication, or a resident's access of the smart medicine cabinet 800 at a time that does not correspond to the time that a scheduled dose of medicine is due. For example, the resident may access the smart medicine cabinet 800 early, before the scheduled dose is due to be taken, or the resident may access the smart medicine cabinet 800 at the wrong time. The method starts in step 875 with the smart medicine cabinet 800 connected to the HAPPIE home unit 103. In step 876, the smart medicine cabinet 800 detects that the door 801 has been opened, based upon signals from contacts 819, or by motion detectors 152, or based upon video detected by video cameras 818.

In step 877 a determination is made concerning whether the time that the door 801 was opened is within a predetermined period of time for a scheduled dose of medicine. If the smart medicine cabinet 800 is accessed within the predetermined period of time corresponding to a scheduled dose of medicine, as indicated in step 878, the method proceeds to step 879 to follow a method for the corresponding scheduled dose of medicine, as indicated, for example, in FIG. 66. If the smart medicine cabinet 800 is not accessed within the predetermined period of time corresponding to a scheduled dose of medicine, as indicated in step 880, the method proceeds to step 881, where the HAPPIE home unit 103 accesses the video cameras 818 in the smart medicine cabinet 800.

In step 882, the HAPPIE home unit 103 uses the video cameras 818 to determine whether the resident has taken a medicine container from the smart medicine cabinet 800. If the resident does not remove a medicine container from the smart medicine cabinet 800 during a predetermined period of time, as indicated in step 883, the HAPPIE home unit 103 may play a prompt over speakers 157, as indicated in step 884, and ask the resident if he or she needs assistance. If the resident removes a medicine container from the smart medicine cabinet 800, as indicated in step 885, the method proceeds to step 886 where the HAPPIE home unit 103 generates an alert to a caregiver via the caregiver portal 101. In step 887, the HAPPIE home unit 103 prompts the resident via speakers 157 concerning what medicine is being taken. If a response from the resident is not received, as indicated in step 889, the caregiver is alerted via the caregiver portal 101 in step 891. The HAPPIE home unit 103 may compare video data received from the video cameras 818 to determine what medicine was taken by the resident, and include that data, together with other data concerning the time of access and the circumstances, in the alert sent to the caregiver via the caregiver portal 101. If the resident responds, as indicated in step 888, the HAPPIE home unit 103 records the audio response using microphones 113, and in step 890, transmits the recorded audio to the caregiver via the caregiver portal 101.

Figure 70:
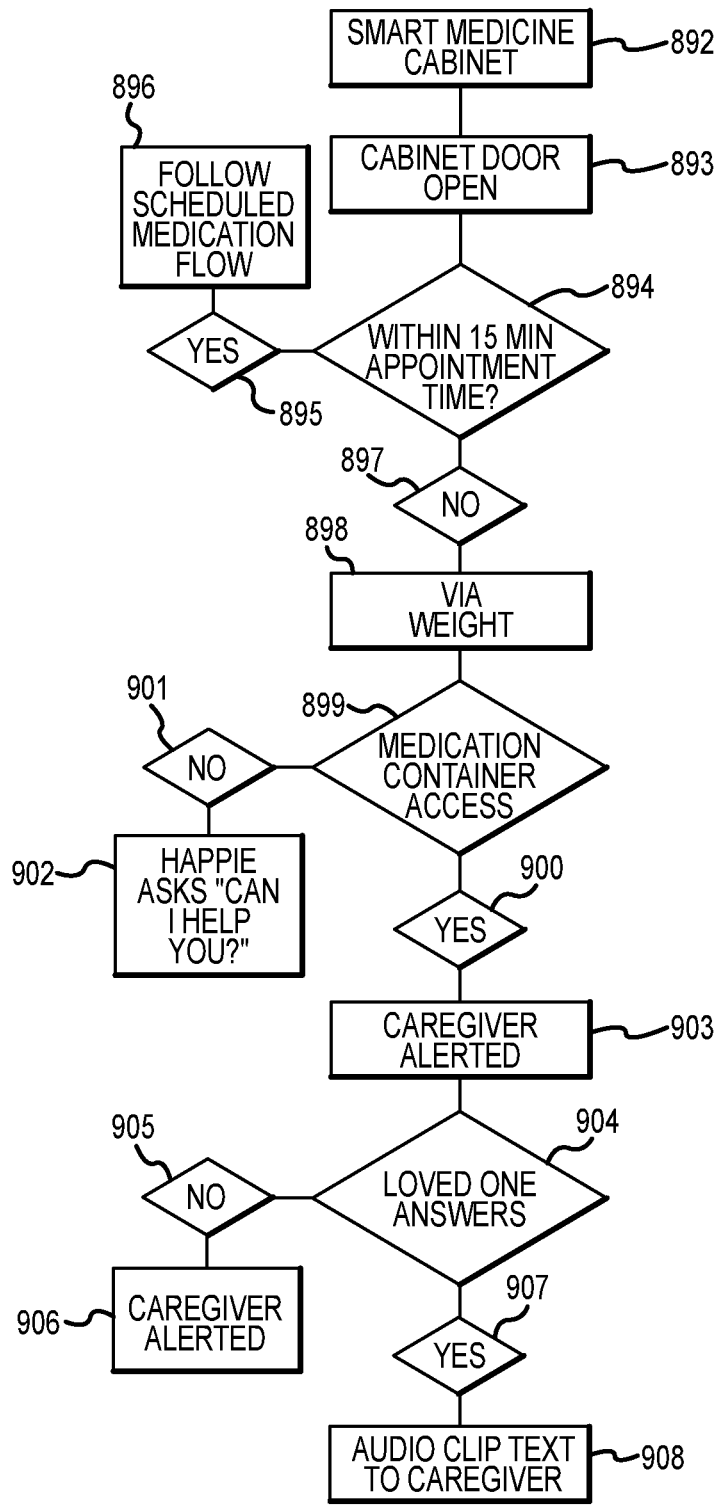
FIG. 70 is a flowchart illustrating the operation of a smart medicine cabinet for unscheduled medication.

FIG. 70 is a flowchart illustrating a method of operation for the smart medicine cabinet 800 for unscheduled medication. The method starts in step 892 with the smart medicine cabinet 800 connected to the HAPPIE home unit 103. In step 893, the smart medicine cabinet 800 detects that the door 801 has been opened. This detection may be based upon signals from contacts 819 that are received by the HAPPIE home unit 103, or upon signals from motion detectors 152. Alternatively, video cameras 818 may be used to detect when the door 801 of the smart medicine cabinet 800 is opened.

In step 894 a determination is made concerning whether the time that the door 801 was opened is within a predetermined period of time for a scheduled dose of medicine. If the smart medicine cabinet 800 is accessed within the predetermined period of time corresponding to a scheduled dose of medicine, as indicated in step 895, the method proceeds to step 896 to follow a method for the corresponding scheduled dose of medicine, as indicated, for example, in FIG. 67. If the smart medicine cabinet 800 is not accessed within the predetermined period of time corresponding to a scheduled dose of medicine, as indicated in step 897, the method proceeds to step 898, where the HAPPIE home unit 103 accesses weight sensors 130 associated with the medicine contained in the smart medicine cabinet 800.

In step 899, the HAPPIE home unit 103 uses weight sensors 130 to determine whether the resident has taken a medicine container from the smart medicine cabinet 800. If the resident does not remove a medicine container from the smart medicine cabinet 800 during a predetermined period of time, as indicated in step 901, the HAPPIE home unit 103 may play a prompt over speakers 157, as indicated in step 902, and ask the resident if he or she needs assistance. If the resident removes a medicine container from the smart medicine cabinet 800, as indicated in step 900, the method proceeds to step 903 where the HAPPIE home unit 103 generates an alert to a caregiver via the caregiver portal 101. In step 904, the HAPPIE home unit 103 prompts the resident via speakers 157 concerning what medicine is being taken. If a response from the resident is not received, as indicated in step 905, the caregiver is alerted via the caregiver portal 101 in step 906. The HAPPIE home unit 103 may compare data from weight sensors 130 to determine what medicine was taken by the resident, and include that data, together with other data concerning the time of access and the circumstances, in the alert sent to the caregiver via the caregiver portal 101. If the resident responds, as indicated in step 907, the HAPPIE home unit 103 records the audio response using microphones 113, and in step 908, transmits the recorded audio to the caregiver via the caregiver portal 101.

Figure 71:
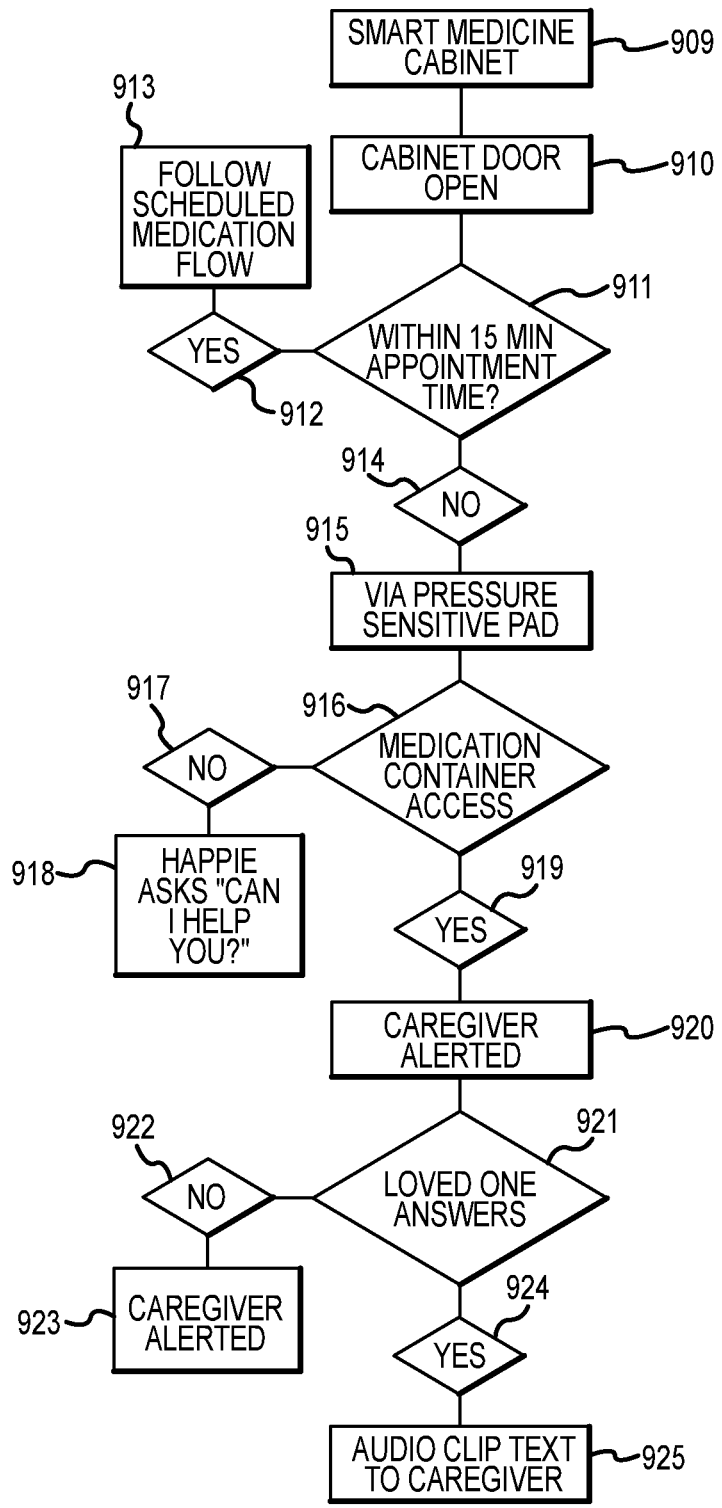
FIG. 71 is a flowchart illustrating the operation of a smart medicine cabinet for unscheduled medication.

FIG. 71 is a flowchart illustrating a method of operation for the smart medicine cabinet 800 for unscheduled medication. The method starts in step 909 with the smart medicine cabinet 800 connected to the HAPPIE home unit 103. In step 910, the smart medicine cabinet 800 detects that the door 801 has been opened.

In step 911, a determination is made concerning whether the time that the door 801 was opened is within a predetermined period of time for a scheduled dose of medicine. If the smart medicine cabinet 800 is accessed within the predetermined period of time corresponding to a scheduled dose of medicine, as indicated in step 912, the method proceeds to step 913 to follow a method for the corresponding scheduled dose of medicine, as indicated, for example, in FIG. 68. If the smart medicine cabinet 800 is not accessed within the predetermined period of time corresponding to a scheduled dose of medicine, as indicated in step 914, the method proceeds to step 915, where the HAPPIE home unit 103 accesses data from the pressure sensitive pads 811 in the smart medicine cabinet 800.

In step 916, the HAPPIE home unit 103 uses the pressure sensitive pads 811 to determine whether the resident has taken a medicine container from the smart medicine cabinet 800. If the resident does not remove a medicine container from the smart medicine cabinet 800 during a predetermined period of time, as indicated in step 917, the HAPPIE home unit 103 may play a prompt over speakers 157, as indicated in step 918, and ask the resident if he or she needs assistance. If the resident removes a medicine container from the smart medicine cabinet 800, as indicated in step 919, the method proceeds to step 920 where the HAPPIE home unit 103 generates an alert to a caregiver via the caregiver portal 101. In step 921, the HAPPIE home unit 103 prompts the resident via speakers 157 concerning why the resident has accessed the smart medicine cabinet 800 or concerning what medicine is being taken. If a response from the resident is not received, as indicated in step 922, the caregiver is alerted via the caregiver portal 101 in step 923. The HAPPIE home unit 103 may compare data from the pressure sensitive pads 811 to determine what medicine was taken by the resident, and include that data, together with other data concerning the time of access and the circumstances, in the alert sent to the caregiver via the caregiver portal 101. If the resident responds, as indicated in step 924, the HAPPIE home unit 103 records the audio response using microphones 113, and in step 925, transmits the recorded audio to the caregiver via the caregiver portal 101.

The methods described in connection with FIG. 69, FIG. 70, and FIG. 71, may be combined, and the HAPPIE home unit 103 may simultaneously use data from video cameras 818, from pressure sensitive pads 811, and from other sensors 130, to process a resident's access to the smart medicine cabinet 800 for unscheduled medication.

Figure 45:
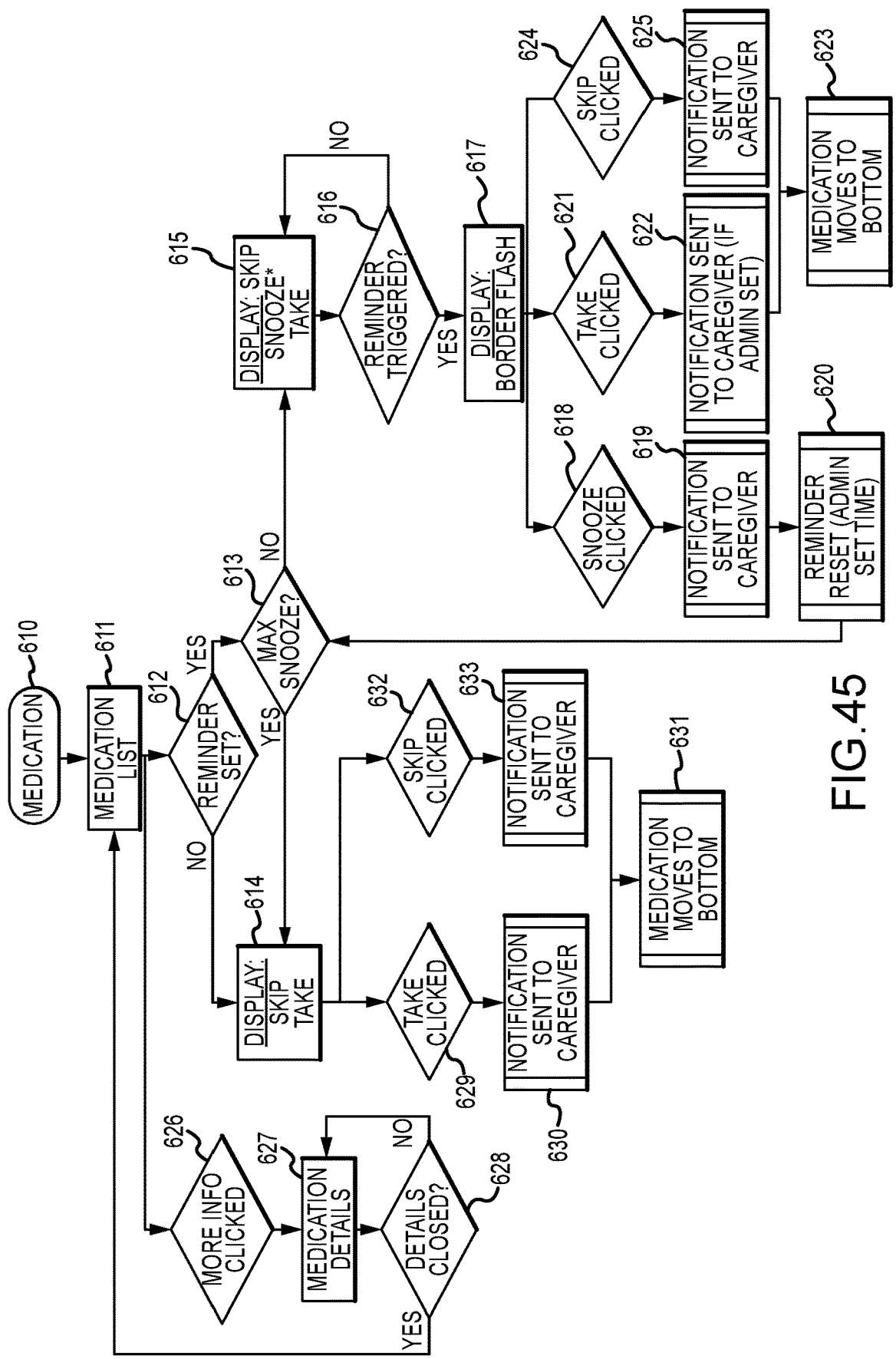
FIG. 45 is a flowchart illustrating a method for medication in accordance with one embodiment of the invention.

FIG. 45 is a flowchart illustrating a method for medication in accordance with one embodiment of the invention. The medication method is invoked at step 610. A medication list is displayed in step 611 corresponding to the medication that the resident is scheduled to take. The displayed list of medicines provides an option for requesting more information concern each medicine, if desired. If the resident requests more information, (for example, by clicking on a designated area of a graphical user interface, or by speaking a request which is picked up by a microphone 113 and analyzed by a speech recognition module), the method proceeds to step 626 to upon detection of the request. In step 627, medication details are provided to the resident, for example, by displaying the information on a video monitor 156, or by playing audio over speakers 157. The method checks in step 628 to determine whether the details have been closed by the resident. If so, the method loops back to step 611. If not, the method loops back to step 627 until the resident is satisfied with the information provided and closes the details.

In step 612, the resident may not wish to take the medicine at the moment that the HAPPIE home unit 103 notifies the resident that it is time for the scheduled dose, and may set a reminder is for a specific medicine. If the reminder is not set in step 612, the method proceeds to step 614 to display to the resident on a video monitor 156 a choice to skip or take the designated dose. If the medicine is taken, the resident so indicates that it was taken by clicking on a designated area of a graphical user interface in step 629. Alternatively, the HAPPIE home unit 103 may analyze video data from a video camera 112 and automatically determine from the analysis whether the resident has taken the medicine. The method proceeds to step 630, and the HAPPIE home unit 103 sends a notification to the caregiver via the caregiver portal 101. Then the medication moves to the bottom of the list in step 631 until it is time to take another dose of the medication. Data is stored in the database 108 indicating that the medicine was taken as prescribed, together with other details such as the time and date taken, and the specific dose taken.

Going back to step 614, if the resident indicates that he or she wants to skip the medicine, the resident may do so in step 632 by clicking on an area of the graphical user interface for indicating a skip. The method proceeds to step 633, and a notification of this is sent to the caregiver via the caregiver portal 102. The method then proceeds to step 631, as previously described.

Going back to step 612, if the resident indicates that he or she wants to snooze the notice that it is time to take a certain medicine, the method proceeds to step 613 to determine, in the event of repeated reminders having been set, whether a predetermined maximum snooze has been reached. If the maximum has been reached, the method proceeds to step 614 (as described above) and does not snooze the medication notice. If the maximum snooze has not been reached in step 613, the method proceeds to step 615 and displays on a video monitor 156 the options to skip, snooze, or take, for the specified medicine.

In step 616, the HAPPIE home unit checks to determine whether a reminder is triggered. If not, the method loops back to step 615. If so, the method proceeds to step 617 and displays a flashing border around the display of the skip, snooze, or take, options displayed on the video monitor 156.

If the resident clicks "snooze," the method proceeds to step 621 upon detection of such input from the resident. In step 622, a notification is sent to the caregiver via the caregiver portal 101 that the medication was taken, and the method proceeds to step 623 to record appropriate data in the database 108 concerning the event, and move the medicine to the bottom of the list.

If the resident clicks "skip," the method proceeds to step 624 upon detection of such input from the resident. In step 625, a notification is sent to the caregiver via the caregiver portal 101 that the medication was skipped, and the method proceeds to step 623 to record appropriate data in the database 108 concerning the event, and move the medicine to the bottom of the list.

If the resident clicks "take," the method proceeds to step 618 upon detection of such input from the resident. In step 619, a notification is sent to the caregiver via the caregiver portal 101 that the medication was snoozed, and the method loops back to step 613.

FIG. 82, FIG. 83, FIG. 84 and FIG. 85 illustrate an alternative embodiment of the smart medicine cabinet 800.

Figure 63:
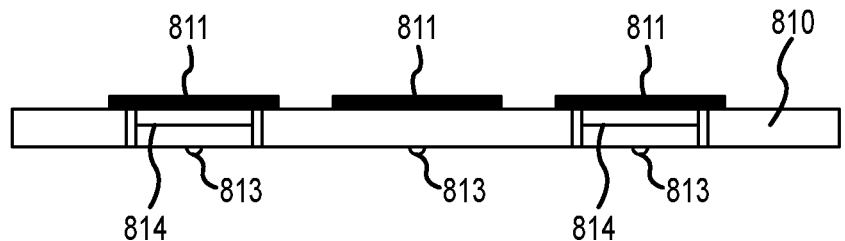
FIG. 63 is a rear view of the shelf of the smart medicine cabinet shown in FIG. 61.
Figure 82:
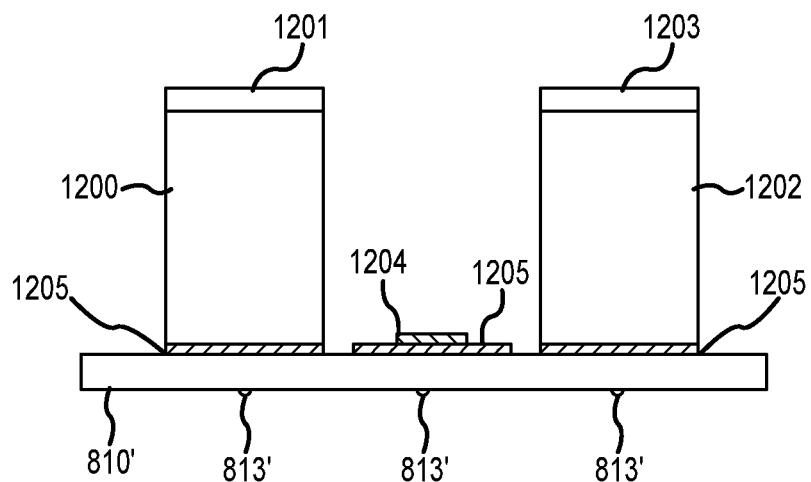
FIG. 82 is a front view of a shelf of an alternative embodiment of a smart medicine cabinet showing a shelf with two locations that have medication containers and a third location between them that does not have a medication container.
Figure 84:
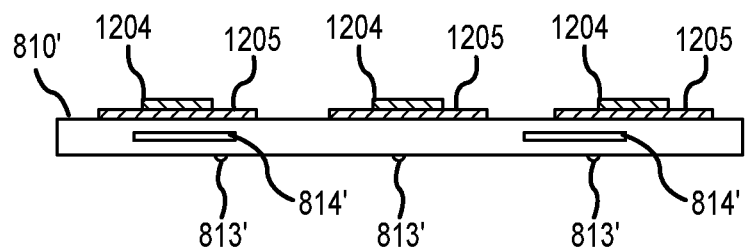
FIG. 84 is a rear view of the shelf of the alternative embodiment of a smart medicine cabinet shown in FIG. 82.
Figure 85:
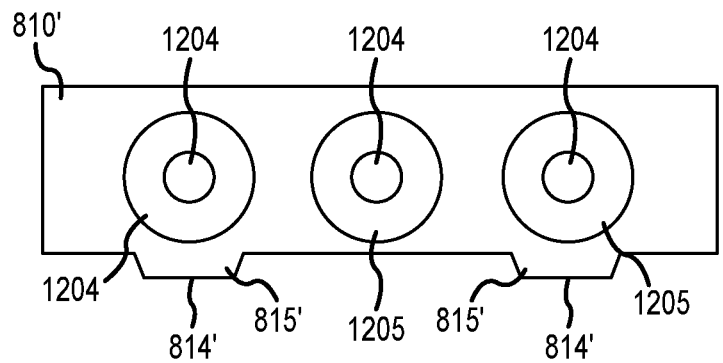
FIG. 85 is a top view of the shelf of the alternative embodiment of a smart medicine cabinet shown in FIG. 82 and FIG. 84.

In this embodiment of the smart medicine cabinet 800, the structure shown in FIG. 61, FIG. 62, and FIG. 63 is modified as shown in FIG. 82, FIG. 84 and FIG. 85, as described more fully below.

Figure 83:
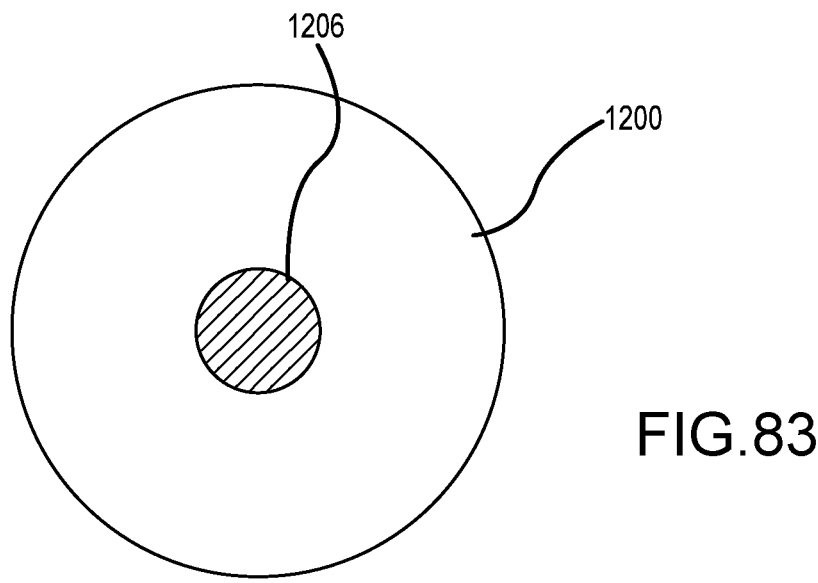
FIG. 83 is a bottom view of a medication container of the type shown in FIG. 82.

In this alternative embodiment of the smart medicine cabinet 800, the shelf 810' is modified to include micro-pads 1205 which are capable of precise weight measurements, and which are in communication with the computational and logic unit 121 and the database 108. Medication is removed from a conventional container that may be received from a pharmacy and placed in a specially configured container or bottle 1200 that is adapted to securely conform to a corresponding micro-pad 1205. In other words, the bottle 1200 is intended to replace the prescription medication container used by a pharmacy. Referring to FIG. 83, the bottom of each bottle 1200 has an individually configured indentation region 1206 that corresponds to, and registers with, a raised region 1204 on an associated micro-pad 1205. Thus, container or bottle 1203 shown in FIG. 82 will have an individually configured indentation region 1206 that is different from bottle 1200. Each bottle 1200 and 1202 has a different configured indentation region 1206 so that the respective bottle 1200 or 1202 corresponds to, and fits or registers with, only one micro-pad 1205 on the shelf 810'. This prevents placing bottle 1200 in a different location on the shelf 810'. If the bottle 1200 is removed from the shelf 810', the bottle 1200 must be placed back onto its corresponding micro-pad 1205, and will not fit on any other micro-pad 1205 on the shelf 810'. This way, the bottle 1200 will always be placed on the same micro-pad 1205 each time it is replaced on the shelf 810' in the smart medicine cabinet 800. Thus, each micro-pad 1205 measurement of the weight of the medication in the bottle 1200 or 1202 associated with that micro-pad 1205 can be associated with corresponding data stored in database 108 for the specific corresponding medication that was originally placed in that location in order to precisely determine the amount of that medication in the associated bottle 1200 or 1202.

Each bottle 1200 and 1202 will register and affix itself securely to one specific associated micro-pad 1205. This eliminates the risk of a bottle 1200 and 1202 being knocked over, or being placed on the wrong micro-pad scale 1205. In a preferred embodiment, the raised region 1204 on each associated micro-pad 1205 can be electrically activated by the computational and logic unit 121 to securely lock the associated bottle 1200 and 1202 in place by securely conforming the corresponding raised region 1204 to the corresponding associated indentation region 1206. All of the bottles 1200 and 1202 on every shelf 810' can be locked, and when the time arrives for a dose of medication to be taken by the resident, the corresponding bottle 1200 or 1203 can be automatically unlocked at the predetermined time by the computational and logic unit 121. This eliminates the risk of the resident taking the wrong medication at that time, because bottles 1200 or 1202 containing medication that is not due to be taken by the resident will remain locked.

The micro-pads 1205 include precision weight sensors that can measure the difference in the weight of a bottle 1200 before a dose of medication is taken, and the weight of the bottle 1200 after the dose of medication was taken. The computational and logic unit 121 receives the weight measurement data from the associated micro-pad 1205, and computes the difference in the weight of the bottle 1200 before a dose of medication is taken, and the weight of the bottle 1200 after the dose of medication was taken. The computational and logic unit 121 compares the result with data stored in the database 108 to determine if the correct dosage was taken by the resident. If any discrepancy is detected, the computational and logic unit 121 may automatically generate an alert to a caregiver via the caregiver portal 101, or alternatively, the computational and logic unit 121 may communicate directly with the resident using speakers 157 and voice recognition of spoken responses picked up by microphones 113, or using video monitors 156, to inquire about the accuracy of the medication dosage that was taken by the resident.

Bottle 1200 is preferably provided with a screw-on top 1201. Bottle 1202 is similarly provided with a screw-on top 1203. if desired, the screw-on tops 1201 and 1203 may be configured to lock onto their respective bottles 1200 and 1202 to make it difficult for the resident to remove the tops 1201 and 1203.

This alternative embodiment of the smart medicine cabinet 800 includes small lights 813' that have a function, operation, and structure the same as the small lights 813 described above in connection with FIG. 60, FIG. 61, FIG. 63, and FIG. 64, and need not be described further. This alternative embodiment includes power & communication ports 814' that have a function, operation, and structure the same as the power & communication ports 814 described above in connection with FIG. 62, FIG. 63, and FIG. 64, and need not be described further. Referring to FIG. 85, this alternative embodiment of the smart medicine cabinet 800 includes tabs 815' that have a function, operation, and structure the same as the tabs 815 described above in connection with FIG. 62, FIG. 63, and FIG. 64, and need not be described further.

Figure 86:
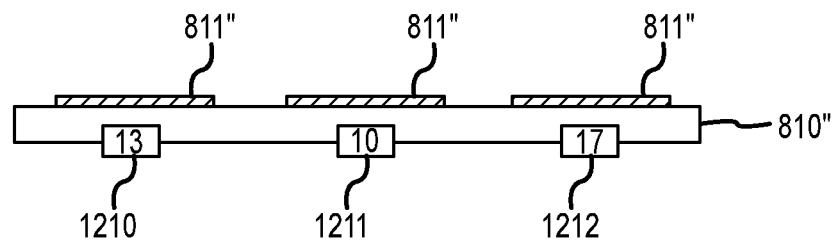
FIG. 86 is a front view of a shelf of yet another alternative embodiment of a smart medicine cabinet showing a shelf having a plurality of digital displays associated with corresponding medication containers.
Figure 87:
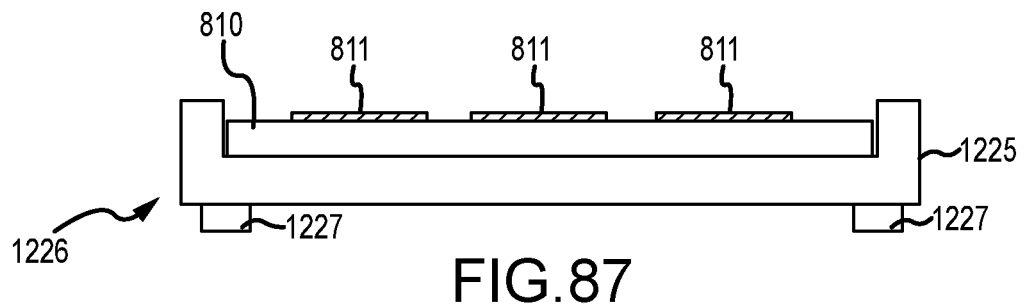
FIG. 87 is a front view of a remote smart medicine cabinet shelf holder.

FIG. 86 illustrates another alternative embodiment of the smart medicine cabinet 800. In this embodiment, the shelf 811" includes a digital display 1210 associated with an individual corresponding pressure sensitive pad 811". The corresponding pressure sensitive pad 811" includes the capability of precisely measuring the weight of medication placed onto the pressure sensitive pad 811". Based upon the weight measured by the pressure sensitive pad 811", the computational and logic unit 121 computes the number of doses of medication for the medication stored in the database 108 associated with that pressure sensitive pad 811". Thus, as each dose of medication is taken by the resident, the digital display 1210 will display the remaining doses of medication that remain. In addition, the number of remaining doses is stored in the database 108. The computational and logic unit 121 compares the number of remaining doses with information stored in the database 108, and when a predetermined number of doses remain, automatically communicates a prescription refill request to medical personnel via the doctor portal 102, or if refills remain associated with that prescription, automatically orders a refill from a pharmacy via the Internet 105. The computational and logic unit 121 automatically generates an informational message to a caretaker via the caretaker portal 101 to inform the caretaker of the status of the medication and any re-fills or resupply orders. A caretaker can use the caretaker portal 101 to configure medication reorder or refill thresholds for each medication individually.

The illustrated embodiment shown in FIG. 86 shows a second digital display 1211 associated with an individual corresponding pressure sensitive pad 811". A third digital display 1212 is shown associated with a different corresponding pressure sensitive pad 811". It will be understood that each pressure sensitive pad 811" in this embodiment has its own associated digital display 1210, 1211 and 1212.

The embodiment of the smart medicine cabinet 800 described in connection with FIG. 86 is otherwise the same as the embodiment of a smart medicine cabinet 800 described above in connection with FIG. 59, FIG. 60, FIG. 62, FIG. 63, FIG. 64 and FIG. 65.

FIG. 87, FIG. 88, FIG. 89, FIG. 90 and FIG. 91 illustrate a remote smart medicine cabinet shelf holder 1226. The remote smart medicine cabinet shelf holder 1226 includes a shelf holder base 1225. The shelf holder base 1225 is adapted to receive a shelf 810 that is removed from the smart medicine cabinet 800, and to securely hold the shelf 810 in place.

Figure 90:
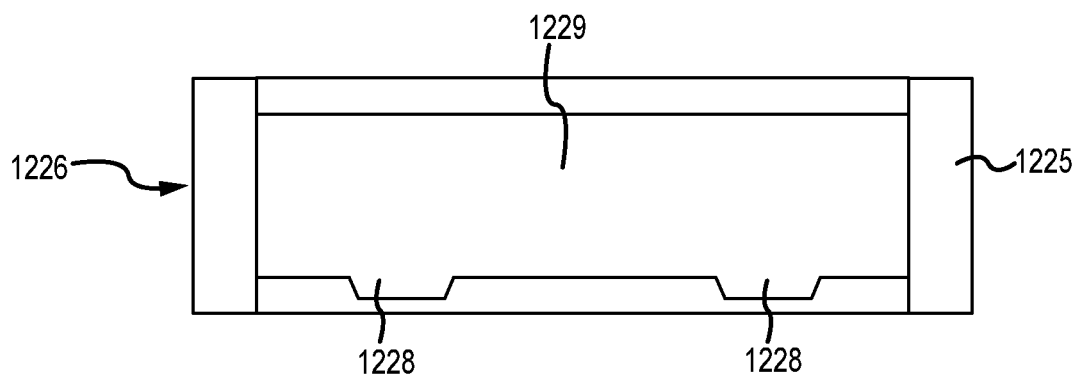
FIG. 90 is a top view of the remote smart medicine cabinet shelf holder shown in FIG. 88, with the shelf removed from the holder.

Referring to FIG. 90, the remote smart medicine cabinet shelf holder 1226 has an empty space 1229 for receiving a shelf 810. The empty space 1229 has a size and shape corresponding to the size and shape of a shelf 810, including indentations 1228 for receiving the tabs 815 of a shelf 810.

Figure 88:
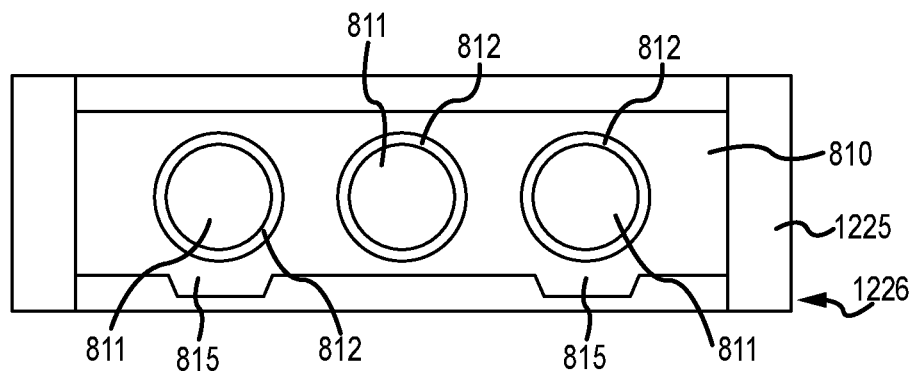
FIG. 88 is a top view of the remote smart medicine cabinet shelf holder shown in FIG. 87, with a shelf in place in the holder.
Figure 89:
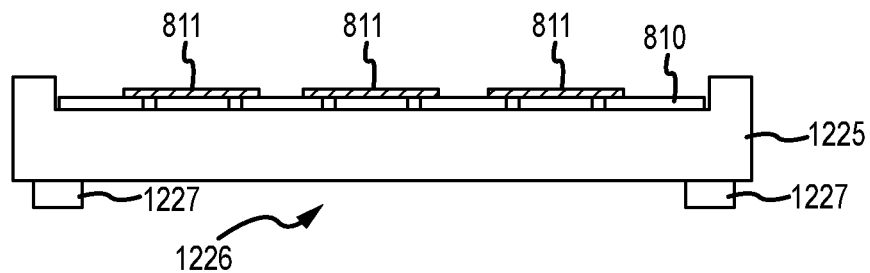

FIG. 88 shows a top view, similar to FIG. 90, but with a shelf 810 placed in secure corresponding registered relationship with the shelf holder base 1225. The shelf 810 is shown with pressure sensitive pads 810 and light rings 812, which function the same as the corresponding components described above, and will not be further described. The shelf 810 has tabs 815 that register with the indentations 1228 in the shelf holder base 1225. Power & communication ports 814 on the tabs 815 make connection with corresponding ports provided in the indentations 1228 in the shelf holder base 1225.

Figure 91:
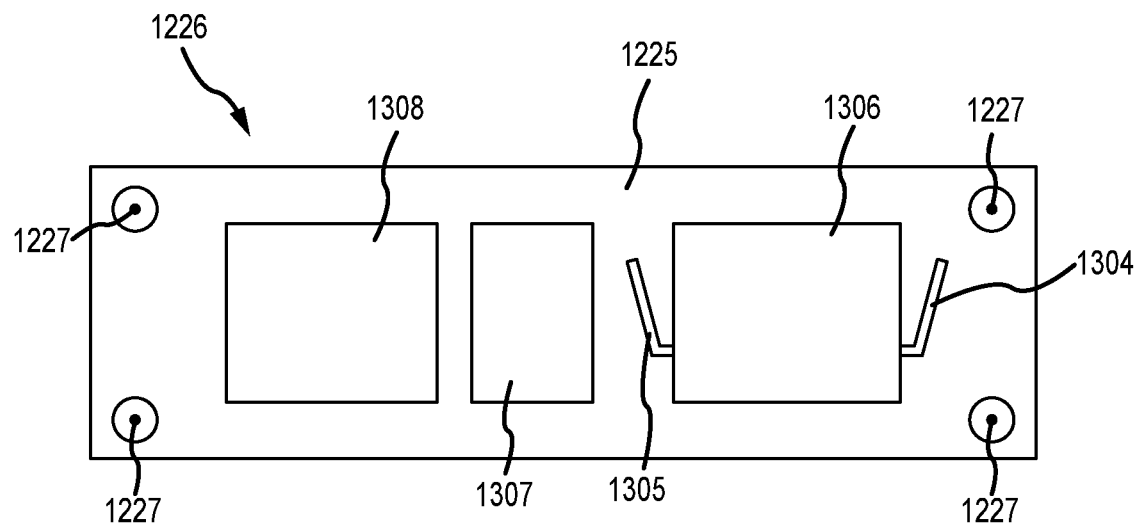
FIG. 91 is a bottom view of the remote smart medicine cabinet shelf holder shown in FIG. 87.

FIG. 91 shows a bottom view of the remote smart medicine cabinet shelf holder 1226. A power supply 1308 is provided to remotely power the shelf 810 via the power & communication ports 814 included in the shelf 810. A communication module 1306 is included to provide wireless data communication via WiFi hotspot 109 with the HAPPIE Home computational and logic unit 121, and also to provide wireless communication with the smart medicine cabinet 800. WiFi antennas 1304 and 1305 may be provided to facilitate wireless data communication with the WiFi hotspot 109 and the smart medicine cabinet 800. In addition, the communication unit 1306 may also include bluetooth communication functionality. A battery backup supply 1307 is preferably provided to supply electrical power when the power supply 1308 is not plugged into commercial power. The battery backup supply 1307 allows portable wireless operation of the shelf 810.

The shelf holder base 1225 is preferably provided with feet or supports 1227, so that the remote smart medicine cabinet shelf holder 1226 can be conveniently placed on any surface.

The remote design of the remote smart medicine cabinet shelf holder 1226 facilitates medication coordination and control at a convenient location away from the smart medicine cabinet 800. For example, it allows a caretaker to more conveniently work with medication contained on the shelves 810 of a smart medicine cabinet 800 in a location other than the bathroom, such as the kitchen countertop or bedroom nightstand. The remote smart medicine cabinet shelf holder or cradle 1226 supplies power and communication with the shelf 810 to the same degree as is available when the shelf 810 is in the smart medicine cabinet 800.

Figure 72:
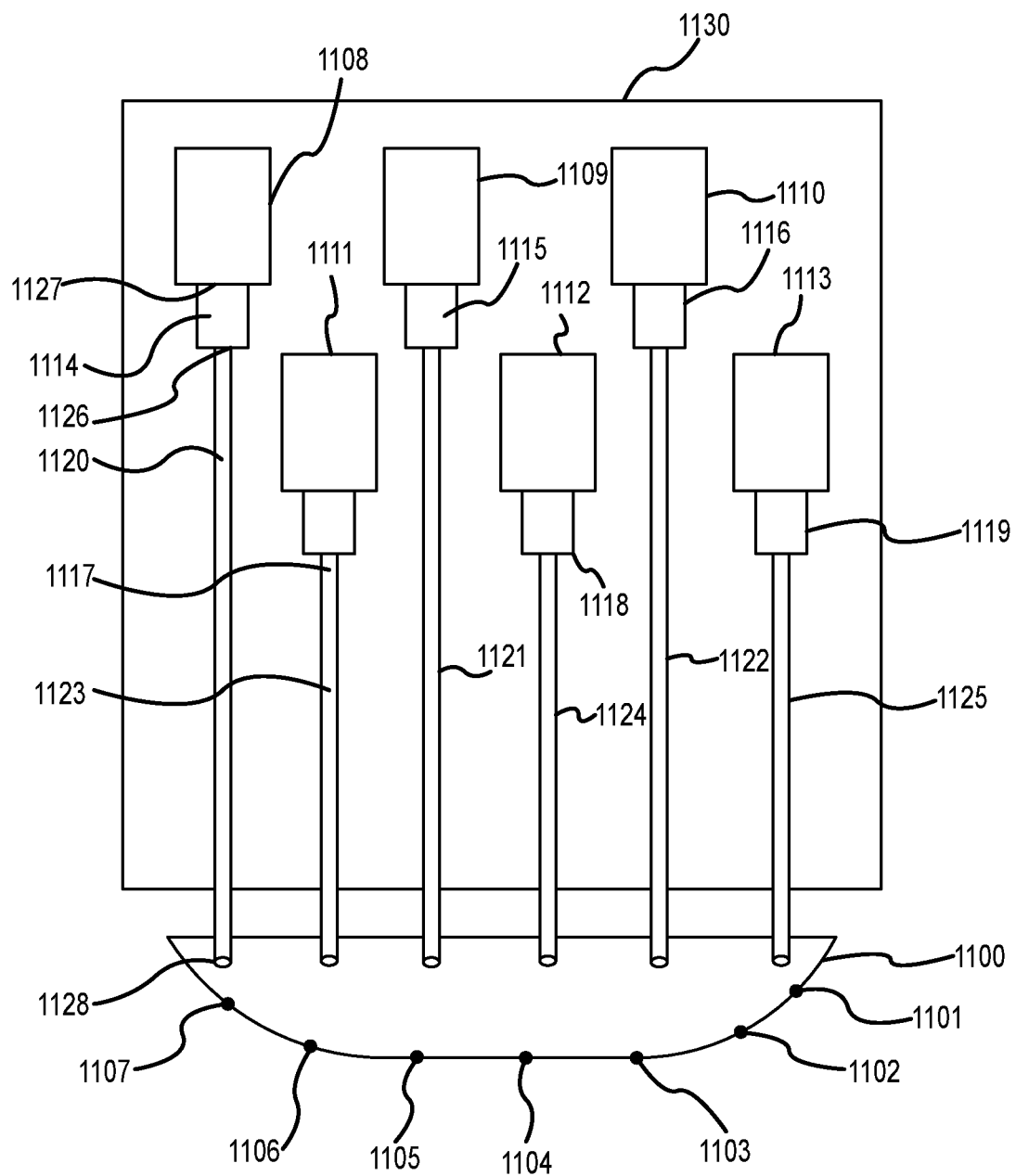
FIG. 72 is a drawing illustrating an alternative embodiment of a smart medicine cabinet for automatically dispensing medications.

FIG. 72 is a drawing illustrating an alternative embodiment of a smart medicine cabinet for automatically dispensing medications. A medicine bottle or container 1108 is provided for this embodiment of the smart medicine cabinet. The medicine bottle 1108 is used to store a plurality of doses of medication or dietary supplements. The medicine bottle 1108 has a pre-dispensary chamber 1114 sized and adapted to permit only one does of medication at a time in the chamber 1114. A first door or gate 1127 may be provided to open and permit only one dose of medication to enter the pre-dispensary chamber 1114, at which time the first door or gate 1127 closes. The first gate 1127 is connected to and controlled by the HAPPIE Home computing and logic unit 121. In a preferred embodiment, gravity is used to drop a dose of medication into the chamber 1114, however, a supplemental vibration device may be provided for vibrating the bottle 1108 when necessary to cause a dose of medication to drop into the chamber 1114. Alternatively, air pressure may be used to move the dose of medication into and down through the chute 1120. Alternatively, a pill-dispenser may be included at the bottom of the pre-dispensary chamber 1114, where the pill-dispenser comprises a wheel with a plurality of slots that are sized for one pill, and which rotate incrementally to move one slot from the bottom of the bottle 1108 to the top of the pre-dispensary chamber 1114 to permit only one pill in a slot to be deposited into the pre-dispensary chamber 1114 at a time. Thus, the exact dose of medication will be pre-stored in the pre-dispensary chamber 1114 until it is time for the resident to take the medication. The medication is weighed and measured in the pre-dispensary chamber 1114 to make sure it is the correct dosage and amount. The smart medicine cabinet is in communication with the HAPPIE Home computing and logic unit 121 and the database 108, where information concerning scheduled medication doses and times is maintained for the resident, and the weight and measurement of the medication in the pre-dispensary chamber 1114 is compared with associated data stored in the database 108 to insure that the pre-stored dose of medication is correct.

When it is time to dispense the dose of medication stored in pre-dispensary chamber 1114, a second door or gate 1126 may be provided in the bottom of the pre-dispensary chamber 1114. The second gate 1126 is connected to and controlled by the HAPPIE Home computing and logic unit 121. The second gate 1126 opens at the scheduled predetermined time, in response to a command from the HAPPIE Home computational and logic unit 121, to permit the prescribed single dose of medication to drop into a chute or tube 1120. The prescribed single dose of medication then falls through the chute 1120 and exits a lower chute opening 1128 to fall into a dispenser service tray 1100. The resident may then remove the medication from the service tray 1100 and take the medication as prescribed. The service tray 1100 has a plurality of sensors 1101, 1102, 1103, 1104, 1105, 1106 and 1107, to sense when the medication is removed from the service tray 1100. The time when the resident removes the medication from the service tray 1100 is recorded and stored in the database 108. The sensors 1101, 1102, 1103, 1104, 1105, 1106 and 1107 can also be used to double-check the weight of the dose of medication, and in the event of any discrepancy between the amount measured in the pre-dispensary chamber 1114 and the amount measured by the sensors associated with the service tray 1100, the HAPPIE Home computational and logic unit 121 automatically generates an alert to a caretaker via caretaker portal 101 for investigation and follow up.

In a preferred embodiment, a plurality of medicine bottles or containers 1108, 1109, 1110, 1111, 1112 and 1113 are provided for the individual separate storage of different medications. Each of the illustrated bottles 1109, 1110, 1111, 1112 and 1113 has an associated pre-dispensary chamber 1115, 1116, 1117, 1118 and 1119, respectively, connected to the bottle 1109, 1110, 1111, 1112 and 1113. Each pre-dispensary chamber 1115, 1116, 1117, 1118 and 1119 is connected to an associated chute or tube 1121, 1122, 1123, 1124 and 1125, respectively. The structure, function and operation of the bottles 1121, 1122, 1123, 1124 and 1125 the associated pre-dispensary chambers 1115, 1116, 1117, 1118 and 1119, and the connected chutes 1121, 1122, 1123, 1124 and 1125, are the same as described in connection with bottle 1108, pre-dispensary chamber 1114, and chute 1120, respectively.

In a preferred embodiment of this smart medicine cabinet, a cabinet 1130 is provided enclosing the bottles 1108, 1109, 1110, 1111, 1112 and 1113 and their associated pre-dispensary chambers 1114, 1115, 1116, 1117, 1118 and 1119. The chutes 1120, 1121, 1122, 1123, 1124 and 1125 extend out of the cabinet 1130 to the service tray 1100. A hinged door may be provided for this embodiment of the smart medicine cabinet to completely enclose, when the door is closed, the contents of the cabinet 1130. The door may be closed and locked, if desired, to securely seal the contents of the medicine bottles 1121, 1122, 1123, 1124 and 1125 from the resident, and access to the contents of the cabinet 1130 may be limited to a caretaker or to medical personnel who may need to service or refill the bottles 1108, 1109, 1110, 1111, 1112 and 1113. In this embodiment, the resident need not open the door of the smart medicine cabinet, because the resident will have access to the contents of the dispenser service tray 1100 even when the door is locked. And if data from the sensors 1101, 1102, 1103, 1104, 1105, 1106, and 1107 indicates that the resident failed to remove the medication from the service tray 1100 at the appropriate time, the HAPPIE Home computational and logic unit 121 may automatically generate an alert to a caretaker via the caretaker portal 101. A door such as the door illustrated and described in connection with FIG. 59 may be used in connection with the smart medicine cabinet according to the embodiment described in connection with FIG. 72, and the door need not be further described.

The embodiment of the smart medicine cabinet described in connection with FIG. 72 allows for multiple medications to be automatically dispensed at the correct prescribed time, in the exact amount and dosage prescribed. This can be advantageous for a resident who is required to take a number of different prescribed medications at different respective times, and this embodiment of a smart medicine cabinet avoids mistakes in taking a plurality of different prescription medications. This embodiment of a smart medicine cabinet insures that the correct medication is taken at the correct time, in the correct amount or dose, and does so even for a resident who may have difficulty remembering what needs to be taken and when it needs to be taken. It will be appreciated that this embodiment of a smart medicine cabinet helps to avoid both missed doses of medication, and mistaken double-doses of medication, if the resident is unable to remember whether he or she has already taken a prescribed dose of medication or that a prescribed does of medication is scheduled to be taken but has not been. This embodiment of a smart medicine cabinet also has advantages for dispensing medication that may be addictive or dangerous if not taken as prescribed. Moreover, this embodiment of a smart medicine cabinet has the advantage of automatically adjusting or changing the dose of medication. For example, some medications may require three pills the first day, two pills the second day, and then one pill of a predetermined number of days thereafter, such as steroid medications administered for allergy conditions. Alternatively, a doctor may change the prescribed dose or frequency of a medication, and the smart medicine cabinet may automatically change the time and dose provided to the resident under the control of the HAPPIE Home computational and logic unit 121.

The rear view of the smart medicine cabinet for the embodiment described in connection with FIG. 72 is substantially the same as shown in FIG. 65, and need not be described again.

Figure 92:
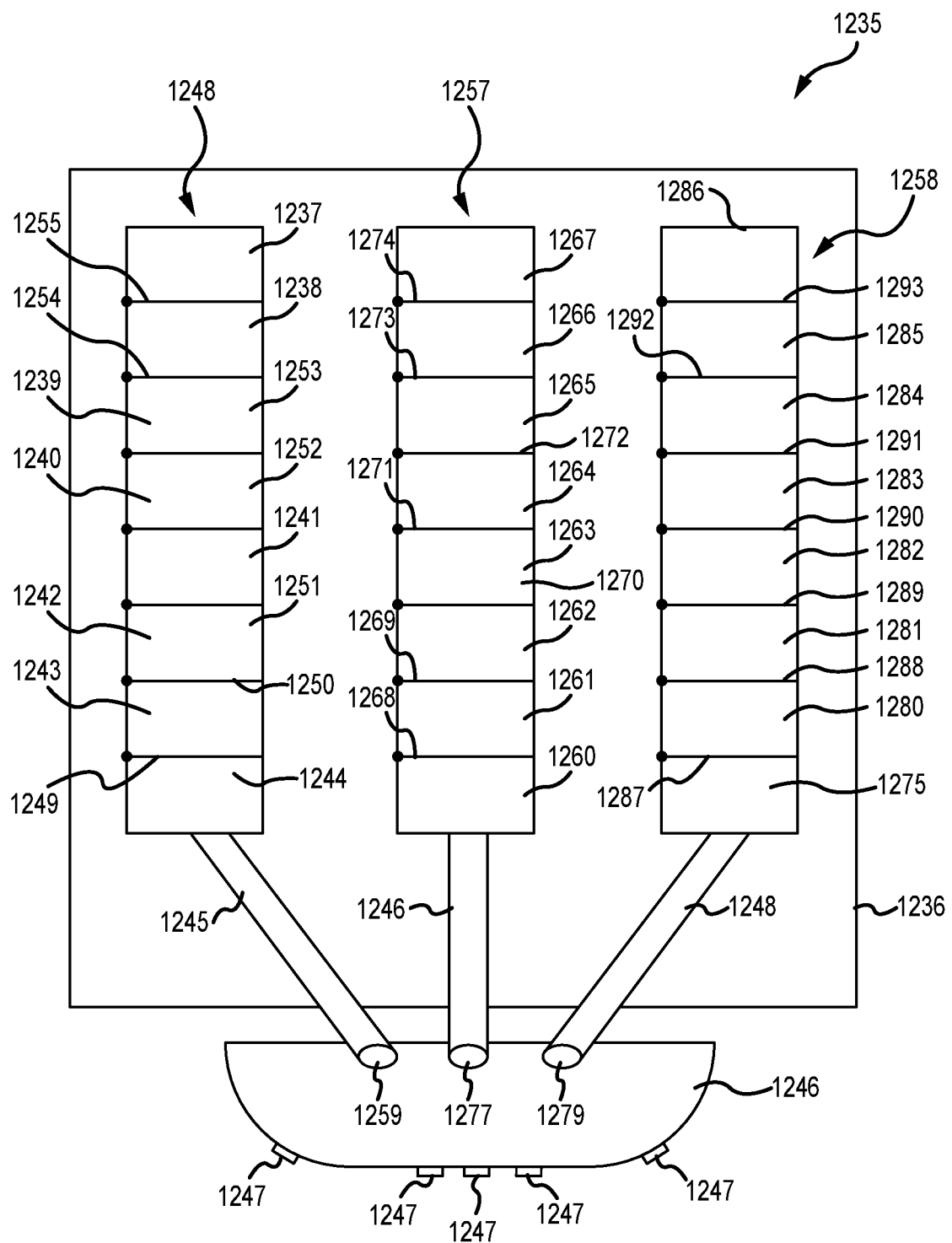
FIG. 92 is a front view of an alternative embodiment of a smart medicine cabinet having removable compartmentalized medication holders.

FIG. 92 illustrates yet another alternative embodiment of a smart medicine cabinet 1235. This smart medicine cabinet 1235 comprises an enclosure 1236 that preferably has a door (attached to the enclosure 1236 at a hinge on the left as shown in the illustrated embodiment) such as the door illustrated and described with reference to FIG. 59. Referring to FIG. 92, the enclosure 1236 includes receptacles for snapping into place a first compartmentalized medication holder 1248, a second compartmentalized medication holder 1257, and a third compartmentalized medication holder 1258.

The first compartmentalized medication holder 1248 comprises an AM medication dispenser chamber 1244 that is connected to a chute or tube 1245 connected to a dispenser service tray 1246. Medication in the form of pills, capsules, or tablets introduced into the AM medication dispenser chamber 1244 will fall down the chute 1245 and into the service tray 1246 to be taken by the resident. The first compartmentalized medication holder 1248 includes a Monday medication chamber 1243 connected to the AM medication dispenser chamber 1244 by a trap door or gate 1249 connected to and controlled by the computational and logic unit 121. In this embodiment, the Monday medication chamber 1243 is filled with all of the medication that the resident is scheduled to take in the morning on the following Monday. Thus, when the trap door 1249 is automatically activated at the prescribed time by the computational and logic unit 121, all of the medication that the resident is prescribed to take on Monday morning falls through the chute 1245, out the lower opening 1259 in the chute, and into the service tray 1246. The service tray 1246 is accessible to the resident even when the door of the enclosure 1236 is closed and locked. The service tray 1246 includes sensors 1247 to detect when the resident scoops the medication out of the service tray 1246.

The first compartmentalized medication holder 1248 includes a Tuesday medication chamber 1242 connected to the AM medication dispenser chamber 1244 by a trap door or gate 1250 connected to and controlled by the computational and logic unit 121. In this embodiment, the Tuesday medication chamber 1242 is filled with all of the medication that the resident is scheduled to take in the morning on the next Tuesday. Thus, when the trap door 1250 is automatically activated at the prescribed time by the computational and logic unit 121, all of the medication that the resident is prescribed to take on Tuesday morning falls through the chute 1245, out the lower opening 1259 in the chute, and into the service tray 1246.

The first compartmentalized medication holder 1248 includes a Wednesday medication chamber 1241 connected to the AM medication dispenser chamber 1244 by a trap door or gate 1251 connected to and controlled by the computational and logic unit 121. In this embodiment, the Wednesday medication chamber 1241 is filled with all of the medication that the resident is scheduled to take in the morning on the next Wednesday. Thus, when the trap door 1251 is automatically activated at the prescribed time by the computational and logic unit 121, all of the medication that the resident is prescribed to take on Wednesday morning falls through the chute 1245, out the lower opening 1259 in the chute, and into the service tray 1246.

Similarly, the first compartmentalized medication holder 1248 includes a Thursday medication chamber 1240 connected to the AM medication dispenser chamber 1244 by a trap door or gate 1252 connected to and controlled by the computational and logic unit 121. The trap door 1252 is automatically activated at the prescribed time by the computational and logic unit 121 to permit all of the medication that the resident is prescribed to take on Thursday morning to fall through the chute 1245 and into the service tray 1246. In like fashion, the first compartmentalized medication holder 1248 includes a Friday medication chamber 1239 connected to the AM medication dispenser chamber 1244 by a trap door or gate 1253 connected to and controlled by the computational and logic unit 121, which is operated at the prescribed time to automatically dispense all of the medication that the resident is to take on Friday morning.

The first compartmentalized medication holder 1248 includes a Saturday medication chamber 1238 connected to the AM medication dispenser chamber 1244 by a trap door or gate 1254 connected to and controlled by the computational and logic unit 121, to dispense Saturday morning medication. The first compartmentalized medication holder 1248 includes a Sunday medication chamber 1237 connected to the AM medication dispenser chamber 1244 by a trap door or gate 1255 connected to and controlled by the computational and logic unit 121, to dispense Sunday morning medication.

As described above, the first compartmentalized medication holder 1248 snaps into place in the enclosure 1236, and consequently, may be removed from the enclosure 1236. The first compartmentalized medication holder 1248 can be removed from the enclosure 1236 by a caretaker or by medical personnel in order to permit convenient re-filling of the medication chambers 1243, 1242, 1241, 1240, 1239, 1238 and 1237. Once the first compartmentalized medication holder 1248 has been filled with prescribed morning medication to be taken by the resident during the succeeding week, it may be conveniently snapped or clicked back into place in the enclosure 1236 ready for operation. In the event that no medication is prescribed for a given day, that corresponding medication chamber may be left empty without compromising the operation of the first compartmentalized medication holder 1248.

Referring to FIG. 92, the structure and operation of the second compartmentalized medication holder 1257 is similar to the first compartmentalized medication holder 1248. The second compartmentalized medication holder 1257 includes a mid-day medication dispenser chamber 1260 that is connected to a chute or tube 1276 connected to the dispenser service tray 1246. Medication in the form of pills, capsules, or tablets introduced into the mid-day medication dispenser chamber 1260 will fall down the chute 1276 and into the service tray 1246 to be taken by the resident. In the intended operation of this embodiment, the second compartmentalized medication holder 1257 is used for medication that the resident is scheduled to take in the middle of the day.

A Monday medication chamber 1261 is connected to the mid-day medication dispenser chamber 1260 by a trap door or gate 1268 connected to and controlled by the computational and logic unit 121, to automatically dispense medication into the service tray 1246 that the resident is prescribed to take mid-day on Monday. A Tuesday medication chamber 1262 is connected to the mid-day medication dispenser chamber 1260 by a trap door or gate 1269 connected to and controlled by the computational and logic unit 121, to automatically dispense medication into the service tray 1246 that the resident is prescribed to take mid-day on Tuesday. A Wednesday medication chamber 1263 is connected to the mid-day medication dispenser chamber 1260 by a trap door or gate 1270 connected to and controlled by the computational and logic unit 121, to automatically dispense medication into the service tray 1246 that the resident is prescribed to take mid-day on Wednesday.

Similarly, the second compartmentalized medication holder 1257 has a Thursday medication chamber 1264 connected to the mid-day medication dispenser chamber 1260 by a trap door or gate 1271 that is connected to and controlled by the computational and logic unit 121, in order to automatically dispense medication into the service tray 1246 that the resident is prescribed to take mid-day on Thursday. A Friday medication chamber 1265 is connected to the mid-day medication dispenser chamber 1260 by a trap door or gate 1272 connected to and controlled by the computational and logic unit 121, to automatically dispense medication into the service tray 1246 that the resident is prescribed to take mid-day on Friday. A Saturday medication chamber 1266 is connected to the mid-day medication dispenser chamber 1260 by a trap door or gate 1273 connected to and controlled by the computational and logic unit 121, to automatically dispense medication into the service tray 1246 that the resident is prescribed to take mid-day on Saturday. And a Sunday medication chamber 1267 is connected to the mid-day medication dispenser chamber 1260 by a trap door or gate 1274 connected to and controlled by the computational and logic unit 121, to automatically dispense medication into the service tray 1246 that the resident is prescribed to take mid-day on Sunday.

As described above, the second compartmentalized medication holder 1257 may be removed from the enclosure 1236, and conveniently re-filled by a caretaker or by medical personnel as described above in connection with the first compartmentalized medication holder 1248, and then snapped or clicked back into place in the enclosure 1236.

The third compartmentalized medication holder 1258 has a PM medication dispenser chamber 1275 that is connected to a chute or tube 1278 connected to a dispenser service tray 1246. Medication in the form of pills, capsules, or tablets introduced into the PM medication dispenser chamber 1275 will fall down the chute 1278 and into the service tray 1246 to be taken by the resident. In the intended operation of the illustrated embodiment, the third compartmentalized medication holder 1258 is filled with the medication that the resident is prescribed to take each day in the evening.

The third compartmentalized medication holder 1258 includes a Monday medication chamber 1280 connected to the PM medication dispenser chamber 1275 by a trap door or gate 1287 connected to and controlled by the computational and logic unit 121. In this embodiment, the Monday medication chamber 1280 is filled with all of the medication that the resident is scheduled to take in the evening on Monday. Thus, when the trap door 1287 is automatically activated at the prescribed time by the computational and logic unit 121, all of the medication that the resident is prescribed to take on Monday evening falls through the chute 1278, out the lower opening 1279 in the chute, and into the service tray 1246.

The third compartmentalized medication holder 1258 has a Tuesday medication chamber 1281 connected to the PM medication dispenser chamber 1275 by a trap door or gate 1288 that is connected to and controlled by the computational and logic unit 121, in order to automatically dispense medication into the service tray 1246 that the resident is prescribed to take on Tuesday evening. The third compartmentalized medication holder 1258 has a Wednesday medication chamber 1282 connected to the PM medication dispenser chamber 1275 by a trap door or gate 1289 that is connected to and controlled by the computational and logic unit 121, in order to automatically dispense medication into the service tray 1246 that the resident is prescribed to take on Wednesday evening.

The third compartmentalized medication holder 1258 has a Thursday medication chamber 1283 connected to the PM medication dispenser chamber 1275 by a trap door or gate 1290 that is connected to and controlled by the computational and logic unit 121, in order to automatically dispense medication into the service tray 1246 that the resident is prescribed to take on Thursday evening. The third compartmentalized medication holder 1258 has a Friday medication chamber 1284 connected to the PM medication dispenser chamber 1275 by a trap door or gate 1291 that is connected to and controlled by the computational and logic unit 121, in order to automatically dispense medication into the service tray 1246 that the resident is prescribed to take on Friday evening.

Similarly, the third compartmentalized medication holder 1258 has a Saturday medication chamber 1285 connected to the PM medication dispenser chamber 1275 by a trap door or gate 1292 that is connected to and controlled by the computational and logic unit 121, in order to automatically dispense medication into the service tray 1246 that the resident is prescribed to take on Saturday evening. Finally, the third compartmentalized medication holder 1258 has a Sunday medication chamber 1286 connected to the PM medication dispenser chamber 1275 by a trap door or gate 1293 that is connected to and controlled by the computational and logic unit 121, in order to automatically dispense medication into the service tray 1246 that the resident is prescribed to take on Sunday evening.

Figure 93:
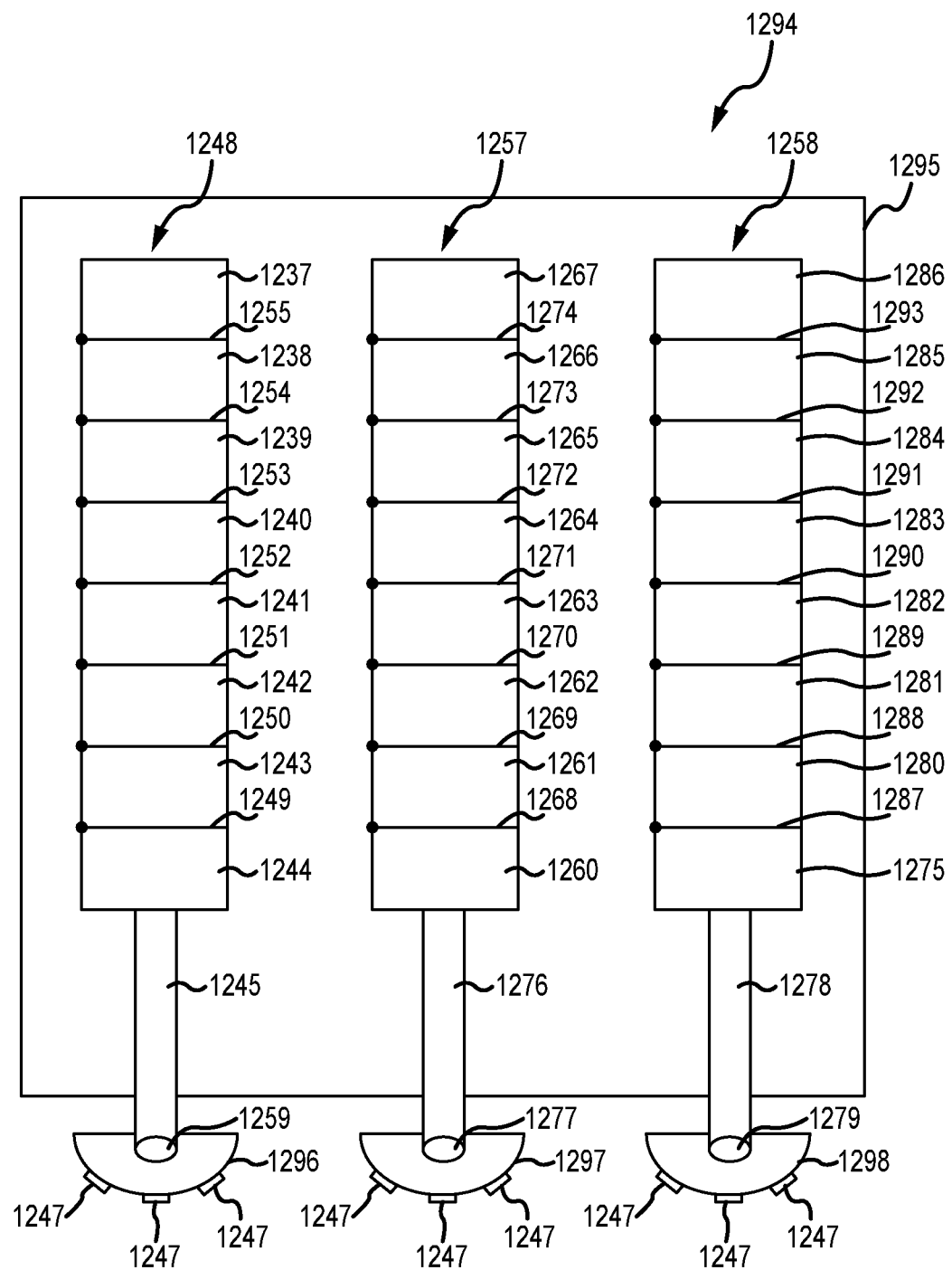
FIG. 93 is a front view of an alternative embodiment of a smart medicine cabinet having removable compartmentalized medication holders, and including three dispenser service trays.

FIG. 93 illustrates an alternative embodiment of a smart medicine cabinet 1294. This embodiment of a smart medicine cabinet 1294 includes an enclosure 1295 that has a door (attached to the enclosure 1295 at a hinge on the left as shown in the illustrated embodiment) similar to the door illustrated and described with reference to FIG. 59. Referring to FIG. 93, the enclosure 1295 includes receptacles for snapping into place a first compartmentalized medication holder 1248, a second compartmentalized medication holder 1257, and a third compartmentalized medication holder 1258. Similar to the embodiment described with reference to FIG. 92, in the embodiment shown in FIG. 93, the first compartmentalized medication holder 1248 holds medication that is to be taken each day in the morning. The second compartmentalized medication holder 1257 contains medication that is scheduled to be taken at mid-day on each day, and third compartmentalized medication holder 1258 has medication that is to be taken each day during the evening.

The embodiment shown in FIG. 93 is different in that a first dispenser service tray 1296, a second dispenser service tray 1297, and a third dispenser service tray 1298 are provided. The first chute or tube 1245 dispenses medication into the first dispenser service tray 1296. The second chute or tube 1276 dispenses medication into the second dispenser service tray 1297. And the third chute or tube 1278 dispenses medication into the third dispenser service tray 1298. Referring to FIG. 93, the operation of components having the same reference numeral shown in FIG. 92 is the same as that described in connection with FIG. 92.

Figure 94:
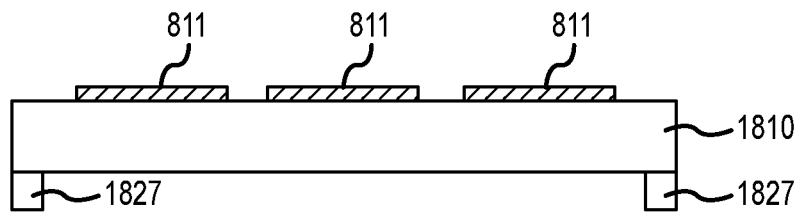
FIG. 94 is a front view of an embodiment of a remote smart medicine cabinet shelf.
Figure 95:
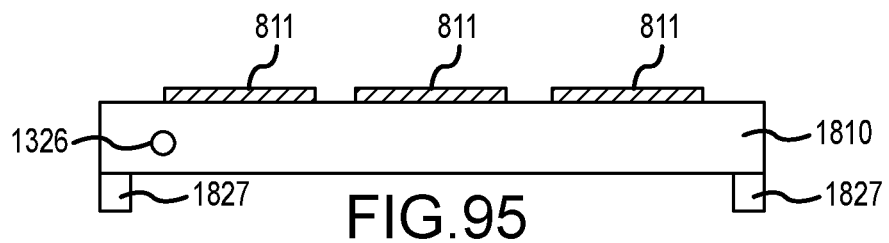
FIG. 95 is a rear view of the embodiment of a remote smart medicine cabinet shelf shown in FIG. 94.
Figure 96:
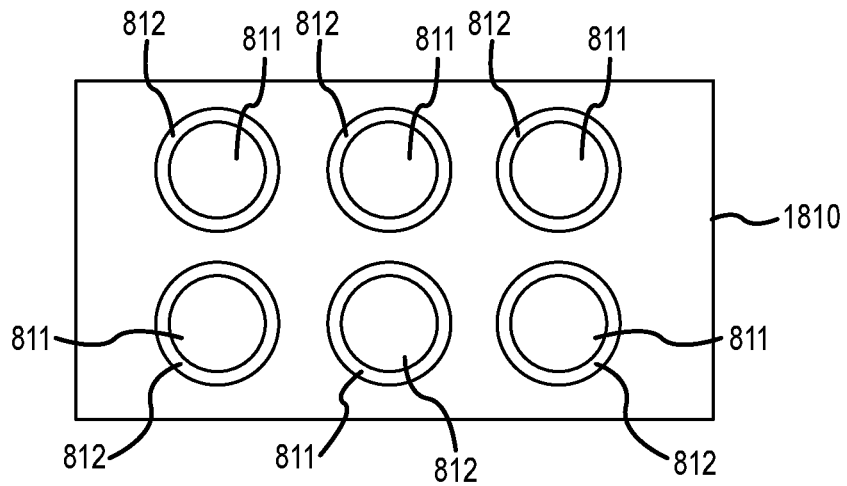
FIG. 96 is a top view of the embodiment of a remote smart medicine cabinet shelf shown in FIG. 94.
Figure 97:
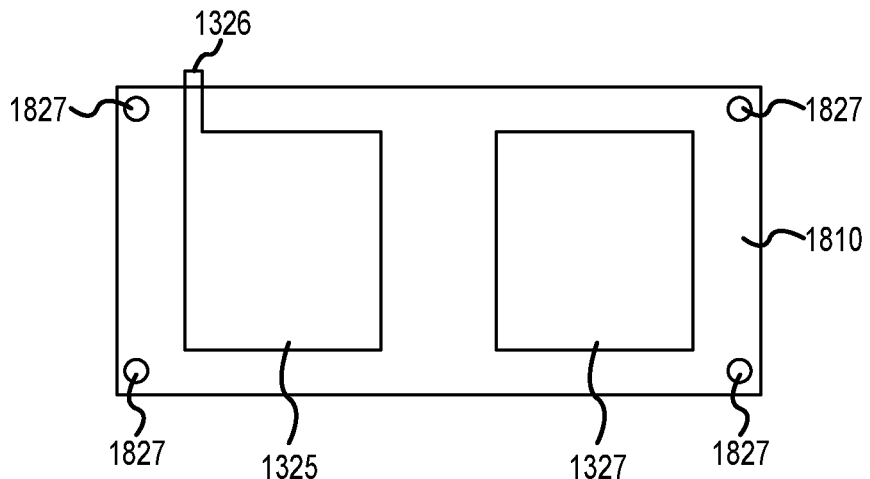
FIG. 97 is a bottom view of the embodiment of a remote smart medicine cabinet shelf shown in FIG. 94.

FIG. 94 is a front view of an embodiment of a remote smart medicine cabinet shelf 1810. FIG. 95, FIG. 96, and FIG. 97, show a rear view, a top view, and a bottom view, respectively, of this embodiment of a remote smart medicine cabinet shelf 1810. This embodiment of a remote smart medicine cabinet shelf 1810 provides a remote shelf for the storing, dispensing, measuring and reporting of medications taken. This embodiment of a remote smart medicine cabinet shelf 1810 has many of the same features and functionality as the shelves 810 described above in connection with the smart medicine cabinet 800, including weight sensitive pads 811 that measure the dosage taken, as well as the halo light design 812 described above to direct the resident to the correct bottle of medication to be taken.

This embodiment of a remote smart medicine cabinet shelf 1810 shown in FIG. 94, FIG. 95, FIG. 96, and FIG. 97, is self-contained with a power supply and battery backup 1325, and a wireless communications module 1327 providing WiFi and Bluetooth communications with the HAPPIE Home unit 103. This self-contained embodiment of a remote smart medicine cabinet shelf 1810 may, in various embodiments, accommodate three, six and nine microscale, weight sensitive pads 811 and halo light configurations 812. FIG. 96 illustrates an embodiment having six weight sensitive pads 811 and halo light configurations 812, but it will be understood that alternative embodiments may have three, or nine, or any other convenient number of weight sensitive pads 811 and halo light configurations 812 to correspond to the different number of individual medications that must be taken by the resident. Thus, this embodiment can be expanded, as needed, and additional shelf size and configurations can be provided due to an increase in prescription medications taken, as the resident ages naturally, or to combat specific health conditions and illnesses. There are not any current size constraints, as this self-contained embodiment of a remote smart medicine cabinet shelf 1810 is not necessarily intended to be mounted within a smart medicine cabinet 800.

This self-contained embodiment of a remote smart medicine cabinet shelf 1810 operates using a power supply that plugs into power plug 1326, where the power supply (not shown) typically comprises a conventional converter for converting standard electrical power available via a conventional electrical wall outlet to 12-volt direct current or other suitable low voltage current for the remote smart medicine cabinet shelf 1810. A back-up battery pack 1325 is included in the remote smart medicine cabinet shelf 1810, as shown in FIG. 97. A built-in wireless communication link is provided by the wireless communications module 1327 between the smart medicine cabinet 800, the HAPPIE Home unit 103, and the remote smart medicine cabinet shelf 1810. One benefit of the remote smart medicine cabinet shelf 1810 is that that this embodiment provides medication monitoring and tracking of prescription medication taken by the resident while away from home or on vacation.

This self-contained embodiment of a remote smart medicine cabinet shelf 1810 has feet 1827 attached to the bottom of the shelf 1810. These feet 1827 provide a convenient support for the remote smart medicine cabinet shelf 1810 when it is placed on a table or other support surface.

Figure 42:
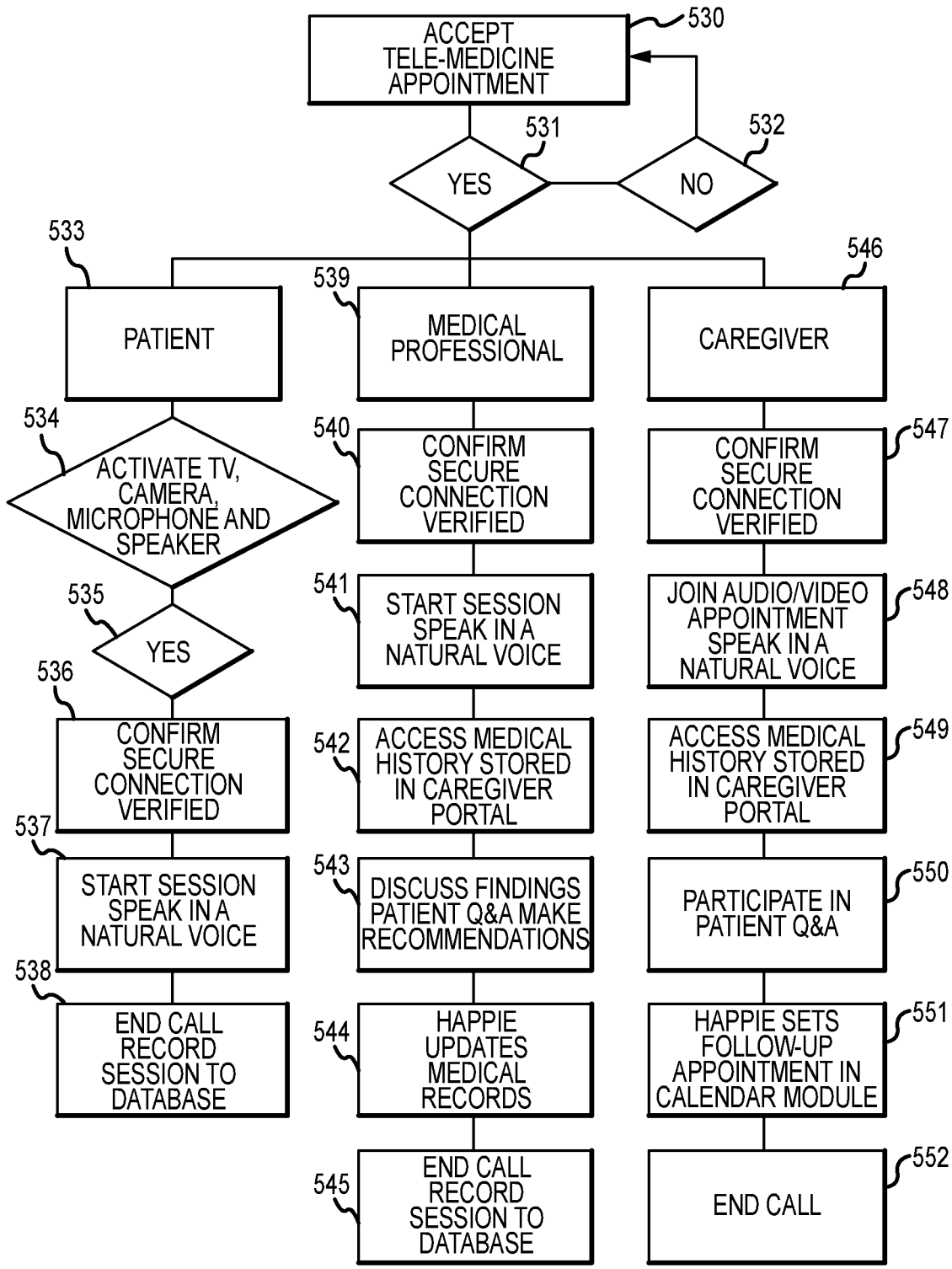
FIG. 42 is a flowchart illustrating a method associated with a telemedicine feature in accordance with one embodiment of the invention.

Referring to FIG. 42, a telemedicine feature according to one embodiment of the invention is illustrated. This feature is provided in connection with the caregiver portal 101, the doctor portal 102, and the resident's TV or video monitors 156 available at the residence. The HAPPIE home unit 103 preferably has a telemedicine module configured to execute the steps of the method described herein. This functionality may also be accessed via an app on the caregiver's smartphone 178 or the resident's smartphone 111.

The HAPPIE home unit 103 includes architecture designed to treat authorized medical professionals as approved caregivers possessing a unique feature set that includes three-way conference calling between the resident, the caregiver, and the medical professional. Medical professionals have access to specific modules, data and reporting provided by the doctor portal 102. Either the medical professional or the resident may initiate a three-way connection that includes the resident, the caregiver, and the medical professional. Referring to FIG. 42, a three-way connection is initiated in step 530. If the three-way connection is not successful, as indicated in step 532, the method loops back for another attempt. If the three-way connection is successful in step 531, the method proceeds to connect the resident in step 533, connect the medical professional in step 539, and connect the caregiver in step 546.

The telemedicine module in accordance with the present invention offers the ability to speak with a medical professional by established an audio or audio video connection, which may be initiated by the caregiver or the resident who wish to speak with an independent health care provider or in-plan health insurance health care provider to ask medically related questions. Audio and video recordings of the call are made and stored in the database 108 provided with the HAPPIE home unit 103. Such recordings may be revisited or reviewed at a later time, and provide a permanent record concerning the resident's health care.

The telemedicine module in accordance with the present invention offers the ability to schedule health care related consultation at a predetermined time. An audio or audio-video connection may be initiated by the medical professional, the patient, or the caregiver. The HAPPIE home unit 103 can remind the resident and the caregiver of an upcoming call that has been scheduled. The HAPPIE home unit 103 can then initiate the call to the appropriate parties at the predetermined scheduled time. Audio and video recordings of the call are recorded and logged into the HAPPIE home unit 103 for storage on the database 108 for revisiting at a later time or as a permanent record.

The telemedicine module in accordance with the present invention offers the ability to generate patient status alerts concerning the resident. Health status parameters may be set by the medical professional. Status updates and alerts can be tied to medical monitoring devices 160 and to wearable sensors 158, and made available to both the caregiver portal 101 and to the doctor portal 102 when a threshold is crossed to trigger the alert.

As shown in FIG. 42, in the case of the resident 533, in step 534 if the resident's TV or video monitors 156 are off, the HAPPIE home unit 103 will activate or turn on the TV or video monitors 156 when a reminder indicates that a scheduled conference with a medical professional (e.g., doctor or nurse) is due or is about to occur. In step 535, the resident has the option to accept the scheduled or incoming telemedicine conference. Alternatively, if the resident does not accept the medical consultation appointment at the scheduled time in step 535, the appointment is postponed. The HAPPIE home unit 103 may reschedule the appointment at this time, or at a later point in time. If the resident does not accept the medical consultation appointment at the scheduled time in step 535, the medical professional is notified of the resident's decision not to take the consultation or to reschedule via the doctor portal 102, and the caregiver is notified via the caregiver portal 101.

If the resident accepts the consultation in step 535, the HAPPIE home unit 103 proceeds to step 536 to verify the credentials of the medical professional and the caregiver, ensure that the communication link is secure, and then connects the resident, the medical professional, and the caregiver together via a three-way communication link. In the event that the caregiver is not available, the resident has the option of accepting the medical consultation with the medical professional without the caregiver's participation, and the HAPPIE home unit 103 converts the communication circuit to a two-way connection between the resident and the medical professional via the doctor portal 102. Referring to FIG. 42, in step 537, after a secure connection has been established and verified by the HAPPIE home unit 103, the resident may begin the consultation with the medical professional by speaking in a normal voice, which will be picked up by microphones 113 and transmitted over the secure connection via the doctor portal 102. The medical professional will be displayed to the resident on the resident's TV or video monitor 156. In addition, the medical professional may display other information on the resident's TV or video monitor 156, such as the results of tests, instructions for physical therapy exercises, medication instructions, instructional videos, etc. The medical professional will also have access, via the doctor portal 102, to data from medical equipment 160, such as blood pressure sensors 163, pulse monitor 165, patient temperature sensor 161, Fitbit™ wristband 164, Mediwand™ device 162, etc.

Normally, a caregiver will be included, via the caregiver portal 101, in a three-way communication link between the resident via the HAPPIE home unit 103, and the medical professional via the doctor portal 102.

Referring to FIG. 42, when a three-way telemedicine consultation is established with the caregiver in step 546, the HAPPIE home unit 103 verifies and confirms that the connection is secure in step 547. As illustrated in step 548, the caregiver typically will be able to view everything that appears on the resident's TV or video monitors 156, unless such access is restricted by the HAPPIE home unit 103. The caregiver will be able to communicate via the caregiver portal 101 with both the medical professional at the doctor portal 102, and with the resident using the HAPPIE home unit 103. The caregiver may speak in a natural voice, as indicated in step 548. The caregiver will be able to access medical history and medical records concerning the resident, which are stored in the database 108, via the caregiver portal 101. The caregiver will also be able to access medical history and medical records concerning the resident, which are stored at the caregiver portal 101, as indicated in step 549. As indicated in step 550, the caregiver is able to participate in, and assist the resident if necessary, in any question and answer session involving the medical professional, such as providing the medical professional with information concerning medical history, allergies to medicines, and list of medications. In step 551, the HAPPIE home unit 103 sets any follow-up appointments on the resident's calendar, illustrated for example in FIGS. 10, 11, and 12, and also provides the appointment data to the caregiver's calendar. In step 552, the HAPPIE home unit 103 terminates the connection with the caregiver portal 101 when the consultation ends.

Referring to FIG. 42, a secure connection with a medical professional is established in step 539. The HAPPIE home unit 103 verifies that the connection is secure in step 540. In step 541, the medical professional is able to communicate by speaking in a normal voice, and live video is transmitted from a camera provided at the doctor portal 102. The medical professional may be a doctor, nurse, physical therapist, pharmacist, lab technician, instructor for a medical device, or any person trained in medicine or related sciences.

The medical professional is able to access, via the doctor portal 102, medical data and medical records stored in the database 108 maintained by the HAPPIE home unit 103. The medical professional is also able to access, via the doctor portal 102, medical data and medical records stored at the caregiver portal 101, as illustrated in step 542. Using the doctor portal 102, the medical professional is able to discuss findings with the resident and the caregiver, conduct question and answer sessions, and make recommendations, as shown in step 543. As indicated in step 544, the HAPPIE home unit 103 stores any other medical data or information on the database 108, which may be input or otherwise received during the telemedicine consultation, such as new prescriptions, new appointments, new or revised schedule information, and doctor notes. The HAPPIE home unit 103 also records the entire audio and video session, and stores it on the database 108 at the end of the call, as indicated in step 545. A voice recognition module 167 may be employed to transcribe the entire consultation, and to provide a text searchable record of the consultation that is stored in the database 108. The HAPPIE home unit 103 terminates the connection with the doctor portal 102 when the consultation ends.

The HAPPIE home unit 103 offers significant advantages for a caregiver to remotely check on the status of the resident, using the caregiver portal 102, without requiring the caregiver to travel to the residence and without requiring a resident nurse or other caregiver. This is facilitated by a method provided by the HAPPIE home unit 103 for locating the resident at any time. This method normally is provided as a caregiver tool, and is not intended to display on the resident's TV console or video monitors 156. Optionally, this method may be run remotely at the caregiver portal 102, or on a mobile device app on the caregiver's smartphone 178 or other wireless computing device.

Figure 43:
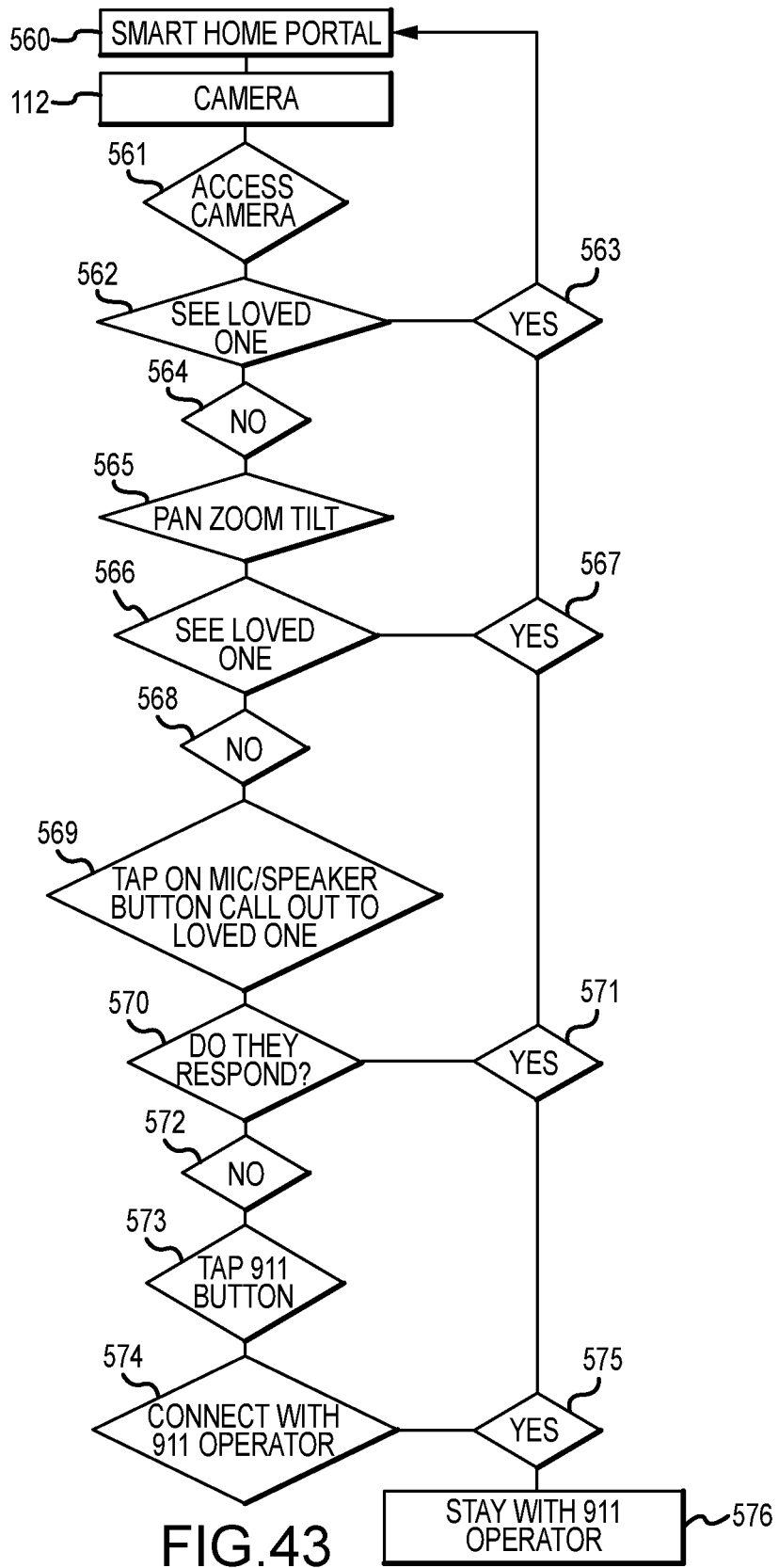
FIG. 43 is a flowchart illustrating a method for locating the resident associated with the HAPPIE home unit in accordance with one embodiment of the invention.

When the resident is being located, three are generally three possibilities or circumstances that may require different treatment. First, the resident may be readily visible on an image provided by one of the cameras 112 at the residence monitored by the HAPPIE home unit 103, when the caregiver logs into the HAPPIE home unit 103 at the residence. Second, the resident may be located within a short period of time after scrolling through the camera views provided by a plurality of video cameras 112, and it is apparent from the view of the resident that the resident is doing well. Third, the resident may be out of camera range, and his or her status is unknown. Fourth, the resident may be located while scrolling through the camera views provided by a plurality of video cameras 112, and the resident appears to be unresponsive, or other circumstances indicate that emergency services 106 may be needed. As illustrated in FIG. 43, a method provided by the HAPPIE home unit 103 for locating the resident, which is capable of dealing will all such circumstances.

Referring to FIG. 43, a caregiver may access the HAPPIE home unit via a smart home portal 560. In step 561, the caregiver accesses video cameras 112 via the caregiver portal 101. In step 562, a determination is made whether the resident is visible in the video images provided by video cameras 112. If the resident is located, as indicated in step 563, the method loops back and is completed.

If the resident is not located, as indicated in step 564, the method proceeds to pan, tilt, and zoom the video cameras 112 in step 565, in an effort to locate the resident. In step 566, a determination is made whether the resident is visible in the video images provided by video cameras 112 after the cameras 112 are zoomed out, and panned and tilted around. If the resident is located, as indicated in step 567, the method loops back and is completed.

If the resident is not located, as indicated in step 568, the method proceeds to activate a microphone located at the caregiver portal 102 so that the caregiver may call out to the resident, which audio is transmitted to the HAPPIE home unit 103 via the caregiver portal 102 and broadcast via speakers 157 at the residence, as indicated in step 569. Microphones 113 at the residence are activated to pick up any response from the resident, and transmit the received audio to the caregiver portal 102. A determination is made in step 570 concerning whether any response is received from the resident. If a satisfactory response is received, and the resident is doing well, as indicated in step 571, the method loops back and is completed.

If no response is received, as indicated in step 572, or the resident is located and appears unresponsive or in distress, the caregiver may initiate, via the caregiver portal 102, an emergency call for help via the emergency services portal 106, as illustrated in step 574. In step 575, the HAPPIE home unit 103 establishes a three-way audio-video communication link with the caregiver via the caregiver portal 102 and with emergency services via the emergency services portal 106. Using the three-way communication link, the caregiver is able to communicate the situation and circumstances to emergency services via the caregiver portal 101. In addition, the emergency services has access to information from the microphones 113 and the video cameras 112 at the residence, and can observe the premises remotely via the emergency services portal 106. This access may be especially advantageous, if for example, the caregiver discovers that an intruder is in the residence, or that a robbery or other crime is in progress. Emergency services may also be given access via the emergency service portal 106 to data stored in the database 108 concerning the resident's activities prior to the event, such as food and hydration consumption by the resident, whether prescribed medication was taken on schedule, as well as vital signs and other health data from wearable sensors 158, which may be especially advantageous in a medical emergency, because better decisions can be made concerning the appropriate emergency response based upon such additional information. A record of the audio picked up by microphones 113, video recorded by video cameras 112, and other sensor readings during and immediately prior to the event from sensors 130, and from medical equipment 160, is stored in the database 108 for evidentiary purposes, or as useful diagnostic information for medical professionals. The caregiver may stay connected with the emergency services personnel as indicated in step 576. Or alternatively, at the option of the caregiver, the method may loop back in step 575 and is completed.

In an emergency, or when otherwise desired, the caregiver may broadcast, via the caregiver portal 102, a request to others involved with the resident concerning the status of the resident. For example, the caregiver may inquire whether anyone else knows the whereabouts of the resident. Or the caregiver may ask who was the last person to see the resident, and when that occurred.

An automated home care system for senior care may advantageously take advantage of machine learning and artificial intelligence for improved care of a resident. Machine learning within the system enables the system to accurately track the patterns and routines of the resident who is being monitored by the system. Sensors 130 throughout the residence feed current data to the computational and logic unit 121 to be stored in the database 108, and machine learning is applied to compare the resident's location within the residence, in real time, as it relates to historical data stored on the database 108. The computational and logic unit 121 uses the data to predict where the resident is likely to move to next in the residence. Inconsistencies between the current location of the resident and predicted location of the resident may be used to trigger an automatic alert to a caregiver via the caregiver portal 101, when the deviation exceeds certain predetermined levels. the alert to the caregiver may be a text alert, or email alert, or phone call, or any other type of communication that is designed to bring the information to the attention of the appropriate caregiver.

Wearable sensors 158 may be used to gather data concerning the resident's current position and posture, based upon the height and location of the sensor that is being worn by the resident. Height data may indicate whether the resident is sitting, lying down, standing, or walking around in the residence. Wearable sensors 158 in the form of a pin, necklace, wrist band with a chip, smart device, smart watch, or other wearable sensors such as a FitBit™ device 164, may be advantageously used for this purpose. Any medical and health and wellness monitoring device 136 that can be worn by the resident can be used.

Discrepancies in the height measured for the wearable sensor, not associated with a fall, can be merged with data from a posture detection system to determine if the resident is slouching over, walking with a bias, slumping, or otherwise not displaying a normal or typical posture for the resident. The absence of new motion data may indicate that the resident has become unconscious, if combined with data indicating a lack of any response from the resident to audible inquiries automatically generated by the computational and logic unit 121 and played over the speakers 157. The absence of new motion data may also indicate that the wearable sensor 158 has been removed by the resident, or has ceased to function correctly. Any of these circumstances can cause the computational and logic unit 121 to automatically generate an alert to a caregiver via the caregiver portal 101. Given the historical data that is stored in the database 108, the computational and logic unit 121 develops an individualized posture profile for a particular resident, and deviations are measured based upon departures from that typical posture profile, rather than from some average posture for individuals in the general population.

Loss of consciousness may be difficult to detect when the resident is in a sitting position, or a reclining position, or is lying on a bed. Changes in breathing, minor involuntary movements, facial tics, or other slight visual cues or signs can be detected by the computational and logic unit 121 based upon visual data from cameras 112 and audio data from microphones 113, which might not be noticeable to a casual observer. The computational and logic unit 121 compares variances in such visual data and audio data with historical data stored in the database 108, and automatically triggers an alert to a caregiver via the caregiver portal 101 when the variation exceeds a predetermined level of deviation.

Fainting or loss of consciousness will likely result in the resident ending up on the floor. Upon fainting, a person will typically crumple or fall straight down to the floor or ground. It is rare that a person will make loud noises, comments, screams, or crying under such circumstances. Typically, a person who faints will come to rest on the floor or ground and not exhibit any further movement for a period of time. Video data received from cameras 112 is analyzed by the computational and logic unit 121 to detect a fainting or unconsciousness event, together with data collected by wearable sensors 158, motion detectors 152, and audio data from microphones 113, to determine if the resident has experienced a fall due to loss of consciousness or fainting. The computational and logic unit 121 predicts a resident's likelihood of distress and may automatically generate an alert to a caregiver via the caregiver portal 101, or may automatically contact emergency services via the emergency services portal 106, or both.

Fainting or loss of consciousness can be distinguished from a slip and fall event. In the case of a slip and fall event, it will typically be accompanied by loud noises, comments, screams, or crying. When a person slips and falls, the person may remain conscious while lying on the floor and can verbally request help or assistance. The loud noises, spoken utterances, screams, or cries from the resident will be picked up by microphones 113 and analyzed by the computational and logic unit 121. Words spoken, stress levels detected in the resident's voice, and speaking volume are all detected and analyzed as indicators that a slip and fall event has occurred, or some other event out of the normal. Data collected by wearable sensors 158, data collected by motion sensors 152, video data collected by cameras 112, audio data collected by microphones 113, and data collected by other sensors 130 (such as floor sensors 153), will all be analyzed by the computational and logic unit 121 to determine if the resident has experienced a fall. Verbal requests from the resident are received by microphones 113 and analyzed using voice recognition, along with any other spoken words uttered by the resident. The computational and logic unit 121 can respond to a slip and fall event by generating an alert to a caregiver via the caregiver portal 101 and/or by summoning emergency assistance (calling an ambulance or EMT personnel, for example) via the emergency services portal 106.

Figure 73:
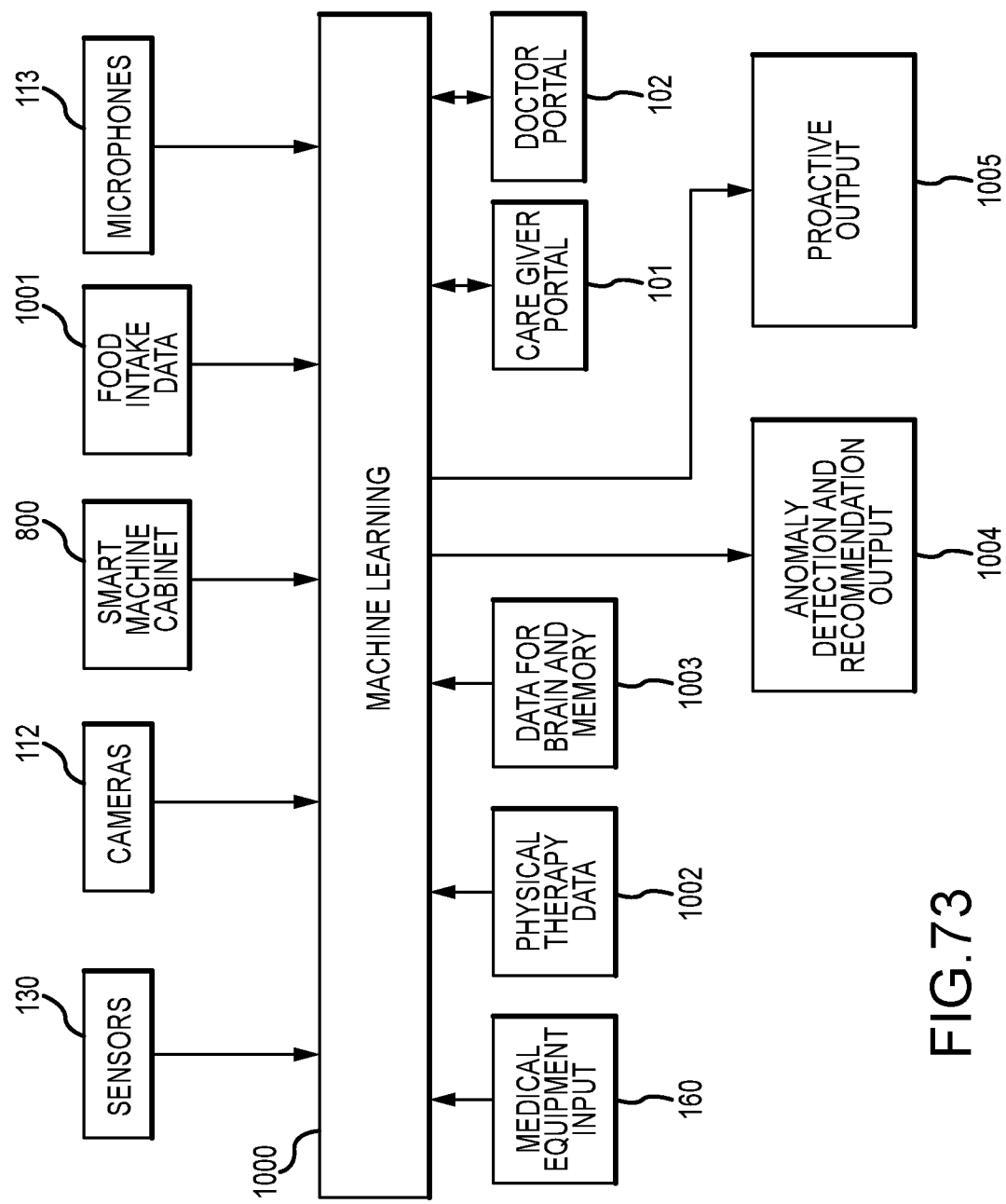
FIG. 73 is a block diagram illustrating an alternative embodiment that includes a machine learning module.

FIG. 73 illustrates one preferred embodiment of an automated home system for senior care that includes a machine learning module 1000. The machine learning module 1000 is preferably included within the HAPPIE home unit 103. In the embodiment shown in FIG. 73, the machine learning module 1000 receives inputs from video cameras 112 and microphones 113. Home sensors 130 may also provide data to the machine learning module 1000, including input from motion detectors 152, bed sensors 151, floor sensors 153, intelligent heat detectors 194, security sensors 147, temperature and humidity sensors 149, fire and smoke sensors 150, and water sensors 148, (as shown in FIG. 4). Referring to FIG. 73, the illustrated embodiment includes input from the smart medicine cabinet 800.

As shown in FIG. 73, the machine learning module 1000 receives input data from medical equipment 160, such as equipment that measures the resident's temperature 161, blood pressure measuring equipment 163, pulse monitor 165, weight scale 166, and Mediwand 162. The machine learning module 1000 may also receive medical input data from wearable sensors 158, a FitBit 164, and similar devices.

Referring to FIG. 73, food intake data 1001 may be provided as an input to the embodiment using a machine learning module 1000. Food intake data 1001 includes data concerning the food that has been eaten by the resident of the automated home, and the nutrition received by the resident. Food intake data 1001 may be input manually for the resident. However, food intake data 1001 may be advantageously captured automatically by the pantry 119, the refrigerator 115, and the coffee maker 118, as well as with an intelligent analysis of video data from cameras 112 when the resident eats a meal or a snack. In addition, the resident may verbally speak what food has been consumed by the resident, and audio from microphones 113 can be analyzed using speech recognition to provide data to the machine learning module 1000. Food intake data 1001 may also be provided by a caregiver via the caregiver portal 101.

Referring to FIG. 73, physical therapy data 1002 may be provided as an input to the machine learning module 1000. For example, if the resident participates in physical therapy exercises, data associated with that activity may be input into the machine learning module 1000 either directly or via the doctor portal 102. Alternatively, the resident may verbally speak a summary of physical therapy activities completed by the resident, and audio from microphones 113 can be analyzed using speech recognition to provide data to the machine learning module 1000. The physical therapy data 1002 may include data captured in connection with the wellness module 204.

Referring to FIG. 73, data relating to brain function, cognition, and memory 1003 may be provided as an input to the machine learning module 1000. For example, brain function, cognition, and memory data 1003 may include data captured in connection with the memory strength module 206. Alternatively, data relating to brain function, cognition, and memory 1003 may be provided by a caregiver via the caregiver portal 101, or by medical personnel via the doctor portal 102.

Input data to the machine learning module 1000 may also be provided through the Internet 105. For example, weather reports and forecasts may be obtained by the machine learning module 1000 via the Internet.

The machine learning module 1000 may analyze the data received via various inputs, optionally compare it against a dataset of data representing a normal baseline of such inputs, and provide anomaly detection alerts 1004 when the input data deviates significantly from the information in the stored dataset. The machine learning module 1000 may produce recommendations output 1004 when the input data deviates significantly from the information in the stored baseline dataset or normal dataset. For example, if the input data from the weight scale 166 indicates a significant increase in the resident's weight, and food intake data 1001 indicates a significant increase in caloric intake, the machine learning module 1000 may generate a recommendation to the resident concerning what the resident should consider having for lunch or dinner, or generate a recommendation if the smart refrigerator 115 indicates that the resident has opened the refrigerator door, which recommendation may be displayed on video monitors 156 or an audio output may be spoken over speakers 157. The machine learning module 1000 may automatically generate alerts or recommendations 1004 which may be sent to a caregiver via the caregiver portal 101, or to medical personnel via the doctor portal 102, when the input data deviates significantly from a normalized baseline represented by information stored in the dataset.

The machine learning module 1000 may generate proactive outputs 1005 when the input data deviates significantly from a baseline stored in the reference dataset. For example, the medical equipment input 160 may include data from a blood sugar monitor. If the blood sugar level rises above a predetermined level, the machine learning module 1000 could generate a proactive output 1005 alerting a diabetic resident to take a prescribed dose of insulin. Alternatively, if the data inputs indicate a chance of rain, the machine learning module 1000 may generate a proactive output 1005 recommending that the resident take an umbrella or wear rain gear if the resident is going out.

Recommendations 1004 and proactive alerts 1005 may generate outputs based upon a single input and algorithms executed by the machine learning module 1000. However, an embodiment of the present invention can use a plurality of inputs provided to the machine learning module 1000 to identify anomalous conditions based upon the plurality of inputs. For example, a small decline in the data 1003 from a memory strength module combined with missing an appointment could indicate could indicate a condition that produces an output 1004 when any single input, considered alone, might be insufficient. In the embodiment illustrated in FIG. 73, the machine learning module 1000 and anomaly detection module 1004 can develop recommendations and alerts based upon a combined data set.

Figure 74:
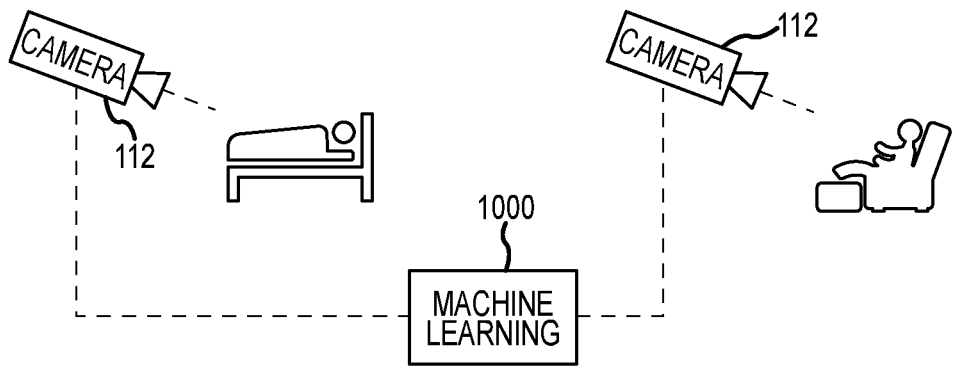
FIG. 74 is a schematic diagram showing a machine learning module receiving video data input from video cameras.

Referring to FIG. 74, the machine learning module 1000 may advantageously analyze data from video cameras 112. This includes data gathered while a resident is sleeping, or is watching TV, or is engaged in other activities. For example, the machine learning module 1000 may perform pose analysis of images of the resident captured by the video cameras 112. If an analysis of the data from the video cameras 112 represent a significant deviation from the normal pose of the resident, this may generate alerts to a caregiver or to medical personnel.

Figure 75:
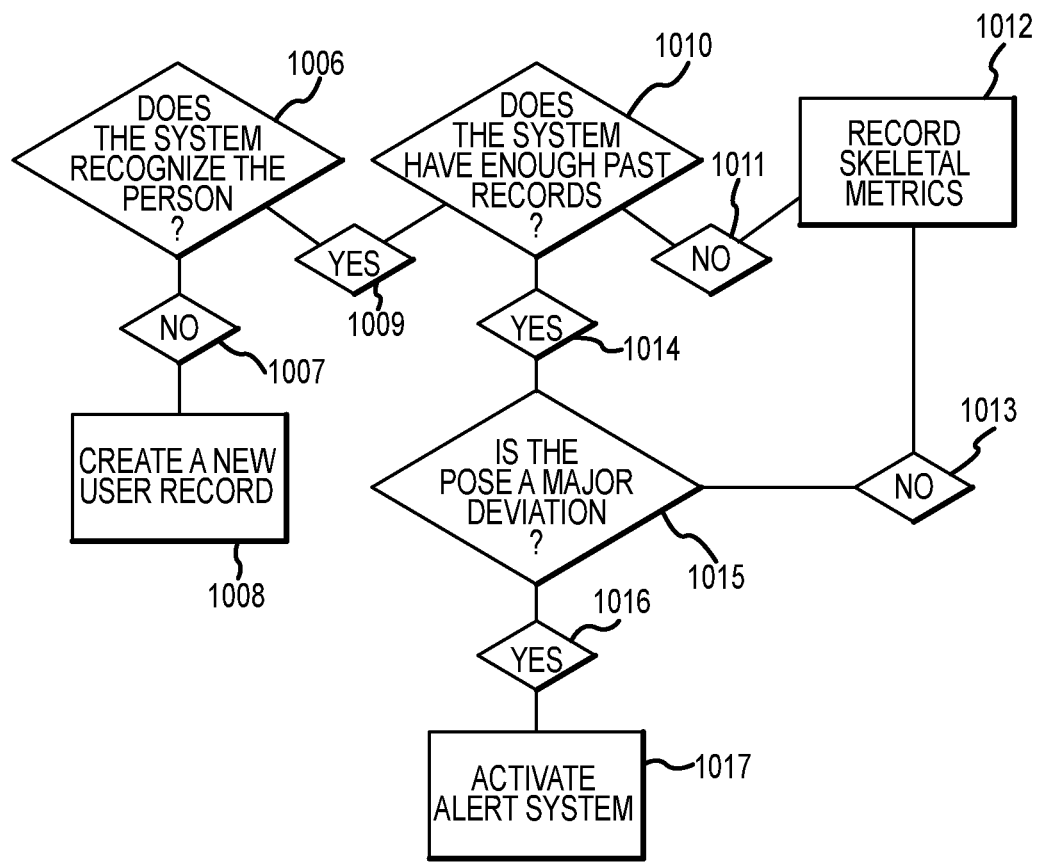
FIG. 75 is a flow chart illustrating a method of using video data to detect an abnormal pose by a person.

FIG. 75 illustrates a flow chart diagram of a method for activating an alert based upon an analysis of pose data from the video cameras 112. In step 1006 a determination is made whether the person captured by the video camera 112 is recognized and can be identified. If the person is not recognized as a known person, in step 1007, a new record is created for that person in step 1008. If the person is recognized in step 1009, the system determines whether it has enough past records in step 1010. If the system determines in step 1011 that it does not have enough past records to make an accurate normal pose determination, the system will record skeletal metrics in step 1012 and add those records to the data set. An open-source algorithm like OpenPose may be used for the skeletal analysis to produce a data set of skeletal pose data. For example, OpenPose can be used to convert a video image of a human pose into a series of points in 3-dimensional space, or into points associated with a vector indicating the direction of the bone and its length, which may be flattened into 2-dimensional space for analysis or storage in a data set.

Referring to FIG. 75, if the system determines in step 1014 that it has enough past records to make a pose analysis, in step 1015 a determination is made whether the pose is a major deviation from normal. if it is not, as illustrated in step 1013, the skeletal metrics are recorded and added to the data set. If the results of the analysis in step 1015 is a determination in step 1016 that the pose is a major deviation from normal, that the system automatically activates an alert in step 1017 without human intervention.

Figure 76:
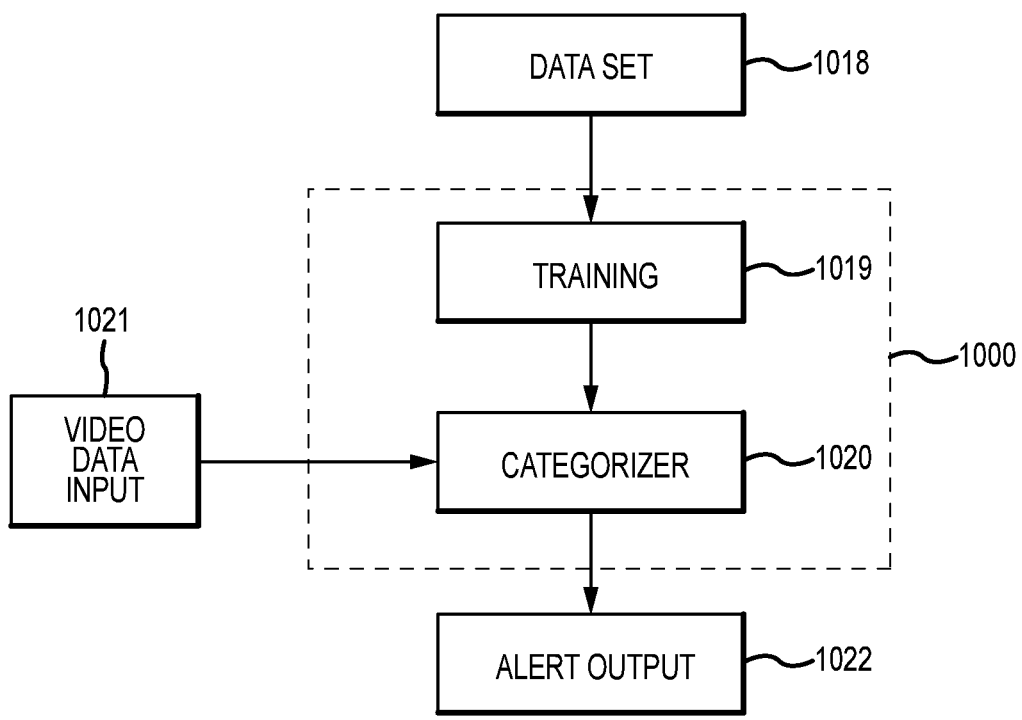
FIG. 76 is a block diagram of an embodiment of a machine learning module for analyzing video data.

FIG. 76 shows further details of the machine learning module 1000 in an embodiment that analyzes video data 1021 to detect whether the resident has fallen or is unconscious. A predetermined data set 1018 is used to provide data representative of a person who has fallen or is unconscious on the floor. In practice, a relatively small number of reference data examples, for example ten or more, is typically sufficient for this purpose. The reference data set 1018 is fed into a training module 1019 in the machine learning module 1000. The training module 1019 then feeds its results into a categorizer module 1020 in the machine learning module 1000. The categorizer module 1020 compares the output of the training module 1019 to data received from the video data input 1021 to determine whether the resident has fallen or is unconscious on the floor. An alert output 1022 is generated when a determination is made that the resident has fallen, or is unconscious on the floor.

Figure 77:
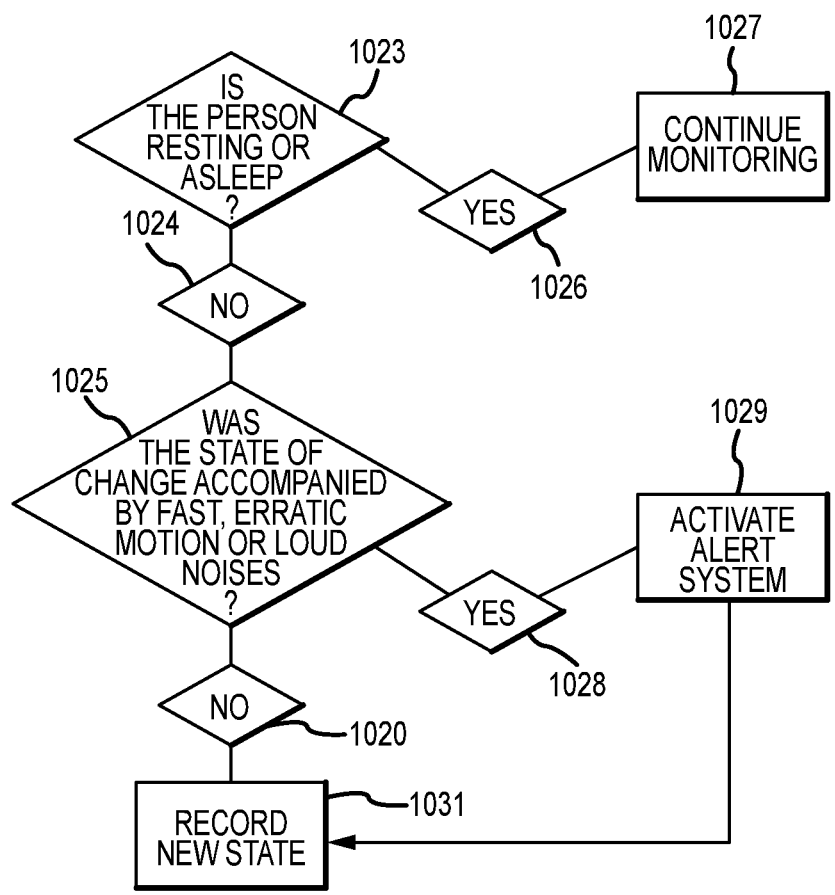
FIG. 77 is a flow chart illustrating a method for activating alerts based upon an analysis of video data.

Referring to FIG. 77, a flow chart is shown illustrating a method of generating an alert based upon analysis of video data by the machine learning module 1000. In step 1023, a determination is made whether the resident is resting or asleep. If the answer is yes in step 1026, the system continues monitoring as shown in step 1027.

In FIG. 77, if a determination is made that the resident is not resting or asleep in step 1024, a determination is made in step 1025 whether the state of change was accompanied by fast, erratic motion (based on video data from video cameras 112) or by loud noises (based upon audio data from microphones 113). If the answer is no, as shown in step 1030, the method proceeds to step 1031 to record the new state. If the answer is yes, as shown in step 1028, the method proceeds to automatically activate an alert system in step 1029.

Figure 78:
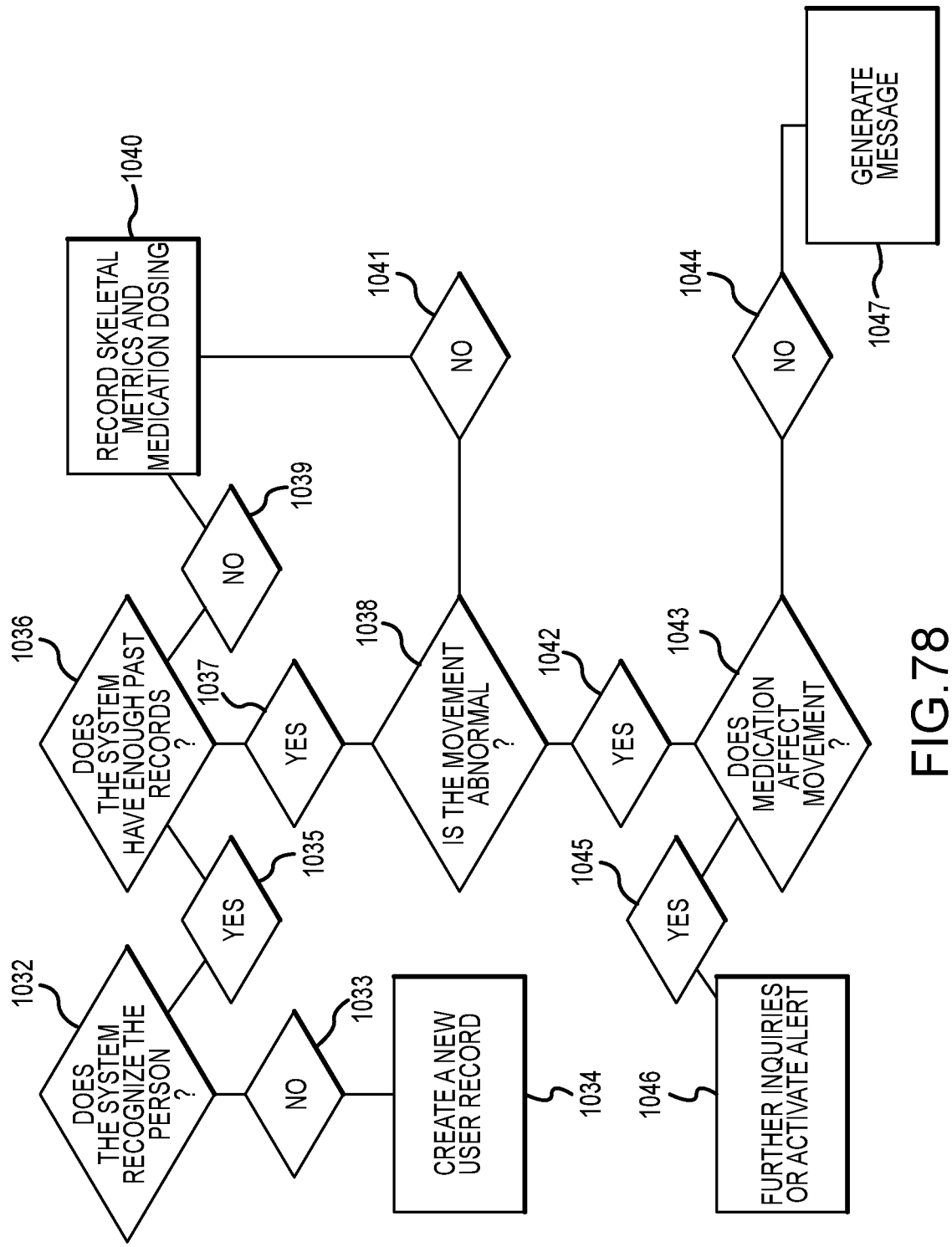
FIG. 78 is a flow chart illustrating another method for activating alerts based upon an analysis of video data.

FIG. 78 illustrates a flow chart for one method of generating alerts based upon multiple inputs. In step 1032, a determination is made whether the person is recognized. If the person is not recognized or identified, as shown in step 1033, the method proceeds to step 1034 to create a new record for this person. If the person is recognized, as shown in step 1035, the method proceeds to step 1036 to determine whether the system has enough past records for the identified person to reliably analyze the person's pose and movement. If the answer is no, as shown in step 1039, the method proceeds to step 1040 to record skeletal metrics for this person. In addition, in this embodiment, the system also includes data concerning medication associated with this person.

In step 1036 shown in FIG. 78, if a determination is made that the system has enough past records, as shown in step 1037, the method proceeds to step 1038 to determine whether the movement is abnormal for this person. If the movement is not abnormal, as indicated by step 1041 in FIG. 78, the method proceeds to step 1040. If the movement is abnormal, as indicated by step 1042 in FIG. 78, the method proceeds to step 1043 to determine whether the person (normally the resident) is taking medication that affects movement. If the answer is no, the method proceeds to step 1044, and generates a message or alert in step 1047 to a caregiver via the caregiver portal 101. If the answer is yes, as shown by step 1045 in FIG. 78, the method proceeds to step 1046 to automatically initiate further inquiries of the resident or alternatively to activate an alert to a caregiver via the caregiver portal 101, or to medical personnel via the doctor portal 102, to check on the resident or to investigate further.

Figure 79:
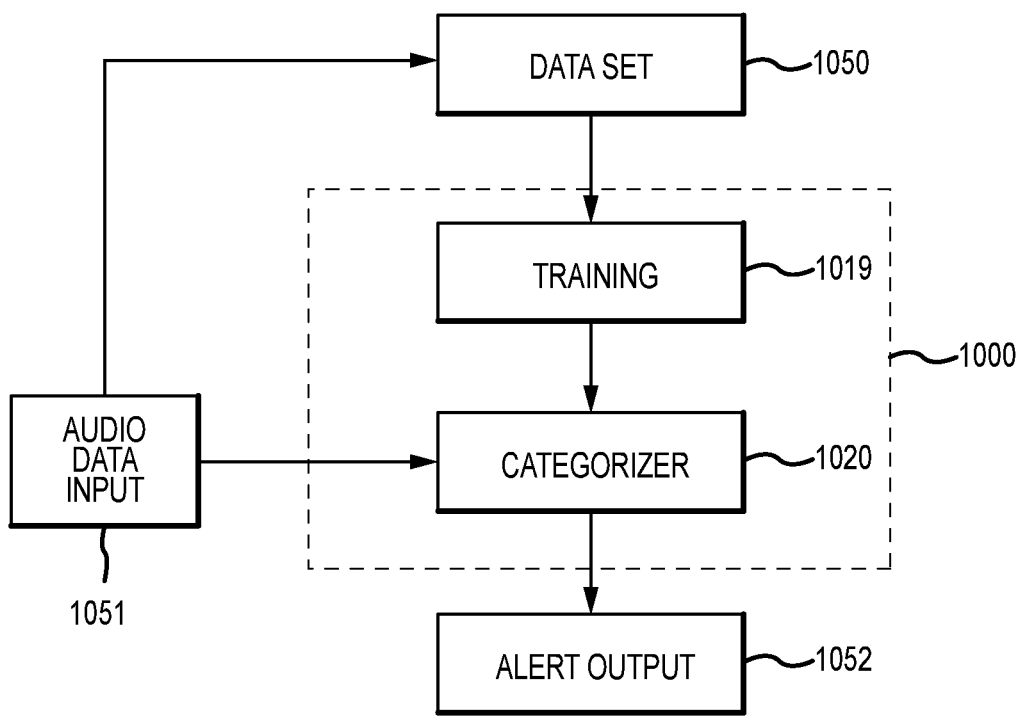
FIG. 79 is a block diagram of an embodiment using a machine learning module to analyze speech patterns and generate alerts.

FIG. 79 is a block diagram of an embodiment using the machine learning module 1000 to analyze speech patterns and generate alerts in appropriate circumstances. A data set 1050 of the resident's speech patterns is provided in storage. This data is fed to a training module 1019 in the machine learning module 1000. Audio data feed 1051 is provided from microphones 113. The audio data input 1051 is coupled to the training module 1019 to provide constant training concerning the resident's speech. The audio data input 1051 is coupled to the categorizer 1020. The output of the training module 1019 is also connected to the categorizer 1020. If abnormal speech patterns are detected, an alert is automatically generated and sent to alert output 1052. An alert or notification is sent to a caregiver, for example, via caregiver portal 101, that a speech pattern out of the ordinary has been detected.

Figure 80:
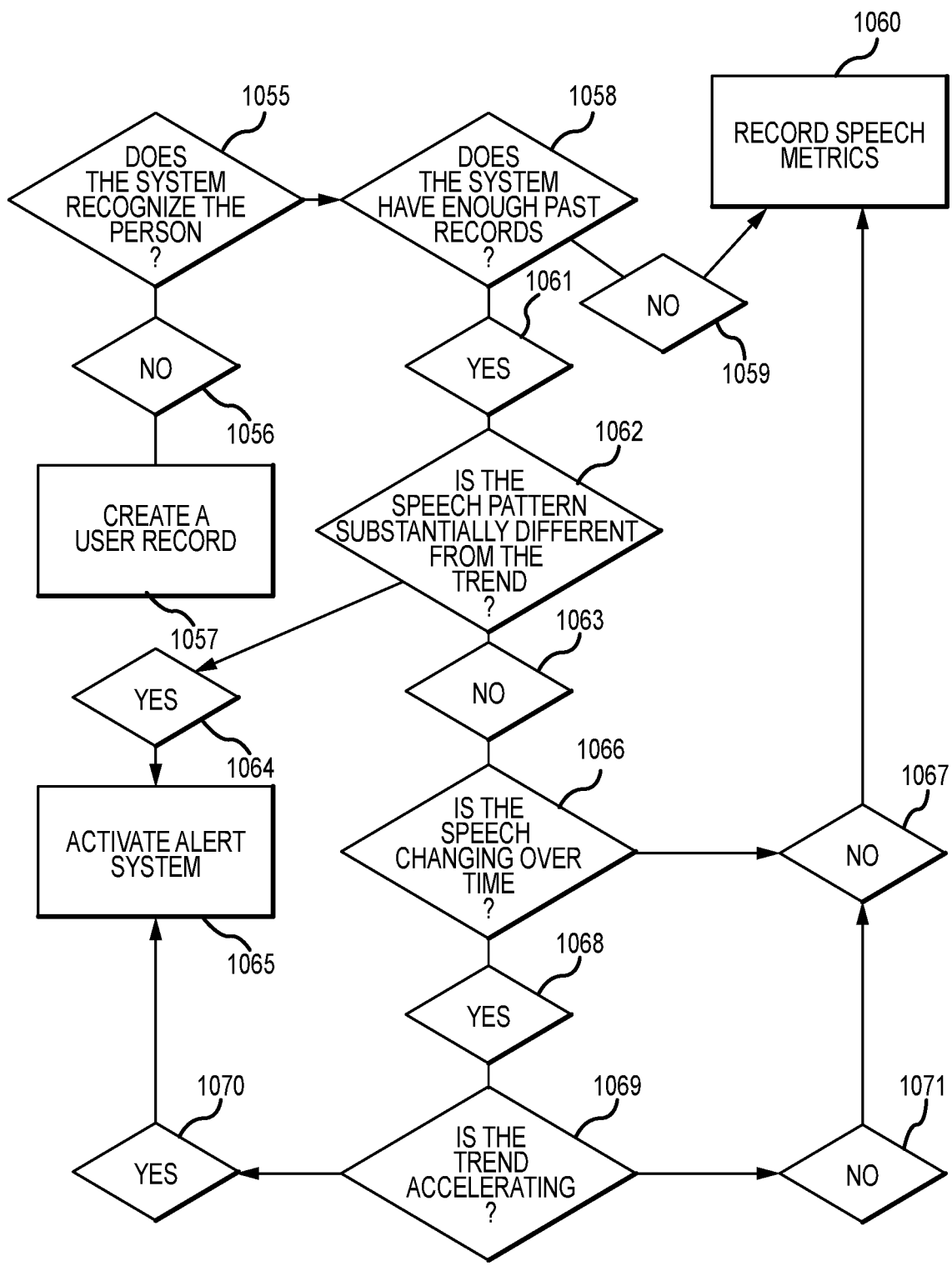
FIG. 80 is a flowchart illustrating a method of analyzing speech patterns and generating alerts.

FIG. 80 is a flowchart illustrating a method of analyzing speech patterns and generating alerts. In step 1055, a determination is made whether the person's voice is recognized, wherein the voice is picked up by microphones 113. In most instances, the system will be dealing with the voice of the resident. But the system will also recognize the voice patterns of caregivers, family members, and friends. In a preferred embodiment, the system will supplement voice recognition with facial recognition by simultaneously using video data from video cameras 112.

Referring to FIG. 80, if the person's voice is not recognized, as indicated by step 1056, the method will proceed to step 1057, where a new record for the person will be created. If the person's voice is recognized, the method proceeds to step 1058, where a determination is made whether the system has enough past records to construct a normal speech pattern for that person. if the system does not have enough records, as shown in step 1059, the method proceeds to step 1060 where the person's speech metrics are recorded and stored, so that the system can determine a normal baseline speech pattern for the person. In step 1058, if the system determines that it has enough past records, as shown in step 1061, the method proceeds to step 1062 where a determination is made whether the speech pattern is substantially different from that person's normal or baseline speech pattern. If the answer is yes, as shown in step 1064, the system proceeds to automatically activate an alert, as shown in step 1065.

In step 1062, if a determination is made that the person's speech pattern is not substantially different, as shown in step 1063, the method proceeds to step 1066 where a determination is made whether the person's speech is changing over time. If not, as shown by step 1067, the method proceeds to step 1060. If the person's speech pattern is changing over time, as shown by step 1068 in FIG. 80, the method proceeds to step 1069 where a determination is made whether the speech pattern represents an accelerating trend. If the answer is yes, as indicated by step 1070, the method proceeds to step 1065 to automatically generate an alert. If the answer is no, in step 1071 the method may record data concerning the speech results in database 108, and optionally produces a report to a caregiver via caregiver portal 101, and the method then loops back to step 1060.

Figure 81:
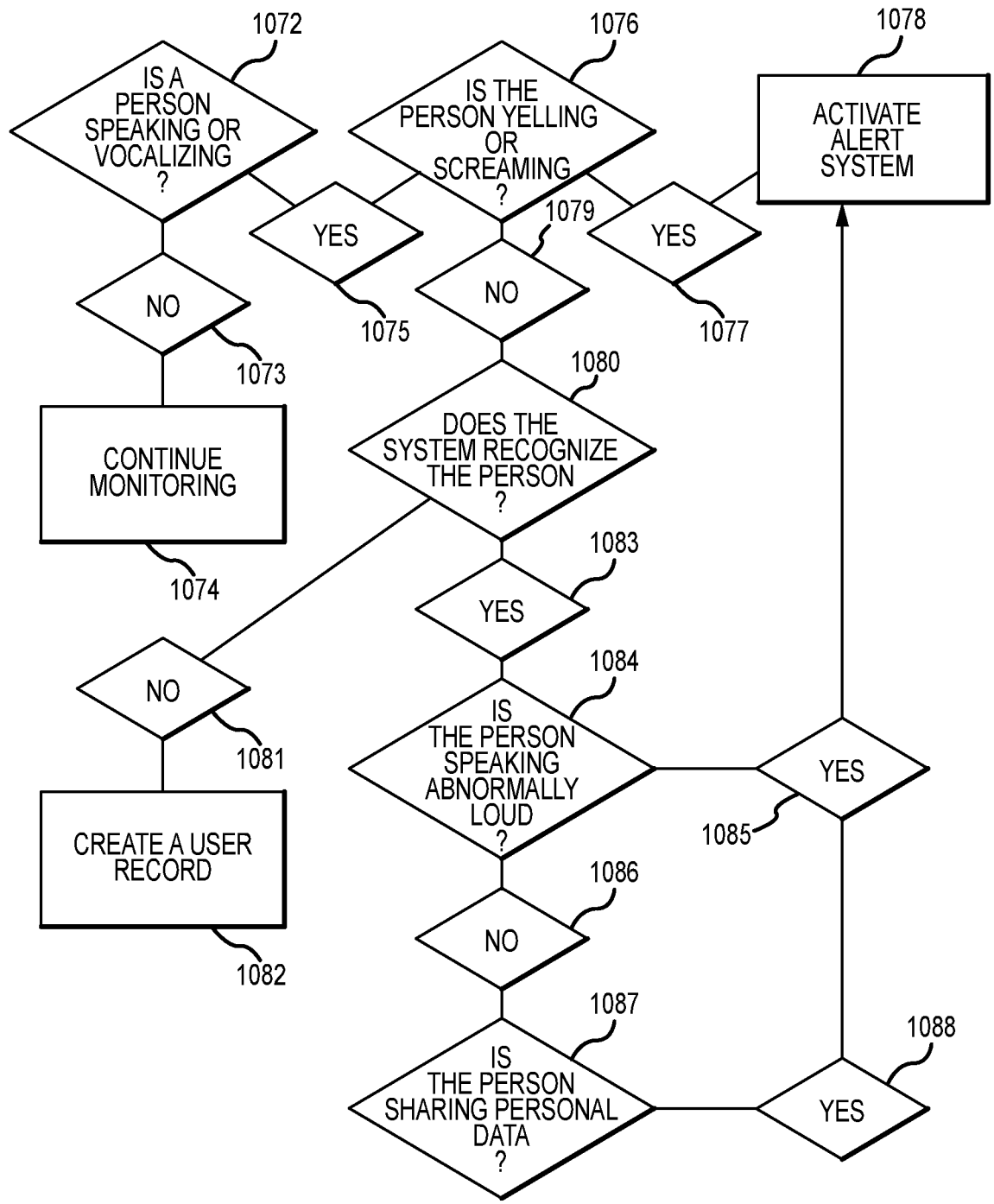
FIG. 81 is a flowchart illustrating another method of analyzing speech patterns and generating alerts.

FIG. 81 is a flowchart illustrating another method of analyzing speech patterns and generating alerts. In step 1072, a determination is made whether the person is speaking or vocalizing. If the answer is no, as indicated by step 1073, the method proceeds to step 1074 to continue monitoring. if the answer is yes, as indicated by step 1075, the method proceeds to step 1076 where a determination is made whether the person is yelling or screaming. If the answer is yes, as indicated by step 1077, the method proceeds to step 1078 to activate an alert.

If a determination is made that the person is not yelling or screaming, as indicated by step 1079, the method proceeds to step 1080 to determine whether the person can be recognized by the system. If the person is not recognized, as indicated by step 1081, the method proceeds to step 1082 where a new record is created for that person. If the person is recognized, as indicated by step 1083, the method proceeds to step 1084 where a determination is made whether the person is speaking abnormally loud. If so, as indicated by step 1085, the method proceeds to step 1078. If the person is not speaking abnormally loud, as indicated by step 1086, the method proceeds to step 1087 to determine where the person is sharing personal data. For example, if the resident is giving out his or her social security number, credit card number, or other personal data, as indicated by step 1088, the method proceeds to step 1078. The system considers other data, such as whether the resident is communicating with medical personal via the doctor portal 102, and if the context is one where personal data is expected to be shared, the system will not generate an alert.

Figure 44:
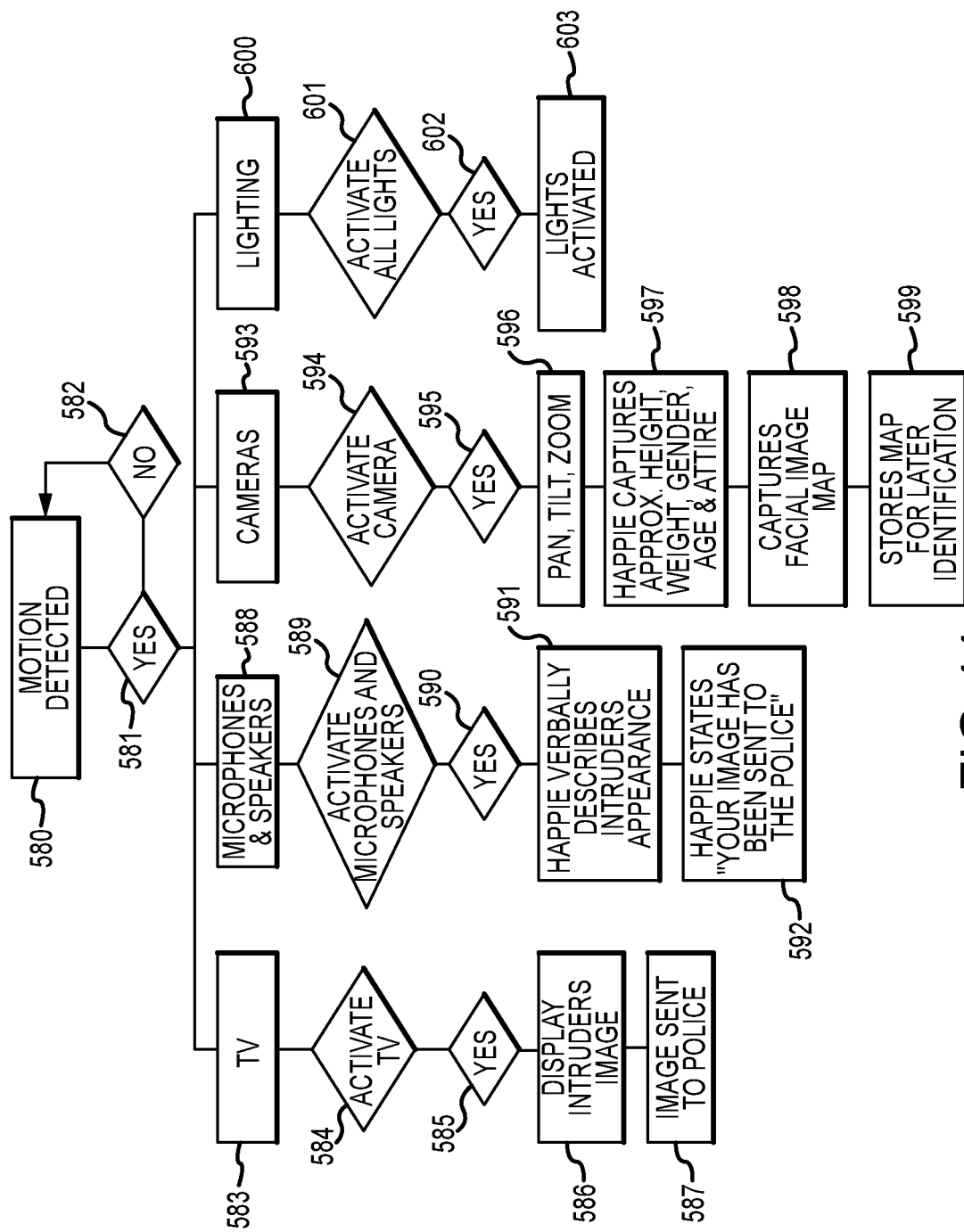
FIG. 44 is a flowchart illustrating a method for home security provided by the HAPPIE home unit in accordance with one embodiment of the invention.

The HAPPIE home unit 103 provides many advantageous features for home security. FIG. 44 is a flowchart illustrating a method for home security provided by the HAPPIE home unit 103 in accordance with one embodiment of the invention. When this method is activated, alerts may be simultaneously sent to emergency services via the emergency services portal 106, and to caregivers via the caregiver portal 101. When this method is activated, video from cameras 112 and audio from microphones 113 may be accessed and viewed remotely using an app on the caregiver's smartphone 178 or other wireless computing device 179, as well as via the caregiver portal 102.

In one example illustrated in FIG. 44, motion sensors 152 are monitored in step 580. The system may constantly scan for motion detection. If no motion is detected, as shown in step 582, the system continues to scan for a motion detection. if motion is detected, as illustrated in step 581, the method proceeds as shown in FIG. 44, to access the resident's TV or video monitors 156 in step 583, access microphones 113 and speakers 157 in step 588, access video cameras 112 in step 593, and access lighting controls 159 in step 600.

In connection with the resident's TV or video monitors 583, a determination is made whether to activate TV and video monitors 156 at the residence in step 584. For example, in the case of an intruder detection, the TV and video monitors 156 would typically be activated in step 585. As a deterrent, in step 586 the image of the intruder may be displayed on the TV and video monitors 156 to demonstrate to the intruder that he or she has been detected and his or her image is being recorded and stored in the database 108. Preferably, the database 108 is located in a secure and locked location in the residence, so that an intruder cannot easily access it and destroy the database 108. The information and data may also be simultaneously transmitted to a remote server 100 and stored on a remote database 175 that is not physically accessible from the residence. In step 587, the image of the intruder may be sent to the police via the emergency services portal 106.

In connection with microphones and speakers 588 at the residence, a determination is made whether to activate microphones 113 and speakers 157 in step 589. The microphones 113 and speakers 157 are activated in step 590. As a deterrent, in step 591 the HAPPIE home unit 103 may broadcast over the speakers 157 a verbal description of the intruder, and also transmit that description with accompanying images of the intruder (captured by video cameras 112) to the police via the emergency services portal 106. As a deterrent, in step 592, the HAPPIE home unit 103 may broadcast over the speakers 157 a warning to the intruder that his or her image has been sent to the police, and that the police have been summoned and are on their way. The HAPPIE home unit 103 further instructs the intruder to leave immediately, or else the intruder will face prosecution.

In connection with video cameras 593 at the residence, a determination is made whether to activate video cameras 112 in step 594. The video cameras 112 are activated in step 595. In step 596, the HAPPIE home unit may use data from motion sensors 152, floor sensors 153, intelligent heat detectors 194, and other security sensors 147 to locate zones of interest and probable location of the intruder, and pan, tilt, and zoom video cameras 112 accordingly to capture images of the intruder. In step 597, the information from the video cameras 112 is used by the HAPPIE home unit 103 to determine estimates of the intruder's height, weight, gender, age, and attire. This information is included in the description sent to the police via the emergency services portal 106.

In step 598, the HAPPIE home unit 103 employs a plurality of video cameras 112 to capture a 3D facial image map of the intruders face. In step 599, images of the intruder together with the 3D facial image map are stored in the database 108, and also preferably transmitted to a remote server 100 for storage in a remote database 175, for later identification. Optionally, a real-time facial recognition function may be activated for the images of the intruder, and compared with information maintained in a remote database 175 in order to identify the intruder. If facial recognition is successful, the description of the intruder broadcast in step 591 may also include calling the intruder by name.

In connection with lighting 159 at the residence, a determination is made whether to activate the lights 159 in step 601. The lights 159 are activated in step 602. In step 603, the lights 159 may be activated by turning them on constantly at their brightest setting, or alternatively, the lights 159 may be flashed on and off in order to draw attention and as a deterrent to the intruder. A strobe mode for the lights 159 may also be employed in order to disorient the intruder.

The HAPPIE home unit 103 may receive data and instructions from the police via the emergency services portal 106. The police may send updated instructions to the resident via the emergency services portal 106. In addition, the police may speak directly to the intruder via the emergency services portal 106 using the speakers 157 and microphones 113 at the residence. In an optional embodiment, one of more TASER™ devices may be located at strategic locations in the residence, or alternatively other devices employing nonlethal force, and which may be remotely activated by the police using the emergency services portal 106, in order to disable or disarm the intruder. The police may send an "all clear" signal to the HAPPIE home unit 103 via the emergency services portal 106 in order to deactivate the method for home security, for example, when the intruder is captured or detained, or when the police are able to determine that there is no immediate threat or the threat has passed. Alternatively, the caregiver may issue an "all clear" signal using the caregiver portal 101, or the resident may do so locally using a key pad with a security code, or by saying a predetermined code word that is received via the microphones 113 and recognized by the HAPPIE home unit 103, using speech recognition, as a disarm code.

For convenience, the method for home security has been described in connection with the detection of motion by motion sensors 152. However, it will be understood by those skilled in the art that the method illustrated in FIG. 44 may also be activated upon detection of glass breakage by glass breakage detectors 146, upon detection of a perimeter door opening by door sensors 137, upon detection of a window opening by window sensors 145, upon a signal received from predetermined perimeter floor sensors 153, upon detection of a garage door opening by garage door sensor 144, upon a signal from other perimeter sensors 143, and upon receipt of a signal from a panic button pressed by the resident.

Figure 46:
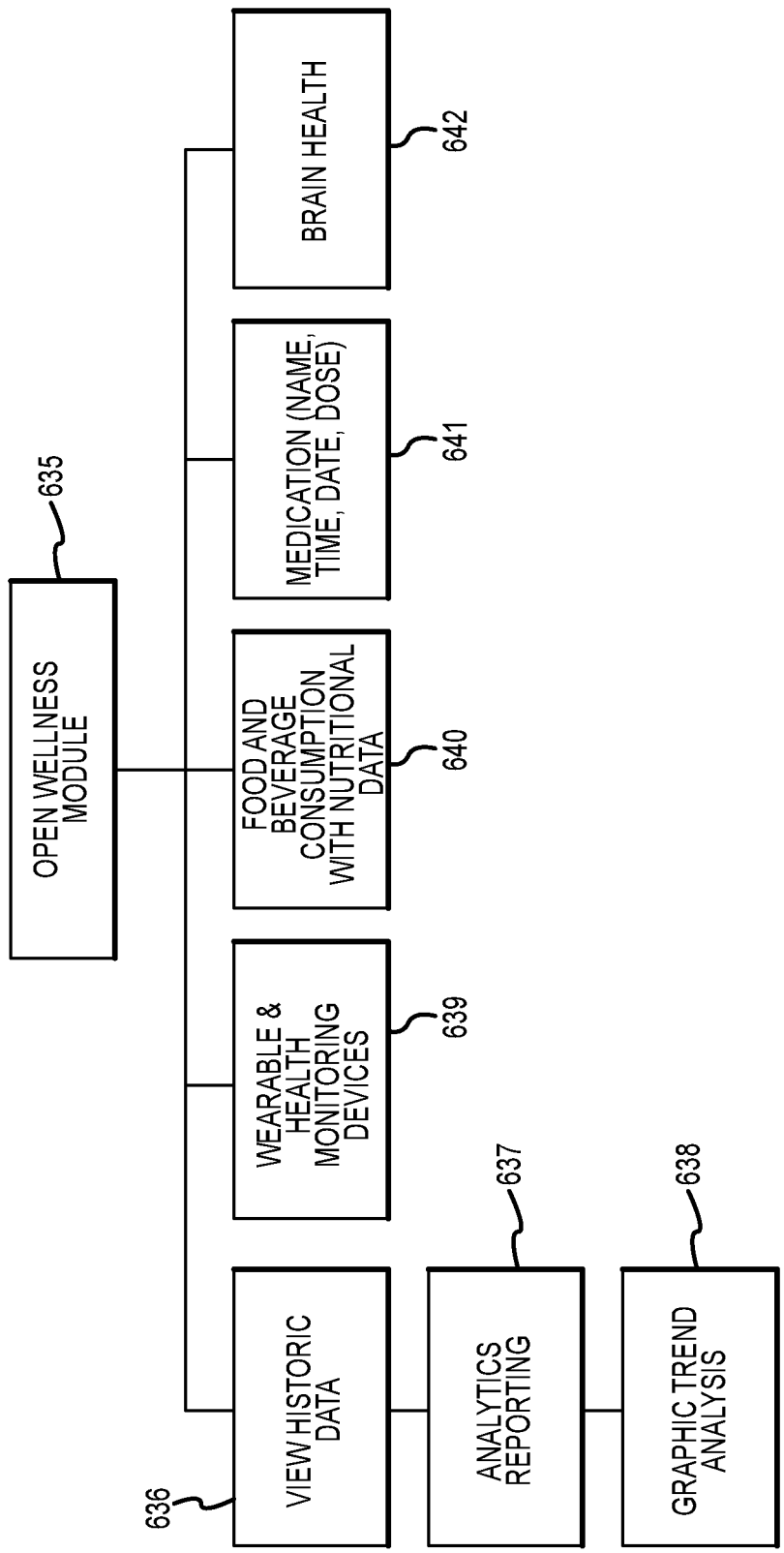
FIG. 46 is a block diagram illustrating modules that may be used in connection with the caregiver portal.

FIG. 46 is a block diagram illustrating modules that may be used in connection with the caregiver portal. A wellness module 662 may display on a display or video monitor at the caregiver portal 101. The wellness module 662 may incorporate medication monitoring, physical therapy, a data port for health monitoring devices and wearable technology, mental health, memory strengthening, diet, exercise, and nutrition monitoring and records, thereby providing a comprehensive picture concerning the resident's well being and health. The wellness module 662 may include an interface for viewing historic data concerning the resident, as indicated by reference numeral 636 in FIG. 46. Historic data stored on the database 108 may be accessed and viewed by the caregiver via the caregiver portal 101, including historic data concerning medication, exercise, nutrition, data from health monitoring devices 160, and any data or information stored on the database 108 concerning the resident. The functionality includes analytics reporting 637, including analysis of information from bed sensors 151 and floor sensors 153 concerning the resident's periods of activity and rest, information from the resident's TV 156 concerning program viewing, nutritional analysis concerning food and beverages consumed from the smart pantry 119 and the smart refrigerator 115, and any data concerning incidents or events. Graphic trend analysis 638 is provided, for example, if data from the resident's weight scale 166 shows that the resident is steadily gaining weight.

The wellness module 662 includes an interface 639 with wearable sensors and monitoring devices 158 and other health monitoring devices 160 associated with the resident, such as a weight scale 166, blood pressure monitor 163, heart rate or pulse monitor 165, thermometer or temperature device 161, Mediwand™ device 162, or any other health monitoring device 160. Data from health monitoring devices 165 and 163, and data from wearable tech devices or sensors 158, is uploaded to the HAPPIE home unit 103 and stored in the database 108 in one of two ways. One, on a routine schedule programmed into the calendar module 650 of the HAPPIE home unit 103. Two, when the resident walks past a mic pack 142 located anywhere in the residence.

The wellness module 662 includes an interface 640 with data stored in the database 108 concerning food and beverage consumption available to the HAPPIE home unit 103 from the smart refrigerator 115 and the smart pantry 119. In addition, food and beverage consumption data may be manually entered in the database 108 by the caregiver, either locally or via the caregiver portal 101.

The wellness module 662 includes an interface 641 with data stored in the database 108 concerning the resident's medication, including data and information provided to the HAPPIE home unit 103 from a smart medicine cabinet concerning medicine taken by the resident. Data and information concerning medicine taken may also be manually entered by a caregiver, either locally or via the caregiver portal 101. The data stored in the database 108 concerning medication may include historical information concerning name of medicine, time, date, and dose taken by the resident. The wellness module 662 also includes information concerning drug interactions, and analyzes each medicine prescribed for the resident with other medications being taken by the resident to identify any potential drug interactions or potential warnings concerning particular drugs or medicines being taken at the same time. If appropriate, alerts will be automatically generated and sent to a medical professional via the doctor portal 102, and to a caregiver via the caregiver portal 101. In addition, the wellness module 662 uses data stored in the database 108 concerning food and beverages from the smart pantry 119 and the smart refrigerator 115 to identify any food or beverages that should not be consumed together with a particular medicine. If appropriate, alerts will be automatically generated and sent to a medical professional via the doctor portal 102, and to a caregiver via the caregiver portal 101, in the event that food or beverages are selected from the smart pantry 119 and the smart refrigerator 115 which should not be consumed together with certain medicines that have been recently taken by the resident, or which are schedule to be taken in the near future.

The wellness module includes an interface with a brain health module 642. This includes the ability to conduct brain health exercises with the resident, and to view historical data concerning brain health measurement data stored on the database 108.

In addition to displaying on a display or video monitor at the caregiver portal 101, the wellness module may also display on video monitors 156 at the residence, or on an app running on the resident's smartphone 111. The resident can use the features of the wellness module for the resident's personal health monitoring, and nutrition tracking, for example. The resident may use the wellness module to initiate brain health exercises and tests. The resident may use the wellness module to check on medications and schedules for medicines. The resident may generally access any functionality provided by the wellness module, if desired.

Figure 47:
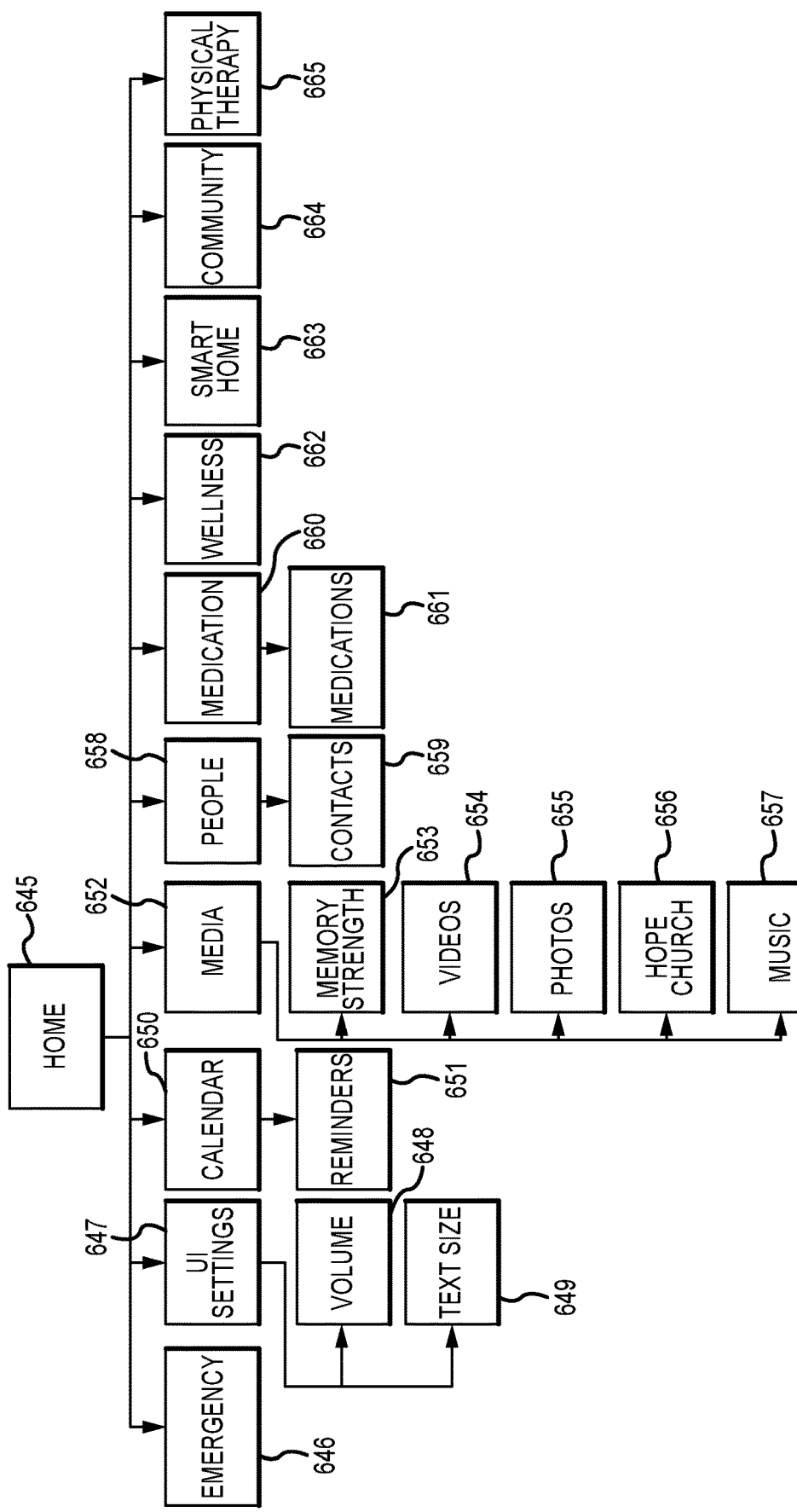
FIG. 47 is a block diagram illustrating a suite of modules that may be used in connection with an embodiment of the invention.
Figure 52:
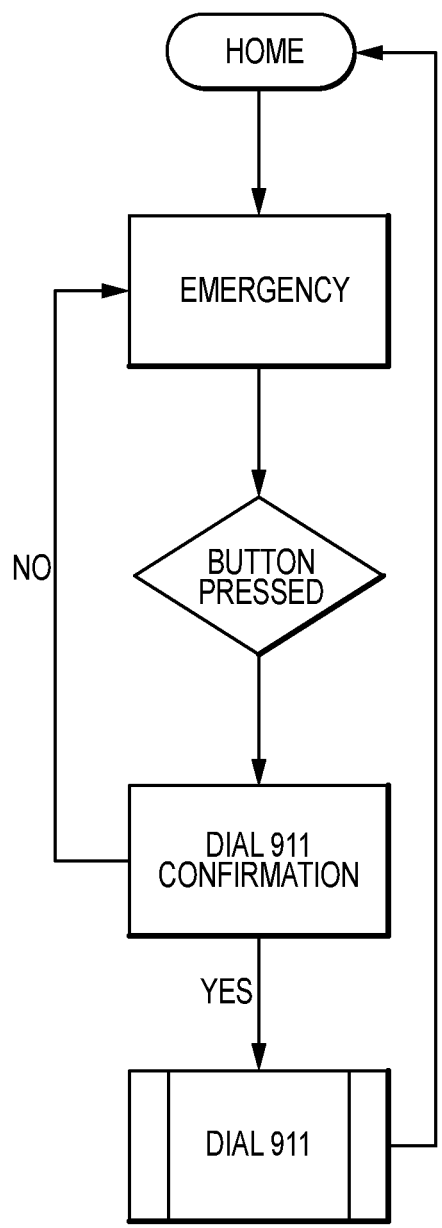
FIG. 52 is a flowchart that illustrates one example of an emergency module that may be used with the invention.

FIG. 47 is a block diagram of a possible configuration of modules in a HAPPIE home unit 103 in accordance with one embodiment of the invention. In this embodiment, the HAPPIE home unit 103 provides a home module that displays a home screen 645 on the TV and monitors 156 connected to the HAPPIE home unit 103. An emergency module 646 is always readily accessible. The emergency screen shot depicted in FIG. 39 may be employed in the emergency module 646. The method for home security illustrated in FIG. 44 may be employed in the emergency module 646. The flowchart of FIG. 52 illustrates one example of the operation of the emergency module 646 that may be utilized.

Figure 49:
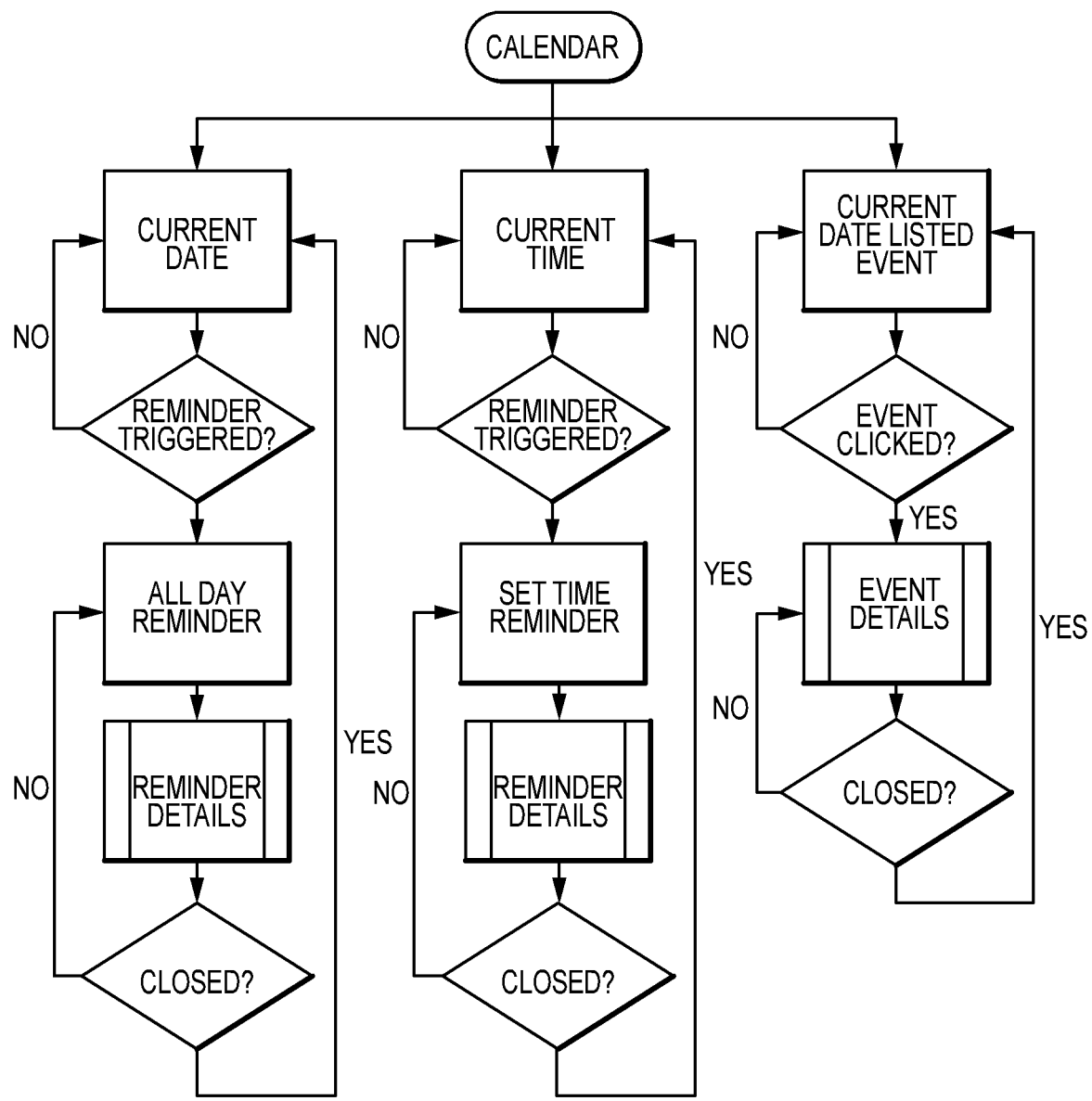
FIG. 49 is a flowchart illustrating the operation of a calendar module that may be used in connection with an embodiment of the invention.

A calendar module 650 is provided for managing appointments, including doctor appointments and physical therapy appointments, although the module is capable of managing any type of calendar event. The calendar module 650 can generate reminders and alerts 651 for any appointment or scheduled event. The calendar module 650 can include scheduled medication, and provide reminders 651 when medication is due to be taken. In this regard, the calendar module 650 interfaces with the medication module 660. The medication module 660 may include the method depicted in FIG. 45. The medication module 660 also provides the resident with information concerning medications 661, and monitors for possible drug interactions. The calendar module 650 may include the method of operation shown in the flowchart of FIG. 49.

A wellness module 662 is provided. The wellness module 662 may be employed to provide a comprehensive picture of all available data stored on the database 108 relating to health and wellness. The wellness module 662 may include information concerning nutrition, hydration, medication, physical therapy, health monitoring devices, wearable technology, mental health data, memory strengthening, diet, and exercise. The wellness module 662 provides a graphical user interface to the resident via the TV or video monitors 156, or via a smartphone 111. The wellness module 662 may also be accessed via the caregiver portal 101, or via the caregiver's smartphone 178. The wellness module 662 may include the features and functions described in connection with FIG. 46. The wellness module 662 may be used to provide access to wearable sensors 158 and health monitoring devices 165 and 163 that have been connected with the HAPPIE home unit 103. The wellness module 662 can be used to provide a convenient view of historic data, analytic reporting and graphic trend analysis, using data from such devices. The wellness module 662 can be used to provide a convenient view of food and beverage consumption, complete with nutritional data. The wellness module 662 can be used to provide a convenient display of points of intersection between medications taken (time, date, dose), food consumed, and beverage or hydration consumption. The HAPPIE home unit 103 provides for expanded functionality as additional wearable and health monitoring devices 160 can be integrated with the HAPPIE home unit 103, and the invention is not limited to the examples illustrated in FIG. 4.

Figure 50:
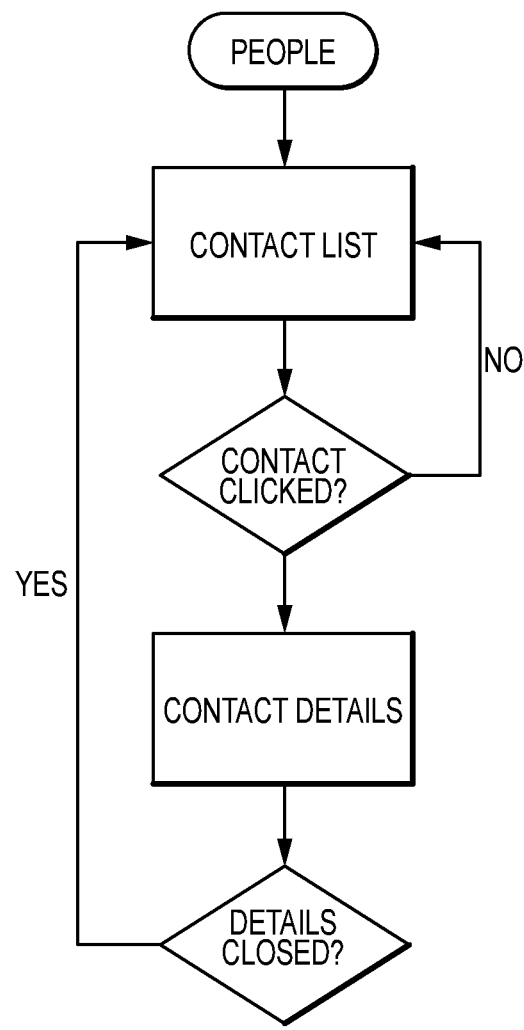
FIG. 50 is a flowchart illustrating the operation of a people module that may be used in connection with an embodiment of the invention.

A people module 658 is provided, which includes contact information 659 for the resident's family, medical professionals, and friends. Preferably, photos stored in the database 108 are associated with each contact in order to provide a memory aide for any resident suffering from dementia. The flowchart of FIG. 50 illustrates an example of the operation of the people module 658.

Figure 54:
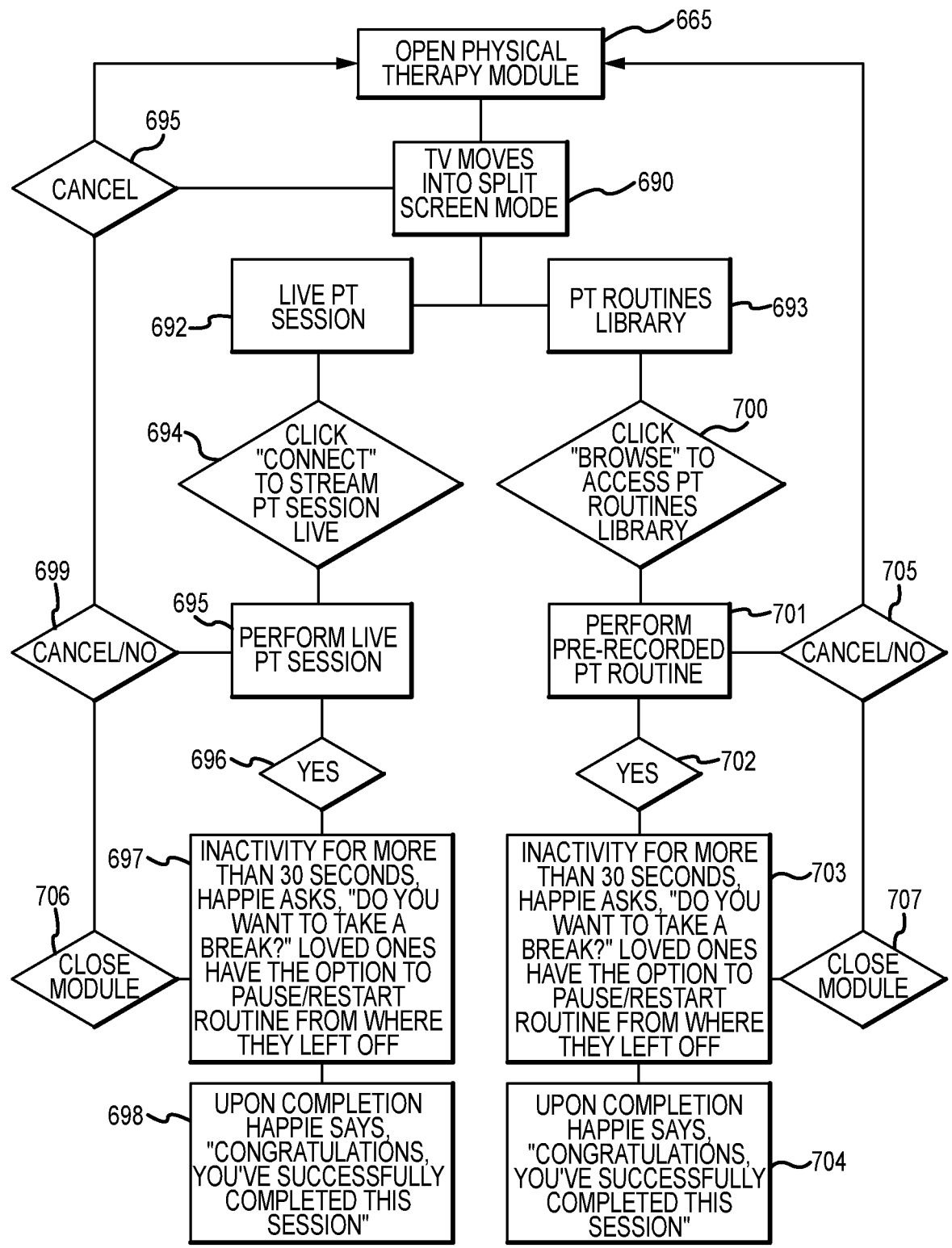
FIG. 54 is a flowchart illustrating the operation of a physical therapy module that may be used in connection with an embodiment of the invention.

A physical therapy module 665 is provided. The physical therapy module 665 may include instructional videos for the resident to watch concerning physical therapy. The physical therapy module 665 can interface with health monitoring devices 160 during a physical therapy session, and wearable sensors 158, and track the physical therapy sessions taken by the resident, storing the data in the database 108. The instructional videos may be stored in the database 108 and accessed at any time in order to make it easier to participate in needed physical therapy. The flowchart of FIG. 54 illustrates an example of the operation of the physical therapy module 665.

Figure 53:
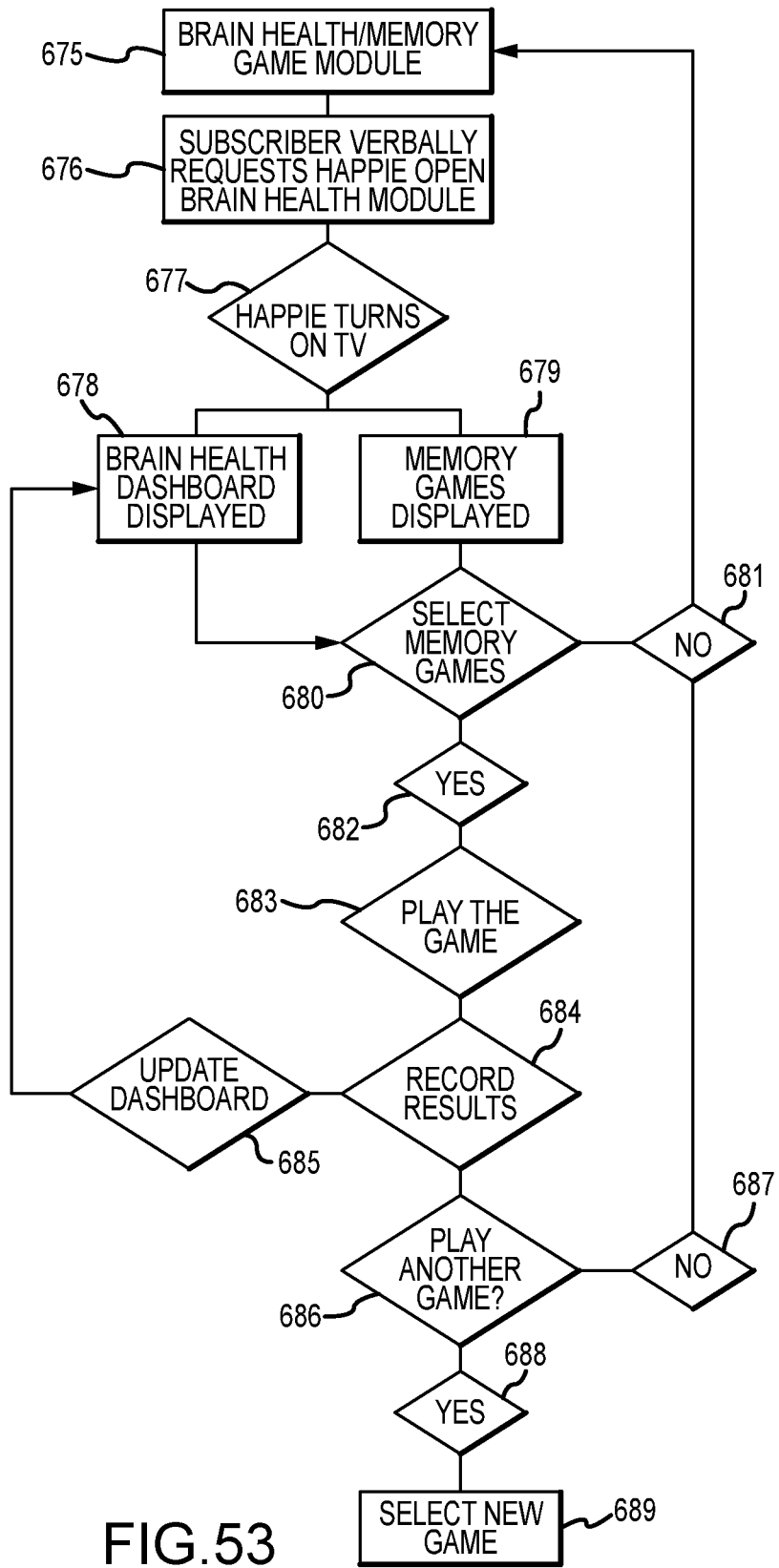
FIG. 53 is a flowchart that illustrates one example of a brain health and memory strength module that may be used with the invention.

The HAPPIE home unit 103 includes a media module 652. The media module 652 includes a video module 654 for accessing videos stored in the database 108, and for accessing videos available via the Internet 105. The media module 652 includes a photos module 655 for accessing photos stored in the database 108. The database 108 may include photos of family and friends, and events in the life of the resident. A photo gallery of this nature can be particularly useful for residents with dementia. The photos module 655 may also be used for accessing photos available via the Internet 105. The media module 652 includes a church module 656 for interfacing with the resident's church or faith support group. The church module 656 includes the capability of watching church services from the resident's home, either live streaming video or recordings of the services. The church module 656 also includes an interface for the resident to communicate with church personnel and church friends in time of spiritual need. The media module 652 also includes a music module 657 for accessing and playing music. The available music may include music stored on the database 108, and music accessible via the Internet 105. The media module 652 includes a memory strength module 653, which may provide brain exercises and tests for the resident. This may be particularly useful for a resident with dementia. An example of a method that may be employed in connection with the memory strength module 653 is illustrated in the flowchart of FIG. 53.

The video displays and televisions 156 are preferably connected to the home entertainment system 120 through the core 121 of the HAPPIE home unit 103, and may be used in connection with the media module 652 to show a television program or movie, or otherwise used for entertainment purposes.

Figure 48:
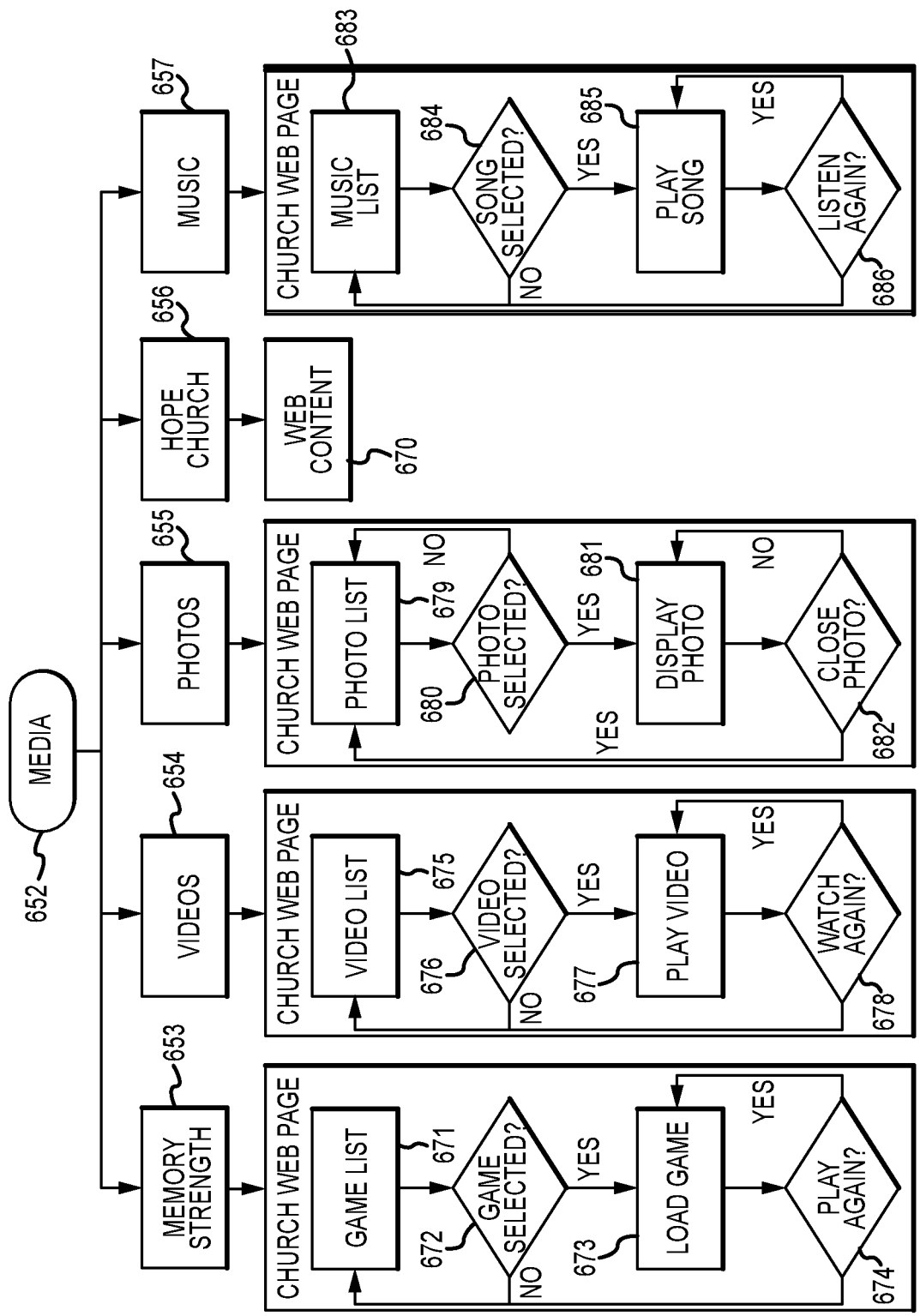
FIG. 48 is a block diagram illustrating a media module that may be used in connection with an embodiment of the invention.

An example of an implementation of the media module 652 is shown in further detail in FIG. 48. The memory strength module 653 shown in FIG. 48 may include a list of games 671 that have a memory strengthening feature to the games. A memory game may be selected in 672, in which event the game will be loaded 673, and the resident may play the game again 674 as many times as desired. The video module 654 may be used to access a list of videos 675, and to select videos 676. A selected video is played 677, and the resident is provided with the option to watch the video again 678. The photo module 655 may be used to access a list of photos 679, and to select photos 680, at which point the selected photo is displayed 681. The resident is provided with the option to close the photo 682 when the resident is finished viewing the display. The church module 656 may be used to access web content 670 provided by the resident's church. The music module 657 may be used to display a list of music 683. A song may be selected 684, in which event the music will be played 685. The resident is provided with the option to play the song again 686. In the illustrated example, most of the content is provided by a church. However, the scope of the invention is not limited to content that may be provided in that fashion, but includes relevant content for the illustrated modules regardless of source.

Figure 55:
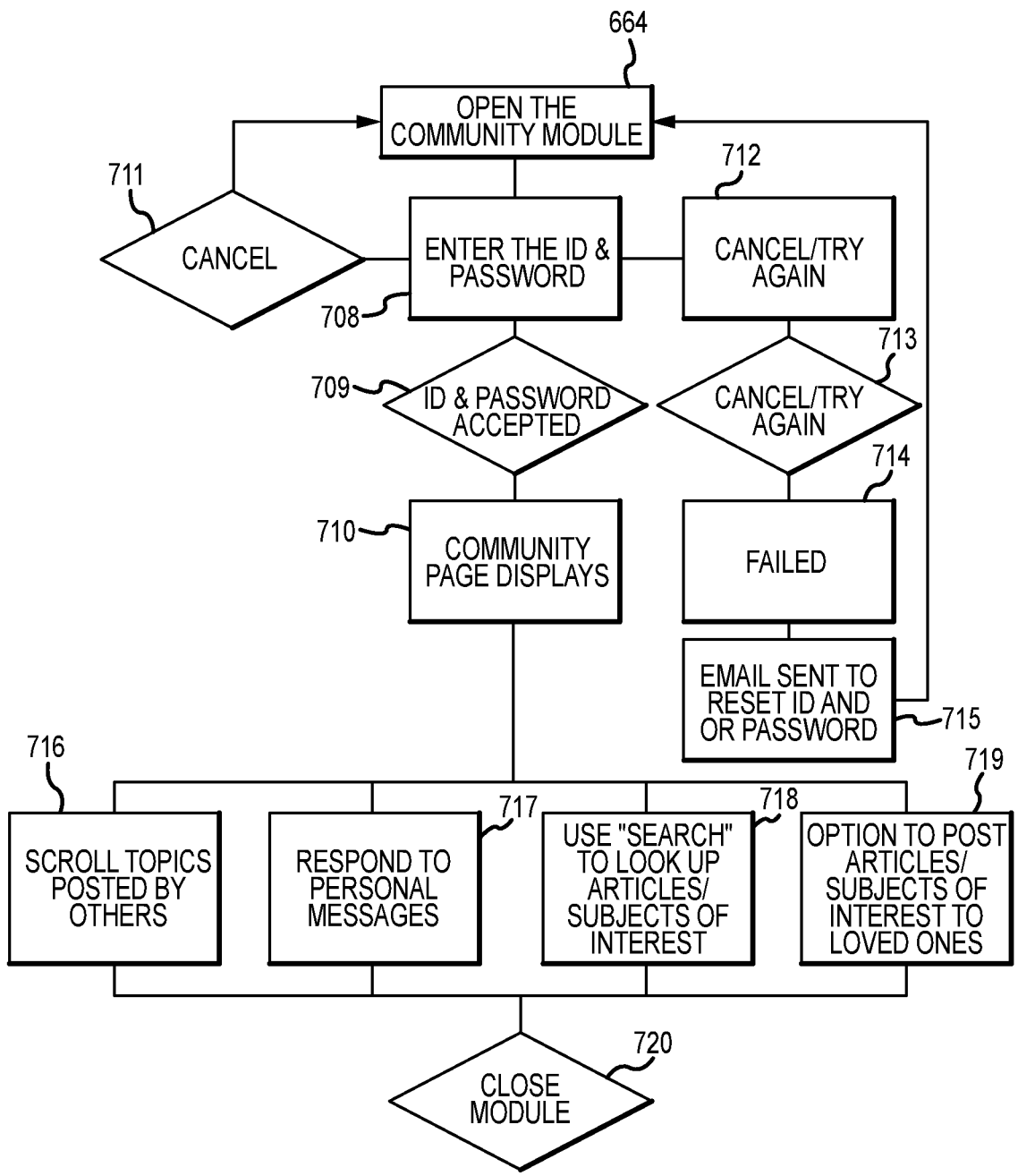
FIG. 55 is a flowchart illustrating the operation of a community module that may be used in connection with an embodiment of the invention.
Figure 56:
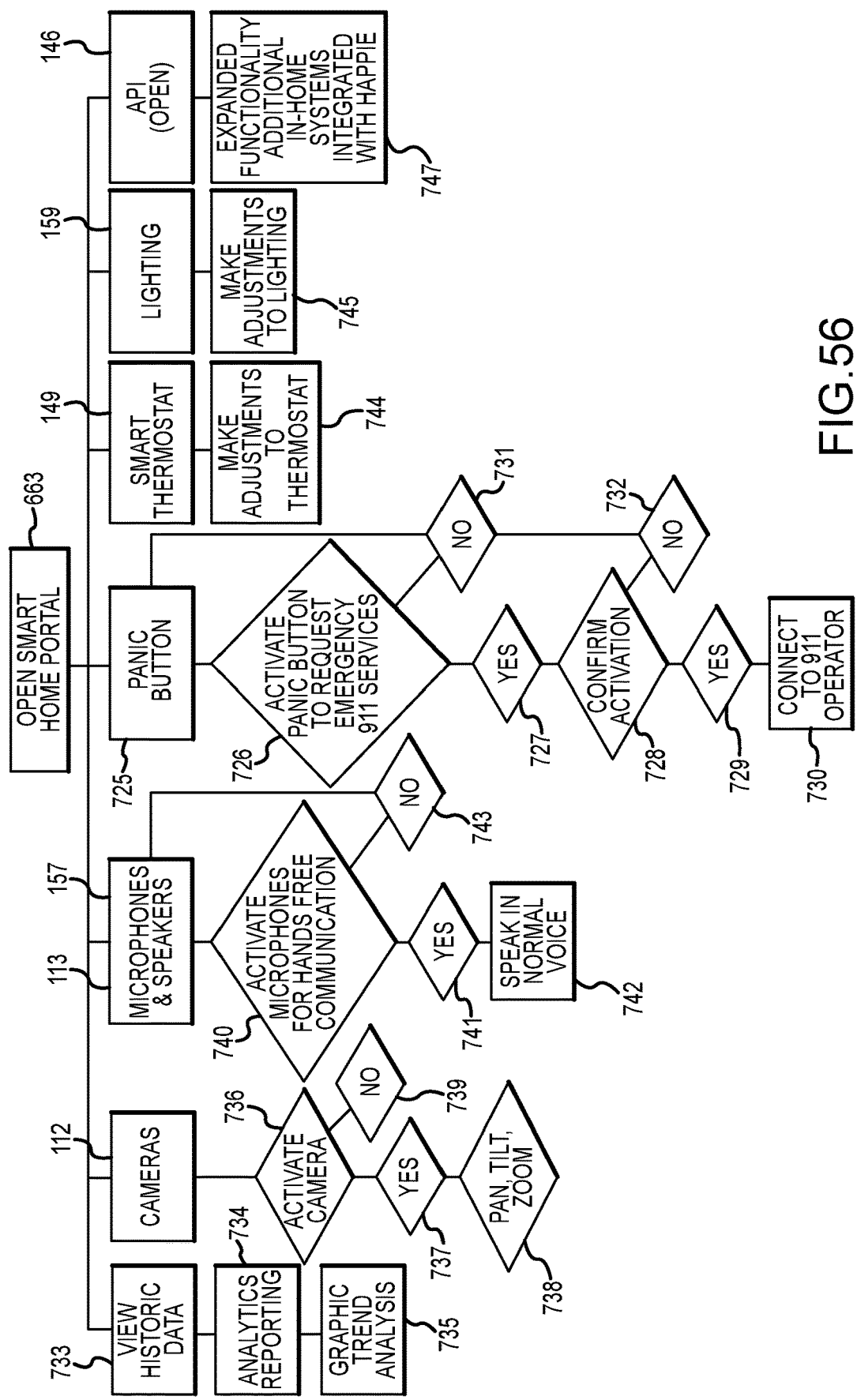
FIG. 56 is a flowchart illustrating the operation of a smart home module that may be used in connection with an embodiment of the invention.

As shown in FIG. 47, a smart home module 663 is provided for the HAPPIE home unit 103. The flowchart of FIG. 56 illustrates an example of the operation of the smart home module 663. A community module 664 is also provided. The community module 664 provides caregiver support groups, including live chat and video conferencing for caregivers. The community module 664 provides limited access chat groups, text messaging, and video conferencing for multiple caregivers associated with a resident that they may have in common, where access to the group is limited to authorized caregivers. The community module 664 provides caregivers with subject matter alerts from published web articles and news stories. Consolidation of all medical records are made available for secure sharing amongst doctors and medical professionals via the doctor portal 102, and for caregivers via the caregiver portal 101. The HAPPIE home unit 103 has been architected to include peer-to-peer connections between caregivers, residents, and medical professionals. Messaging between caregivers, residents, and medical professionals can go directly to another caregiver, resident, or medical professional connected with the HAPPIE home unit 103. It is not mandatory that community messages go through the Internet 105. The flowchart of FIG. 55 illustrates an example of the operation of the community module 664.

Figure 51:
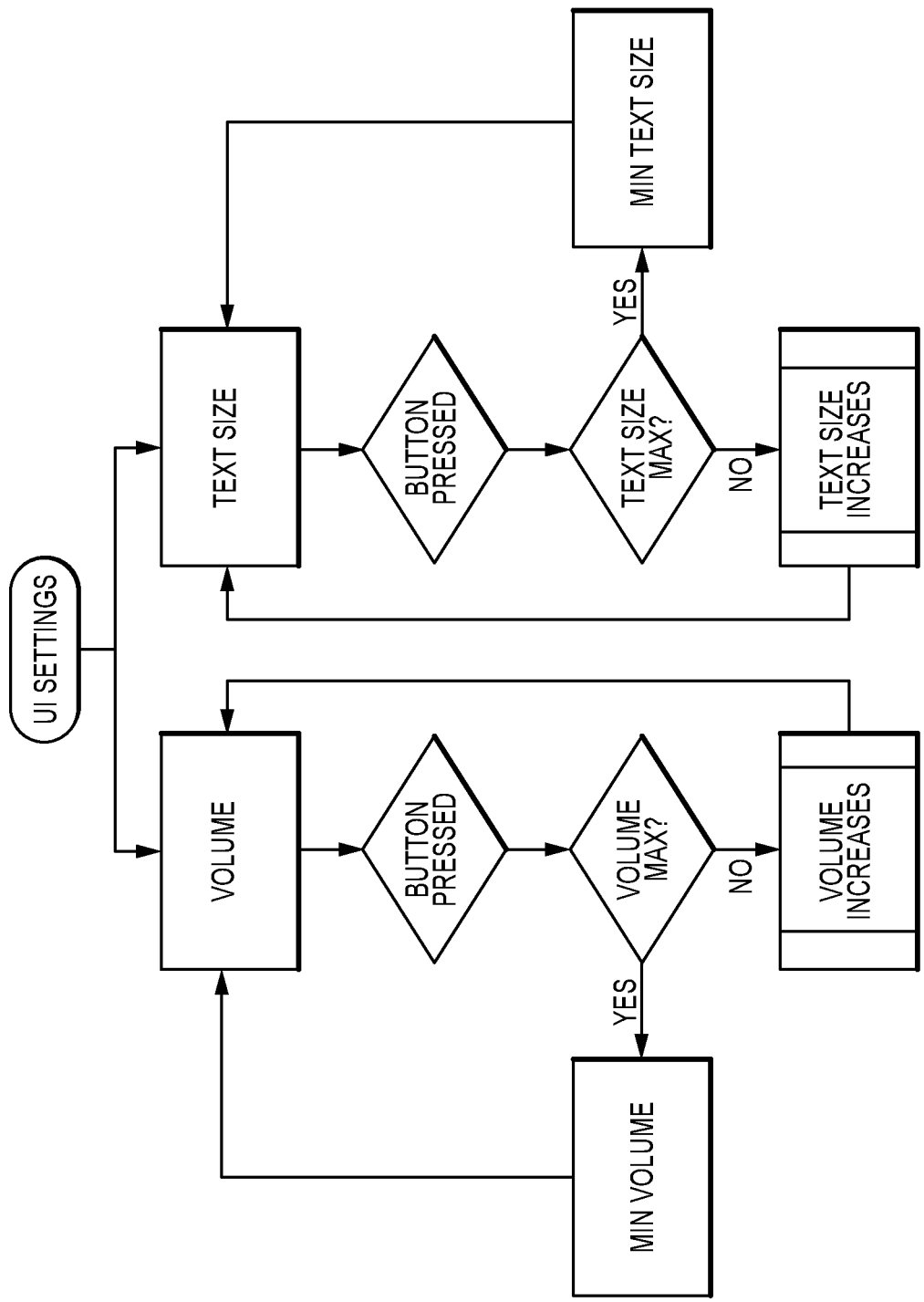
FIG. 51 is a flowchart illustrating the operation of a user interface settings module that may be used in connection with an embodiment of the invention.

A user interface settings module 647 is provided, which includes adjustment of volume settings 648 and adjustment of text size 649. The flowchart of FIG. 51 illustrates an example of the operation of the user interface setting module 647.

As shown in FIG. 53, the HAPPIE home unit 103 may include a brain health-memory strength module 675. The brain health-memory strength module 675 is designed to help a resident work towards staying mentally fit longer, while slowing the effects of aging on brain function and memory. The brain health-memory strength module 675 may also assess the impact that the resident's lifestyle plays in his or her brain health, and identify changes that could possibly improve the resident's overall brain health. Typically, the brain health-memory strength module 675 will display on the resident's TV or video monitors 156.

Referring to FIG. 53, the brain health-memory strength module 675 may be accessed from the resident's TV 156. In step 676, the resident may activate the brain health-memory strength module 675 using a voice command. In step 677, the HAPPIE home unit 103 turns on the TV 156, if it is not already on. In step 678, the HAPPIE home unit 103 displays a memory strength dashboard or other appropriate display on the TV 156. Alternatively, in step 679, the HAPPIE home unit 103 stages a game that is to be played by the resident. If the TV 156 is already running, the HAPPIE home unit 103 can pause the current television program and display the memory strength dashboard or stage a particular game that is to be played. The brain health dashboard is a graphic display of the profound impact of what you eat and drink, how much you exercise, how well you sleep, the way you socialize, and how you manage stress, which are all believed to be important to brain health.

In step 680, the resident may select a memory game or exercise to be played. Preferably, the resident may make this selection by speaking out loud in a normal speaking voice, which is transmitted to the HAPPIE home unit via microphones 113. If the resident makes the selection to engage in a game, the method proceeds to step 682. If the resident decides not to do so at the present time, the method proceeds to step 681. The resident can direct the HAPPIE home unit 103 to begin a game immediately, set a future time to begin the game, or request that the game begin after the current television program ends. Memory games and routines may be scheduled through the Calendar module 650, and reminders alert the resident when it is time to engage the brain health-memory strength module 675.

In step 683, the memory strength game is played. In step 684, the HAPPIE home unit 103 records, on the database 108, the games that were played, the scores achieved, and provides the results to the resident as well as the caregiver via the caregiver portal 101. Graphic trend analysis is available for review at any time. The HAPPIE home unit 103 tracks the time of day, and days of the week, when the games are played.

In step 685, data collected from the brain health-memory strength module 675, as well as all other wellness modules, is combined to draw correlations between brain health-memory strength performance on the one hand, and diet, exercise, nutrition, hydration, stress, sleep patterns and medication patterns on the other hand. As each memory strength game is played, the data is updated for the dashboard in step 685. The updated dashboard may be displayed in step 678. Alerts can be established by factors the resident wishes to track, as well as performance milestones. For example, if the resident achieves an all time best score, the resident may configure the HAPPIE home unit 103 to generate an alert.

In step 686, the resident may determine whether to play another game. If the resident decides to do so, the method proceeds to step 688, and a new game is selected in step 689. If the resident decides not to play another game, the method proceeds to step 687, and loops back to the beginning.

It should be appreciated that the brain health-memory strength module 675 may be displayed on the resident's smartphone 111. The brain health-memory strength module 675 may also display on the caregiver portal 101.

FIG. 54 is a flowchart illustrating the operation of a physical therapy module 665 that may be used in connection with an embodiment of the invention, when the physical therapy module 665 is opened. In one embodiment, the TV 156 changes to a split screen mode in step 690. If the resident cancels the physical therapy module 665 at this point, the method proceeds to step 691 and loops back to the beginning.

In the case of a live physical therapy session as indicated in step 692, the resident clicks to connect to a live video stream with a physical therapy instructor in step 694. In step 695, a peer-to-peer video connection is preferably employed using a WebRTC stream, and the live physical therapy session is displayed on the TV or video monitors 156 and audio is played over the speakers 157. The resident participates remotely in the live physical therapy session in step 696. If the resident cancels the session, the method proceeds to step 699 and loops back to the beginning.

In the event of inactivity for more than a predetermined period of time, for example 30 seconds, the HAPPIE home unit 103 will prompt the resident by playing audio over the speakers 157 asking if the resident wishes to take a break, as illustrated in step 697. The resident has the option to pause and restart the physical therapy routine from where he or she left off, and the HAPPIE home unit 103 will continue to record the live video conference and store it on the database 108 for later playback. Upon completion of the prescribed physical therapy session, in step 698 the HAPPIE home unit 103 will play audio over the speakers 157 saying "congratulations, you have successfully completed this session." In step 706, the HAPPIE home unit 103 will close the physical therapy module 665 and loop back to the beginning.

Referring to FIG. 54, in the event that the resident wishes to participate in a recorded physical therapy session, in step 693 the resident will be presented with a display of the library of physical therapy video recordings stored on the database 108. Alternatively, the display may also include recorded physical therapy session available remotely via the Internet 105. In step 700, the resident may browse the list of available physical therapy sessions. In step 701, the HAPPIE home unit 103 plays the recorded physical therapy video using video monitors 156 and speakers 157. If the resident cancels the session, the method proceeds to step 705 and loops back to the beginning.

The resident participates in the recorded physical therapy session in step 702. In the event of inactivity for more than a predetermined period of time, for example 30 seconds, the HAPPIE home unit 103 will prompt the resident by playing audio over the speakers 157 asking if the resident wishes to take a break, as illustrated in step 703. The resident has the option to pause and restart the physical therapy routine from where he or she left off, and the HAPPIE home unit 103. Upon completion of the prescribed physical therapy session, in step 704 the HAPPIE home unit 103 will play audio over the speakers 157 saying "congratulations, you have successfully completed this session." In step 707, the HAPPIE home unit 103 will close the physical therapy module 665 and loop back to the beginning.

Activity or inactivity from the physical therapy module 665 is integrated with records of food and beverage consumption stored on the database 108. The database 108 includes records of calorie burning values, which are available for display in the wellness module 662 and are measured by activity type, length of time for the routine, and intensity. Graphic trend analysis is available to display potential correlations between food, beverage, and medication consumption, as impacted by physical activity. Alerts can be established in the HAPPIE home unit 103 should a downward trend or potential health challenges be detected by the HAPPIE home unit 103 or the remote HAPPIE server 100.

FIG. 55 is a flowchart illustrating the operation of a community module 664 that may be used in connection with an embodiment of the invention. The community module 664 is intended to provide a safe and secure connection for the resident, his or her friends, his or her family members, and caregivers. The community module 664 may be opened on the HAPPIE home unit 103 and an appropriate display is provided on video monitor 156. In step 708, the resident's ID and password is entered. If valid credentials are entered, the ID and password are accepted in step 709. In step 710, the community home screen is displayed on video monitor 156.

On the community home screen, the resident may scroll topics posted by others in step 716. In step 717, the resident may respond to personal messages. In step 718, the resident may use a search engine to look up articles and materials of interest. In step 719, the resident has the option to post articles or messages of interest to the community. In step 720, the community module 664 is closed.

Referring to FIG. 55, in step 708, the resident has the option to cancel the community module in step 711, in which case it will close and loop back to the home module 645. In step 708, if the ID and password entered are not valid, the method proceeds to step 712 and the resident is given the opportunity to enter his or her ID and password again. In step 713, the process is repeated. In step 714, if a predetermined number of attempts to enter credentials does not result in the recognition of a valid ID and password by the HAPPIE home unit 103, the login fails in step 714. The HAPPIE home unit 103 will send the resident an email to reset his or her ID and password in step 715. The method then loops back to the home module 645.

Although the community module 664 has been described from the perspective of the resident, the community module 664 is also available remotely to a caregiver via the caregiver portal 101, and to friends and family members via the Internet 105.

FIG. 56 is a flowchart illustrating the operation of a smart home module 663 that may be used in connection with an embodiment of the invention. The resident opens the smart home module 663 to control the lights 159, thermostat 149, cameras 112, and any other smart home equipment that is digitally controllable. The resident may access the smart thermostat 149, and make adjustments to the temperature in step 744. The resident may access the lights 159, and make adjustments to the lighting in step 745, including turning lights on and off, and dimming lights, as desired.

Using the smart home module 663, the resident may control cameras 112. Cameras 112 can be activated in step 736. If a particular camera 112 is selected in step 737, then the resident can pan, tilt, and zoom that camera 112 in step 738. The resident can control microphones 113 and speakers 157 using the smart home module 663. A microphone 113 can be selected in step 740 for activation. If a selected microphone 113 is activated in step 741, the microphone can be used for hands free communication, and the resident may speak in a normal voice. Alternatively, if the resident wishes to listen in on a particular area of the residence, for example, if the resident hears a sound outside at night, the resident may select a particular microphone 113 for activation for that purpose as well.

Using the smart home module 663, the resident may use a "panic button", as indicated in step 725, to request emergency services via the emergency services portal 106. If the "panic button" is activated in step 727, the HAPPIE home unit 103 may confirm activation in step 728, and if confirmed in step 729, make a connection to a 911 operator in step 730, or otherwise request emergency services via the emergency services portal 106.

Using the smart home module 663, the resident may view historic data, as indicated in step 733. the resident may also examine analytics reporting in step 734. This may include, for example, electricity usage, or thermostat settings over the last several days, or any other analytical data collected by the HAPPIE home unit 103 and stored in the database 108. The HAPPIE home unit 103 also performs trend analysis of such data stored in the database 108, and can display it graphically to the resident, as indicated in step 735.

The smart home module 663 provides an open port 746 for expanded functionality and the integration of additional home systems with the HAPPIE home unit 103, as indicated in step 747. Any device that utilizes the Internet of Things technology, or "IoT," can be interfaced with the HAPPIE home unit 103 via the API 746. For example, if the resident installs solar panels on the residence, the smart home module 663 may interface with the solar energy equipment and provide historical data concerning the amount of electricity generated by the solar equipment, an analysis of the amount of electricity provided to the utility grid, and the amount of savings achieved to the resident based upon the electricity generated locally by the solar panels. If the resident has an electric car, and installs a charging cable in the residence, the charging equipment may be interfaced with the HAPPIE home unit 103 via the API 746, and reports can be provided for the resident concerning the charging history and amount of home electricity used for powering the electric car. Automatic smart self-propelled home vacuum cleaners may be interfaced with, and controlled by, the HAPPIE home unit 103 using the API 746.

Although the smart home module 663 has been described from the perspective of the resident, the smart home module 663 is also available remotely to a caregiver via the caregiver portal 101.

The HAPPIE home unit 103 is connected to the resident's TV 156. The HAPPIE home unit 103 may be attached in-line with the resident's TV 156, between the cable box and the TV 156. The HAPPIE home unit 103 adds an interface that slides in on the TV screen regardless of what TV channel or program the resident is watching on the TV 156. This slide in interface overlays the display on the TV screen, and can alert the resident to take medication, eat, or of upcoming appointments. The slide in interface can also allow the resident to answer phone calls and to video conference right on the screen of the resident's TV 156. The HAPPIE home unit 103 alerts and activities will simply slide in from the edge of the TV screen and will display information to the resident. The resident can also speak to the HAPPIE home unit 103 via microphones 113 and see prompts and feedback on the television screen. The HAPPIE home unit 103 can capture images of what is on the TV screen at regular intervals, and use this data to interpret what channels or programs the resident is watching.

In a preferred embodiment, as the resident or caretaker is browsing through the HAPPIE home unit 103, or when the HAPPIE home unit 103 is idle, it will listen for updated user-interface files on the server 100. These are different from operating system or program files. These are the content screens for the main display on video monitors 156 connected to the HAPPIE home unit 103. They can be updated anytime on the server 100 and will sometimes be laid out differently or have different options based on the configuration of the HAPPIE home unit 103. These screens will be monitored and updated as available.

The HAPPIE home unit 103 will monitor the quality of service of the connection to the server 100 and will not swap the local copy of screens until all the associated layout and graphics have been successfully downloaded and verified. In the case of a resident's data (contacts, appointments, etc.) and media, results are cached each time the HAPPIE home unit 103 connects to the main server 100. This way, if the connection goes down, the HAPPIE home unit 103 is still available to the resident. If the connection is live, results are updated and re-cached as they are downloaded.

In one embodiment, each HAPPIE home unit 103 (main console and remote processing units) is responsible for updating its own software and content. In a preferred embodiment, each HAPPIE home unit 103 may share its updates with other HAPPIE home units 103 to reduce download sizes. Currently when a HAPPIE home unit 103 boots, it downloads a catalog from the main server 100 based on its function (main console or remote processing unit) and it compares all of its files to the files listed in the catalog. Once the HAPPIE home unit 103 has compiled a list of discrepancies, it sends that list to the server 100 along with its current file version numbers. The server 100 decides which files are the highest priority and takes the amount of bandwidth currently available into account. The server 100 tells the HAPPIE home unit 103 which files to download and when. The HAPPIE home unit 103 will update and reboot if necessary.

In the case of large files, the update catalog can also recommend "patching" the existing file. Instead of downloading an entirely new file, the server 100 can decide it is faster to patch parts of the existing file, because a plethora of the file contents have not changed. This saves bandwidth and time. A "hash" is then computed for the resulting file (a mathematical algorithm which computes a number that represents the file contents) and sends it to the server 100. If the hash of the local file and the server file do not match, the server 100 will assume the patch failed and will recommend a complete file replacement.

In addition to the embodiments described herein, a plurality of HAPPIE home units 103 may deployed in a single residence, and can be interconnected. In the case of multiple HAPPIE home units 103, one HAPPIE home unit 103 will act as the server with the additional HAPPIE home units 103 communicating to the server unit 103 over a peer-to-peer network.

The video monitors 156 may be used with the HAPPIE home unit 103 to surf or otherwise access the Internet 105 using a conventional web browser running on the HAPPIE home unit 103.

It will be apparent to those skilled in the art that the various embodiments described above are simply representative examples of the described system within the scope of this invention, and that other modifications and configurations will also fall within its scope. In addition, various modifications of the illustrated embodiments will be apparent to a person skilled in the art after having the benefit of this disclosure. For example, in all instances where information or data is stored on the local database 108 maintained by the HAPPIE home unit 103, such information and data may also be simultaneously transmitted to a central server 100 and stored on a central database 175. Those skilled in the art will also appreciate that equivalent devices and materials, and equivalent method steps, may be substituted for those illustrated in the described examples, without departing from the spirit and scope of the invention.

What is claimed is:

1. A smart medicine cabinet comprising:
   a plurality of micro-pads including a first micro-pad;
   a plurality of containers including a first container;
   a database configured to store an allowed dosage weight for a medicine;
   each of the plurality of micro-pads configured for weight measurements of each of a plurality of containers, respectively, after each of a plurality of containers is replaced back onto each of the respective plurality of micro-pads;
   each of the plurality of micro-pads configured to communicate the weight measurements to a processor and store the weight measurements in a database;
   the processor is configured to compare a first weight measurement after the first container is replaced back onto the first micro-pad a first time to a second weight measurement after the first container is replaced back onto the micro-pad a second time;
   the processor is further configured to determine a taken dosage weight based on a difference between the first weight measurement and the second weight measurement;
   the processor is further configured to determine if the taken dosage weight corresponds to the allowed dosage weight;
   the processor is further configured to provide a notification, in response to the taken dosage weight being different from the allowed dosage weight;
   each of the plurality of micro-pads include a raised region;
   each of the plurality of containers is configured to securely conform to each of the plurality of micro-pads, respectively;
   each of the plurality of containers include an indentation region;
   the indentation region corresponding with, and registering with, the raised region;
   each indentation region being unique from other indentation regions such that one of the indentation regions only corresponds with, and registers with, one of the raised regions;
   each of the plurality of micro-pads is configured to receive an electrical activation;
   the electrical activation being configured to lock each of the plurality of containers to each of the plurality of micro-pads, respectively; and
   at a predetermined time, one of the plurality of micro-pads is configured to receive a deactivation signal that is configured to deactivate the electrical activation and unlock one of the plurality of containers from one of the plurality of micro-pads.

2. The smart medicine cabinet of claim 1, wherein the notification includes at least one of an alert sent to a caregiver via a caregiver portal, a communication via speakers or a communication via video monitors.

3. The smart medicine cabinet of claim 2, wherein the first container includes a screw-on top configured to lock to the first container.

4. The smart medicine cabinet of claim 3, further comprising a light ring around the first micro-pad.

5. The smart medicine cabinet of claim 4, further comprising a display associated with the first container, wherein the display is configured to indicate a number of doses remaining in the first container based on the allowed dosage weight.

6. The smart medicine cabinet of claim 5, wherein the processor is further configured to send a prescription refill request to at least one of a caretaker via a caretaker portal, a doctor via a doctor portal or a pharmacy via the internet, in response to a predetermined number of doses remaining.

7. The smart medicine cabinet of claim 6, further comprising a shelf having tabs received into indentations on a shelf holder base, wherein the first micro-pad is located on top of the shelf, and wherein power and communication ports on the tabs connect with corresponding power and communication ports on the indentations.

8. The smart medicine cabinet of claim 7, further comprising a power supply configured to power the shelf via the power and communication ports, a communication module configured to provide wireless data communication as a WiFi hotspot via the power and communication ports, a backup battery supply for the power and communication ports and Bluetooth communication functionality for the power and communication ports.

9. The smart medicine cabinet of claim 8, further comprising supports on the shelf, wherein the shelf is configured to be moved and placed on a surface remote from the smart medicine cabinet.

\* \* \* \* \*